(12) United States Patent
Tsantrizos et al.

(10) Patent No.: US 8,377,960 B2
(45) Date of Patent: Feb. 19, 2013

(54) INHIBITORS OF HUMAN IMMUNODEFICIENCY VIRUS REPLICATION

(75) Inventors: Youla S. Tsantrizos, Laval (CA); Murray D. Bailey, Pierrefonds (CA); François Bilodeau, Laval (CA); Rebekah J. Carson, Mascouche (CA); Lee Fader, St-Lazare (CA); Teddy Halmos, Laval (CA); Stephen Kawai, Montreal (CA); Serge R. Landry, St-Jerome (CA); Steven Laplantea, Bois-des-Filion (CA); Bruno Simoneau, Laval (CA)

(73) Assignee: Gilead Sciences, Inc., Foster City, CA (US)

( * ) Notice: Subject to any disclaimer, the term of this patent is extended or adjusted under 35 U.S.C. 154(b) by 196 days.

(21) Appl. No.: 12/743,138

(22) PCT Filed: Nov. 3, 2008

(86) PCT No.: PCT/CA2008/001941
§ 371 (c)(1), (2), (4) Date: Jul. 8, 2010

(87) PCT Pub. No.: WO2009/062289
PCT Pub. Date: May 22, 2009

(65) Prior Publication Data
US 2011/0028464 A1 Feb. 3, 2011

Related U.S. Application Data

(60) Provisional application No. 60/988,327, filed on Nov. 15, 2007.

(51) Int. Cl.
*A61K 31/47* (2006.01)
(52) U.S. Cl. ............................ 514/311; 546/152
(58) Field of Classification Search ............ 546/152
See application file for complete search history.

(56) References Cited

U.S. PATENT DOCUMENTS

| 5,686,486 A | 11/1997 | Tomich et al. |
| 5,700,810 A | 12/1997 | Natsugari et al. |
| 5,731,321 A | 3/1998 | Mederski et al. |
| 6,018,049 A | 1/2000 | Hajima et al. |
| 6,069,151 A | 5/2000 | Dyke et al. |
| 6,670,377 B1 | 12/2003 | MeKouar et al. |
| 7,176,220 B2 | 2/2007 | Satoh et al. |
| 7,939,545 B2 | 5/2011 | Tsantrizos et al. |
| 2005/0165052 A1 | 7/2005 | Fakhfakh et al. |
| 2005/0261336 A1 | 11/2005 | Mousnier et al. |
| 2006/0094755 A1 | 5/2006 | Rajagopalan et al. |
| 2010/0311735 A1 | 12/2010 | Tsantrizos et al. |

FOREIGN PATENT DOCUMENTS

| CA | 2446324 A1 | 11/2002 |
| CA | 2606282 A1 | 11/2006 |
| CA | 2622639 A1 | 4/2007 |
| CA | 2626956 A1 | 5/2007 |
| CA | 2600832 C | 12/2011 |
| CL | 239203 | 11/2004 |
| CL | 236004 | 8/2005 |
| EP | 0403535 A1 | 12/1990 |
| EP | 0447164 A1 | 9/1991 |
| EP | 1541558 A1 | 6/2005 |
| JP | 01063518 A | 3/1989 |
| JP | 03227923 A | 10/1991 |
| WO | WO-89/07939 | 9/1989 |
| WO | WO-99/33825 A8 | 8/1999 |
| WO | WO-01/57021 A3 | 2/2002 |
| WO | WO-03/030893 A1 | 4/2003 |
| WO | WO-03/039539 A3 | 11/2003 |
| WO | WO-2004050643 A2 | 6/2004 |
| WO | WO-2005058834 A2 | 6/2005 |
| WO | WO-2006129134 A1 | 12/2006 |
| WO | 2007131350 A1 | 11/2007 |
| WO | WO-2009/062289 | 5/2009 |
| WO | WO-2009/0622825 | 5/2009 |

OTHER PUBLICATIONS

International Search Report, Form PCT/ISA/210, for corresponding PCT/CA2008/001941; date of mailing: Feb. 13, 2008.
Kohl,H.; Synthesis and Biological Activity of Quinolyl Acetic Acid Derivatives; Journal of Pharmaceuticals Sciences; 1973; 2028-30.
Fehnel,E.; Friedlander Syntheses with o-Aminoaryl Ketones. III. Acid Catalyzed Condensations of o-Aminobenzophenone with Polyfunctional Carbonyl Compounds (1,2); Journal of Heterocyclic Chemistry; 1967; 565-570.
Mekouar, K.; Styryquinoline Derivatives: A New Class of Potent HIV-1 Integrase Inhibitors That Block HIV-1 Replication in CEM Cells; J. Med. Chem.; 1998; 41; 2846-2857.
Zoubiri, F.; Structure-Activity Relationships and Binding Mode of Styryquinolines as Potent Inhibitors of HIV-1 Integrase and Replication of HIV-1 in Cell Culture; J. Med. Chem.; 2000; 1533-1540.
International Preliminary Report on Patentability, Form PCT/IB/373, for PCT/CA2007/000845, mailed Nov. 17, 2008, 6 pages.
Written Opinion, Form PCT/ISA/237, for PCT/CA2007/000845, mailed Aug. 31, 2007, 5 pages.

(Continued)

*Primary Examiner* — Brian McDowell

(57) ABSTRACT

Compounds of formula I: wherein c, $R^2$, $R^3$, $R^4$, $R^5$, $R^6$, $R^7$ and $R^8$ are defined herein, are useful as inhibitors of HIV replication.

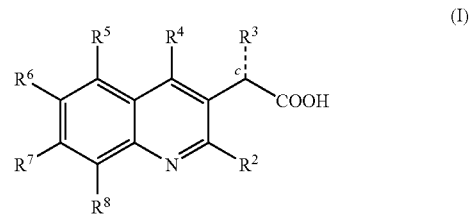

13 Claims, No Drawings

OTHER PUBLICATIONS

International Search Report, Form PCT/ISA/210, for PCT/CA2007/000845, mailed Aug. 31, 2007, 5 pages.
International Preliminary Report on Patentability, Form PCT/IB/373, for PCT/CA2008/001611, mailed May 27, 2010, 7 pages.
International Search Report, Form PCT/ISA/210, for PCT/CA2008/001611, mailed Dec. 4, 2008, 6 pages.
Written Opinion, Form PCT/ISA/237, for PCT/CA2008/001611, mailed Dec. 4, 2008, 6 pages.
International Preliminary Report on Patentability, Form PCT/IB/373, for PCT/CA2008/001941, mailed May 18, 2010, 6 pages.
Written Opinion, Form PCT/ISA/237, for PCT/CA2008/001941, mailed Feb. 13, 2009, 5 pages.
Partial International Search Report, Annex to Form PCT/ISA/206, for PCT/US2012/032026, mailed Jun. 13, 2012, 2 pages.
Notice of Allowance received for U.S. Appl. No. 11/746,303 dated Jan. 10, 2011, 4 pages.
Non Final Office Action received for U.S. Appl. No. 11/746,303 dated Aug. 9, 2010, 12 pages.
Office Communication received for U.S. Appl. No. 11/746,303 dated Mar. 31, 2011, 2 pages.
U.S. Appl. No. 11/746,303 Restriction Requirement, dated Apr. 22, 2010.
Notice of Allowance received for U.S. Appl. No. 12/742,997, dated May 18, 2012. 7 pages.
Notice of Allowance received for U.S. Appl. No. 12/742,997, dated Aug. 27, 2012, 7 pages.
Ali, Acta Chimica Academiae Scientiarum Hungaricae, 79(4):455-456, 1973.
Tang, W. et al., A General and Special Catalyst for Suzuki-Miyaura Coupling Processes, Angew. Chem. Int. Ed., 49(34):5879-5883, 2010.
Anzini, M. et al., Novel, Potent, and Selective 5-HT3 Receptor Antagonists Based on the Arylpiperazine Skeleton: Synthesis, Structure, Biological Activity, and comparative Molecular Field Analysis Studies, J. Med. Chem., 38(14):2692-2704, 1995.
Bénarda, C. et al., Linker-modified quinoline derivatives targeting HIV-1 integrase: synthesis and biological activity, Bioorganic & Medicinal Chemistry Letters, 14(10):2473-2476, 2004.
Bedoya, Luis M. et al, "4-Phenylcoumarins as HIV transcription inhibitors," Bioorganic & Medicinal Chemistry Letters: 15(2), 4447-4450, Oct. 15, 2005.
Cheng, C-C. et al., "The Friedlander Synthesis of Quinolines," Org. Reactions, 28:37-57, 1982.
Doi, F. et al., Synthesis of Chroman Derivatives by the Ring Expansion Reaction of Spirodienones, and and Assesment of the Plant Growth Inhibition, Bull. Chem. Soc. Jpn., 77:2257-2263, 2004.
Fakhfakha, M.A. et al., Synthesis and biological evaluation of substituted quinolines: potential treatment of protozoal and retroviral co-infections, Bioorganic & medicinal Chemistry, 11(23):5013-5023, 2003.
Feliu, L. et al., Conversion of a 4-quinolone into a 1,6-diazaphenalene, Tetrahedron, 53(12):4511-4520, 1997.
Forgione, P. et al., Unexpected Intermolecular Pd-Catalyzed Cross-Coupling Reaction Employing Heteroaromatic Carboxylic Acids as Coupling Partners, J. Am. Chem. Soc., 128(35):11350-11351, 2006.
Frye, S.V. et al., Synthesis of 2-aminobenzophenones via rapid halogen-lithium exchange in the presence of a 2-amino-N-methoxy-N-methylbenzamide, J. Org. Chem., 56(11):3750-3752, 1991.
Hahn, N.D. et al., Efficient and regioselective chromium(0)-catalyzed reaction of 2-substituted furans with diazo compounds: stereoselective synthesis of (2E,4Z)-2-aryl-hexadienedioic acid diesters, J. Organometal. Chem., 689(16):2662-2673, 2004.
Pitchai, P. et al., Photo induced synthesis of methyl derivative of cryptosanguinolentine, Indian J. Chem. Sec. B. Org. Chem. Including Med. Chem., 48B(5):692-696, 2009.
Chen, Y.C. et al., Multiple Dendritic Catalysts for Asymmetric Transfer Hydrogenation, J. Org. Chem., 67(15):5301-5306, 2002.
Kadzimirsz, D. et al., A Domino Annulation Reaction under Willgerodt-Kindler Conditions, J. Org. Chem., 73(12):4644-4649, 2008.
Jung, S.H. and Kim, S.H., Futher Understandings of Regio- and Stereoselectivity in the Diels-Alder Reaction: Diels-Alder Reaction of Allenic Ester with 4-(Bulky)alkyl-substituted 3-siloxy-1,3-butadiene, Bull. Korean Chem. Soc., 24(1):13-14, 2003.
Lin, H. and Paquette, L.A., A Convenient method for Determining the Concentration of Grignard Reagents, Synth. Commun., 24(17):2503-2506, 1994.
Love, B. et al., Benzazepinones. Synthesis of the monoaza analog of diazepam, and the correct structure of the benzoylpropionanilide cyclization product, J. Med. Chem., 14(9):849-852, 1971.
Mederski, W.W.K.R. et al., 1,4-diaryl-2-oxo-1,2-dihydro-quinoline-3-carboxylic acids as endothelin receptor antagonists, Bioorg. & Med. Chem. Lett., 7(14):1883-1886, 1997.
Michel, S. and Ley, S.V., Synthesis of Enantiomers of Butane-1,2-diacetal-Protected Glyceraldehyde and of (R,R)-Butane-1,2-diacetal-Protected Glycolic Acid, Synthesis, 2003(10):1598-1602, 2003.
Gengan, R.M. et al., Convenient and Efficient Microwave-Assisted Synthesis of a Methyl Derivative of the Fused Indoloquinoline Alkaloid Cryptosanguinolentine, Molecules, 15(5):3171-3178, 2010.
Movassaghi, M. et al., Direct Synthesis of Pyridine Derivatives, J. Am. Chem. Soc., 129(33):10096-10097, 2007.
Tang, W. et al., Efficient Monophosphorus Ligands for Palladium-Catalyzed Miyaura Borylation, Org. Lett., 13(6):1366-1369, 2011.
Paramasivam, K. et al, "Synthesis of Benzo[k]phenanthridines: Part Ivt," Indian J. Chem., Section B: Organic Chem Including Med. Chem., 23B(4):311-315, 1984.
Paramasivam, K., et al., Furoquinolines; Part XI. A Novel AICL3-Catalysed Rearrangement of 4-phenyl-2,3-dihydrofuro[2,3-b]quinolines. A New Route to the 5,6-Benzophenanthridine System, Synthesis, 11:768-770, 1977.
Sekar, M. and Prasad, K.J.R., Quinoline Alkaloids: Synthesis of Pyrano[2,3-b]quinolines, Khaplofoline, Lunacrine, and Demethoxy Lunacrine, J. Nat. Prod., 61:294-296, 1998.
Sivakamasundari, S. et al., Pyrroloquinolines: Part Ivt-Synthesis of 1-Aryl-1H-pyrrolo[2,3b]quinolines, Indian J. Chem., Section B: Organic Chem Including Med. Chem., 26B(8):744-747, 1987.
Takeuchi, Y. et al., Syntheses and antifungal activity of dl-griseofulvin and its congeners. III., Chem. Pharm. Bull. (Tokyo), 45(12):2011-2015, 1997.
Wolf, C. et al., Acid-Mediated Halogen Exchange in Heterocyclic Arenes: A Highly Effective Iodination Method, Synlett, 2003(12):1801-1804, 2003.
Zou, G. et al., Cross-coupling of arylboronic acids with terminal alkynes in air, Tetrahedron Lett., 44(48):8709-8711, 2003.
Zouhiri, F. et al., Structure-Activity Relationships and Binding Mode of Styrylquinolines as Potent Inhibitors of HIV-1 Integrase and Replication of HIV-1 in Cell Culture, J. Med. Chem., 43:1533-1540, 2000.

INHIBITORS OF HUMAN IMMUNODEFICIENCY VIRUS REPLICATION

RELATED APPLICATIONS

This application claims benefit of U.S. Ser. No. 60/988,327, filed Nov. 15, 2007, which is herein incorporated by reference.

FIELD OF THE INVENTION

The present invention relates to compounds, compositions and methods for the treatment of human immunodeficiency virus (HIV) infection. In particular, the present invention provides novel inhibitors of HIV replication, pharmaceutical compositions containing such compounds and methods for using these compounds in the treatment of HIV infection. More specifically, the present invention provides novel inhibitors of the HIV integrase enzyme, pharmaceutical compositions containing such compounds and methods for using these compounds to reduce HIV replication and in the treatment of HIV infection.

BACKGROUND OF THE INVENTION

Acquired immune deficiency syndrome (AIDS) is caused by the human immunodeficiency virus (HIV), particularly the HIV-1 strain. Most currently approved therapies for HIV infection target the viral reverse transcriptase and protease enzymes. There is additionally one approved drug targeting gp41 to inhibit viral entry and one approved drug targeting the integrase enzyme. Within the reverse transcriptase inhibitor and protease inhibitor classes, resistance of HIV to existing drugs is a problem. Therefore, it is important to discover and develop new antiretroviral compounds.

SUMMARY OF THE INVENTION

The present invention provides a novel series of compounds having inhibitory activity against HIV replication. Furthermore, representative compounds of the invention have activity as inhibitors in a cell-based HIV replication assay. Further objects of this invention arise for the one skilled in the art from the following description and the examples. The compounds of the present invention have an affinity for the HIV integrase enzyme. Therefore, the compounds of the invention may be used to inhibit the activity of HIV integrase and may be used to reduce HIV replication.

One aspect of the invention provides an isomer, racemate, enantiomer or diastereomer of a compound of formula (I):

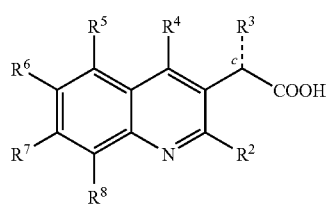

(I)

wherein
$R^2$ is selected from:
a) $(C_{2-6})$alkenyl, $(C_{2-6})$alkynyl, $(C_{1-6})$haloalkyl, $(C_{3-7})$cycloalkyl, aryl, Het, halo, nitro or cyano;
b) —C(=O)—$R^{11}$, —C(=O)—O—$R^{11}$, —S—$R^{11}$, —SO—$R^{11}$, —SO$_2$—$R^{11}$, —$(C_{1-6})$alkylene-$R^{11}$, —$(C_{1-6})$alkylene-C(=O)—$R^{11}$, —$(C_{1-6})$alkylene-C(=O)—O—$R^{11}$, —$(C_{1-6})$alkylene-O—$R^{11}$, —$(C_{1-6})$alkylene-S—$R^{11}$, —$(C_{1-6})$alkylene-SO—$R^{11}$ or —$(C_{1-6})$alkylene-SO$_2$—$R^{11}$;
wherein $R^{11}$ is in each instance independently selected from H, $(C_{1-6})$alkyl, $(C_{2-6})$alkenyl, $(C_{2-6})$alkynyl, $(C_{1-6})$haloalkyl, $(C_{3-7})$cycloalkyl, aryl and Het; and
wherein each of the aryl and Het is optionally substituted with 1 to 3 substituents each independently selected from:
i) halo, oxo, thioxo, $(C_{2-6})$alkenyl, $(C_{1-6})$haloalkyl, $(C_{3-7})$cycloalkyl, $(C_{3-7})$cycloalkyl-$(C_{1-6})$alkyl-, —OH, —O$(C_{1-6})$alkyl, —O$(C_{1-6})$haloalkyl, —SH, —S$(C_{1-6})$alkyl, —SO$(C_{1-6})$alkyl, —SO$_2$$(C_{1-6})$alkyl, —C(=O)—NH$_2$, —C(=O)—NH$(C_{1-4})$alkyl, —C(=O)—N$((C_{1-4})$alkyl$)_2$, —C(=O)-aryl, —C(=O)—Het, NH$_2$, —NH$(C_{1-6})$alkyl and —N$((C_{1-6})$alkyl$)_2$;
ii) $(C_{1-6})$alkyl optionally substituted with —OH, —O—$(C_{1-6})$haloalkyl, or —O—$(C_{1-6})$alkyl; and
iii) aryl or Het, wherein each of the aryl and Het is optionally substituted with halo, $(C_{1-6})$alkyl or COOH; and
c) —O—$R^{8a}$
wherein $R^{8a}$ is selected from H, $(C_{2-6})$alkenyl, $(C_{2-6})$alkynyl, $(C_{1-6})$haloalkyl, $(C_{3-7})$cycloalkyl, aryl and Het;
d) —N($R^9$)$R^{10}$, —C(=O)—N($R^9$)$R^{10}$, —O—C(=O)—N($R^9$)$R^{10}$, —SO$_2$—N($R^9$)$R^{10}$, —$(C_{1-6})$alkylene-N($R^9$)$R^{10}$, —$(C_{1-6})$alkylene-C(=O)—N($R^9$)$R^{10}$, —$(C_{1-6})$alkylene-O—C(=O)—N($R^9$)$R^{10}$, or —$(C_{1-6})$alkylene-SO$_2$—N($R^9$)$R^{10}$ wherein
$R^9$ is in each instance independently selected from H, $(C_{1-6})$alkyl and $(C_{3-7})$cycloalkyl; and
$R^{10}$ is in each instance independently selected from $R^{11}$, —$(C_{1-6})$alkylene-$R^{11}$, —SO$_2$—$R^{11}$, —C(=O)—$R^{11}$, —C(=O)O$R^{11}$ and —C(=O)N($R^9$)$R^{11}$;
wherein $R^{11}$ and $R^9$ are as defined above; or
$R^2$ may also be H, $(C_{1-6})$alkyl or —O—$(C_{1-6})$alkyl when one of $R^5$ or $R^8$ is other than H or when one of $R^6$ or $R^7$ is other than H, halo, $(C_{1-6})$alkyl or $(C_{1-6})$haloalkyl,
$R^5$ and $R^8$ are each independently selected from:
a) halo, nitro or cyano;
b) $R^{11}$, —C(=O)—$R^{11}$, —C(=O)—O—$R^{11}$, —O—$R^{11}$, —S—$R^{11}$, —SO—$R^{11}$, —SO$_2$—$R^{11}$, —$(C_{1-6})$alkylene-$R^{11}$, —$(C_{1-6})$alkylene-C(=O)—$R^{11}$, —$(C_{1-6})$alkylene-C(=O)—O—$R^{11}$, —$(C_{1-6})$alkylene-O—$R^{11}$, —$(C_{1-6})$alkylene-S—$R^{11}$, —$(C_{1-6})$alkylene-SO—$R^{11}$ or —$(C_{1-6})$alkylene-SO$_2$—$R^{11}$;
wherein $R^{11}$ is in each instance independently selected from H, $(C_{1-6})$alkyl, $(C_{2-6})$alkenyl, $(C_{2-6})$alkynyl, $(C_{1-6})$haloalkyl, $(C_{3-7})$cycloalkyl, aryl and Het; and
wherein each of the aryl and Het is optionally substituted with 1 to 3 substituents each independently selected from:
i) halo, oxo, thioxo, $(C_{2-6})$alkenyl, $(C_{1-6})$haloalkyl, $(C_{3-7})$cycloalkyl, $(C_{3-7})$cycloalkyl-$(C_{1-6})$alkyl-, —OH, —O$(C_{1-6})$alkyl, —O$(C_{1-6})$haloalkyl, —SH, —SO$(C_{1-6})$alkyl, —SO$_2$$(C_{1-6})$alkyl, —C(=O)—NH$_2$, —C(=O)—NH$(C_{1-4})$alkyl, —C(=O)—N$((C_{1-4})$alkyl$)_2$, —C(=O)-aryl, —C(=O)—Het, NH$_2$, —NH$(C_{1-6})$alkyl and —N$((C_{1-6})$alkyl$)_2$;
ii) $(C_{1-6})$alkyl optionally substituted with —OH, —O—$(C_{1-6})$haloalkyl, or —O—$(C_{1-6})$alkyl; and iii) aryl or Het, wherein each of the aryl and Het is optionally substituted with halo, $(C_{1-6})$alkyl or COOH; and c) $—N(R^9)R^{10}$, $—C(=O)—N(R^9)R^{10}$, $—SO_2—N(R^9)R^{10}$, $—(C_{1-6})$alkylene-$N(R^9)R^{10}$, $—(C_{1-6})$alkylene-$C(=O)—N(R^9)R^{10}$, $—(C_{1-6})$alkylene-$O—C(=O)—N(R^9)R^{10}$, or $—(C_{1-6})$alkylene-$SO_2—N(R^9)R^{10}$ wherein
$R^9$ is in each instance independently selected from H, $(C_{1-6})$alkyl and $(C_{3-7})$cycloalkyl; and
$R^{10}$ is in each instance independently selected from $R^{11}$, $—(C_{1-6})$alkylene-$R^{11}$, $—SO_2—R^{11}$, $—C(=O)—R^{11}$, $—C(=O)OR^{11}$ and $—C(=O)N(R^9)R^{11}$;
wherein $R^{11}$ and $R^9$ are as defined above;

$R^6$ is selected from:
a) $(C_{2-6})$alkenyl, $(C_{2-6})$alkynyl, $(C_{3-7})$cycloalkyl, nitro, cyano, aryl and Het;
b) $—C(=O)—R^{11}$, $—C(=O)—O—R^{11}$, $—O—R^{11}$, $—S—R^{11}$, $—SO—R^{11}$, $—SO_2—R^{11}$, $—(C_{1-6})$alkylene-$R^{11}$, $—(C_{1-6})$alkylene-$C(=O)—R^{11}$, $—(C_{1-6})$alkylene-$C(=O)—O—R^{11}$, $—(C_{1-6})$alkylene-$O—R^{11}$, $—(C_{1-6})$alkylene-$S—R^{11}$, $—(C_{1-6})$alkylene-$SO—R^{11}$ or $—(C_{1-6})$alkylene-$SO_2—R^{11}$;
wherein $R^{11}$ is in each instance independently selected from H, $(C_{1-6})$alkyl, $(C_{2-6})$alkenyl, $(C_{2-6})$alkynyl, $(C_{1-6})$haloalkyl, $(C_{3-7})$cycloalkyl, aryl and Het; and
c) $—N(R^9)R^{10}$ $—O—C(=O)—N(R^9)R^{10}$, $—SO_2—N(R^9)R^{10}$, $—(C_{1-6})$alkylene-$N(R^9)R^{10}$, $—(C_{1-6})$alkylene-$C(=O)—N(R^9)R^{10}$, $—(C_{1-6})$alkylene-$O—C(=O)—N(R^9)R^{10}$, or $—(C_{1-6})$alkylene-$SO_2—N(R^9)R^{10}$ wherein
$R^9$ is in each instance independently selected from H, $(C_{1-6})$alkyl and $(C_{3-7})$cycloalkyl; and
$R^{10}$ is in each instance independently selected from $R^{11}$, $—(C_{1-6})$alkylene-$R^{11}$, $—SO_2—R^{11}$, $—C(=O)—R^{11}$, $—C(=O)OR^{11}$ and $—C(=O)N(R^9)R^{11}$;
wherein $R^{11}$ and $R^9$ are as defined above;

wherein each of the aryl and Het is optionally substituted with 1 to 3 substituents each independently selected from:
i) halo, oxo, thioxo, $(C_{2-6})$alkenyl, $(C_{1-6})$haloalkyl, $(C_{3-7})$cycloalkyl, $(C_{3-7})$cycloalkyl-$(C_{1-6})$alkyl-, $—OH$, $—O(C_{1-6})$alkyl, $—O(C_{1-6})$haloalkyl, $—SH$, $—S(C_{1-6})$alkyl, $—SO(C_{1-6})$alkyl, $—SO_2(C_{1-6})$alkyl, $—NH_2$, $—NH(C_{1-6})$alkyl and $—N((C_{1-6})$alkyl$)_2$;
ii) $(C_{1-6})$alkyl optionally substituted with $—OH$, $—O—(C_{1-6})$haloalkyl, or $—O—(C_{1-6})$alkyl; and
iii) aryl or Het, wherein each of the aryl and Het is optionally substituted with halo, $(C_{1-6})$alkyl or COOH; and $R^6$ may also be H, halo, $(C_{1-6})$alkyl, or $(C_{1-6})$haloalkyl when at least one of $R^5$ or $R^8$ is other than H or when $R^7$ is other than H, halo, $(C_{1-6})$alkyl, or $(C_{1-6})$haloalkyl or when $R^2$ is other than H, $(C_{1-6})$alkyl, or $—O—(C_{1-6})$alkyl;

$R^7$ is selected from:
a) $(C_{2-6})$alkenyl, $(C_{2-6})$alkynyl, $(C_{3-7})$cycloalkyl, nitro, cyano, aryl and Het;
b) $—C(=O)—R^{11}$, $—C(=O)—O—R^{11}$, $—S—R^{11}$, $—SO—R^{11}$, $—SO_2—R^{11}$, $—(C_{1-6})$alkylene-$R^{11}$, $—(C_{1-6})$alkylene-$C(=O)—R^{11}$, $—(C_{1-6})$alkylene-$C(=O)—O—R^{11}$, $—(C_{1-6})$alkylene-$O—R^{11}$, $—(C_{1-6})$alkylene-$S—R^{11}$, $—(C_{1-6})$alkylene-$SO—R^{11}$ or $—(C_{1-6})$alkylene-$SO_2—R^{11}$;
wherein $R^{11}$ is in each instance independently selected from H, $(C_{1-6})$alkyl, $(C_{2-6})$alkenyl, $(C_{2-6})$alkynyl, $(C_{1-6})$haloalkyl, $(C_{3-7})$cycloalkyl, aryl and Het; and
c) $—N(R^9)R^{10}$, $—C(=O)—N(R^9)R^{10}$, $—O—C(=O)—N(R^9)R^{10}$, $—SO_2—N(R^9)R^{10}$, $—(C_{1-6})$alkylene-$N(R^9)R^{10}$, $—(C_{1-6})$alkylene-$C(=O)—N(R^9)R^{10}$, $—(C_{1-6})$alkylene-$O—C(=O)—N(R^9)R^{10}$, or $—(C_{1-6})$alkylene-$SO_2—N(R^9)R^{10}$ wherein $R^9$ is in each instance independently selected from H, $(C_{1-6})$alkyl and $(C_{3-7})$cycloalkyl; and
$R^{10}$ is in each instance independently selected from $R^{11}$, $—(C_{1-6})$alkylene-$R^{11}$, $—SO_2—R^{11}$, $—C(=O)—R^{11}$, $—C(=O)OR^{11}$ and $—C(=O)N(R^9)R^{11}$;
wherein $R^{11}$ and $R^9$ are as defined above;

wherein each of the aryl and Het is optionally substituted with 1 to 3 substituents each independently selected from:
i) halo, oxo, thioxo, $(C_{2-6})$alkenyl, $(C_{1-6})$haloalkyl, $(C_{3-7})$cycloalkyl, $(C_{3-7})$cycloalkyl-$(C_{1-6})$alkyl-, $—OH$, $—O(C_{1-6})$alkyl, $—O(C_{1-6})$haloalkyl, $—SH$, $—S(C_{1-6})$alkyl, $—SO(C_{1-6})$alkyl, $—SO_2(C_{1-6})$alkyl, $—NH_2$, $—NH(C_{1-6})$alkyl and $—N((C_{1-6})$alkyl$)_2$;
ii) $(C_{1-6})$alkyl optionally substituted with $—OH$, $—O—(C_{1-6})$haloalkyl, or $—O—(C_{1-6})$alkyl; and
iii) aryl or Het, wherein each of the aryl and Het is optionally substituted with halo, $(C_{1-6})$alkyl or COOH; and $R^7$ may also be H, halo, $(C_{1-6})$alkyl, or $(C_{1-6})$haloalkyl when at least one of $R^5$ or $R^8$ is other than H or when $R^6$ is other than H, halo, $(C_{1-6})$alkyl, or $(C_{1-6})$haloalkyl or when $R^2$ is other than H, $(C_{1-6})$alkyl, or $—O—(C_{1-6})$alkyl;

or $R^5$ and $R^6$, together with the C to which they are attached, $R^6$ and $R^7$, together with the C to which they are attached, or $R^7$ and $R^8$, together with the C to which they are attached; may be linked to form a 5- or 6-membered carbocycle or a 4- to 7-membered heterocycle optionally further containing 1 to 3 heteroatoms each independently selected from N, O and S, wherein each S heteroatom may, independently and where possible, exist in an oxidized state such that it is further bonded to one or two oxygen atoms to form the groups SO or $SO_2$;
wherein the carbocycle or heterocycle is optionally substituted with 1 to 3 substituents each independently selected from halo, $(C_{1-6})$alkyl, $(C_{2-6})$alkenyl, $(C_{1-6})$haloalkyl, $(C_{3-7})$cycloalkyl, $—OH$, $—O(C_{1-6})$alkyl, $—SH$, $—S(C_{1-6})$alkyl, $—NH_2$, $—NH(C_{1-6})$alkyl and $—N((C_{1-6})$alkyl$)_2$;

$R^3$ is $(C_{1-6})$alkyl, $(C_{1-6})$haloalkyl, $(C_{2-6})$alkenyl, $(C_{2-6})$alkynyl, $(C_{3-7})$cycloalkyl-$(C_{1-6})$alkyl-, aryl-$(C_{1-6})$alkyl-, Het-$(C_{1-6})$alkyl- or $—Y—R^{31}$, and bond c is a single bond; or
$R^3$ is $(C_{1-6})$alkylidene and bond c is a double bond;
wherein Y is O or S and $R^{31}$ is $(C_{1-6})$alkyl, $(C_{1-6})$haloalkyl, $(C_{2-6})$alkenyl, $(C_{2-6})$alkynyl, $(C_{3-7})$cycloalkyl, aryl, $(C_{3-7})$cycloalkyl-$(C_{1-6})$alkyl-, aryl-$(C_{1-6})$alkyl- or Het-$(C_{1-6})$alkyl-;
wherein each of the $(C_{1-6})$alkylidene, $(C_{1-6})$alkyl, $(C_{1-6})$haloalkyl, $(C_{2-6})$alkenyl, $(C_{2-6})$alkynyl, $(C_{3-7})$cycloalkyl-$(C_{1-6})$alkyl-, Het-$(C_{1-6})$alkyl- and $—Y—R^{31}$ is optionally substituted with 1 to 3 substituents each independently selected from $(C_{1-6})$alkyl, halo, cyano, oxo and $—O(C_{1-6})$alkyl;

$R^4$ is aryl or Het, wherein each of the aryl and Het is optionally substituted with 1 to 5 substituents each independently selected from halo, $(C_{1-6})$alkyl, $(C_{2-6})$alkenyl, $(C_{1-6})$haloalkyl, $(C_{3-7})$cycloalkyl, $—OH$, $—O(C_{1-6})$alkyl, $—SH$, $—S(C_{1-6})$alkyl, $—NH_2$, $—NH(C_{1-6})$alkyl and $—N((C_{1-6})$alkyl$)_2$; wherein the $(C_{1-6})$alkyl is optionally substituted with hydroxy, $—O(C_{1-6})$alkyl, cyano or oxo;

wherein Het is a 4- to 7-membered saturated, unsaturated or aromatic heterocycle having 1 to 4 heteroatoms each independently selected from O, N and S, or a 7- to 14-membered saturated, unsaturated or aromatic heteropolycycle having wherever possible 1 to 5 heteroatoms, each independently selected from O, N and S; wherein each N heteroatom may, independently and where possible, exist in an oxidized state such that it is further bonded to an oxygen atom to form an N-oxide group and wherein each S heteroatom may, independently and where possible, exist in an oxidized state such that it is further bonded to one or two oxygen atoms to form the groups SO or $SO_2$;

or a salt or an ester thereof.

Another aspect of this invention provides a compound of formula (I) or a pharmaceutically acceptable salt or ester thereof, as a medicament.

Still another aspect of this invention provides a pharmaceutical composition comprising a therapeutically effective amount of a compound of formula (I) or a pharmaceutically acceptable salt or ester thereof; and one or more pharmaceutically acceptable carriers.

According to an embodiment of this aspect, the pharmaceutical composition according to this invention additionally comprises at least one other antiviral agent.

The invention also provides the use of a pharmaceutical composition as described hereinabove for the treatment of an HIV infection in a mammal having or at risk of having the infection.

A further aspect of the invention involves a method of treating an HIV infection in a mammal having or at risk of having the infection, the method comprising administering to the mammal a therapeutically effective amount of a compound of formula (I), a pharmaceutically acceptable salt or ester thereof, or a composition thereof as described hereinabove.

Another aspect of the invention involves a method of treating an HIV infection in a mammal having or at risk of having the infection, the method comprising administering to the mammal a therapeutically effective amount of a combination of a compound of formula (I) or a pharmaceutically acceptable salt or ester thereof, and at least one other antiviral agent; or a composition thereof.

Also within the scope of this invention is the use of a compound of formula (I) as described herein, or a pharmaceutically acceptable salt or ester thereof, for the treatment of an HIV infection in a mammal having or at risk of having the infection.

Another aspect of this invention provides the use of a compound of formula (I) as described herein, or a pharmaceutically acceptable salt or ester thereof, for the manufacture of a medicament for the treatment of an HIV infection in a mammal having or at risk of having the infection.

An additional aspect of this invention refers to an article of manufacture comprising a composition effective to treat an HIV infection; and packaging material comprising a label which indicates that the composition can be used to treat infection by HIV; wherein the composition comprises a compound of formula (I) according to this invention or a pharmaceutically acceptable salt or ester thereof.

Still another aspect of this invention relates to a method of inhibiting the replication of HIV comprising exposing the virus to an effective amount of the compound of formula (I), or a salt or ester thereof, under conditions where replication of HIV is inhibited.

Further included in the scope of the invention is the use of a compounds of formula (I) to inhibit the activity of the HIV integrase enzyme.

Further included in the scope of the invention is the use of a compound of formula (I), or a salt or ester thereof, to inhibit the replication of HIV.

DETAILED DESCRIPTION OF THE INVENTION

Definitions

As used herein, the following definitions apply unless otherwise noted:

The term "substituent", as used herein and unless specified otherwise, is intended to mean an atom, radical or group which may be bonded to a carbon atom, a heteroatom or any other atom which may form part of a molecule or fragment thereof, which would otherwise be bonded to at least one hydrogen atom. Substituents contemplated in the context of a specific molecule or fragment thereof are those which give rise to chemically stable compounds, such as are recognized by those skilled in the art.

The term "$(C_{1-n})$alkyl" as used herein, wherein n is an integer, either alone or in combination with another radical, is intended to mean acyclic, straight or branched chain alkyl radicals containing from 1 to n carbon atoms. "$(C_{1-6})$alkyl" includes, but is not limited to, methyl, ethyl, propyl (n-propyl), butyl (n-butyl), 1-methylethyl (iso-propyl), 1-methylpropyl (sec-butyl), 2-methylpropyl (iso-butyl), 1,1-dimethylethyl (tent-butyl), pentyl and hexyl. The abbreviation Me denotes a methyl group; Et denotes an ethyl group, Pr denotes a propyl group, iPr denotes a 1-methylethyl group, Bu denotes a butyl group and tBu denotes a 1,1-dimethylethyl group.

The term "$(C_{1-n})$alkylidene" as used herein, wherein n is an integer, either alone or in combination with another radical, is intended to mean acyclic, straight or branched chain alkyl radicals containing from 1 to n carbon atoms which are bonded to a molecule or fragment thereof, as a substituent thereof, by a double bond. "$(C_{1-6})$alkylidene" includes, but is not limited to, $CH_2=$, $CH_3CH=$, $CH_3CH_2CH=$,

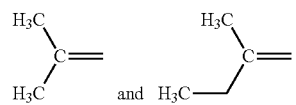

groups. Unless specified otherwise, the term "$(C_{2-n})$alkylidene" is understood to encompass individual stereoisomers where possible, including but not limited to (E) and (Z) isomers, and mixtures thereof. When a $(C_{2-n})$alkylidene group is substituted, it is understood to be substituted on any carbon atom thereof which would otherwise bear a hydrogen atom, unless specified otherwise, such that the substitution would give rise to a chemically stable compound, such as are recognized by those skilled in the art.

The term "$(C_{1-n})$alkylene" as used herein, wherein n is an integer, either alone or in combination with another radical, is intended to mean acyclic, straight or branched chain divalent alkyl radicals containing from 1 to n carbon atoms. "$(C_{1-6})$alkylene" includes, but is not limited to, $—CH_2—$, $—CH_2CH_2—$,

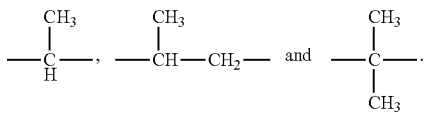

The term "$(C_{2-n})$alkenyl", as used herein, wherein n is an integer, either alone or in combination with another radical, is intended to mean an unsaturated, acyclic straight or branched chain radical containing two to n carbon atoms, at least two of which are bonded to each other by a double bond. Examples of such radicals include, but are not limited to, ethenyl (vinyl), 1-propenyl, 2-propenyl, and 1-butenyl. Unless specified otherwise, the term "$(C_{2-n})$alkenyl" is understood to encompass individual stereoisomers where possible, including but not limited to (E) and (Z) isomers, and mixtures thereof. When a $(C_{2-n})$alkenyl group is substituted, it is understood to be substituted on any carbon atom thereof which would otherwise bear a hydrogen atom, unless specified otherwise, such that the substitution would give rise to a chemically stable compound, such as are recognized by those skilled in the art.

The term "$(C_{2-n})$alkynyl", as used herein, wherein n is an integer, either alone or in combination with another radical, is intended to mean an unsaturated, acyclic straight or branched chain radical containing two to n carbon atoms, at least two of which are bonded to each other by a triple bond. Examples of such radicals include, but are not limited to, ethynyl, 1-propynyl, 2-propynyl, and 1-butynyl. When a $(C_{2-n})$alkynyl group is substituted, it is understood to be substituted on any carbon atom thereof which would otherwise bear a hydrogen atom, unless specified otherwise, such that the substitution would give rise to a chemically stable compound, such as are recognized by those skilled in the art.

The term "$(C_{3-m})$cycloalkyl" as used herein, wherein m is an integer, either alone or in combination with another radical, is intended to mean a cycloalkyl substituent containing from 3 to m carbon atoms and includes, but is not limited to, cyclopropyl, cyclobutyl, cyclopentyl, cyclohexyl and cycloheptyl.

The term "$(C_{3-m})$cycloalkyl-$(C_{1-n})$alkyl-" as used herein, wherein n and m are both integers, either alone or in combination with another radical, is intended to mean an alkyl radical having 1 to n carbon atoms as defined above which is itself substituted with a cycloalkyl radical containing from 3 to m carbon atoms as defined above. Examples of $(C_{3-7})$cycloalkyl-$(C_{1-6})$alkyl- include, but are not limited to, cyclopropylmethyl, cyclobutylmethyl, cyclopentylmethyl, cyclohexylmethyl, 1-cyclopropylethyl, 2-cyclopropylethyl, 1-cyclobutylethyl, 2-cyclobutylethyl, 1-cyclopentylethyl, 2-cyclopentylethyl, 1-cyclohexylethyl and 2-cyclohexylethyl. When a $(C_{3-m})$cycloalkyl-$(C_{1-n})$alkyl-group is substituted, it is understood that substituents may be attached to either the cycloalkyl or the alkyl portion thereof or both, unless specified otherwise, such that the substitution would give rise to a chemically stable compound, such as are recognized by those skilled in the art.

The term "aryl" as used herein, either alone or in combination with another radical, is intended to mean a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, 1-naphthyl, 2-naphthyl, tetrahydronaphthyl and dihydronaphthyl.

The term "aryl-$(C_{1-n})$alkyl-" as used herein, wherein n is an integer, either alone or in combination with another radical, is intended to mean an alkyl radical having 1 to n carbon atoms as defined above which is itself substituted with an aryl radical as defined above. Examples of aryl-$(C_{1-n})$alkyl- include, but are not limited to, phenylmethyl (benzyl), 1-phenylethyl, 2-phenylethyl and phenylpropyl. When an aryl-$(C_{1-n})$alkyl-group is substituted, it is understood that substituents may be attached to either the aryl or the alkyl portion thereof or both, unless specified otherwise, such that the substitution would give rise to a chemically stable compound, such as are recognized by those skilled in the art.

The term "carbocycle" as used herein, either alone or in combination with another radical, is intended to mean a cyclic compound, either aromatic or non-aromatic, saturated or unsaturated, in which all of the ring members are carbon atoms. The carbocycle group may containing 5 or 6 carbon atom and may be further fused to a second 5- or 6-membered carbocyclic group which may be aromatic, saturated or unsaturated.

The term "Het" as used herein, either alone or in combination with another radical, is intended to mean a 4- to 7-membered saturated, unsaturated or aromatic heterocycle having 1 to 4 heteroatoms each independently selected from O, N and S, or a 7- to 14-membered saturated, unsaturated or aromatic heteropolycycle having wherever possible 1 to 5 heteroatoms, each independently selected from O, N and S, unless specified otherwise; wherein each N heteroatom may, independently and where possible, exist in an oxidized state such that it is further bonded to an oxygen atom to form an N-oxide group and wherein each S heteroatom may, independently and where possible, exist in an oxidized state such that it is further bonded to one or two oxygen atoms to form the groups SO or $SO_2$. When a Het group is substituted, it is understood that substituents may be attached to any carbon atom or heteroatom thereof which would otherwise bear a hydrogen atom, unless specified otherwise, such that the substitution would give rise to a chemically stable compound, such as are recognized by those skilled in the art.

The term "Het-$(C_{1-n})$alkyl-" as used herein and unless specified otherwise, wherein n is an integer, either alone or in combination with another radical, is intended to mean an alkyl radical having 1 to n carbon atoms as defined above which is itself substituted with a Het substituent as defined above. Examples of Het-$(C_{1-n})$alkyl- include, but are not limited to, thienylmethyl, furylmethyl, piperidinylethyl, 2-pyridinylmethyl, 3-pyridinylmethyl, 4-pyridinylmethyl, quinolinylpropyl, and the like. When an Het-$(C_{1-n})$alkyl-group is substituted, it is understood that substituents may be attached to either the Het or the alkyl portion thereof or both, unless specified otherwise, such that the substitution would give rise to a chemically stable compound, such as are recognized by those skilled in the art.

The term "heteroatom" as used herein is intended to mean O, S or N.

The term "heterocycle" as used herein and unless specified otherwise, either alone or in combination with another radical, is intended to mean a 3- to 7-membered saturated, unsaturated or aromatic heterocycle containing from 1 to 4 heteroatoms each independently selected from O, N and S; or a monovalent radical derived by removal of a hydrogen atom therefrom. Examples of such heterocycles include, but are not limited to, azetidine, pyrrolidine, tetrahydrofuran, tetrahydrothiophene, thiazolidine, oxazolidine, pyrrole, thiophene, furan, pyrazole, imidazole, isoxazole, oxazole, isothiazole, thiazole, triazole, tetrazole, piperidine, piperazine, azepine, diazepine, pyran, 1,4-dioxane, 4-morpholine, 4-thiomorpholine, pyridine, pyridine-N-oxide, pyridazine, pyrazine and pyrimidine, and saturated, unsaturated and aromatic derivatives thereof.

The term "heteropolycycle" as used herein and unless specified otherwise, either alone or in combination with another radical, is intended to mean a heterocycle as defined above fused to one or more other cycle, including a carbocycle, a heterocycle or any other cycle; or a monovalent radical derived by removal of a hydrogen atom therefrom. Examples of such heteropolycycles include, but are not limited to, indole, isoindole, benzimidazole, benzothiophene, benzofuran, benzopyran, benzodioxole, benzodioxane, benzothiazole, quinoline, isoquinoline, and naphthyridine, and saturated, unsaturated and aromatic derivatives thereof.

The term "halo" as used herein is intended to mean a halogen substituent selected from fluoro, chloro, bromo or iodo.

The term "$(C_{1-n})$haloalkyl" as used herein, wherein n is an integer, either alone or in combination with another radical, is intended to mean an alkyl radical having 1 to n carbon atoms as defined above wherein one or more hydrogen atoms are each replaced by a halo substituent. Examples of $(C_{1-n})$haloalkyl include but are not limited to chloromethyl, chloroethyl, dichloroethyl, bromomethyl, bromoethyl, dibromoethyl, fluoromethyl, difluoromethyl, trifluoromethyl, fluoroethyl and difluoroethyl.

The terms "—O—$(C_{1-n})$alkyl" or "$(C_{1-n})$alkoxy" as used herein interchangeably, wherein n is an integer, either alone or in combination with another radical, is intended to mean an oxygen atom further bonded to an alkyl radical having 1 to n carbon atoms as defined above. Examples of —O—$(C_{1-n})$alkyl include but are not limited to methoxy ($CH_3O$—), ethoxy ($CH_3CH_2O$—), propoxy ($CH_3CH_2CH_2O$—), 1-methylethoxy (iso-propoxy; $(CH_3)_2CH$—O—) and 1,1-dimethylethoxy (tert-butoxy; $(CH_3)_3C$—O—). When an —O—$(C_{1-n})$alkyl radical is substituted, it is understood to be substituted on the $(C_{1-n})$alkyl portion thereof, such that the substitution would give rise to a chemically stable compound, such as are recognized by those skilled in the art.

The term "—O—$(C_{1-n})$haloalkyl", wherein n is an integer, either alone or in combination with another radical, is intended to mean an oxygen atom further bonded to a haloalkyl radical having 1 to n carbon atoms as defined above. When an —O—$(C_{1-n})$haloalkyl radical is substituted, it is understood to be substituted on the $(C_{1-n})$alkyl portion thereof.

The terms "—S—$(C_{1-n})$alkyl" or "$(C_{1-n})$alkylthio" as used herein interchangeably, wherein n is an integer, either alone or in combination with another radical, is intended to mean an sulfur atom further bonded to an alkyl radical having 1 to n carbon atoms as defined above. Examples of —S—$(C_{1-n})$alkyl include but are not limited to methylthio ($CH_3S$—), ethylthio ($CH_3CH_2S$—), propylthio ($CH_3CH_2CH_2S$—), 1-methylethylthio (isopropylthio; $(CH_3)_2CH$—S—) and 1,1-dimethylethylthio (tert-butylthio; $(CH_3)_3C$—S—). When —S—$(C_{1-n})$alkyl radical, or an oxidized derivative thereof, such as an —SO—$(C_{1-n})$alkyl radical or an —$SO_2$—$(C_{1-n})$alkyl radical, is substituted, each is understood to be substituted on the $(C_{1-n})$alkyl portion thereof, such that the substitution would give rise to a chemically stable compound, such as are recognized by those skilled in the art.

The term "oxo" as used herein is intended to mean an oxygen atom attached to a carbon atom as a substituent by a double bond (=O).

The term "thioxo" as used herein is intended to mean a sulfur atom attached to a carbon atom as a substituent by a double bond (=S).

The term "cyano" as used herein is intended to mean a carbon atom attached to a nitrogen atom as a substituent by a triple bond.

The term "COOH" as used herein is intended to mean a carboxyl group (—C(=O)—OH). It is well known to one skilled in the art that carboxyl groups may be substituted by functional group equivalents. Examples of such functional group equivalents contemplated in this invention include, but are not limited to, esters, amides, imides, boronic acids, phosphonic acids, phosphoric acids, tetrazoles, triazoles, N-acylsulfamides ($RCONHSO_2NR_2$), and N-acylsulfonamides ($RCONHSO_2R$).

The term "functional group equivalent" as used herein is intended to mean an atom or group that may replace another atom or group which has similar electronic, hybridization or bonding properties.

The term "protecting group" as used herein is intended to mean protecting groups that can be used during synthetic transformation, including but not limited to examples which are listed in Greene, "Protective Groups in Organic Chemistry", John Wiley & Sons, New York (1981), and more recent editions thereof, herein incorporated by reference.

The following designation

is used in sub-formulas to indicate the bond which is connected to the rest of the molecule as defined.

The term "salt thereof" as used herein is intended to mean any acid and/or base addition salt of a compound according to the invention, including but not limited to a pharmaceutically acceptable salt thereof.

The term "pharmaceutically acceptable salt" as used herein is intended to mean a salt of a compound according to the invention which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. Lists of suitable salts are found in, for example, S. M. Birge et al., J. Pharm. Sci., 1977, 66, pp. 1-19, herein incorporated by reference.

The term "pharmaceutically-acceptable acid addition salt" as used herein is intended to mean those salts which retain the biological effectiveness and properties of the free bases and which are not biologically or otherwise undesirable, formed with inorganic acids including but not limited to hydrochloric acid, hydrobromic acid, sulfuric acid, sulfamic acid, nitric acid, phosphoric acid and the like, and organic acids including but not limited to acetic acid, trifluoroacetic acid, adipic acid, ascorbic acid, aspartic acid, benzenesulfonic acid, benzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, hexanoic acid, formic acid, fumaric acid, 2-hydroxyethanesulfonic acid (isethionic acid), lactic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, pivalic acid, propionic acid, pyruvic acid, salicylic acid, stearic acid, succinic acid, sulfanilic acid, tartaric acid, p-toluenesulfonic acid, undecanoic acid and the like.

The term "pharmaceutically-acceptable base addition salt" as used herein is intended to mean those salts which retain the biological effectiveness and properties of the free acids and which are not biologically or otherwise undesirable, formed with inorganic bases including but not limited to ammonia or the hydroxide, carbonate, or bicarbonate of ammonium or a metal cation such as sodium, potassium, lithium, calcium, magnesium, iron, zinc, copper, manganese, aluminum and the like. Particularly preferred are the ammonium, potassium, sodium, calcium, and magnesium salts. Salts derived from pharmaceutically-acceptable organic nontoxic bases include but are not limited to salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins and the like. Particularly preferred organic nontoxic bases are isopropylamine, diethylamine, ethanolamine, trimethylamine, dicyclohexylamine, choline, and caffeine.

The term "ester thereof" as used herein is intended to mean any ester of a compound according to the invention in which any of the —COOH substituents of the molecule is replaced by a —COOR substituent, in which the R moiety of the ester is any carbon-containing group which forms a stable ester moiety, including but not limited to alkyl, alkenyl, alkynyl, cycloalkyl, cycloalkylalkyl, aryl, arylalkyl, heterocyclyl, heterocyclylalkyl, each of which being optionally further substituted. The term "ester thereof" includes but is not limited to pharmaceutically acceptable esters thereof.

The term "pharmaceutically acceptable ester" as used herein is intended to mean esters of the compound according to the invention in which any of the COOH substituents of the molecule are replaced by a —COOR substituent, in which the R moiety of the ester is selected from alkyl (including, but not limited to, methyl, ethyl, propyl, 1-methylethyl, 1,1-dimethylethyl, butyl); alkoxyalkyl (including, but not limited to methoxymethyl); acyloxyalkyl (including, but not limited to acetoxymethyl); arylalkyl (including, but not limited to, benzyl); aryloxyalkyl (including, but not limited to, phenoxymethyl); and aryl (including, but not limited to phenyl) optionally substituted with halogen, $(C_{1-4})$alkyl or $(C_{1-4})$alkoxy. Other suitable esters can be found in Design of Prodrugs, Bundgaard, H. Ed. Elsevier (1985), herein incorporated by reference. Such pharmaceutically acceptable esters are usually hydrolyzed in vivo when injected into a mammal and transformed into the acid form of the compound according to the invention. With regard to the esters described above, unless otherwise specified, any alkyl moiety present preferably contains 1 to 16 carbon atoms, more preferably 1 to 6 carbon atoms. Any aryl moiety present in such esters preferably comprises a phenyl group. In particular the esters may be a $(C_{1-16})$alkyl ester, an unsubstituted benzyl ester or a benzyl ester substituted with at least one halogen, $(C_{1-6})$alkyl, $(C_{1-6})$alkoxy, nitro or trifluoromethyl.

The term "mammal" as used herein is intended to encompass humans, as well as non-human mammals which are susceptible to infection by HIV. Non-human mammals include but are not limited to domestic animals, such as cows, pigs, horses, dogs, cats, rabbits, rats and mice, and non-domestic animals.

The term "treatment" as used herein is intended to mean the administration of a compound or composition according to the present invention to alleviate or eliminate symptoms of HIV infection and/or to reduce viral load in a patient. The term "treatment" also encompasses the administration of a compound or composition according to the present invention post-exposure of the individual to the virus but before the appearance of symptoms of the disease, and/or prior to the detection of the virus in the blood, to prevent the appearance of symptoms of the disease and/or to prevent the virus from reaching detectable levels in the blood, and the administration of a compound or composition according to the present invention to prevent perinatal transmission of HIV from mother to baby, by administration to the mother before giving birth and to the child within the first days of life.

The term "antiviral agent" as used herein is intended to mean an agent that is effective to inhibit the formation and/or replication of a virus in a mammal, including but not limited to agents that interfere with either host or viral mechanisms necessary for the formation and/or replication of a virus in a mammal.

The term "inhibitor of HIV replication" as used herein is intended to mean an agent capable of reducing or eliminating the ability of HIV to replicate in a host cell, whether in vitro, ex vivo or in vivo.

The term "HIV integrase" or "integrase", used herein interchangeably, means the integrase enzyme encoded by the human immunodeficiency virus type 1.

The term "therapeutically effective amount" means an amount of a compound according to the invention, which when administered to a patient in need thereof, is sufficient to effect treatment for disease-states, conditions, or disorders for which the compounds have utility. Such an amount would be sufficient to elicit the biological or medical response of a tissue system, or patient that is sought by a researcher or clinician. The amount of a compound according to the invention which constitutes a therapeutically effective amount will vary depending on such factors as the compound and its biological activity, the composition used for administration, the time of administration, the route of administration, the rate of excretion of the compound, the duration of the treatment, the type of disease-state or disorder being treated and its severity, drugs used in combination with or coincidentally with the compounds of the invention, and the age, body weight, general health, sex and diet of the patient. Such a therapeutically effective amount can be determined routinely by one of ordinary skill in the art having regard to their own knowledge, the state of the art, and this disclosure.

Preferred Embodiments

In the following preferred embodiments, groups and substituents of the compounds of formula (I):

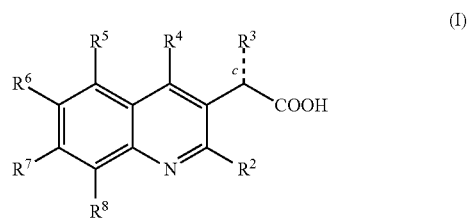

according to this invention are described in detail.

Core:

Core-A: In one embodiment, the compounds of the invention are represented by formula (Ia):

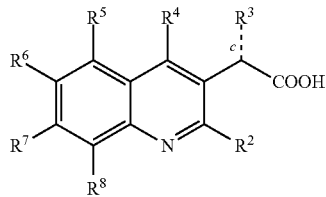

(Ia)

wherein c, $R^2$, $R^3$, $R^4$, $R^5$, $R^6$, $R^7$ and $R^8$ are as defined herein.

It will be apparent to a person skilled in the art that, when bond c is a single bond, the carbon atom bonded to the —COOH and $R^3$ substituents can exist in two possible stereochemical configurations, as shown in formulas (Ib) and (Ic) below:

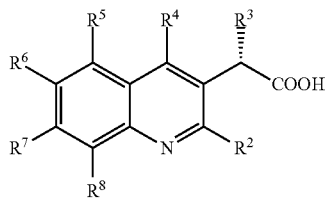

(Ib)

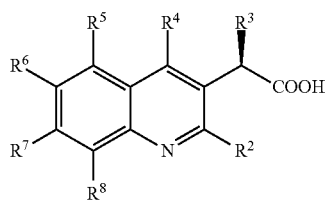

(Ic)

wherein $R^2$, $R^3$, $R^4$, $R^5$, $R^6$, $R^7$ and $R^8$ are as defined herein.

It has been found that compounds of formula (Ib) have improved activity over compounds of formula (Ic).

Core-B: In one embodiment, the compounds of the invention are represented by formula (Ib):

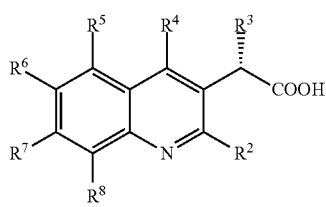

(Ib)

wherein $R^2$, $R^3$, $R^4$, $R^5$, $R^6$, $R^7$ and $R^8$ are as defined herein.

Core-C: In an alternative embodiment, the compounds of the invention are represented by formula (Ic):

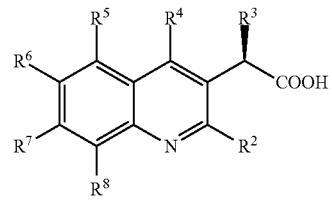

(Ic)

wherein $R^2$, $R^3$, $R^4$, $R^5$, $R^6$, $R^7$ and $R^8$ are as defined herein.

Any and each individual definition of the Core as set out herein may be combined with any and each individual definition of $R^2$, $R^3$, $R^4$, $R^5$, $R^6$, $R^7$ and $R^8$ as set out herein.

$R^2$:

$R^2$-A: In one embodiment, $R^2$ is selected from:

a) $(C_{2-6})$alkenyl, $(C_{2-6})$alkynyl, $(C_{1-6})$haloalkyl, $(C_{3-7})$cycloalkyl, aryl, Het, halo, nitro or cyano;

b) —C(=O)—$R^{11}$, —C(=O)—O—$R^{11}$, —S—$R^{11}$, —SO—$R^{11}$, —SO$_2$—$R^{11}$, —$(C_{1-6})$alkylene-$R^{11}$, —$(C_{1-6})$alkylene-C(=O)—$R^{11}$, —$(C_{1-6})$alkylene-C(=O)—O—$R^{11}$, —$(C_{1-6})$alkylene-O—$R^{11}$, —$(C_{1-6})$alkylene-S—$R^{11}$, —$(C_{1-6})$alkylene-SO—$R^{11}$ or —$(C_{1-6})$alkylene-SO$_2$—$R^{11}$;

wherein $R^{11}$ is in each instance independently selected from H, $(C_{1-6})$alkyl, $(C_{2-6})$alkenyl, $(C_{2-6})$alkynyl, $(C_{1-6})$haloalkyl, $(C_{3-7})$cycloalkyl, aryl and Het; and wherein each of the aryl and Het is optionally substituted with 1 to 3 substituents each independently selected from:

i) halo, oxo, thioxo, $(C_{2-6})$alkenyl, $(C_{1-6})$haloalkyl, $(C_{3-7})$cycloalkyl, $(C_{3-7})$cycloalkyl-$(C_{1-6})$alkyl-, —OH, —O$(C_{1-6})$alkyl, —O$(C_{1-6})$haloalkyl, —SH, —S$(C_{1-6})$alkyl, —SO$(C_{1-6})$alkyl, —SO$_2(C_{1-6})$alkyl, —C(=O)—NH$_2$, —C(=O)—NH$(C_{1-4})$alkyl, —C(=O)—N$((C_{1-4})$alkyl$)_2$, —C(=O)-aryl, —C(=O)—Het, NH$_2$, —NH$(C_{1-6})$alkyl and —N$((C_{1-6})$alkyl$)_2$;

ii) $(C_{1-6})$alkyl optionally substituted with —OH, —O—$(C_{1-6})$haloalkyl, or —O—$(C_{1-6})$alkyl; and iii) aryl or Het, wherein each of the aryl and Het is optionally substituted with halo, $(C_{1-6})$alkyl or COOH; and c) —O—$R^{8a}$ wherein $R^{8a}$ is selected from H, $(C_{2-6})$alkenyl, $(C_{2-6})$alkynyl, $(C_{1-6})$haloalkyl, $(C_{3-7})$cycloalkyl, aryl and Het;

d) —N$(R^9)R^{10}$, —C(=O)—N$(R^9)R^{10}$, —SO$_2$—N$(R^9)R^{10}$, —$(C_{1-6})$alkylene-N$(R^9)R^{10}$, —$(C_{1-6})$alkylene-C(=O)—N$(R^9)R^{10}$, —$(C_{1-6})$alkylene-O—C(=O)—N$(R^9)R^{10}$, or —$(C_{1-6})$alkylene-SO$_2$—N$(R^9)R^w$ wherein $R^9$ is in each instance independently selected from H, $(C_{1-6})$alkyl and $(C_{3-7})$cycloalkyl; and $R^{10}$ is in each instance independently selected from $R^{11}$, —$(C_{1-6})$alkylene-$R^{11}$, —SO$_2$—$R^{11}$, —C(=O)—$R^{11}$, —C(=O)O$R^{11}$ and —C(=O)N$(R^9)R^{11}$;

wherein $R^{11}$ and $R^9$ are as defined above; or $R^2$ may also be H, $(C_{1-6})$alkyl or —O—$(C_{1-6})$alkyl when one of $R^5$ or $R^8$ is other than H or when one of $R^6$ or $R^7$ is other than H, halo, $(C_{1-6})$alkyl or $(C_{1-6})$haloalkyl.

$R^2$-B: In an alternative embodiment, $R^2$ is $(C_{1-6})$alkyl or —O$(C_{1-6})$alkyl when one of $R^5$ or $R^8$ is other than H or when one of $R^6$ or $R^7$ is other than H, halo, $(C_{1-6})$alkyl or $(C_{1-6})$haloalkyl.

R²-C: In another embodiment, R² is (C₁₋₆)alkyl when one of R⁵ and R⁸ is other than H or when one of R⁶ or R⁷ is other than H, halo, (C₁₋₆)alkyl or (C₁₋₆)haloalkyl.

R²-D: In another embodiment, R² is —CH₃ or —CH₂CH₃ when one of R⁵ or R⁸ is other than H or when one of R⁶ or R⁷ is other than H, halo, (C₁₋₆)alkyl or (C₁₋₆)haloalkyl.

R²-E: In another embodiment, R² is —CH₃ when one of R⁵ or R⁸ is other than H or when one of R⁶ or R⁷ is other than H, halo, (C₁₋₆)alkyl or (C₁₋₆)haloalkyl.

R²-F: In another embodiment, R² is —(C₁₋₆)alkylene-Het, —(C₁₋₆)alkylene-aryl, —(C₁₋₆)alkylene-O-Het, —(C₁₋₆)alkylene-O-aryl, Het or aryl, all being optionally substituted with (C₁₋₆)alkyl, (C₁₋₆)haloalkyl, or —O(C₁₋₆)alkyl.

R²-G: In another embodiment, R² is —(C₁₋₆)alkylene-Het, —(C₁₋₆)alkylene-aryl, —(C₁₋₆)alkylene-O-Het or —(C₁₋₆)alkylene-O-aryl.

R²-H: In another embodiment, R² is —(C₁₋₆)alkylene-Het, —(C₁₋₆)alkylene-aryl, —(C₁₋₆)alkylene-O-Het or —(C₁₋₆)alkylene-O-aryl; or
(C₁₋₆)alkyl, when one of R⁵ or R⁸ is other than H or when one of R⁶ or R⁷ is other than H, halo, (C₁₋₆)alkyl or (C₁₋₆)haloalkyl.

R²-I: In another embodiment, R² is

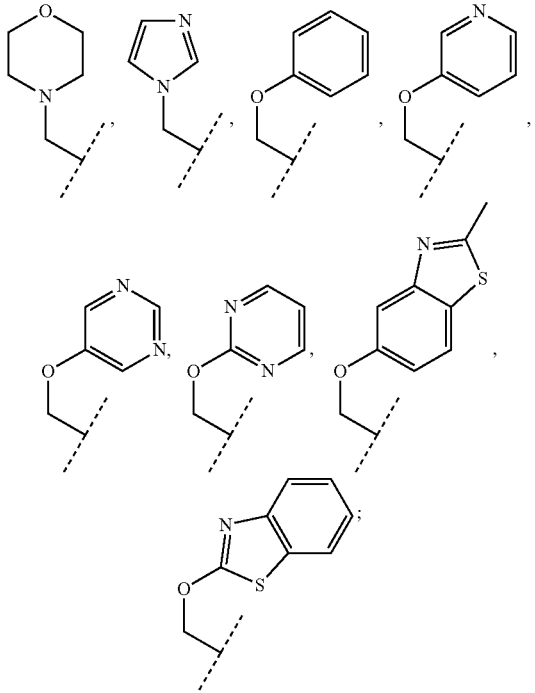

or
CH₃, when one of R⁵ or R⁸ is other than H or when one of R⁶ or R⁷ is other than H, halo, (C₁₋₆)alkyl or (C₁₋₆)haloalkyl.

Any and each individual definition of R² as set out herein may be combined with any and each individual definition of the Core, c, R³, R⁴, R⁵, R⁶, R⁷ and R⁸ as set out herein.

R³:

R³-A: In one embodiment, R³ is (C₁₋₆)alkyl, (C₁₋₆)haloalkyl, (C₂₋₆)alkenyl, (C₂₋₆)alkynyl, (C₃₋₇)cycloalkyl-(C₁₋₆)alkyl-, aryl-(C₁₋₆)alkyl-, Het-(C₁₋₆)alkyl- or —Y—R³¹, and bond c is a single bond; or
R³ is (C₁₋₆)alkylidene and bond c is a double bond;

wherein Y is O or S and R³¹ is (C₁₋₆)alkyl, (C₁₋₆)haloalkyl, (C₂₋₆)alkenyl, (C₂₋₆)alkynyl, (C₃₋₇)cycloalkyl, aryl, (C₃₋₇)cycloalkyl-(C₁₋₆)alkyl-, aryl-(C₁₋₆)alkyl- or Het-(C₁₋₆)alkyl-;
wherein each of the (C₁₋₆)alkylidene, (C₁₋₆)alkyl, (C₁₋₆)haloalkyl, (C₂₋₆)alkenyl, (C₂₋₆)alkynyl, (C₃₋₇)cycloalkyl-(C₁₋₆)alkyl-, Het-(C₁₋₆)alkyl- and —Y—R³¹ is optionally substituted with 1 to 3 substituents each independently selected from (C₁₋₆)alkyl, halo, cyano, oxo and —O(C₁₋₆)alkyl.

R³-B: In one embodiment, R³ is (C₁₋₆)alkyl, (C₁₋₆)haloalkyl, (C₂₋₆)alkenyl, (C₂₋₆)alkynyl, (C₃₋₇)cycloalkyl-(C₁₋₆)alkyl-, aryl-(C₁₋₆)alkyl- or Het-(C₁₋₆)alkyl-;
wherein each of the (C₁₋₆)alkyl, (C₁₋₆)haloalkyl, (C₂₋₆)alkenyl, (C₂₋₆)alkynyl, (C₃₋₇)cycloalkyl-(C₁₋₆)alkyl-, aryl-(C₁₋₆)alkyl- and Het-(C₁₋₆)alkyl- is optionally substituted with 1 to 3 substituents each independently selected from (C₁₋₆)alkyl, halo, cyano, oxo and —O(C₁₋₆)alkyl; and
bond c is a single bond.

R³-C: In another embodiment, R³ is (C₁₋₆)alkyl or (C₂₋₆)alkenyl; and
bond c is a single bond.

R³-D: In an alternative embodiment, R³ is —Y—(C₁₋₆)alkyl, —Y—(C₂₋₆)alkenyl, —Y—(C₂₋₆)alkynyl, —Y—(C₃₋₇)cycloalkyl, —Y-aryl, (C₃₋₇)cycloalkyl-(C₁₋₆)alkyl-Y—, aryl-(C₁₋₆)alkyl-Y— or Het-(C₁₋₆)alkyl-Y—;
wherein Y is O or S; and
wherein each of the —Y—(C₁₋₆)alkyl, —Y—(C₂₋₆)alkenyl, —Y—(C₂₋₆)alkynyl, —Y—(C₃₋₇)cycloalkyl, —Y-aryl, (C₃₋₇)cycloalkyl-(C₁₋₆)alkyl-Y—, and Het-(C₁₋₆)alkyl-Y— is optionally substituted with 1 to 3 substituents each independently selected from (C₁₋₆)alkyl, halo, cyano, oxo and —O(C₁₋₆)alkyl;
and
bond c is a single bond.

R³-E: In another embodiment, R³ is —O—(C₁₋₆)alkyl, —O—(C₂₋₆)alkenyl, —O—(C₂₋₆)alkynyl, —O—(C₃₋₇)cycloalkyl, —O-aryl, (C₃₋₇)cycloalkyl-(C₁₋₆)alkyl-O—, aryl-(C₁₋₆)alkyl-O— or Het-(C₁₋₆)alkyl-O—;
wherein each of the —O—(C₁₋₆)alkyl, —O—(C₂₋₆)alkenyl, —O—(C₂₋₆)alkynyl, —O—(C₃₋₇)cycloalkyl, —O-aryl, (C₃₋₇)cycloalkyl-(C₁₋₆)alkyl-O—, aryl-(C₁₋₆)alkyl-O— and Het-(C₁₋₆)alkyl-O— is optionally substituted with 1 to 3 substituents each independently selected from (C₁₋₆)alkyl, halo, cyano, oxo and —O(C₁₋₆)alkyl;
and
bond c is a single bond.

R³-F: In another embodiment, R³ is —O(C₁₋₆)alkyl, —O—(C₁₋₆)haloalkyl, —O—(C₂₋₆)alkenyl, —O(C₂₋₆)alkynyl, —O—(C₃₋₇)cycloalkyl, —O-aryl, (C₃₋₇)cycloalkyl-(C₁₋₃)alkyl-O— or Het-(C₁₋₃)alkyl-O—;
wherein Het is a 5- or 6-membered heterocycle having 1 to 3 heteroatoms each independently selected from N, O and S; and
wherein each of the —O(C₁₋₆)alkyl, —O—(C₃₋₇)cycloalkyl and Het-(C₁₋₃)alkyl-O— is optionally substituted with 1 to 3 substituents each independently selected from (C₁₋₃)alkyl, cyano, oxo and —O(C₁₋₆)alkyl; and
bond c is a single bond.

R³-G: In another embodiment, R³ is —O(C₁₋₆)alkyl, —O—(C₁₋₆)haloalkyl, —O(C₂₋₆)alkenyl, —O(C₂₋₆)alkynyl or —O—(C₃₋₇)cycloalkyl;
wherein each of the —O(C₁₋₆)alkyl and —O—(C₃₋₇)cycloalkyl is optionally substituted with 1 to 3 substituents each independently selected from (C$_{1-3}$)alkyl, cyano, oxo and —O(C$_{1-6}$)alkyl; and
bond c is a single bond.

R$^3$—H: In another embodiment, R$^3$ is —O(C$_{1-4}$)alkyl; wherein the —O(C$_{1-4}$)alkyl is optionally substituted with 1 to 2 substituents each independently selected from cyano, oxo and —O(C$_{1-6}$)alkyl; and
bond c is a single bond.

R$^3$-I: In another embodiment, R$^3$ is —OC(CH$_3$)$_3$; and bond c is a single bond.

R$^3$-J: In another embodiment, R$^3$ is selected from:

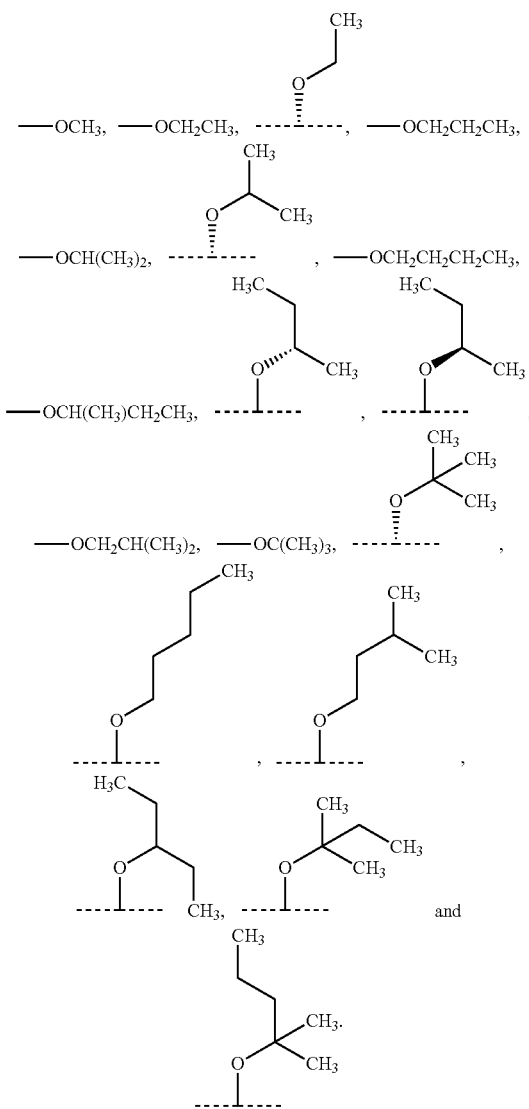

Any and each individual definition of c and R$^3$ as set out herein may be combined with any and each individual definition of the Core, R$^2$, R$^4$, R$^5$, R$^6$, R$^7$ and R$^8$ as set out herein.

R$^4$:

R$^4$-A: In one embodiment, R$^4$ is aryl optionally substituted with 1 to 5 substituents each independently selected from halo, (C$_{1-6}$)alkyl, (C$_{2-6}$)alkenyl, (C$_{1-6}$)haloalkyl, (C$_{3-7}$)cycloalkyl, —OH, —O(C$_{1-6}$)alkyl, —SH, —S(C$_{1-6}$)alkyl, —NH$_2$, —NH(C$_{1-6}$)alkyl and —N((C$_{1-6}$)alkyl)$_2$; wherein the (C$_{1-6}$)alkyl is optionally substituted with hydroxy, —O(C$_{1-6}$)alkyl, cyano or oxo.

R$^4$-B: In another embodiment, R$^4$ is naphthyl or phenyl, wherein the phenyl is optionally substituted with 1 to 3 substituents each independently selected from halo, (C$_{1-4}$)alkyl, (C$_{2-4}$)alkenyl, (C$_{1-4}$)haloalkyl, (C$_{3-7}$)cycloalkyl, —OH, —SH, —S(C$_{1-4}$)alkyl, —NH$_2$, —NH(C$_{1-4}$)alkyl and —N((C$_{1-4}$)alkyl)$_2$;
wherein the (C$_{1-4}$)alkyl is optionally substituted with hydroxy, —O(C$_{1-6}$)alkyl, cyano or oxo.

R$^4$-C: In another embodiment, R$^4$ is phenyl optionally substituted with 1 to 3 substituents each independently selected from halo, (C$_{1-4}$)alkyl and (C$_{1-4}$)haloalkyl.

R$^4$-D: In another embodiment, R$^4$ is phenyl optionally substituted with 1 or 2 substituents each independently selected from F, Cl, Br, —CH$_3$, —CH$_2$CH$_3$, —CH$_2$CH$_2$CH$_3$, —CH(CH$_3$)$_2$ and —C(CH$_3$)$_3$.

R$^4$-E: In another embodiment, R$^4$ is a group of formula:

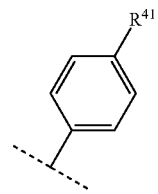

wherein R$^{41}$ is selected from halo, (C$_{1-4}$)alkyl and (C$_{1-4}$)haloalkyl.

R$^4$-F: In an alternative embodiment, R$^4$ is Het optionally substituted with 1 to 4 substituents each independently selected from halo, (C$_{1-6}$)alkyl, (C$_{2-6}$)alkenyl, (C$_{1-6}$)haloalkyl, (C$_{3-7}$)cycloalkyl, —OH, —O(C$_{1-6}$)alkyl, —SH, —S(C$_{1-6}$)alkyl, —NH$_2$, —NH(C$_{1-6}$)alkyl and —N((C$_{1-6}$)alkyl)$_2$; wherein the (C$_{1-6}$)alkyl is optionally substituted with hydroxy, cyano or oxo.

R$^4$-G: In another alternative embodiment, R$^4$ is Het optionally substituted with 1 to 3 substituents each independently selected from halo and (C$_{1-6}$)alkyl;
wherein the Het is a 5- or 6-membered heterocycle having 1 to 3 heteroatoms each independently selected from N, O and S; or the Het is a 9- or 10-membered heteropolycycle having 1 to 3 heteroatoms each independently selected from N, O and S.

R$^4$-H: In another alternative embodiment, R$^4$ is Het optionally substituted with 1 to 3 substituents each independently selected from halo, (C$_{1-6}$)alkyl and —O(C$_{1-6}$)alkyl;
wherein the Het is selected from:

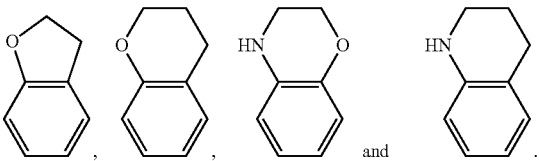

R$^4$-I: In another alternative embodiment, R$^4$ is Het optionally substituted with 1 to 3 substituents each independently selected from halo, (C$_{1-6}$)alkyl and —O(C$_{1-6}$)alkyl;

wherein the Het is selected from:
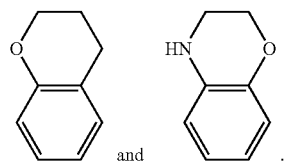 [SMILES: c1ccc2c(c1)CCCO2 ; c1ccc2c(c1)NCCO2]
and
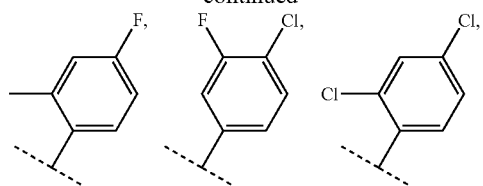
R⁴-J: In another alternative embodiment, R⁴ is selected from:
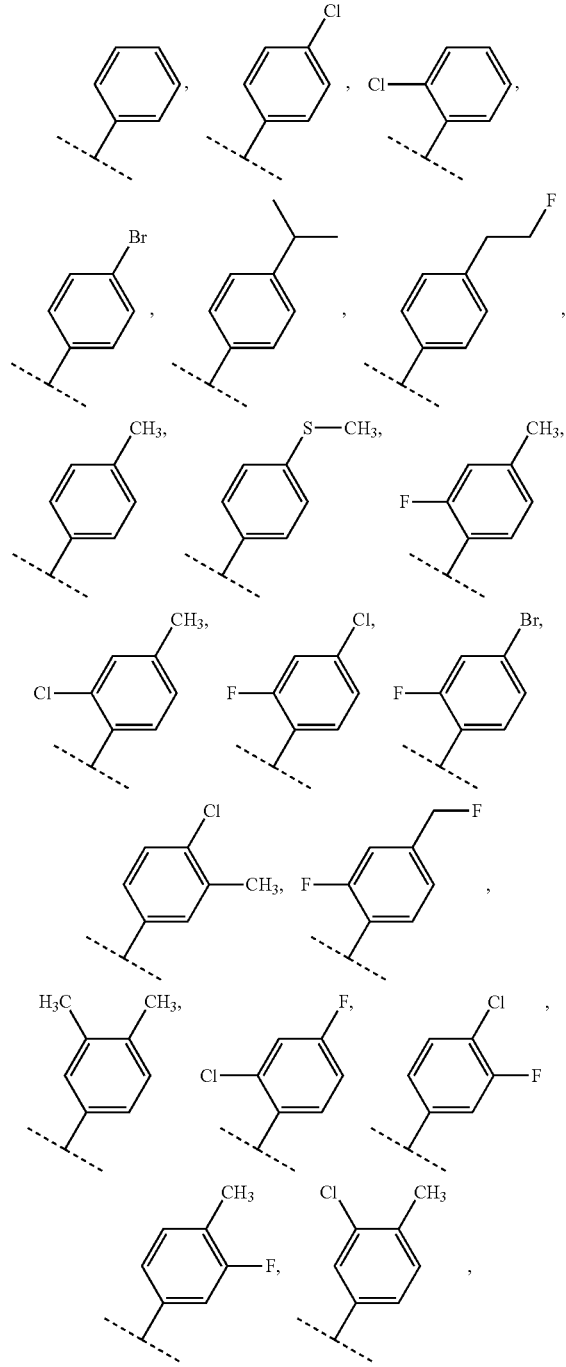
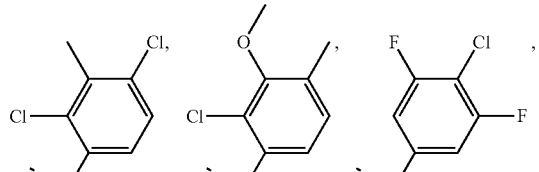
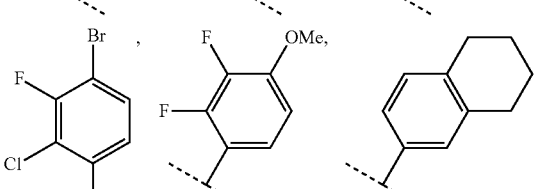
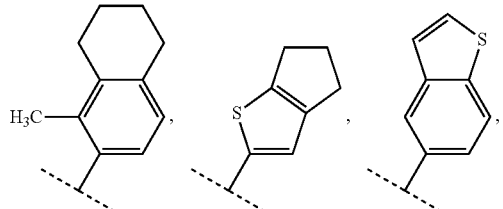
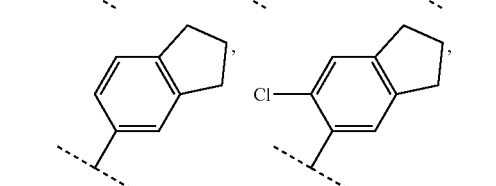
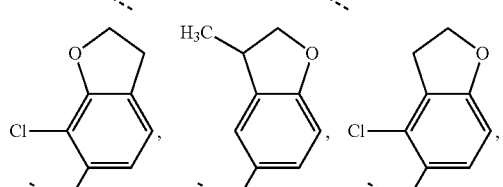
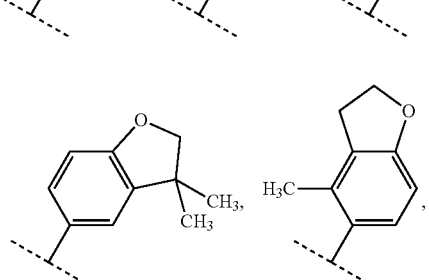
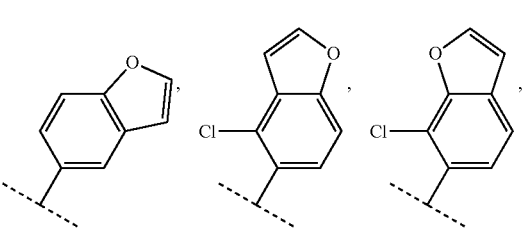

21
-continued
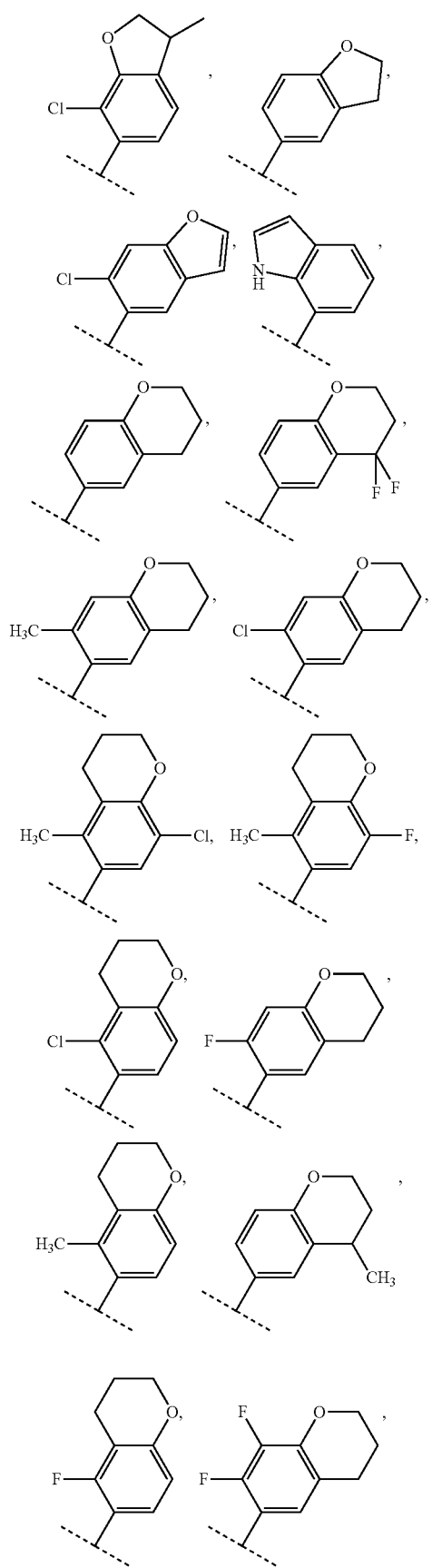
22
-continued
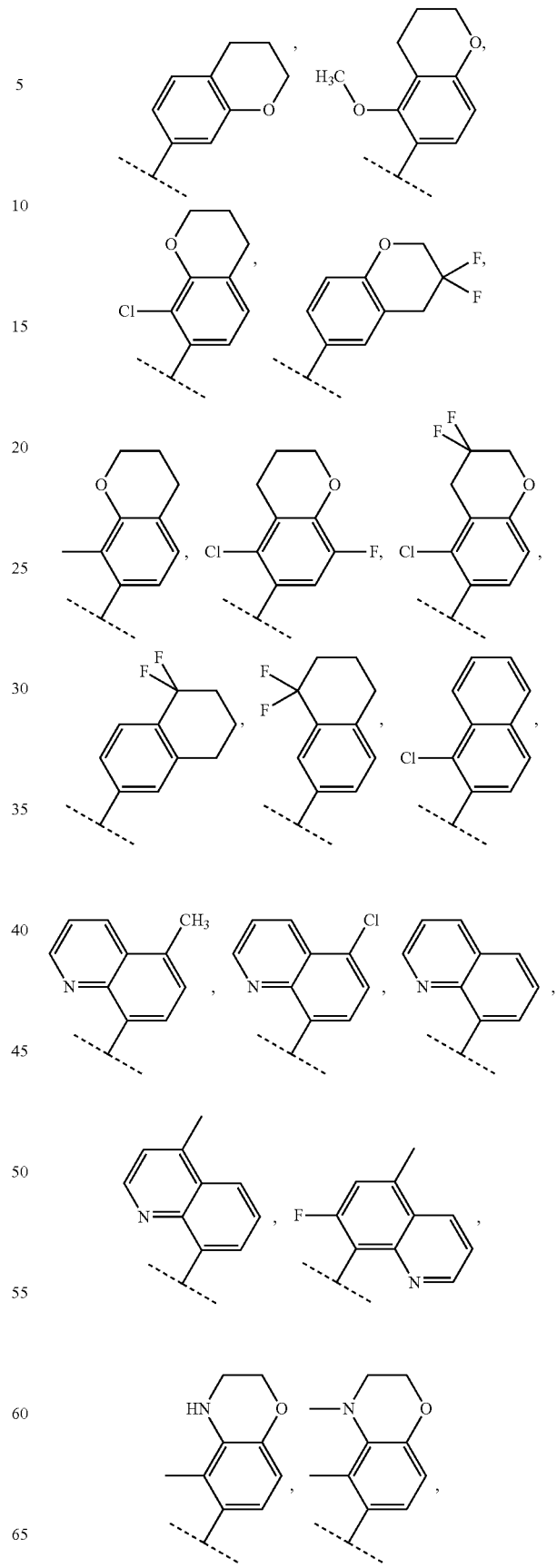

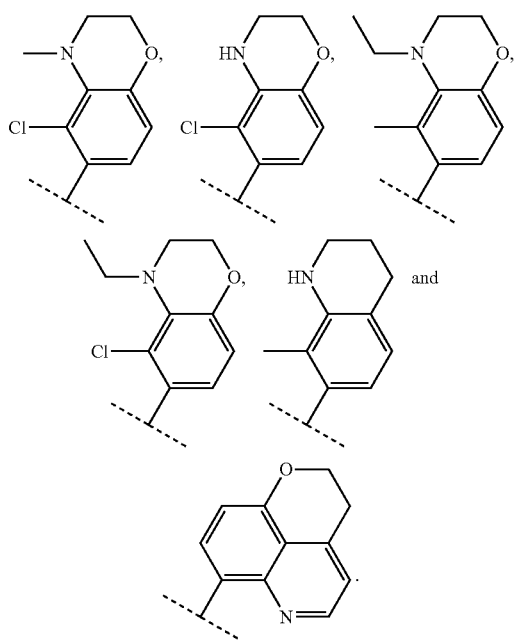

R⁴-K: In another alternative embodiment, R⁴ is selected from:

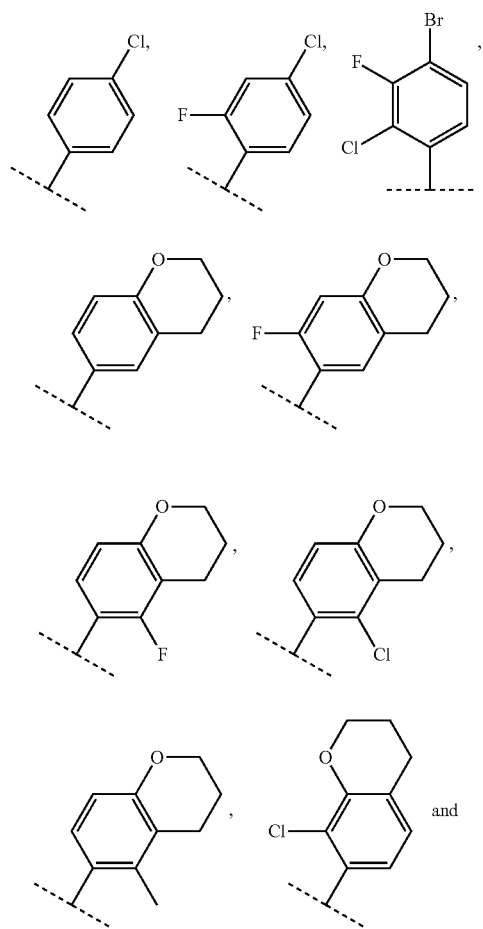

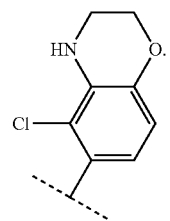

One skilled in the art will recognize that when the R⁴ substituent is not symmetrically substituted about the axis of rotation of the bond attaching R⁴ to Core, rotational isomers or atropisomers are possible. Compounds of the invention in which the R⁴ substituent is not symmetrically substituted about the axis of rotation of the bond attaching R⁴ to Core and in which the carbon atom bonded to the —COOH and R³ substituents is chiral, as described above, will have two chiral centers, a chiral carbon atom and a rotational axis of asymmetry, and thus the atropisomers will exist as diastereomers. However, individual diastereomeric atropisomers may or may not be detectable and/or separable, depending upon the relative amounts of each atropisomer formed during synthesis, present at equilibrium, and the degree of steric hindrance to rotation about the C-4 chiral axis, and therefore, the rate at which interconversion between these atropoisomers occurs. Once separated, individual atropoisomers may be very stable or interconvert, rapidly or slowly, with each other to form an equilibrium mixture of atropoisomers.

R⁴-L: In another alternative embodiment, R⁴ is selected from:

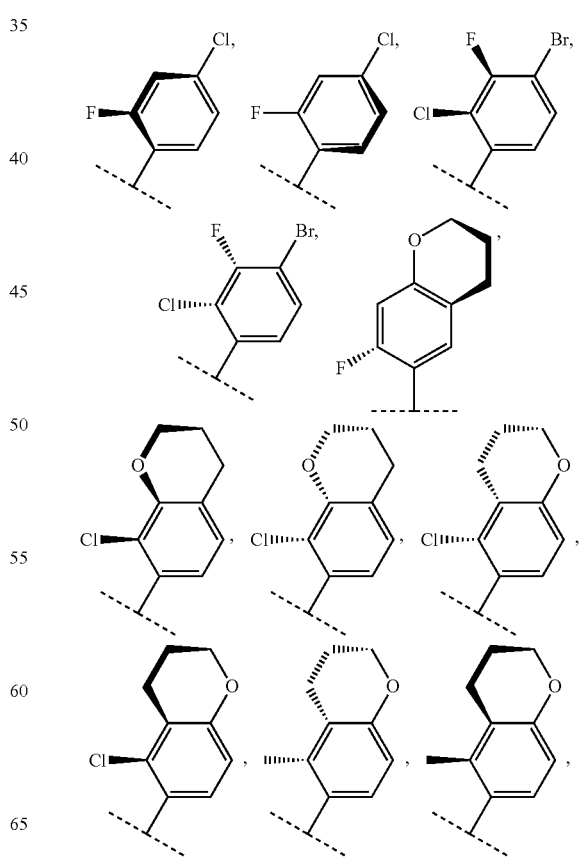

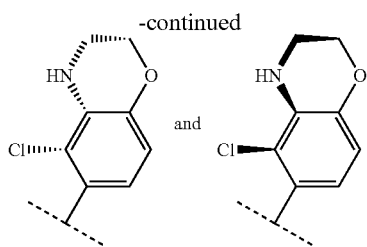

and

Any and each individual definition of $R^4$ as set out herein may be combined with any and each individual definition of the Core, c, $R^2$, $R^3$, $R^5$, $R^6$, $R^7$ and $R^8$ as set out herein.

$R^5$:

$R^5$-A: In one embodiment, $R^5$ is selected from:
a) halo, nitro or cyano;
b) $R^{11}$, —C(=O)—$R^{11}$, —C(=O)—O—$R^{11}$, —S—$R^{11}$, —SO—$R^{11}$, —SO$_2$—$R^{11}$, —(C$_{1-6}$)alkylene-$R^{11}$, —(C$_{1-6}$)alkylene-C(=O)—$R^{11}$, —(C$_{1-6}$)alkylene-C(=O)—O—$R^{11}$, —(C$_{1-6}$)alkylene-O—$R^{11}$, —(C$_{1-6}$)alkylene-S—$R^{11}$, —(C$_{1-6}$)alkylene-SO—$R^{11}$ or —(C$_{1-6}$)alkylene-SO$_2$—$R^{11}$;
wherein $R^{11}$ is in each instance independently selected from H, (C$_{1-6}$)alkyl, (C$_{2-6}$)alkenyl, (C$_{2-6}$)alkynyl, (C$_{1-6}$)haloalkyl, (C$_{3-7}$)cycloalkyl, aryl and Het; and
wherein each of the aryl and Het is optionally substituted with 1 to 3 substituents each independently selected from:
i) halo, oxo, thioxo, (C$_{2-6}$)alkenyl, (C$_{1-6}$)haloalkyl, (C$_{3-7}$)cycloalkyl, (C$_{3-7}$)cycloalkyl-(C$_{1-6}$)alkyl-, —OH, —O(C$_{1-6}$)alkyl, —O (C$_{1-6}$)haloalkyl, —SH, —S(C$_{1-6}$)alkyl, —SO(C$_{1-6}$)alkyl, —SO$_2$(C$_{1-6}$)alkyl, —C(=O)—NH$_2$, —C(=O)—NH(C$_{1-4}$)alkyl, —C(=O)—N((C$_{1-4}$)alkyl)$_2$, —C(=O)-aryl, —C(=O)—Het, NH$_2$, —NH(C$_{1-6}$)alkyl and —N((C$_{1-6}$)alkyl)$_2$;
ii) (C$_{1-6}$)alkyl optionally substituted with —OH, —O—(C$_{1-6}$)haloalkyl, or —O—(C$_{1-6}$)alkyl; and
iii) aryl or Het, wherein each of the aryl and Het is optionally substituted with halo, (C$_{1-6}$)alkyl or COOH; and
c) —N(R$^9$)R$^{10}$, —C(=O)—N(R$^9$)R$^{10}$, —SO$_2$—N(R$^9$)R$^{10}$, —(C$_{1-6}$)alkylene-N(R$^9$)R$^{10}$, —(C$_{1-6}$)alkylene-C(=O)—N(R$^9$)R$^{10}$, —(C$_{1-6}$)alkylene-O—C(=O)—N(R$^9$)R$^{10}$, or —(C$_{1-6}$)alkylene-SO$_2$—N(R$^9$)R$^{10}$ wherein
R$^9$ is in each instance independently selected from H, (C$_{1-6}$)alkyl and (C$_{3-7}$)cycloalkyl; and
R$^{10}$ is in each instance independently selected from R$^{11}$, —(C$_{1-6}$)alkylene-R$^{11}$, —SO$_2$—R$^{11}$, —C(=O)—R$^{11}$, —C(=O)OR$^{11}$ and —C(=O)N(R$^9$)R$^{11}$;
wherein R$^{11}$ and R$^9$ are as defined above; or
or $R^5$ and $R^6$, together with the C to which they are attached, may be linked to form a 5- or 6-membered carbocycle or a 4- to 7-membered heterocycle optionally further containing 1 to 3 heteroatoms each independently selected from N, O and S, wherein each S heteroatom may, independently and where possible, exist in an oxidized state such that it is further bonded to one or two oxygen atoms to form the groups SO or SO$_2$;
wherein the carbocycle or heterocycle is optionally substituted with 1 to 3 substituents each independently selected from halo, (C$_{1-6}$)alkyl, (C$_{2-6}$)alkenyl, (C$_{1-6}$)haloalkyl, (C$_{3-7}$)cycloalkyl, —OH, —O(C$_{1-6}$)alkyl, —SH, —S(C$_{1-6}$)alkyl, —NH$_2$, —NH(C$_{1-6}$)alkyl and —N((C$_{1-6}$)alkyl)$_2$.

$R^5$-B: In one embodiment, $R^5$ is H, halo, (C$_{1-6}$)alkyl, (C$_{1-6}$)haloalkyl or —O(C$_{1-6}$)alkyl.

$R^5$-C: In one embodiment, $R^5$ is H, halo, (C$_{1-4}$)alkyl or (C$_{1-4}$)haloalkyl.

$R^5$-D: In one embodiment, $R^5$ is H, halo or (C$_{1-4}$)alkyl.

$R^5$-E: In one embodiment, $R^5$ is F or H.

$R^5$-F: In one embodiment, $R^5$ is H, F or CH$_3$.

$R^5$-G: In one embodiment, $R^5$ is H.

Any and each individual definition of $R^5$ as set out herein may be combined with any and each individual definition of the Core, c, $R^2$, $R^3$, $R^4$, $R^6$, $R^7$ and $R^8$ as set out herein.

$R^6$:

$R^6$-A: In one embodiment, $R^6$ is selected from:
a) (C$_{2-6}$)alkenyl, (C$_{2-6}$)alkynyl, (C$_{3-7}$)cycloalkyl, nitro, cyano, aryl and Het;
b) —C(=O)—$R^{11}$, —C(=O)—O—$R^{11}$, —O—$R^{11}$, —S—$R^{11}$, —SO—$R^{11}$, —SO$_2$—$R^{11}$, —(C$_{1-6}$)alkylene-$R^{11}$, —(C$_{1-6}$)alkylene-C(=O)—$R^{11}$, —(C$_{1-6}$)alkylene-C(=O)—O—$R^{11}$, —(C$_{1-6}$)alkylene-O—$R^{11}$, —(C$_{1-6}$)alkylene-S—$R^{11}$, —(C$_{1-6}$)alkylene-SO—$R^{11}$ or —(C$_{1-6}$)alkylene-SO$_2$—$R^{11}$;
wherein $R^{11}$ is in each instance independently selected from H, (C$_{1-6}$)alkyl, (C$_{2-6}$)alkenyl, (C$_{2-6}$)alkynyl, (C$_{1-6}$)haloalkyl, (C$_{3-7}$)cycloalkyl, aryl and Het;
c) —N(R$^9$)R$^{10}$, —C(=O)—N(R$^9$)R$^{10}$, —O—C(=O)—N(R$^9$)R$^{10}$, —SO$_2$—N(R$^9$)R$^{10}$, —(C$_{1-6}$)alkylene-N(R$^9$)R$^{10}$, —(C$_{1-6}$)alkylene-C(=O)—N(R$^9$)R$^{10}$, —(C$_{1-6}$)alkylene-O—C(=O)—N(R$^9$)R$^{10}$, or —(C$_{1-6}$)alkylene-SO$_2$—N(R$^9$)R$^{10}$ wherein
R$^9$ is in each instance independently selected from H, (C$_{1-6}$)alkyl and (C$_{3-7}$)cycloalkyl; and
R$^{10}$ is in each instance independently selected from R$^{11}$, —(C$_{1-6}$)alkylene-R$^{11}$, —SO$_2$—R$^{11}$, —C(=O)—R$^{11}$, —C(=O)OR$^{11}$ and —C(=O)N(R$^9$)R$^{11}$;
wherein R$^{11}$ and R$^9$ are as defined above;
wherein each of the aryl and Het is optionally substituted with 1 to 3 substituents each independently selected from:
i) halo, oxo, thioxo, (C$_{2-6}$)alkenyl, (C$_{1-6}$)haloalkyl, (C$_{3-7}$)cycloalkyl, (C$_{3-7}$)cycloalkyl-(C$_{1-6}$)alkyl-, —OH, —O(C$_{1-6}$)alkyl, —O (C$_{1-6}$)haloalkyl, —SH, —S(C$_{1-6}$)alkyl, —SO(C$_{1-6}$)alkyl, —SO$_2$(C$_{1-6}$)alkyl, —NH$_2$, —NH(C$_{1-6}$)alkyl and —N((C$_{1-6}$)alkyl)$_2$;
ii) (C$_{1-6}$)alkyl optionally substituted with —OH, —O—(C$_{1-6}$)haloalkyl, or —O—(C$_{1-6}$)alkyl; and
iii) aryl or Het, wherein each of the aryl and Het is optionally substituted with halo, (C$_{1-6}$)alkyl or COOH; and R$^6$ may also be H, halo, (C$_{1-6}$)alkyl, or (C$_{1-6}$)haloalkyl when at least one of R$^5$ or R$^8$ is other than H or when R$^7$ is other than H, halo, (C$_{1-6}$)alkyl, or (C$_{1-6}$)haloalkyl or when R$^2$ is other than H, (C$_{1-6}$)alkyl, or —O—(C$_{1-6}$)alkyl; or
R$^5$ and R$^6$, together with the C to which they are attached or R$^6$ and R$^7$, together with the C to which they are attached may be linked to form a 5- or 6-membered carbocycle or a 4- to 7-membered heterocycle optionally further containing 1 to 3 heteroatoms each independently selected from N, O and S, wherein each S heteroatom may, independently and where possible, exist in an oxidized state such that it is further bonded to one or two oxygen atoms to form the groups SO or SO$_2$;
wherein the carbocycle or heterocycle is optionally substituted with 1 to 3 substituents each independently selected from halo, (C$_{1-6}$)alkyl, (C$_{2-6}$)alkenyl, (C$_{1-6}$)haloalkyl, (C$_{3-7}$)cycloalkyl, —OH, —O(C$_{1-6}$)alkyl, —SH, —S(C$_{1-6}$)alkyl, —NH$_2$, —NH(C$_{1-6}$)alkyl and —N((C$_{1-6}$)alkyl)$_2$.

$R^6$-B: In one embodiment, $R^6$ is selected from:
  a) $(C_{2-6})$alkenyl, aryl and Het; and
  b) —O—$(C_{1-6})$alkyl; or
  $R^6$ may also be halo when at least one of $R^5$ or $R^8$ is other than H or when $R^7$ is other than H, halo, $(C_{1-6})$alkyl, or $(C_{1-6})$haloalkyl or when $R^2$ is other than H, $(C_{1-6})$alkyl, or —O—$(C_{1-6})$alkyl.

$R^6$-C: In one embodiment, $R^6$ is H, halo, $(C_{1-6})$alkyl or $(C_{1-6})$haloalkyl, when at least one of $R^5$ or $R^8$ is other than H or when $R^7$ is other than H, halo, $(C_{1-6})$alkyl, or $(C_{1-6})$haloalkyl or when $R^2$ is other than H, $(C_{1-6})$alkyl, or —O—$(C_{1-6})$alkyl.

$R^6$-D: In another embodiment, $R^6$ is CH=$CH_2$, phenyl, $OCH_3$; or
  $CH_3$, $CH_2CH_3$, H, F, Cl or Br when at least one of $R^5$ or $R^8$ is other than H or when $R^7$ is other than H, halo, $(C_{1-6})$alkyl, or $(C_{1-6})$haloalkyl or when $R^2$ is other than H, $(C_{1-6})$alkyl, or —O—$(C_{1-6})$alkyl.

$R^6$-E: In another embodiment, $R^6$ is CH=$CH_2$, phenyl, or $OCH_3$; or
  H, Br, $CH_3$ or $CH_2CH_3$ when at least one of $R^5$ or $R^8$ is other than H or when $R^7$ is other than H, halo, $(C_{1-6})$alkyl, or $(C_{1-6})$haloalkyl or when $R^2$ is other than H, $(C_{1-6})$alkyl, or —O—$(C_{1-6})$alkyl.

$R^6$-F: In another embodiment, $R^6$ is H when at least one of $R^5$ or $R^8$ is other than H or when $R^7$ is other than H, halo, $(C_{1-6})$alkyl, or $(C_{1-6})$haloalkyl or when $R^2$ is other than H, $(C_{1-6})$alkyl, or —O—$(C_{1-6})$alkyl.

$R^6$-G: In another embodiment, $R^6$ is C≡CH, CH=$CH_2$, phenyl or $OCH_3$; or
  H, Br when at least one of $R^5$ or $R^8$ is other than H or when $R^7$ is other than H, halo, $(C_{1-6})$alkyl, or $(C_{1-6})$haloalkyl or when $R^2$ is other than H, $(C_{1-6})$alkyl, or —O—$(C_{1-6})$alkyl.

Any and each individual definition of $R^6$ as set out herein may be combined with any and each individual definition of the Core, c, $R^2$, $R^3$, $R^4$, $R^5$, $R^7$ and $R^8$ as set out herein.

$R^7$:

$R^7$-A: In one embodiment, $R^7$ is selected from:
  a) $(C_{2-6})$alkenyl, $(C_{2-6})$alkynyl, $(C_{3-7})$cycloalkyl, nitro, cyano, aryl and Het;
  b) —C(=O)—$R^{11}$, —C(=O)—O—$R^{11}$, —O—$R^{11}$, —S—$R^{11}$, —SO—$R^{11}$, —$SO_2$—$R^{11}$, —$(C_{1-6})$alkylene-$R^{11}$, —$(C_{1-6})$alkylene-C(=O)—$R^{11}$, —$(C_{1-6})$alkylene-C(=O)—O—$R^{11}$, —$(C_{1-6})$alkylene-O—$R^{11}$, —$(C_{1-6})$alkylene-S—$R^{11}$, —$(C_{1-6})$alkylene-SO—$R^{11}$ or —$(C_{1-6})$alkylene-$SO_2$—$R^{11}$;
  wherein $R^{11}$ is in each instance independently selected from H, $(C_{1-6})$alkyl, $(C_{2-6})$alkenyl, $(C_{2-6})$alkynyl, $(C_{1-6})$haloalkyl, $(C_{3-7})$cycloalkyl, aryl and Het; and
  c) —N($R^9$)$R^{10}$, —C(=O)—N($R^9$)$R^{10}$, —O—C(=O)—N($R^9$)$R^{10}$, —$SO_2$—N($R^9$)$R^{10}$, —$(C_{1-6})$alkylene-N($R^9$)$R^{10}$, —$(C_{1-6})$alkylene-C(=O)—N($R^9$)$R^{10}$, —$(C_{1-6})$alkylene-O—C(=O)—N($R^9$)$R^{10}$, or —$(C_{1-6})$alkylene-$SO_2$—N($R^9$)$R^{10}$ wherein
  $R^9$ is in each instance independently selected from H, $(C_{1-6})$alkyl and $(C_{3-7})$cycloalkyl; and
  $R^{10}$ is in each instance independently selected from $R^{11}$, —$(C_{1-6})$alkylene-$R^{11}$, —$SO_2$—$R^{11}$, —C(=O)—$R^{11}$, —C(=O)O$R^{11}$ and —C(=O)N($R^9$)$R^{11}$;
  wherein $R^{11}$ and $R^9$ are as defined above;
wherein each of the aryl and Het is optionally substituted with 1 to 3 substituents each independently selected from:
  i) halo, oxo, thioxo, $(C_{2-6})$alkenyl, $(C_{1-6})$haloalkyl, $(C_{3-7})$cycloalkyl, $(C_{3-7})$cycloalkyl-$(C_{1-6})$alkyl-, —OH, —O$(C_{1-6})$alkyl, —O$(C_{1-6})$haloalkyl, —SH, —S$(C_{1-6})$alkyl, —SO$(C_{1-6})$alkyl, —$SO_2$$(C_{1-6})$alkyl, —$NH_2$, —NH$(C_{1-6})$alkyl and —N($(C_{1-6})$alkyl$)_2$;
  ii) $(C_{1-6})$alkyl optionally substituted with —OH, —O—$(C_{1-6})$haloalkyl, or —O—$(C_{1-6})$alkyl; and
  iii) aryl or Het, wherein each of the aryl and Het is optionally substituted with halo, $(C_{1-6})$alkyl or COOH; and $R^7$ may also be H, halo, $(C_{1-6})$alkyl, or $(C_{1-6})$haloalkyl when at least one of $R^5$ or $R^8$ is other than H or when $R^6$ is other than H, halo, $(C_{1-6})$alkyl, or $(C_{1-6})$haloalkyl or when $R^2$ is other than H, $(C_{1-6})$alkyl, or —O—$(C_{1-6})$alkyl; or
  $R^6$ and $R^7$, together with the C to which they are attached, or $R^7$ and $R^8$, together with the C to which they are attached; may be linked to form a 5- or 6-membered carbocycle or a 4- to 7-membered heterocycle optionally further containing 1 to 3 heteroatoms each independently selected from N, O and S, wherein each S heteroatom may, independently and where possible, exist in an oxidized state such that it is further bonded to one or two oxygen atoms to form the groups SO or $SO_2$;

wherein the carbocycle or heterocycle is optionally substituted with 1 to 3 substituents each independently selected from halo, $(C_{1-6})$alkyl, $(C_{2-6})$alkenyl, $(C_{1-6})$haloalkyl, $(C_{3-7})$cycloalkyl, —OH, —O$(C_{1-6})$alkyl, —SH, —$NH_2$, —NH$(C_{1-6})$alkyl and —N($(C_{1-6})$alkyl$)_2$.

$R^7$-B: In one embodiment, $R^7$ is selected from:
  a) $(C_{2-6})$alkenyl, $(C_{2-6})$alkynyl, $(C_{3-7})$cycloalkyl, nitro, cyano, aryl and Het;
  b) —$(C_{1-6})$alkylene-$R^{11}$, —$(C_{1-6})$alkylene-O—$R^{11}$,
  wherein $R^{11}$ is in each instance independently selected from H, $(C_{1-6})$alkyl, $(C_{2-6})$alkenyl, $(C_{2-6})$alkynyl, $(C_{1-6})$haloalkyl, $(C_{3-7})$cycloalkyl, aryl and Het; and
  c) —N($R^9$)$R^{10}$, —C(=O)—N($R^9$)$R^{10}$, —$(C_{1-6})$alkylene-N($R^9$)$R^{10}$, —$(C_{1-6})$alkylene-C(=O)—N($R^9$)$R^{10}$, wherein
  $R^9$ is in each instance independently selected from H, $(C_{1-6})$alkyl and $(C_{3-7})$cycloalkyl; and
  $R^{10}$ is in each instance independently selected from $R^{11}$, —$(C_{1-6})$alkylene-$R^{11}$, —$SO_2$—$R^{11}$, —C(=O)—$R^{11}$, —C(=O)O$R^{11}$ and —C(=O)N($R^9$)$R^{11}$;
  wherein $R^{11}$ and $R^9$ are as defined above;
wherein each of the aryl and Het is optionally substituted with 1 to 3 substituents each independently selected from:
  i) halo, oxo, thioxo, $(C_{2-6})$alkenyl, $(C_{1-6})$haloalkyl, $(C_{3-7})$cycloalkyl, $(C_{3-7})$cycloalkyl-$(C_{1-6})$alkyl-, —OH, —O$(C_{1-6})$alkyl, —O$(C_{1-6})$haloalkyl, —SH, —S$(C_{1-6})$alkyl, —SO$(C_{1-6})$alkyl, —$SO_2$$(C_{1-6})$alkyl, —$NH_2$, —NH$(C_{1-6})$alkyl and —N($(C_{1-6})$alkyl$)_2$;
  ii) $(C_{1-6})$alkyl optionally substituted with —OH, —O—$(C_{1-6})$haloalkyl, or —O—$(C_{1-6})$alkyl; and
  iii) aryl or Het, wherein each of the aryl and Het is optionally substituted with halo, $(C_{1-6})$alkyl or COOH; or $R^7$ may also be H, halo, $(C_{1-6})$alkyl, or $(C_{1-6})$haloalkyl when at least one of $R^5$ or $R^8$ is other than H or when $R^6$ is other than H, halo, $(C_{1-6})$alkyl, or $(C_{1-6})$haloalkyl or when $R^2$ is other than H, $(C_{1-6})$alkyl, or —O—$(C_{1-6})$alkyl.

$R^7$-C: In one embodiment, $R^7$ is selected from:
  a) $(C_{2-6})$alkenyl, $(C_{3-7})$cycloalkyl, nitro, cyano, aryl and Het;
  b) —$(C_{1-6})$alkylene-$R^{11}$,
  wherein $R^{11}$ is in each instance independently selected from H, $(C_{2-6})$alkenyl, $(C_{2-6})$alkynyl, $(C_{1-6})$haloalkyl, $(C_{3-7})$cycloalkyl, aryl and Het; and c) —N(R$^9$)R$^{10}$, —C(=O)—N(R$^9$)R$^{10}$, wherein R$^9$ is in each instance independently selected from H, (C$_{1-6}$)alkyl and (C$_{3-7}$)cycloalkyl; and R$^{10}$ is in each instance independently selected from R$^{11}$, —(C$_{1-6}$)alkylene-R$^{11}$, —SO$_2$—R$^{11}$, —C(=O)—R$^{11}$, —C(=O)OR$^{11}$ and —C(=O)N(R$^6$)R$^{11}$; wherein R$^{11}$ and R$^9$ are as defined above;

wherein each of the aryl and Het is optionally substituted with 1 to 3 substituents each independently selected from:

i) halo, oxo, thioxo, (C$_{2-6}$)alkenyl, (C$_{1-6}$)haloalkyl, (C$_{3-7}$)cycloalkyl, (C$_{3-7}$)cycloalkyl-(C$_{1-6}$)alkyl-, —OH, —O(C$_{1-6}$)alkyl, —O(C$_{1-6}$)haloalkyl, —SH, —S(C$_{1-6}$)alkyl, —SO(C$_{1-6}$)alkyl, —SO$_2$(C$_{1-6}$)alkyl, —NH$_2$, —NH(C$_{1-6}$)alkyl and —N((C$_{1-6}$)alkyl)$_2$;

ii) (C$_{1-6}$)alkyl optionally substituted with —OH, —O—(C$_{1-6}$)haloalkyl, or —O—(C$_{1-6}$)alkyl; and iii) aryl or Het, wherein each of the aryl and Het is optionally substituted with halo, (C$_{1-6}$)alkyl or COOH;

R$^7$ may also be H, halo, (C$_{1-6}$)alkyl, or (C$_{1-6}$)haloalkyl when at least one of R$^5$ or R$^8$ is other than H or when R$^6$ is other than H, halo, (C$_{1-6}$)alkyl, or (C$_{1-6}$)haloalkyl or when R$^2$ is other than H, (C$_{1-6}$)alkyl, or —O—(C$_{1-6}$)alkyl.

R$^7$-D: In one embodiment, R$^7$ is selected from:

a) aryl or Het; and b) -(C$_{1-6}$)alkylene-R$^{11}$, wherein R$^{11}$ is in each instance independently selected from aryl and Het;

wherein said aryl and Het is optionally substituted with 1 to 3 substituents each independently selected from:

i) halo, oxo, thioxo, (C$_{1-6}$)haloalkyl, —OH, —O(C$_{1-6}$) alkyl, —O (C$_{1-6}$)haloalkyl, —SH, —S(C$_{1-6}$)alkyl, —SO(C$_{1-6}$)alkyl, —SO$_2$(C$_{1-6}$)alkyl, —NH$_2$, —NH (C$_{1-6}$)alkyl and —N((C$_{1-6}$)alkyl)$_2$; and ii) (C$_{1-6}$)alkyl.

R$^7$-E: In one embodiment, R$^7$ is CH$_2$OH, CN, OCH$_3$, CH=CH$_2$, cyclopropyl, NH$_2$, NO$_2$, CONH$_2$, NHC(=O)CH$_3$,

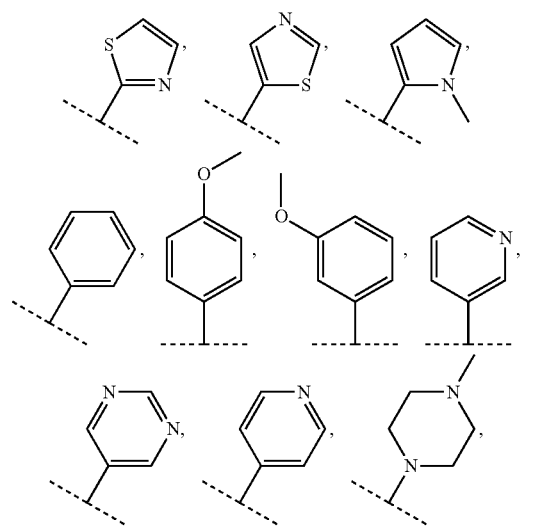

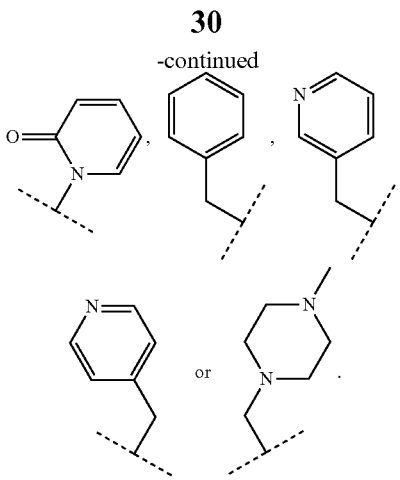

R$^7$-F: In one embodiment, R$^7$ is CH$_2$OH, CN, OCH$_3$, CH=CH$_2$, cyclopropyl, NH$_2$, NO$_2$, CONH$_2$, NHC(=O)CH$_3$,

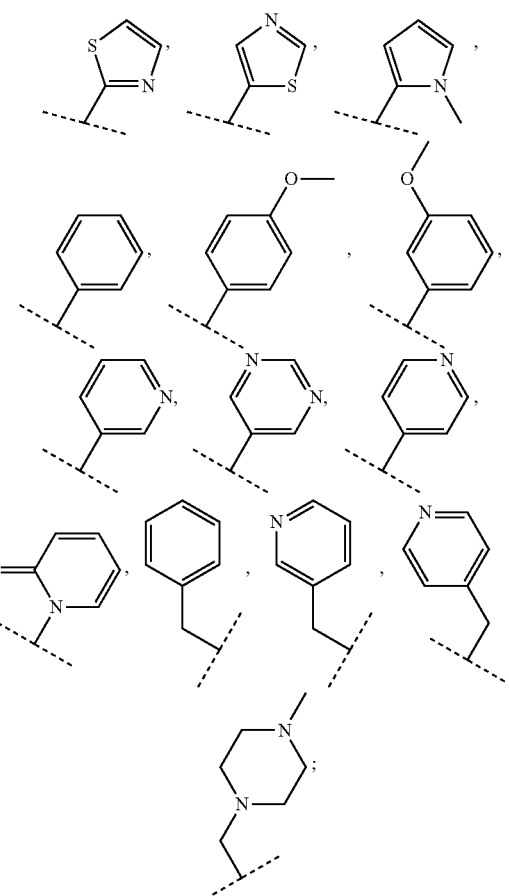

H, when at least one of R$^5$ or R$^8$ is other than H or when R$^6$ is other than H, halo, (C$_{1-6}$)alkyl, or (C$_{1-6}$)haloalkyl or when R$^2$ is other than H, (C$_{1-6}$)alkyl, or —O—(C$_{1-6}$) alkyl.

R$^7$-G: In one embodiment, R$^7$ is H, when at least one of R$^5$ or R$^8$ is other than H or when R$^6$ is other than H, halo, (C$_{1-6}$) alkyl, or (C$_{1-6}$)haloalkyl or when R$^2$ is other than H, (C$_{1-6}$)alkyl, or —O—(C$_{1-6}$)alkyl.

Any and each individual definition of $R^7$ as set out herein may be combined with any and each individual definition of the Core, c, $R^2$, $R^3$, $R^4$, $R^5$, $R^6$ and $R^8$ as set out herein.

$R^8$:

$R^8$-A: In another embodiment, $R^8$ is selected from:
  a) halo, nitro or cyano;
  b) $R^{11}$, —C(=O)—O—$R^{11}$, —S—$R^{11}$, —S—$R^{11}$, —SO—$R^{11}$, —SO$_2$—$R^{11}$, —(C$_{1-6}$)alkylene-$R^{11}$, —(C$_{1-6}$)alkylene-C(=O)—$R^{11}$, —(C$_{1-6}$)alkylene-C(=O)—O—$R^{11}$, —(C$_{1-6}$)alkylene-O—$R^{11}$, —(C$_{1-6}$)alkylene-S—$R^{11}$, —(C$_{1-6}$)alkylene-SO—$R^{11}$ or —(C$_{1-6}$)alkylene-SO$_2$—$R^{11}$;
    wherein $R^{11}$ is in each instance independently selected from H, (C$_{1-6}$)alkyl, (C$_{2-6}$)alkenyl, (C$_{2-6}$)alkynyl, (C$_{1-6}$)haloalkyl, (C$_{3-7}$)cycloalkyl, aryl and Het; and
    wherein each of the aryl and Het is optionally substituted with 1 to 3 substituents each independently selected from:
      i) halo, oxo, thioxo, (C$_{2-6}$)alkenyl, (C$_{1-6}$)haloalkyl, (C$_{3-7}$)cycloalkyl, (C$_{3-7}$)cycloalkyl-(C$_{1-6}$)alkyl-, —OH, —O(C$_{1-6}$)alkyl, —O (C$_{1-6}$)haloalkyl, —SH, —SO(C$_{1-6}$)alkyl, —SO$_2$(C$_{1-6}$)alkyl, —C(=O)—NH$_2$, —C(=O)—NH(C$_{1-4}$)alkyl, —C(=O)—N((C$_{1-4}$)alkyl)$_2$, —C(=O)-aryl, —C(=O)—Het, —NH$_2$, —NH(C$_{1-6}$)alkyl and —N((C$_{1-6}$)alkyl)$_2$;
      ii) (C$_{1-6}$)alkyl optionally substituted with —OH, —O—(C$_{1-6}$)haloalkyl, or —O—(C$_{1-6}$)alkyl; and
      iii) aryl or Het, wherein each of the aryl and Het is optionally substituted with halo, (C$_{1-6}$)alkyl or COOH; and
  c) —N($R^9$)$R^{10}$, —C(=O)—N($R^9$)$R^{10}$, —O—C(=O)—N($R^9$)$R^{10}$, —SO$_2$—N($R^9$)$R^{10}$, —(C$_{1-6}$)alkylene-N($R^9$)$R^{10}$, —(C$_{1-6}$)alkylene-C(=O)—N($R^9$)$R^{10}$, —(C$_{1-6}$)alkylene-O—C(=O)—N($R^9$)$R^{10}$, or —(C$_{1-6}$)alkylene-SO$_2$—N($R^9$)$R^{10}$ wherein
    $R^9$ is in each instance independently selected from H, (C$_{1-6}$)alkyl and (C$_{3-7}$)cycloalkyl; and
    $R^{10}$ is in each instance independently selected from $R^{11}$, —(C$_{1-6}$)alkylene-$R^{11}$, —SO$_2$—$R^{11}$, —C(=O)—$R^{11}$, —C(=O)O$R^{11}$ and —C(=O)N($R^9$)$R^{11}$; wherein $R^{11}$ and $R^9$ are as defined above;
  or $R^7$ and $R^8$, together with the C to which they are attached;
    may be linked to form a 5- or 6-membered carbocycle or a 4- to 7-membered heterocycle optionally further containing 1 to 3 heteroatoms each independently selected from N, O and S, wherein each S heteroatom may, independently and where possible, exist in an oxidized state such that it is further bonded to one or two oxygen atoms to form the groups SO or SO$_2$;
    wherein the carbocycle or heterocycle is optionally substituted with 1 to 3 substituents each independently selected from halo, (C$_{1-6}$)alkyl, (C$_{2-6}$)alkenyl, (C$_{1-6}$)haloalkyl, (C$_{3-7}$)cycloalkyl, —OH, —O(C$_{1-6}$)alkyl, —SH, —S(C$_{1-6}$)alkyl, —NH$_2$, —NH(C$_{1-6}$)alkyl and —N((C$_{1-6}$)alkyl)$_2$.

$R^8$-B: In another embodiment, $R^8$ is selected from:
  a) halo;
  b) $R^{11}$, —O—$R^{11}$, or —(C$_{1-6}$)alkylene-$R^{11}$
    wherein $R^{11}$ is in each instance independently selected from H, (C$_{1-6}$)alkyl, (C$_{2-6}$)alkenyl, (C$_{1-6}$)haloalkyl, aryl and Het; and
    wherein each of the aryl and Het is optionally substituted with 1 to 3 substituents each independently selected from:
      i) halo, oxo, thioxo, (C$_{1-6}$)haloalkyl, —OH, —O(C$_{1-6}$)alkyl, —O (C$_{1-6}$)haloalkyl, —C(=O)—NH$_2$, —C(=O)—NH(C$_{1-4}$) alkyl, —C(=O)—N((C$_{1-4}$)alkyl)$_2$, —C(=O)-aryl, —C(=O)—Het, —NH$_2$, —NH(C$_{1-6}$)alkyl and —N((C$_{1-6}$)alkyl)$_2$;
      ii) (C$_{1-6}$)alkyl; and
      iii) aryl or Het, wherein each of the aryl and Het is optionally substituted with halo, (C$_{1-6}$)alkyl or COOH; and
  c) —N($R^9$)$R^{10}$, —O—C(=O)—N($R^9$)$R^{10}$, —SO$_2$—N($R^9$)$R^{10}$, —(C$_{1-6}$)alkylene-N($R^9$)$R^{10}$, —(C$_{1-6}$)alkylene-C(=O)—N($R^9$)$R^{10}$, —(C$_{1-6}$)alkylene-O—C(=O)—N($R^9$)$R^{10}$, or —(C$_{1-6}$)alkylene-SO$_2$—N($R^9$)$R^{10}$ wherein
    $R^9$ is in each instance independently selected from H, (C$_{1-6}$)alkyl and (C$_{3-7}$)cycloalkyl; and
    $R^{10}$ is in each instance independently selected from $R^{11}$, —(C$_{1-6}$)alkylene-$R^{11}$, —SO$_2$—$R^{11}$, —C(=O)—$R^{11}$, —C(=O)O$R^{11}$ and —C(=O)N($R^9$)$R^{11}$; wherein $R^{11}$ and $R^9$ are as defined above.

$R^8$-C: In another embodiment, $R^8$ is selected from:
  a) halo; and
  b) H, (C$_{1-6}$)alkyl, (C$_{1-6}$)haloalkyl, —O—(C$_{1-6}$)haloalkyl, aryl and Het, —(C$_{1-6}$)alkylene-aryl, —(C$_{1-6}$)alkylene-Het;
    wherein each of the aryl and Het is optionally substituted with 1 to 3 substituents each independently selected from:
      i) halo, oxo, thioxo, —O(C$_{1-6}$)alkyl, —O(C$_{1-6}$)haloalkyl, —C(=O)—NH$_2$, —C(=O)—NH(C$_{1-4}$) alkyl, —C(=O)—N((C$_{1-4}$)alkyl)$_2$, —C(=O)-aryl, C(=O)—Het; and
      ii) (C$_{1-6}$)alkyl.

$R^8$-D: In another embodiment, $R^8$ is selected from:
  a) F, Cl, Br; and
  b) H, (C$_{1-3}$)alkyl, —O—(C$_{1-3}$)haloalkyl, phenyl and Het, —(C$_{1-3}$)alkylene-phenyl, —(C$_{1-3}$)alkylene-Het;
    wherein each of the aryl and Het is optionally substituted with 1 to 2 substituents each independently selected from:
      i) oxo, thioxo, —C(=O)—NH$_2$, —C(=O)—NH(C$_{1-4}$) alkyl, —C(=O)—N((C$_{1-4}$)alkyl)$_2$, —C(=O)-aryl, —C(=O)—Het; and
      ii) (C$_{1-6}$)alkyl.

$R^8$-E: In another embodiment, $R^8$ is selected from: H, Br, F, CH$_3$, CH$_2$CH$_3$, OCF$_3$

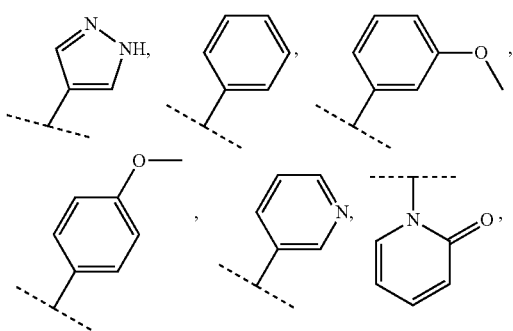

-continued

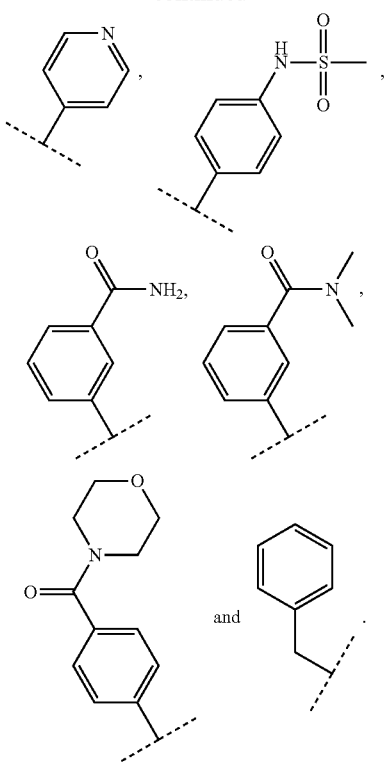

R⁸-F: In another embodiment, R⁸ is H, Br, F, CH₃, CH₂CH₃ or OCF₃.

R⁸-G: In another embodiment, R⁸ is selected from:

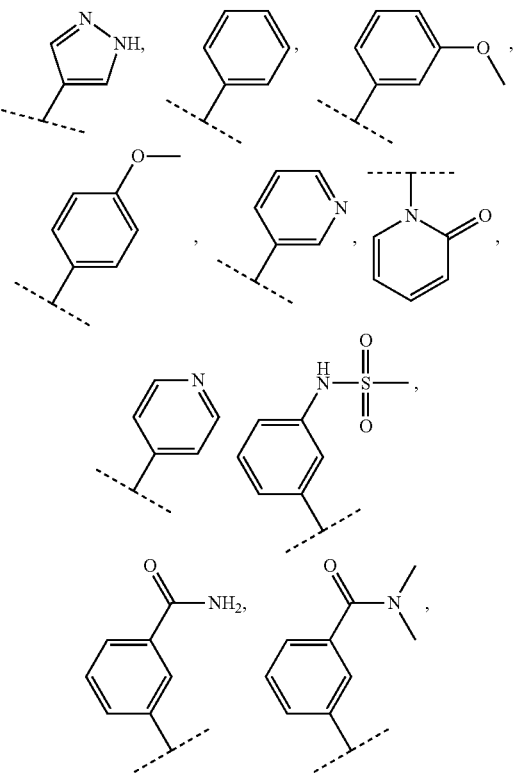

-continued

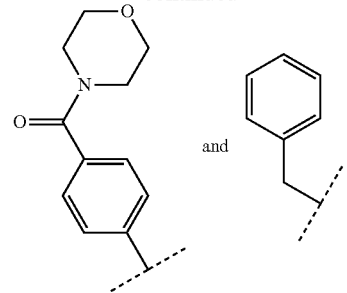

Any and each individual definition of $R^8$ as set out herein may be combined with any and each individual definition of the Core, c, $R^2$, $R^3$, $R^4$, $R^5$, $R^6$ and $R^7$ as set out herein.

Examples of preferred subgeneric embodiments of the present invention are set forth in the following table, wherein each substituent group of each embodiment is defined according to the definitions set forth above:

| Embodiment | Core | $R^2$ | $R^3$ | $R^4$ | $R^5$ | $R^6$ | $R^7$ | $R^8$ |
|---|---|---|---|---|---|---|---|---|
| E-1  | Core-A | $R^2$-I | $R^3$-I | $R^4$-H | $R^5$-D | $R^6$-D | $R^7$-E | $R^8$-D |
| E-2  | Core-A | $R^2$-H | $R^3$-I | $R^4$-I | $R^5$-E | $R^6$-E | $R^7$-D | $R^8$-B |
| E-3  | Core-A | $R^2$-E | $R^3$-I | $R^4$-J | $R^5$-F | $R^6$-F | $R^7$-F | $R^8$-G |
| E-4  | Core-A | $R^2$-I | $R^3$-J | $R^4$-K | $R^5$-G | $R^6$-G | $R^7$-F | $R^8$-E |
| E-5  | Core-A | $R^2$-H | $R^3$-B | $R^4$-L | $R^5$-D | $R^6$-A | $R^7$-D | $R^8$-F |
| E-6  | Core-A | $R^2$-E | $R^3$-C | $R^4$-H | $R^5$-D | $R^6$-G | $R^7$-D | $R^8$-G |
| E-7  | Core-A | $R^2$-H | $R^3$-I | $R^4$-L | $R^5$-F | $R^6$-F | $R^7$-F | $R^8$-E |
| E-8  | Core-A | $R^2$-A | $R^3$-A | $R^4$-K | $R^5$-E | $R^6$-G | $R^7$-B | $R^8$-A |
| E-9  | Core-A | $R^2$-B | $R^3$-D | $R^4$-H | $R^5$-F | $R^6$-D | $R^7$-C | $R^8$-C |
| E-10 | Core-A | $R^2$-C | $R^3$-E | $R^4$-L | $R^5$-G | $R^6$-D | $R^7$-A | $R^8$-C |
| E-11 | Core-A | $R^2$-D | $R^3$-A | $R^4$-B | $R^5$-A | $R^6$-E | $R^7$-D | $R^8$-D |
| E-12 | Core-A | $R^2$-B | $R^3$-F | $R^4$-K | $R^5$-F | $R^6$-D | $R^7$-F | $R^8$-G |
| E-13 | Core-A | $R^2$-C | $R^3$-E | $R^4$-L | $R^5$-G | $R^6$-E | $R^7$-G | $R^8$-E |
| E-14 | Core-A | $R^2$-D | $R^3$-B | $R^4$-J | $R^5$-C | $R^6$-F | $R^7$-B | $R^8$-G |
| E-15 | Core-A | $R^2$-E | $R^3$-G | $R^4$-A | $R^5$-E | $R^6$-G | $R^7$-G | $R^8$-D |
| E-16 | Core-A | $R^2$-G | $R^3$-A | $R^4$-B | $R^5$-A | $R^6$-D | $R^7$-G | $R^8$-E |
| E-17 | Core-A | $R^2$-F | $R^3$-H | $R^4$-E | $R^5$-D | $R^6$-E | $R^7$-A | $R^8$-F |
| E-18 | Core-A | $R^2$-H | $R^3$-C | $R^4$-D | $R^5$-B | $R^6$-F | $R^7$-G | $R^8$-B |
| E-19 | Core-A | $R^2$-I | $R^3$-D | $R^4$-F | $R^5$-D | $R^6$-A | $R^7$-C | $R^8$-C |
| E-20 | Core-A | $R^2$-I | $R^3$-I | $R^4$-C | $R^5$-E | $R^6$-B | $R^7$-G | $R^8$-A |
| E-21 | Core-A | $R^2$-I | $R^3$-I | $R^4$-H | $R^5$-D | $R^6$-D | $R^7$-E | $R^8$-G |
| E-22 | Core-A | $R^2$-H | $R^3$-I | $R^4$-H | $R^5$-D | $R^6$-D | $R^7$-E | $R^8$-G |
| E-23 | Core-A | $R^2$-E | $R^3$-I | $R^4$-H | $R^5$-D | $R^6$-D | $R^7$-E | $R^8$-G |
| E-24 | Core-B | $R^2$-I | $R^3$-I | $R^4$-H | $R^5$-D | $R^6$-D | $R^7$-E | $R^8$-D |
| E-25 | Core-B | $R^2$-H | $R^3$-I | $R^4$-I | $R^5$-E | $R^6$-E | $R^7$-D | $R^8$-B |
| E-26 | Core-B | $R^2$-E | $R^3$-I | $R^4$-J | $R^5$-F | $R^6$-F | $R^7$-F | $R^8$-G |
| E-27 | Core-B | $R^2$-I | $R^3$-J | $R^4$-K | $R^5$-G | $R^6$-G | $R^7$-F | $R^8$-E |
| E-28 | Core-B | $R^2$-I | $R^3$-I | $R^4$-K | $R^5$-G | $R^6$-G | $R^7$-F | $R^8$-E |
| E-29 | Core-B | $R^2$-I | $R^3$-I | $R^4$-K | $R^5$-G | $R^6$-G | $R^7$-G | $R^8$-E |
| E-30 | Core-B | $R^2$-H | $R^3$-B | $R^4$-L | $R^5$-D | $R^6$-A | $R^7$-D | $R^8$-F |
| E-31 | Core-B | $R^2$-E | $R^3$-C | $R^4$-H | $R^5$-D | $R^6$-G | $R^7$-D | $R^8$-G |
| E-32 | Core-B | $R^2$-H | $R^3$-I | $R^4$-L | $R^5$-F | $R^6$-F | $R^7$-F | $R^8$-E |
| E-33 | Core-B | $R^2$-I | $R^3$-I | $R^4$-J | $R^5$-F | $R^6$-B | $R^7$-E | $R^8$-B |
| E-34 | Core-B | $R^2$-E | $R^3$-B | $R^4$-K | $R^5$-G | $R^6$-D | $R^7$-E | $R^8$-D |
| E-35 | Core-B | $R^2$-E | $R^3$-C | $R^4$-J | $R^5$-   | $R^6$-E | $R^7$-D | $R^8$-E |
| E-36 | Core-B | $R^2$-H | $R^3$-E | $R^4$-J | $R^5$-C | $R^6$-C | $R^7$-F | $R^8$-D |
| E-37 | Core-B | $R^2$-H | $R^3$-F | $R^4$-I | $R^5$-D | $R^6$-F | $R^7$-F | $R^8$-B |
| E-38 | Core-B | $R^2$-A | $R^3$-A | $R^4$-K | $R^5$-E | $R^6$-G | $R^7$-B | $R^8$-A |
| E-39 | Core-B | $R^2$-B | $R^3$-D | $R^4$-H | $R^5$-F | $R^6$-D | $R^7$-C | $R^8$-C |
| E-40 | Core-B | $R^2$-C | $R^3$-E | $R^4$-L | $R^5$-G | $R^6$-D | $R^7$-A | $R^8$-C |
| E-41 | Core-B | $R^2$-D | $R^3$-A | $R^4$-B | $R^5$-A | $R^6$-E | $R^7$-D | $R^8$-D |
| E-42 | Core-B | $R^2$-E | $R^3$-J | $R^4$-C | $R^5$-B | $R^6$-A | $R^7$-F | $R^8$-B |
| E-43 | Core-B | $R^2$-F | $R^3$-I | $R^4$-D | $R^5$-D | $R^6$-B | $R^7$-E | $R^8$-B |
| E-44 | Core-B | $R^2$-G | $R^3$-C | $R^4$-E | $R^5$-E | $R^6$-C | $R^7$-D | $R^8$-C |
| E-45 | Core-B | $R^2$-A | $R^3$-D | $R^4$-A | $R^5$-F | $R^6$-C | $R^7$-E | $R^8$-D |
| E-46 | Core-B | $R^2$-B | $R^3$-F | $R^4$-K | $R^5$-F | $R^6$-D | $R^7$-F | $R^8$-G |
| E-47 | Core-B | $R^2$-C | $R^3$-E | $R^4$-L | $R^5$-G | $R^6$-E | $R^7$-G | $R^8$-E |
| E-48 | Core-B | $R^2$-D | $R^3$-B | $R^4$-J | $R^5$-C | $R^6$-F | $R^7$-B | $R^8$-G |
| E-49 | Core-B | $R^2$-E | $R^3$-G | $R^4$-A | $R^5$-E | $R^6$-G | $R^7$-G | $R^8$-D |
| E-50 | Core-B | $R^2$-G | $R^3$-A | $R^4$-B | $R^5$-A | $R^6$-D | $R^7$-G | $R^8$-E |
| E-51 | Core-B | $R^2$-F | $R^3$-H | $R^4$-E | $R^5$-D | $R^6$-E | $R^7$-A | $R^8$-F |

-continued

| Embodiment | Core | $R^2$ | $R^3$ | $R^4$ | $R^5$ | $R^6$ | $R^7$ | $R^8$ |
|---|---|---|---|---|---|---|---|---|
| E-52 | Core-B | $R^2$-H | $R^3$-C | $R^4$-D | $R^5$-B | $R^6$-F | $R^7$-G | $R^8$-B |
| E-53 | Core-B | $R^2$-I | $R^3$-D | $R^4$-F | $R^5$-D | $R^6$-A | $R^7$-C | $R^8$-C |
| E-54 | Core-B | $R^2$-I | $R^3$-I | $R^4$-C | $R^5$-E | $R^6$-B | $R^7$-G | $R^8$-A |
| E-55 | Core-B | $R^2$-I | $R^3$-I | $R^4$-H | $R^5$-D | $R^6$-D | $R^7$-E | $R^8$-G |
| E-56 | Core-B | $R^2$-H | $R^3$-I | $R^4$-H | $R^5$-D | $R^6$-D | $R^7$-E | $R^8$-G |
| E-57 | Core-B | $R^2$-E | $R^3$-I | $R^4$-H | $R^5$-D | $R^6$-D | $R^7$-E | $R^8$-G |
| E-58 | Core-C | $R^2$-I | $R^3$-I | $R^4$-H | $R^5$-D | $R^6$-D | $R^7$-E | $R^8$-D |
| E-59 | Core-C | $R^2$-H | $R^3$-I | $R^4$-I | $R^5$-E | $R^6$-E | $R^7$-D | $R^8$-B |
| E-60 | Core-C | $R^2$-E | $R^3$-I | $R^4$-J | $R^5$-F | $R^6$-F | $R^7$-F | $R^8$-G |
| E-61 | Core-C | $R^2$-H | $R^3$-I | $R^4$-H | $R^5$-D | $R^6$-D | $R^7$-E | $R^8$-G |
| E-62 | Core-C | $R^2$-E | $R^3$-I | $R^4$-H | $R^5$-D | $R^6$-D | $R^7$-E | $R^8$-G |

Examples of most preferred compounds according to this invention are each single compound listed in the following Tables 1 to 4.

In general, all tautomeric and isomeric forms and mixtures thereof, for example, individual tautomers, geometric isomers, stereoisomers, atropisomers, enantiomers, diastereomers, racemates, racemic or non-racemic mixtures of stereoisomers, mixtures of diastereomers, or mixtures of any of the foregoing forms of a chemical structure or compound is intended, unless the specific stereochemistry or isomeric form is specifically indicated in the compound name or structure.

It is well-known in the art that the biological and pharmacological activity of a compound is sensitive to the stereochemistry of the compound. Thus, for example, enantiomers often exhibit strikingly different biological activity including differences in pharmacokinetic properties, including metabolism, protein binding, and the like, and pharmacological properties, including the type of activity displayed, the degree of activity, toxicity, and the like. Thus, one skilled in the art will appreciate that one enantiomer may be more active or may exhibit beneficial effects when enriched relative to the other enantiomer or when separated from the other enantiomer. Additionally, one skilled in the art would know how to separate, enrich, or selectively prepare the enantiomers of the compounds of the present invention from this disclosure and the knowledge in the art.

Preparation of Pure Stereoisomers, e.g. Enantiomers and Diastereomers, or Mixtures of desired enantiomeric excess (ee) or enantiomeric purity, are accomplished by one or more of the many methods of (a) separation or resolution of enantiomers, or (b) enantioselective synthesis known to those of skill in the art, or a combination thereof. These resolution methods generally rely on chiral recognition and include, for example, chromatography using chiral stationary phases, enantioselective host-guest complexation, resolution or synthesis using chiral auxiliaries, enantioselective synthesis, enzymatic and nonenzymatic kinetic resolution, or spontaneous enantioselective crystallization. Such methods are disclosed generally in Chiral Separation Techniques: A Practical Approach (2nd Ed.), G. Subramanian (ed.), Wiley-VCH, 2000; T. E. Beesley and R. P. W. Scott, Chiral Chromatography, John Wiley & Sons, 1999; and Satinder Ahuja, Chiral Separations by Chromatography, Am. Chem. Soc., 2000, herein incorporated by reference. Furthermore, there are equally well-known methods for the quantitation of enantiomeric excess or purity, for example, GC, HPLC, CE, or NMR, and assignment of absolute configuration and conformation, for example, CD, ORD, X-ray crystallography, or NMR.

Pharmaceutical Composition

Compounds of the present invention may be administered to a mammal in need of treatment for HIV infection as a pharmaceutical composition comprising a therapeutically effective amount of a compound according to the invention or a pharmaceutically acceptable salt or ester thereof; and one or more conventional non-toxic pharmaceutically-acceptable carriers, adjuvants or vehicles. The specific formulation of the composition is determined by the solubility and chemical nature of the compound, the chosen route of administration and standard pharmaceutical practice. The pharmaceutical composition according to the present invention may be administered orally or systemically.

When one enantiomer of a chiral active ingredient has a different biological activity than the other, it is contemplated that the pharmaceutical composition according to the invention may comprise a racemic mixture of the active ingredient, a mixture enriched in one enantiomer of the active ingredient or a pure enantiomer of the active ingredient. The mixture enriched in one enantiomer of the active ingredient is contemplated to contain from more than 50% to about 100% of one enantiomer of the active ingredient and from about 0% to less than 50% of the other enantiomer of the active ingredient. Preferably, when the composition comprises a mixture enriched in one enantiomer of the active ingredient or a pure enantiomer of the active ingredient, the composition comprises from more than 50% to about 100% of, or only, the more physiologically active enantiomer and/or the less toxic enantiomer. It is well known that one enantiomer of an active ingredient may be the more physiologically active for one therapeutic indication while the other enantiomer of the active ingredient may be the more physiologically active for a different therapeutic indication; therefore the preferred enantiomeric makeup of the pharmaceutical composition may differ for use of the composition in treating different therapeutic indications.

For oral administration, the compound, or a pharmaceutically acceptable salt or ester thereof, can be formulated in any orally acceptable dosage form including but not limited to aqueous suspensions and solutions, capsules or tablets. For systemic administration, including but not limited to administration by subcutaneous, intracutaneous, intravenous, intramuscular, intra-articular, intrasynovial, intrasternal, intrathecal, and intralesional injection or infusion techniques, it is preferred to use a solution of the compound, or a pharmaceutically acceptable salt or ester thereof, in a pharmaceutically acceptable sterile aqueous vehicle.

Pharmaceutically acceptable carriers, adjuvants, vehicles, excipients and additives as well as methods of formulating pharmaceutical compositions for various modes of administration are well-known to those of skill in the art and are described in pharmaceutical texts such as Remington: The Science and Practice of Pharmacy, 21st Edition, Lippincott Williams & Wilkins, 2005; and L. V. Allen, N. G. Popovish and H. C. Ansel, Pharmaceutical Dosage Forms and Drug Delivery Systems, 8th ed., Lippincott Williams & Wilkins, 2004, herein incorporated by reference.

The dosage administered will vary depending upon known factors, including but not limited to the activity and pharmacodynamic characteristics of the specific compound employed and its mode, time and route of administration; the age, diet, gender, body weight and general health status of the recipient; the nature and extent of the symptoms; the severity and course of the infection; the kind of concurrent treatment; the frequency of treatment; the effect desired; and the judgment of the treating physician. In general, the compound is most desirably administered at a dosage level that will generally afford antivirally effective results without causing any harmful or deleterious side effects.

A daily dosage of active ingredient can be expected to be about 0.001 to about 100 milligrams per kilogram of body weight, with the preferred dose being about 0.01 to about 50 mg/kg. Typically, the pharmaceutical composition of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

Therefore, according to one embodiment, the pharmaceutical composition according to the invention comprises a racemic mixture of the compound of formula (I), or a pharmaceutically acceptable salt or ester thereof.

An alternative embodiment provides a pharmaceutical composition comprising a mixture enriched in one enantiomer of the compound of formula (I), or a pharmaceutically acceptable salt or ester thereof.

A further embodiment provides a pharmaceutical composition comprising a pure enantiomer of the compound of formula (I), or a pharmaceutically acceptable salt or ester thereof.

Combination Therapy

Combination therapy is contemplated wherein a compound according to the invention, or a pharmaceutically acceptable salt or ester thereof, is co-administered with at least one additional antiviral agent. The additional agents may be combined with compounds of this invention to create a single dosage form. Alternatively these additional agents may be separately administered, concurrently or sequentially, as part of a multiple dosage form.

When the pharmaceutical composition of this invention comprises a combination of a compound according to the invention, or a pharmaceutically acceptable salt or ester thereof, and one or more additional antiviral agent, both the compound and the additional agent should be present at dosage levels of between about 10 to 100%, and more preferably between about 10 and 80% of the dosage normally administered in a monotherapy regimen. In the case of a synergistic interaction between the compound of the invention and the additional antiviral agent or agents, the dosage of any or all of the active agents in the combination may be reduced compared to the dosage normally administered in a monotherapy regimen.

Antiviral agents contemplated for use in such combination therapy include agents (compounds or biologicals) that are effective to inhibit the formation and/or replication of a virus in a mammal, including but not limited to agents that interfere with either host or viral mechanisms necessary for the formation and/or replication of a virus in a mammal. Such agents can be selected from:

NRTIs (nucleoside or nucleotide reverse transcriptase inhibitors) including but not limited to zidovudine (AZT), didanosine (ddI), zalcitabine (ddC), stavudine (d4T), lamivudine (3TC), emtricitabine, abacavir succinate, elvucitabine, adefovir dipivoxil, lobucavir (BMS-180194) lodenosine (FddA) and tenofovir including tenofovir disoproxil and tenofovir disoproxil fumarate salt, COMBIVIR™ (contains 3TC and AZT), TRIZIVIR™ (contains abacavir, 3TC and AZT), TRUVADA™ (contains tenofovir and emtricitabine), EPZICOM™ (contains abacavir and 3TC);

NNRTIs (non-nucleoside reverse transcriptase inhibitors) including but not limited to nevirapine, delaviradine, efavirenz, etravirine and rilpivirine;

protease inhibitors including but not limited to ritonavir, tipranavir, saquinavir, nelfinavir, indinavir, amprenavir, fosamprenavir, atazanavir, lopinavir, darunavir (TMC-114), lasinavir and brecanavir (VX-385);

entry inhibitors including but not limited to
  CCR5 antagonists (including but not limited to maraviroc, vicriviroc, INCB9471 and TAK-652),
  CXCR4 antagonists (including but not limited to AMD-11070),
  fusion inhibitors (including but not limited to enfuvirtide (T-20), TR1-1144 and TR1-999) and
  others (including but not limited to BMS-488043);
integrase inhibitors (including but not limited to raltegravir (MK-0518), BMS-707035 and elvitegravir (GS 9137));
TAT inhibitors;
maturation inhibitors (including but not limited to berivimat (PA-457));
immunomodulating agents (including but not limited to levamisole); and
other antiviral agents including hydroxyurea, ribavirin, IL-2, IL-12 and pensafuside.

Furthermore, a compound according to the invention can be used with at least one other compound according to the invention or with one or more antifungal or antibacterial agents (including but not limited to fluconazole).

Therefore, according to one embodiment, the pharmaceutical composition of this invention additionally comprises one or more antiviral agents.

A further embodiment provides the pharmaceutical composition of this invention wherein the one or more antiviral agent comprises at least one NNRTI.

According to another embodiment of the pharmaceutical composition of this invention, the one or more antiviral agent comprises at least one NRTI.

According to yet another embodiment of the pharmaceutical composition of this invention, the one or more antiviral agent comprises at least one protease inhibitor.

According to still another embodiment of the pharmaceutical composition of this invention, the one or more antiviral agent comprises at least one entry inhibitor.

According to a further embodiment of the pharmaceutical composition of this invention, the one or more antiviral agent comprises at least one integrase inhibitor.

A compound according to the present invention may also be used as a laboratory reagent or a research reagent. For example, a compound of the present invention may be used as positive control to validate assays, including but not limited to surrogate cell-based assays and in vitro or in vivo viral replication assays.

Furthermore, a compound according to the present invention may be used to treat or prevent viral contamination of materials and therefore reduce the risk of viral infection of laboratory or medical personnel or patients who come in contact with such materials (e.g. blood, tissue, surgical instruments and garments, laboratory instruments and garments, and blood collection apparatuses and materials).

Derivatives Comprising a Detectable Label

Another aspect of the invention provides a derivative of a compound of formula (I), the derivative comprising a detectable label. Such a label allows recognition either directly or indirectly of the derivative such that it can be detected, measured or quantified. The detectable label may itself be detectable, measurable or quantifiable, or it may interact with one or more other moities which themselves comprise one or more detectable labels, so that the interaction therebetween allows the derivative to be detected, measured or quantified.

Such derivatives may be used as probes to study HIV replication, including but not limited to study of the mechanism of action of viral and host proteins involved in HIV replication, study of conformational changes undergone by such viral and host proteins under various conditions and study of interactions with entities which bind to or otherwise interact with these viral and host proteins. Derivatives according to this aspect of the invention may be used in assays to identify compounds which interact with viral and host proteins, the assays including but not limited to displacement assays which measure the extent to which the derivative is displaced from interacting with the viral and host proteins. A preferred use of derivatives according to this aspect of the invention is in assays to identify HIV integrase inhibitors. Such derivatives may also be used to form covalent or non-covalent interactions with the viral and host proteins or to identify residues of the viral and host proteins which interact with the compounds of the invention.

Detectable labels contemplated for use with derivatives of the compounds of the invention include, but are not limited to, fluorescent labels, chemiluminescent labels, chromophores, antibodies, enzymatic markers, radioactive isotopes, affinity tags and photoreactive groups.

A fluorescent label is a label which fluoresces, emitting light of one wavelength upon absorption of light of a different wavelength. Fluorescent labels include but are not limited to fluorescein; Texas Red; aminomethylcoumarin; rhodamine dyes, including but not limited to tetramethylrhodamine (TAMRA); Alexa dyes including but not limited to Alexa Fluor® 555; cyanine dyes including but not limited to Cy3; europium or lanthanide series based fluorescent molecules; and the like.

A chemiluminescent label is a label which can undergo a chemical reaction which produces light. Chemiluminescent labels include but are not limited to luminol, luciferin, lucigenin, and the like.

A chromophore is a label which selectively absorbs certain wavelengths of visible light while transmitting or reflecting others, thereby causing the compounds which contain the chromophore to appear colored. Chromophores include but are not limited to natural and synthetic dyes.

An antibody is a protein produced by a mammalian immune system in response to a specific antigen, which binds specifically to that antigen. Antibodies contemplated for use as detectable labels according to the invention include but are not limited to antibodies against the following: polyhistidine tags, glutathione-5-transferase (GST), hemagglutinin (HA), FLAG® epitope tags, Myc tag, maltose binding protein (MBP), green fluorescent protein (GFP) and the like.

An enzymatic marker is an enzyme whose presence may be detected by means of an assay specific to the catalytic activity of the enzyme. Enzymatic markers contemplated for use as detectable labels according to the invention include but are not limited to luciferase, horseradish peroxidase (HRP), β-galactosidase and the like.

A radioactive isotope is an isotope of an atom which produces radiation upon radioactive decay. Radioactive isotopes include but are not limited to $^{14}C$, $^{3}H$, $^{31}P$, $^{121}I$, $^{125}I$, and the like.

An affinity tag is a label which has a strong affinity for another moiety, designated herein as a binding partner. Such an affinity tag can be used to form a complex with the binding partner so that the complex may be selectively detected or separated from a mixture. Affinity tags include but are not limited to biotin or a derivative thereof, a histidine polypeptide, a polyarginine, an amylose sugar moiety or a defined epitope recognizable by a specific antibody; suitable epitopes include but are not limited to glutathione-S-transferase (GST), hemagglutinin (HA), FLAG® epitope tags, Myc tag, maltose binding protein (MBP), green fluorescent protein (GFP) and the like.

Furthermore, compounds of the invention used as probes may be labelled with a photoreactive group which is transformed, upon activation by light, from an inert group to a reactive species, such as a free radical. Such a group may be used to activate the derivative so that it can form a covalent bond with one or more residues of a viral or host protein. Photoreactive groups include but are not limited to photoaffinity labels such as benzophenone and azide groups.

Methodology and Synthesis

The synthesis of compounds of formula (I) according to this invention is conveniently accomplished following the general procedure outlined in the schemes below wherein $R^2$, $R^3$, $R^4$, $R^5$, $R^6$, $R^7$ and $R^8$ are as defined herein. Further instruction is provided to one skilled in the art by the specific examples set out herein below.

Scheme 1: Assembly of inhibitors

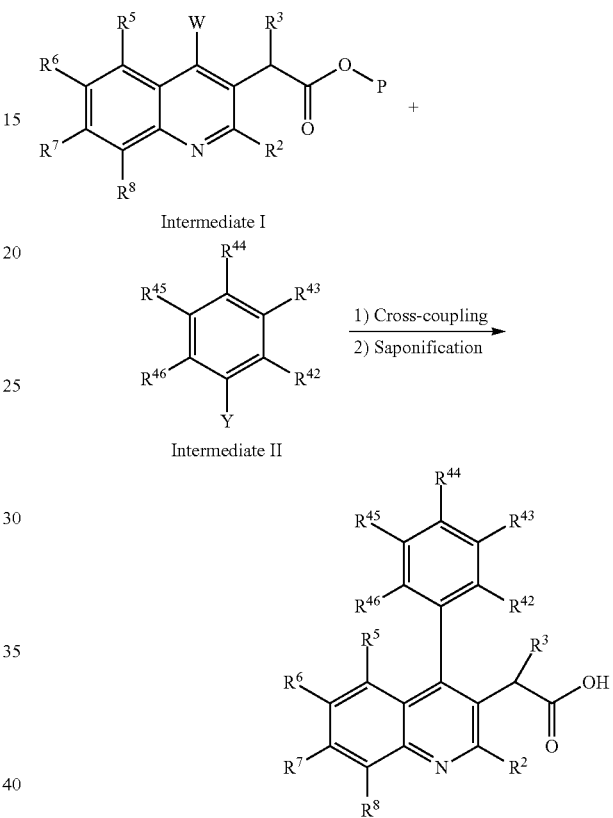

wherein $R^{42}$, $R^{43}$, $R^{44}$, $R^{45}$, and $R^{46}$ may either be substituents on the phenyl moiety or ($R^{42}$ and $R^{43}$), ($R^{43}$ and $R^{44}$), ($R^{44}$ and $R^{45}$) or ($R^{45}$ and $R^{46}$) may be linked so to as to form a carbocycle or heterocycle, W is iodo, bromo, chloro or OTf, Y is $B(OH)_2$ or boronate esters such as $B(OCH_3)_2$ and $B(OC(CH_3)_2C(CH_3)_2O)$, iodo, $SnR_3$ wherein R is $(C_{1-6})$alkyl, ZnX wherein X is halo, and P is a protecting group, such as commonly used protecting groups for carboxylic acids, including, but not limited to a methyl or ethyl ester.

Several coupling methods between the intermediate (I) (i.e. quinoline scaffold) and the intermediate II (i.e. $R^4$ substituent) can be contemplated by those skilled in the art. For examples, but not limited to, Suzuki cross-coupling between the boronic acid or boronate ester derivative of intermediate II and the halo or triflate derivative of intermediate I, copper catalyzed Ullmann cross-coupling between the iodo derivatives of intermediates I and II, Negishi cross-coupling between the arylzinc reagent of the intermediate II and the iodo or triflate derivative of intermediate I, and Stille coupling between the aryltin reagent of II and the bromo or iodo derivative of intermediate I as shown above can lead, after saponification, to the compounds of formula (I).

Alternatively, the same cross-coupling methods can be used by interchanging the coupling partners as shown below. For examples, Suzuki, Negishi, and Stille type cross-coupling between boronic acid or boronate ester derivative, the arylzinc reagent or the aryltin reagent of quinoline intermediate III and the required iodo, bromo, chloro or triflate derivative of intermediate IV can also lead, after saponification, to the compounds of the invention of formula (I).

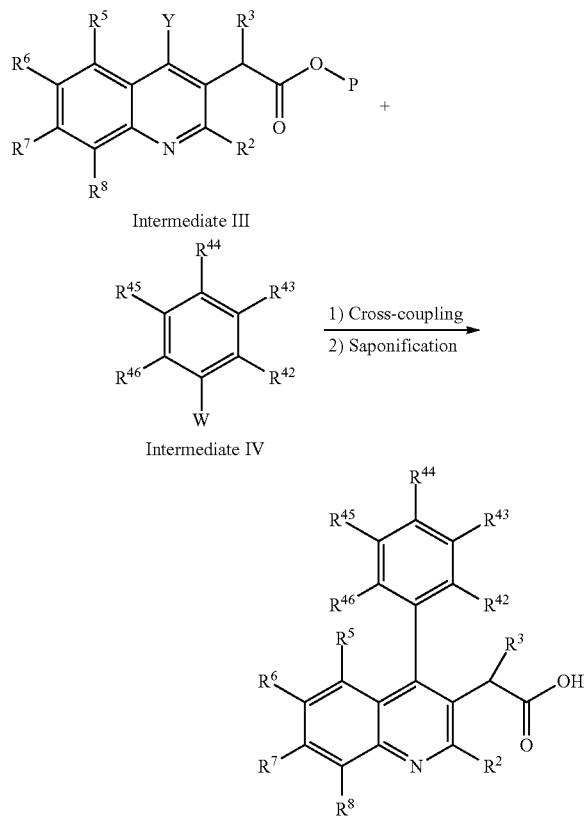

wherein $R^{42}$, $R^{43}$, $R^{44}$, $R^{45}$ and, $R^{46}$ and P are as defined above and W is iodo, bromo, chloro or OTf, Y is $B(OH)_2$ or boronate esters such as $B(OCH_3)_2$ and $B(OC(CH_3)_2C(CH_3)_2O)$, $SnR_3$ wherein R is $(C_{1-6})$alkyl, and ZnX wherein X is halo.

Furthermore, downstream modifications to the product can be contemplated, such as conversion of an aniline-type amine to a chloro or bromo substituent via Sandmeyer reaction or alkylation, or dehalogenation via reduction.

Additionally, intermediate III can be used for decarboxylative biaryl cross-coupling reactions similar to those described by Forgione, Bilodeau and coworkers, J. Am. Chem. Soc. 2006, 128, 11350-11351, herein incorporated by reference, as shown below:

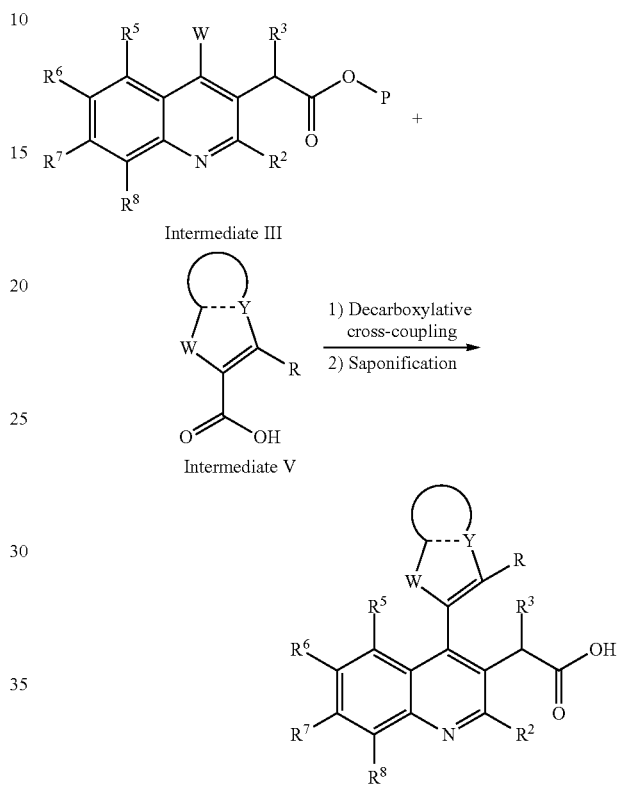

W = O, N, S
Y = CH, N wherein W is iodo, bromo, chloro or OTf, R may be a substituent on the ring and P is as defined herein.

Scheme 1A

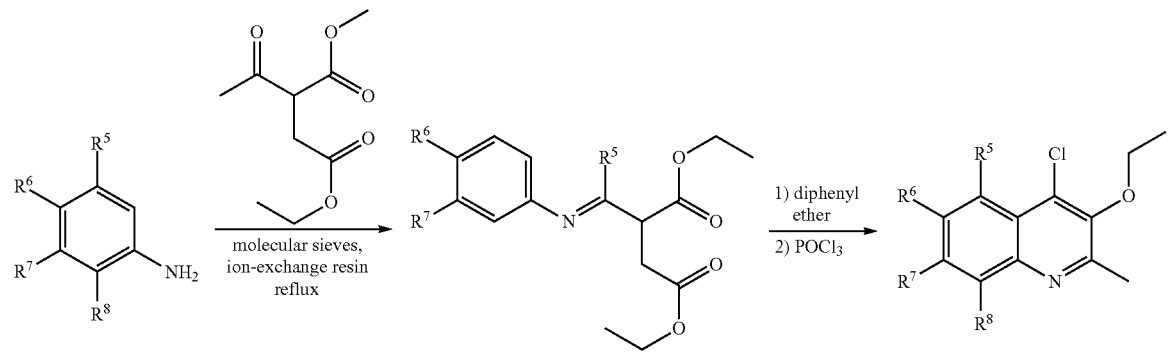

Ia           Ib           Ic

1) HCl 4M in Dioxane
2) NaI, MeCN, reflux• 15 h

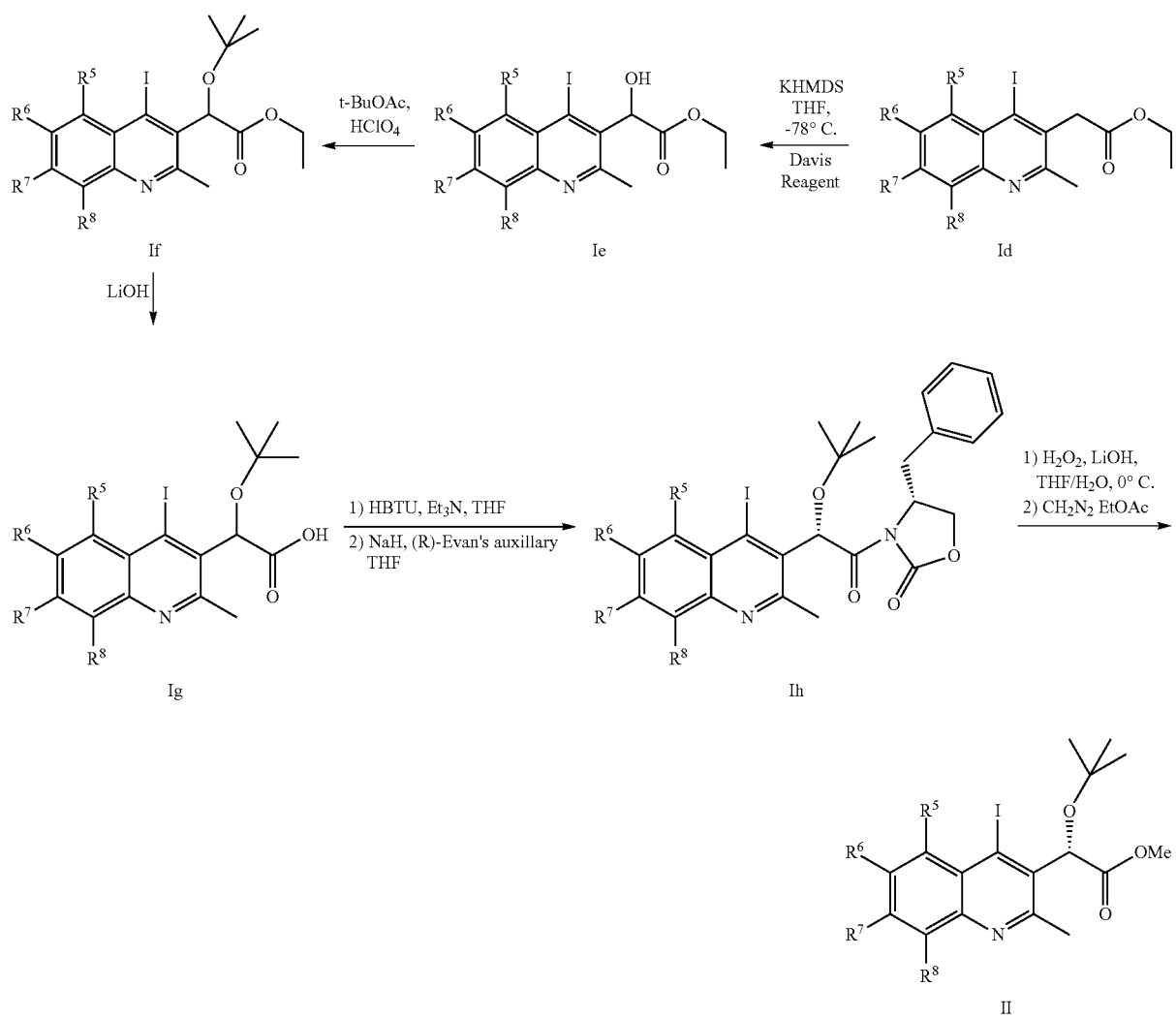

There are a number of transformations known to access quinoline scaffolds. As shown in Scheme 1A, a Friedlander approach can be followed in which appropriately substituted aniline is condensed with a functionalized ketone under dehydration conditions. This intermediate is then cyclized under thermal conditions followed by halogenation of the resulting alcohol. The acetic acid ester side chain can be oxidized and protected to furnish the alpha t-butoxy acetic acid ester moiety as shown. Separation of the enantiomers can be accomplished by formation of diastereomers by addition of a chiral auxiliary such as an oxazolidinone followed by conversion to the corresponding ester by known means.

Alternatively, a modification of this approach can also be used to prepare the quinoline scaffold as is shown in Scheme 2. In this method a properly substituted anthranilic acid derivative can be condensed under dehydration conditions with an appropriate ketone and subsequently cyclized under DMAP/POCl$_3$ conditions to the 4-chloroquinoline. Further elaboration can then be performed as outlined in Scheme 1A.

Scheme 2:

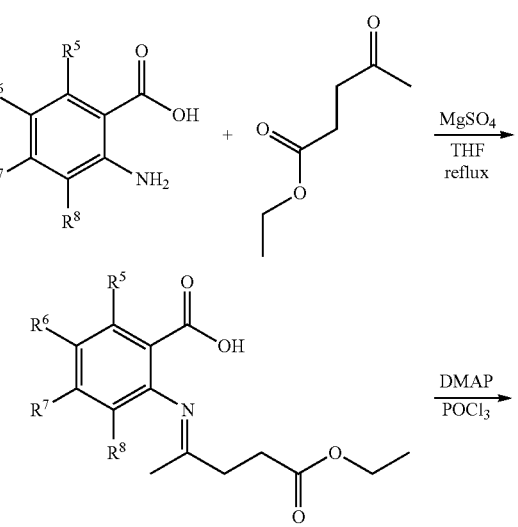

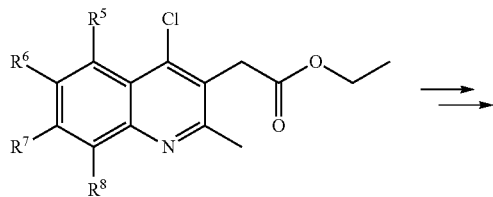

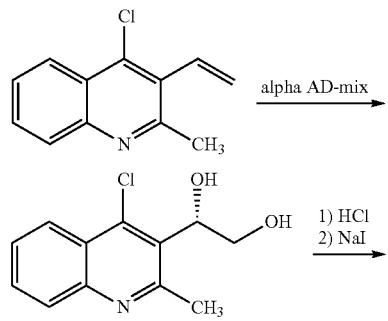

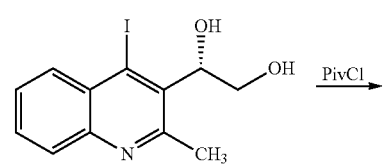

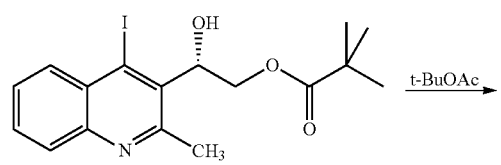

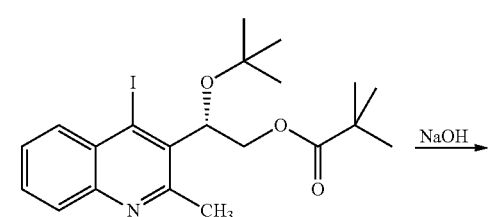

Furthermore, in an alternative route the quinoline scaffold can be accessed in an enantioselective manner as outlined in Scheme 3.

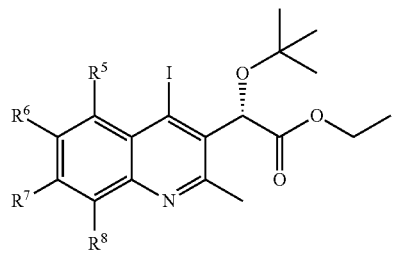

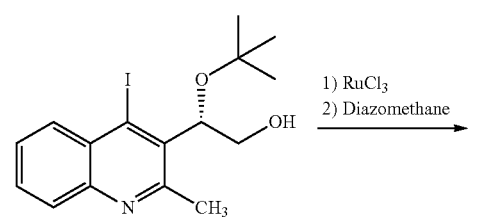

Scheme 3:

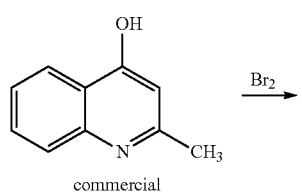

commercial

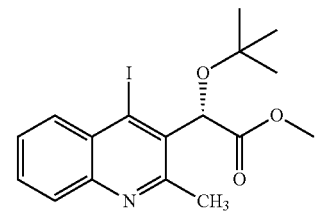

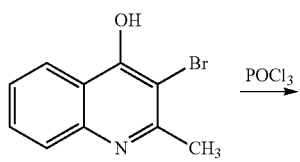

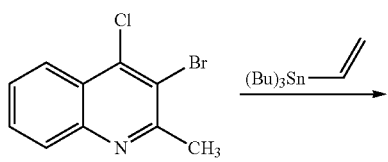

A quinoline precursor can be selectively brominated in the 3-position and subsequently elaborated into the chiral diol by standard methods known in the literature. The chiral diol can be differentially protected to the t-butyl ether followed by liberation of the primary alcohol. This alcohol can then be oxidized to the corresponding carboxylic acid and subsequently protected as the methyl ester to furnish the key chiral 4-iodoquinoline intermediate.

Scheme 4: Alternate synthesis of quinoline scaffold

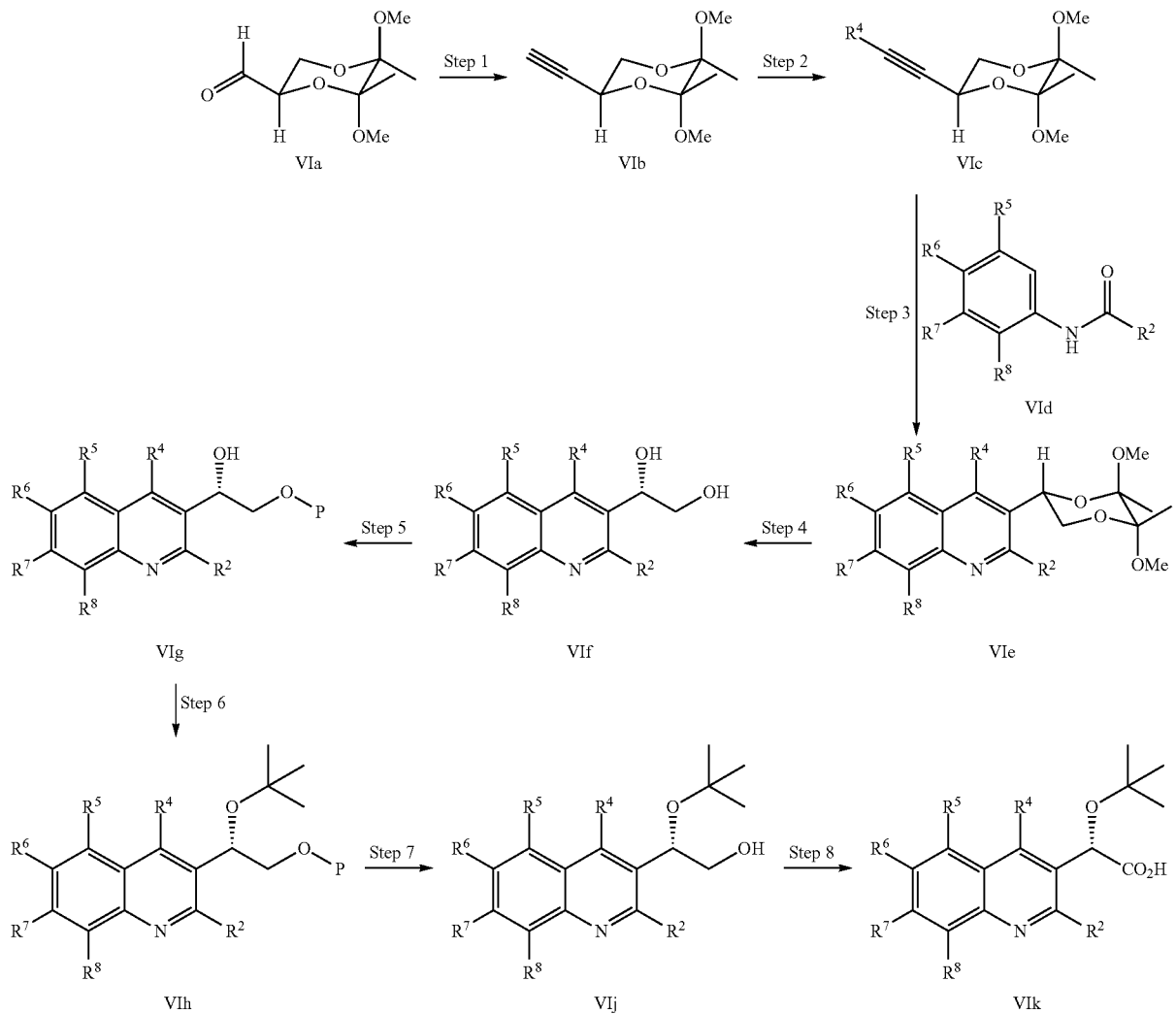

In an alternate route to compounds of general formula I wherein $R^2$ is $(C_{1-6})$alkyl or —O—$C_{1-6}$)alkyl, the known aldehyde VIa is transformed to terminal alkyne VIb. Those skilled in the art will recognize that there are a number of methods for accomplishing this transformation, such as, but not limited to the Bestmann-Ohira reaction or the Corey-Fuchs reaction. The $R^4$ group is then attached to the alkyne using conditions well-known to those skilled in the art, preferentially via a Sonogashira coupling between the alkyne and the aryl iodide derivative of the $R^4$ group, to give the internal alkyne VIc. Other methods may include the Castro-Stevens reaction, or the silver mediated, palladium catalyzed coupling of alkyne VIb and the boronic acid or ester derivative of the $R^4$ fragment as reported by Zou and coworkers (*Tetrahedron Lett.* 2003, 44, 8709-8711). The internal alkyne VIc then undergoes a cyclocondensation with amide VId to give quinoline VIe. Those skilled in the art will recognize this may involve activation of amide VId to facilitate the overall condensation. This is preferentially achieved by the action of triflic anhydride and in the presence of 2-chloropyridine as described by Movassaghi (*J. Am. Chem. Soc.,* 129 (33), 10096-10097, 2007), but may also be achieved in other ways. Amides VId are typically commercially available, although those skilled in the art will recognize that they are also easily obtained from commercially available aniline or nitro arene precursors.

The cyclic diketal is then hydrolyzed to give diol VIf under acidic conditions. The terminal alcohol is then protected to give VIg, where P can be a number of different protecting groups including, but not limited to, a trimethylacetyl group. The secondary alcohol is then derivatized with a tert-butyl group to give compound VIh. Those skilled in the art will recognize that this can be accomplished in more than one way, including an $SN_1$ reaction or acid catalyzed addition to isobutylene. The protecting group is then removed to give primary alcohol VIj, which in turn is oxidized to carboxylic acid VIk. It will be obvious that the oxidation of VIj to VIk can be accomplished in one or two synthetic steps. In the preferred method, Dess-Martin oxidation to an intermediate aldehyde followed by Lindgren oxidation is employed.

Scheme 5: Alternate synthesis of quinoline scaffold

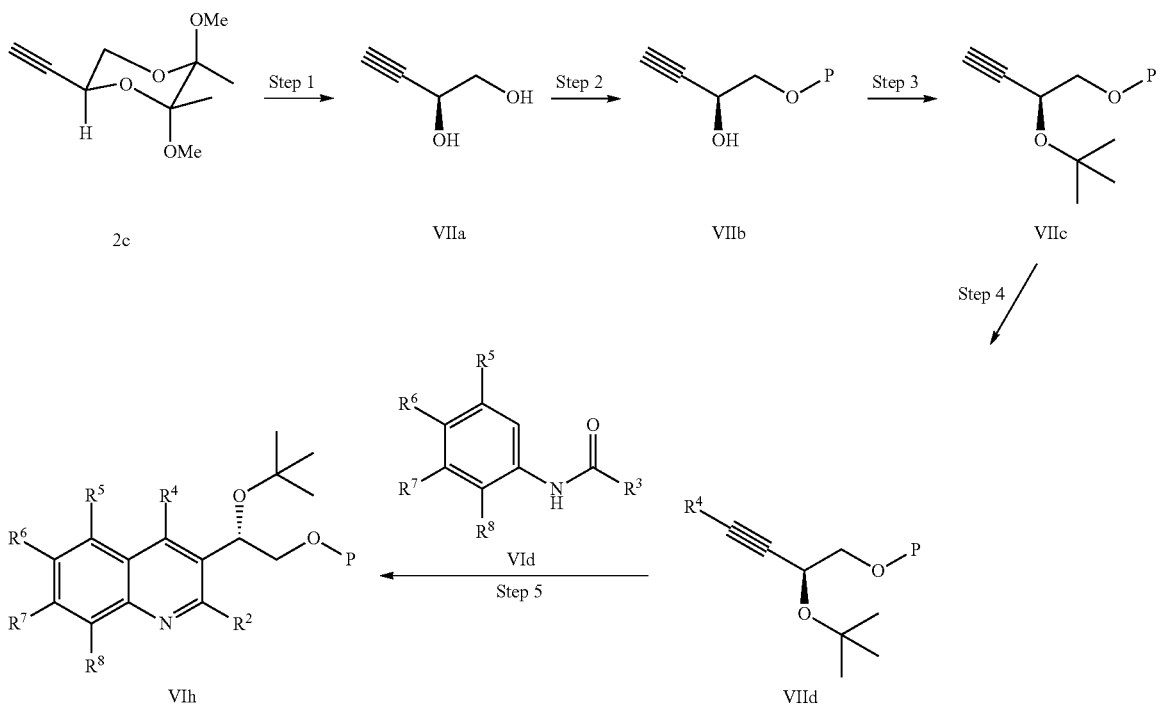

In yet another route to compounds of general formula I, wherein $R^2$ is $(C_{1-6})$alkyl or $-O-C_{1-6}$alkyl, synthesis of intermediate VIh may also be accomplished following a path that begins with acid catalyzed hydrolysis of the cyclic diketal of terminal alkyne VIb to give diol VIIa. The terminal alcohol is then protected to give VIIb, where P can be a number of different protecting groups including, but not limited to, a trimethylacetyl group. The secondary alcohol is then derivatized with the tert-butyl group to give compound VIIc. Those skilled in the art will recognize that this can be accomplished in more than one way, including an $SN_1$ reaction or acid catalyzed addition to isobutylene. The $R^4$ group is then attached to the alkyne using conditions well-known to those skilled in the art, preferentially via a Sonogashira coupling between the alkyne and the aryl iodide derivative of the $R^4$ group, to give the internal alkyne VIId. The internal alkyne VIId then undergoes a cyclocondensation with amide VId to give quinoline VIh, preferentially achieved by the action of triflic anhydride and in the presence of 2-chloropyridine as described for step 3 of Scheme 4. From intermediate VIh, the synthesis of compounds of general formula I is then accomplished following steps 7 and 8 of Scheme 4.

EXAMPLES

Other features of the present invention will become apparent from the following non-limiting examples which illustrate, by way of example, the principles of the invention. It will be apparent to a skilled person that the procedures exemplified below may be used, with appropriate modifications, to prepare other compounds of the invention as described herein.

As is well known to a person skilled in the art, reactions are performed in an inert atmosphere (including but not limited to nitrogen or argon) where necessary to protect reaction components from air or moisture. Temperatures are given in degrees Celsius (° C.). Solution percentages and ratios express a volume to volume relationship, unless stated otherwise. Flash chromatography is carried out on silica gel ($SiO_2$) according to the procedure of W. C. Still et al., J. Org. Chem., (1978), 43, 2923. Mass spectral analyses are recorded using electrospray mass spectrometry. A number of intermediate and final products were are purified using CombiFlash® Companion apparatus, purchased from Teledyne Isco Inc, employing pre-packed silica gel cartridges and EtOAc and hexane as solvents. These cartridges are available either from Silicycle Inc (SiliaFlash, 40-63 microns silica) or from Teledyne Isco (RediSep, 40-63 microns silica). Preparative HPLC is carried out under standard conditions using a SunFire™ Prep C18 OBD 5 µM reverse phase column, 19×50 mm and a linear gradient employing 0.1% TFA/acetonitrile and 0.1% TFA/water as solvents. Compounds are isolated as TFA salts when applicable. Analytical HPLC is carried out under standard conditions using a Combiscreen ODS-AQ C18 reverse phase column, YMC, 50×4.6 mm i.d., 5 µM, 120 Å at 220 nM, elution with a linear gradient as described in the following table (Solvent A is 0.06% TFA in $H_2O$; solvent B is 0.06% TFA in $CH_3CN$):

| Time (min) | Flow (mL/min) | Solvent A (%) | Solvent B (%) |
|---|---|---|---|
| 0 | 3.0 | 95 | 5 |
| 0.5 | 3.0 | 95 | 5 |
| 6.0 | 3.0 | 50 | 50 |
| 10.5 | 3.5 | 0 | 100 |

Abbreviations or symbols used herein include:

| | |
|---|---|
| Ac: | acetyl; |
| AcOH: | acetic acid; |
| Ac$_2$O: | acetic anhydride; |
| BOC or Boc: | tert-butyloxycarbonyl; |
| Bu: | butyl; |
| DABCO: | 1,4-diazabicyclo[2.2.2]octane |
| DBU: | 1,8-diazabicyclo[5.4.0]undec-7-ene; |
| DCE: | dichloroethane; |
| DEAD: | diethyl azodicarboxylate |
| DCM: | dichloromethane; |
| DIAD: | diisopropyl azodicarboxylate; |
| DIBAL: | diisobutyl aluminum hydride; |
| DIPEA: | diisopropylethylamine; |
| DMAP: | N,N-dimethyl-4-aminopyridine; |
| DME: | 1,2-dimethoxyethane; |
| DMF: | N,N-dimethylformamide; |
| DMSO: | dimethylsulfoxide; |
| Dppf: | 1,1'-Bis(diphenylphosphino)ferrocene; |
| EC$_{50}$: | 50% effective concentration; |
| Et: | ethyl; |
| Et$_3$N : | triethylamine; |
| Et$_2$O: | diethyl ether; |
| EtOAc: | ethyl acetate; |
| EtOH: | ethanol; |
| HATU: | O-(7-Azabenzotriazole-1-yl)-N,N,N'N'-tetra-methyluronium hexafluorophosphate; |
| HBTU: | O-Benzotriazole-N,N,N',N'-tetramethyluronium hexafluorophosphate; |
| HPLC: | high performance liquid chromatography; |
| IC$_{50}$: | 50% inhibitory concentration; |
| $^i$Pr or i-Pr: | 1-methylethyl (iso-propyl); |
| KHMDS: | potassium hexamethyl disilazane; |
| LiHMDS: | lithium hexamethyldisilazide; |
| Me: | methyl; |
| MeCN: | acetonitrile; |
| MeOH: | methanol; |
| MOI: | multiplicity of infection; |
| MS: | mass spectrometry (ES: electrospray); |
| n-BuONa: | sodium n-butoxide |
| n-BuOH: | n-butanol; |
| n-BuLI: | n-butyllithium; |
| NMO: | N-methylmorpholine-N-oxide; |
| NMR: | nuclear magnetic resonance spectroscopy; |
| Ph: | phenyl; |
| PhMe: | toluene; |
| PG: | protecting group; |
| PPh$_3$: | triphenylphosphine; |
| Pr: | propyl; |
| RPMI: | Roswell Park Memorial Institute (cell culture medium); |
| RT: | room temperature (approximately 18° C. to 25° C.); |
| SM: | starting material; |
| tert-butyl or t-butyl: | 1,1-dimethylethyl; |
| Tf: | trifluoromethanesulfonyl; |
| Tf$_2$O: | trifluoromethanesulfonic anhydride; |
| TFA: | trifluoroacetic acid; |
| THF: | tetrahydrofuran; and |
| TLC: | thin layer chromatography. |

Example 1

Synthesis of Quinoline Scaffold 1i

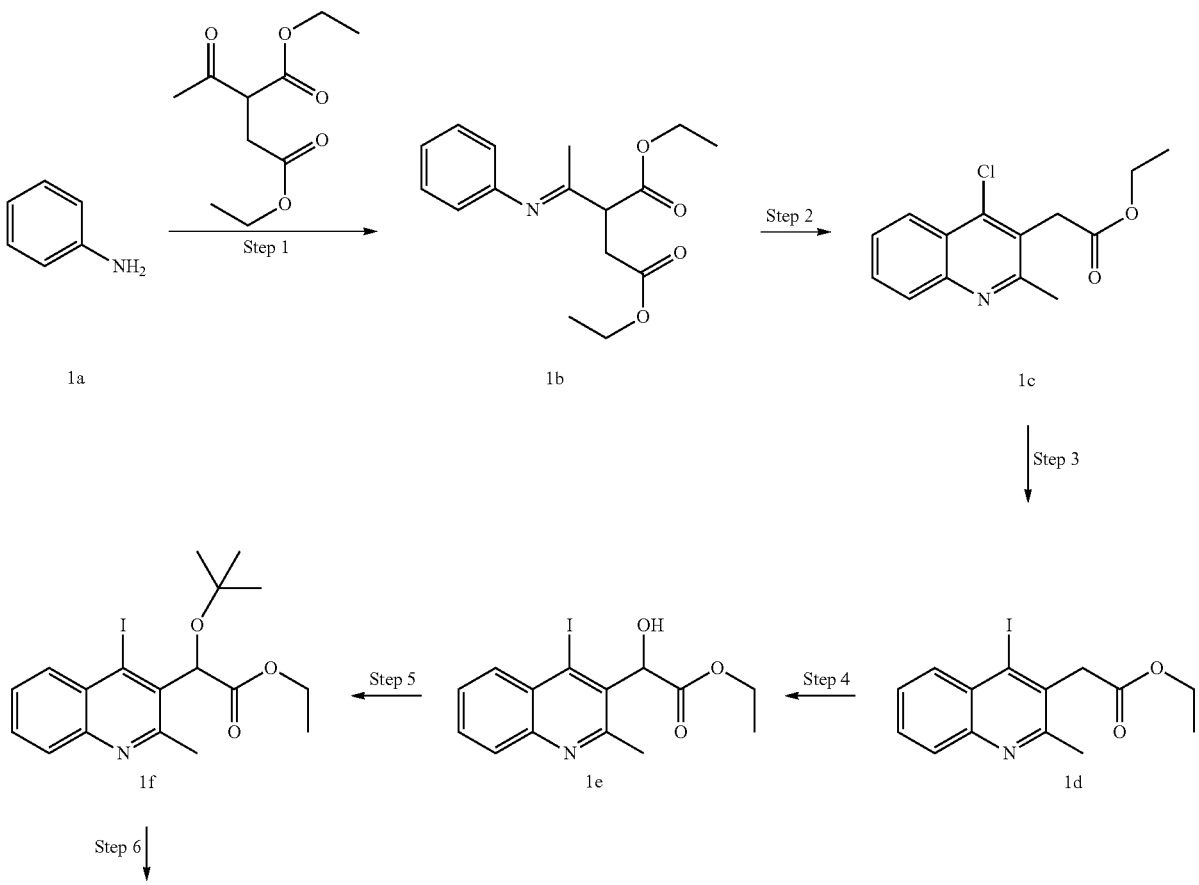

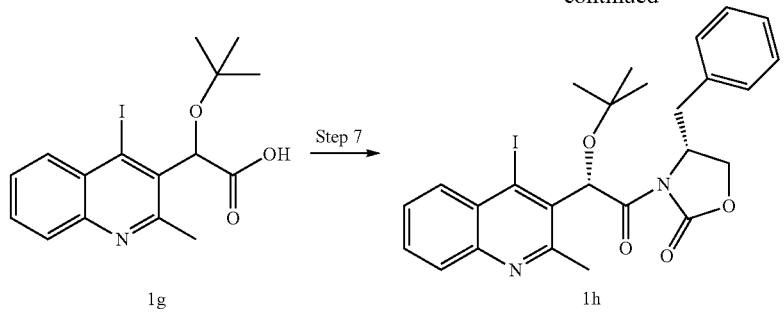

Step 1:

In a 4-neck 500 mL round bottom flask equipped with a magnetic stir bar, condenser and Dean-Stark trap, diethyl acetylsuccinate (6 g, 0.026 mol), aniline 1a (2.5 mL, 0.028 mol), Amberlyst® 15 (0.08 g) and toluene (30 mL) are added. The resulting mixture is heated at reflux temperature for approximately 3 days at which time TLC showed only traces of SM. The reaction mixture is cooled to RT and the Amberlyst® 15 is removed by filtration. The filtrate is concentrated in vacuo to give a suspension of a solid in brown liquid. The filtrate is diluted with diethyl ether and cooled. The solid is filtered and the filtrate is concentrated in vacuo leaving a brown oil (~7.8 g), which contains 1b and some cyclised intermediate. This crude intermediate is used in the next step without further purification.

Step 2:

In a 3-neck 100 mL round bottom flask a mixture of the crude intermediate 1b (7.8 g) and diphenyl ether (50 mL) are heated quickly in a pre-heated (250° C.) heating mantle for 6 min (internal temperature reached ~250° C.) at which time the flask is removed from the heating mantle and is stirred until the internal temperature reaches below 100° C. The reaction mixture is then mixed with hexane (15 mL), at which time a light brown solid is formed. The solid is filtered and washed with hexane (3×10 mL) to give approximately 2.4 g of the intermediate cyclised product. A portion of this sample (1.4 g, 5.87 mmol) is dissolved in phosphorus oxychloride (5 mL) and heated at reflux for 2.5 h. The reaction mixture is cooled to RT and is concentrated on vacuum. The residue is treated with sodium bicarbonate powder then partitioned between EtOAc and water. The combined organic layer is washed with brine, dried over anhydrous $Na_2SO_4$, filtered, passed through a silica gel pad and concentrated to give 1c as a crude light brown solid (2.35 g).

Step 3:

Crude chloro quinoline 1c (1.36 g, 5.17 mmol) is dissolved in THF (20 mL), and HCl in dioxane (4 M, 5.4 mL, 0.022 mol) is added to this solution slowly. The resulting reaction mixture is stirred at RT for 40 min. The solvent is then removed in vacuo and the residue is dried on vacuum. The resulting solid and NaI (3.87 g) are suspended in MeCN (20 mL), and the resulting reaction mixture is heated to reflux for 16 h. The reaction mixture is cooled to RT and treated with a saturated aqueous solution of $NaHCO_3$ (20 mL). The aqueous layer is extracted with DCM, and the combined organic layer is dried over anhydrous $MgSO_4$, filtered and concentrated to give a brown syrup. Purification by silica gel chromatography (30% EtOAc/hexanes) provides iodo quinoline 1d as an off-white solid (1.72 g, 94% yield).

Step 4:

To a solution of KHMDS (0.5 M in toluene, 3 mL, 1.5 mmol) in THF (8 mL) at −78° C. is added a solution of 1d (0.35 g, 0.99 mmol) in THF (8 mL). As the ester is added, the solution becomes a scarlet red. This is allowed to stir at −78° C. for 30 min before being treated with the Davis reagent (0.39 g, 1.5 mmol). After addition of the oxidizing agent, the solution becomes pale yellow and is stirred for an additional 30 min at −78° C. The reaction is quenched with saturated $NH_4Cl$ aqueous solution (8 mL), is warmed to RT and is diluted with EtOAc. The mixture is washed with brine and the organic phase dried ($Na_2SO_4$), filtered and concentrated to afford a solid. Purification by silica gel chromatography (hexanes/EtOAc:6/4) provides 1e as a beige solid (0.50 g, >98% yield).

Step 5:

To a suspension of iodoalcohol 1e (0.53 g, 1.4 mmol) in tert-butyl acetate (12 mL) at RT is added perchloric acid (0.66 mL, 4.6 mmol). The reaction is left to stir for 2 h at RT (suspension turns into a clear solution). The reaction is quenched with water (12 mL) and basified with solid $NaHCO_3$ until pH ~6. The crude product is extracted with EtOAc (3×10 mL), washed with brine (1×10 mL), dried over $MgSO_4$, filtered and concentrated to afford the crude product. Purification by silica gel chromatography (hexanes/EtOAc: 85/15) affords 1f as a pale yellow oil (0.56 g, 91% yield).

Step 6:

Intermediate 1f (0.59 g, 1.4 mmol) is dissolved in a 2 M NaOH aqueous solution (7 mL, 0.014 mol) with ethanol (10 mL) and is stirred for 4 h at RT. The ethanol is then removed in vacuo. The resulting residue is diluted with water (3 mL) and acidified with 2 M HCl solution until pH ~3-4. The residue is then extracted with $CH_2Cl_2$ (3×10 mL), dried over $Na_2SO_4$, filtered, concentrated and dried under high vacuum to afford 1g as a foamy solid (0.56 g, >98% yield).

Step 7:

To a solution of acid 1g (0.39 g, 0.97 mmol) and HBTU (0.48 g, ~1.3 mmol) in anhydrous THF (5 mL) is added diisopropylethylamine (0.5 mL, 2.9 mmol). The mixture is stirred for 5.5 h at 30-35° C. (internal temperature) at which time the sodium salt of R-(+)-benzyloxazolidinone (which is prepared by adding sodium hydride (60% dispersion in mineral oil, 78 mg, 1.95 mmol) to a solution of R-(+)-benzyloxazolidinone (0.35 g, 1.9 mmol) in anhydrous THF (5 mL) is added. The resulting solution is then stirred at RT for 16 h. The solvent is removed in vacuo and partitioned between water and EtOAc. The aqueous phase is then extracted with EtOAc, and the combined organic extracts are dried over anhydrous $Na_2SO_4$, filtered, and concentrated in vacuo to afford a pale yellow solid. The crude product is purified by silica gel chromatography (10->30% EtOAc:hexanes), yielding the desired diastereomer 1h (190 mg, 35% yield, more polar product, >99% ee by chiral column).

Step 8:

To a solution of oxazolidinone 1h (190 mg, 0.34 mmol) in THF/H$_2$O (2 mL/1 mL) at 0° C. is added H$_2$O$_2$ (30%, 0.36 mL, 10.5 eq) followed by LiOH monohydrate (17 mg, 0.41 mmol, 1.2 eq) dissolved in water (1 mL). The reaction mixture is stirred at 0° C. for 30 min at which time 10% Na$_2$SO$_3$ (0.26 mL) is added. The resulting mixture is stirred for ~10 min and then acidified with 2 N HCl to pH ~4-5. The product is then extracted with DCM (3×10 mL). The combined organic extracts are dried over sodium sulfate and concentrated in vacuo to yield the crude acid intermediate as a white foam (0.13 g, 96% yield), which is used in the next step without further purification. The acid (130 mg) is suspended in diethyl ether (3 mL) and treated with diazomethane in diethyl ether until all of the acid SM is consumed (as indicated by TLC). The reaction is quenched with a very small amount of glacial AcOH and then concentrated in vacuo to give an off-white solid. The crude ester product is purified by silica gel chromatography (10-15% EtOAc/hexanes) yielding the quinoline fragment 1i (120 mg, 89% yield) in high enantiomeric purity (>99% ee by chiral HPLC).

Example 2

Synthesis of Fragment 2f

Step 3:

A solution of diol 2d (1.2 g, 14 mmol) and triethylamine (1.7 mL, 12 mmol) in DCM (80 mL) is cooled to 0° C. under N$_2$. Trimethylacetylchloride is added dropwise and the resulting mixture is allowed to come to RT and stir overnight. The reaction is then quenched with MeOH (100 mL) and stirring is continued for 20 min. The mixture is then concentrated under reduced under pressure and the residue is purified by CombiFlash® Companion to give the desired mono ester 2e (550 mg, 40% yield) along with the undesired regioisomeric mono ester (378 mg, 27% yield).

Step 4:

In a sealable reaction flask, a solution of the propargylic alcohol 2e (375 mg, 2.20 mmol) and Amberlyst® H-15 resin (150 mg) in hexane (3 mL) is cooled to −78° C. Isobutene is then bubbled through the solution until the volume approximately doubles. The tube is then sealed, brought to RT and is stirred overnight. The tube is then cooled to −78° C., is opened and brought back to RT. The mixture is then filtered through a plug of SiO$_2$ (EtOAc wash) and concentrated under reduced pressure to provide pure tent-butyl ether 2f (390 mg, 78% yield).

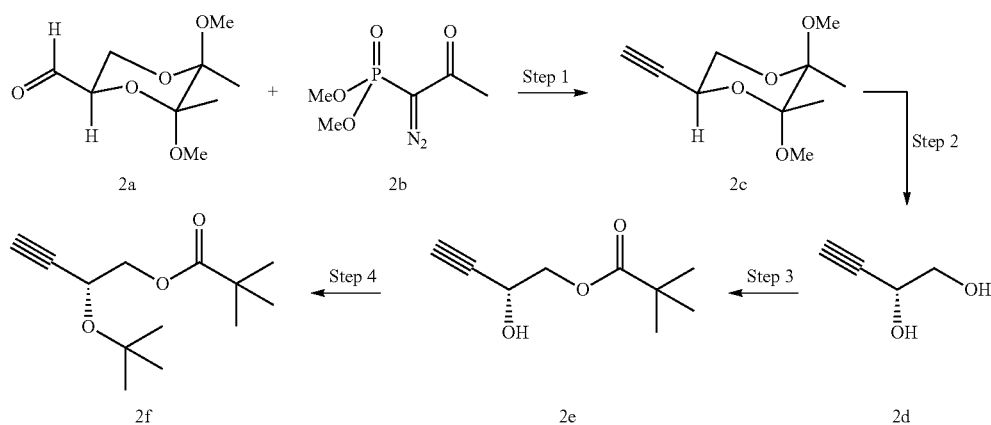

Step 1:

Aldehyde 2a (5.85 g, 28.6 mmol, for preparation see: Michel, P. and Ley, S. V. *Synthesis* 2003, 10, 1598-1602), phoshonate 2b (6.6 g, 34 mmol) and K$_2$CO$_3$ (8.8 g, 64 mmol) are combined in MeOH (125 mL) and the reaction is stirred overnight at RT. The reaction is evaporated nearly to dryness and the residue is partitioned between H$_2$O (250 mL) and EtOAc (500 mL). The water layer is washed with EtOAc (2×250 mL) and the combined organic layers dried over anhydrous Na$_2$SO$_4$ and concentrated to give alkyne 2c (5.55 g, 97% yield).

Step 2:

Alkyne 2c (5.0 g, 25 mmol) is dissolved in TFA (35 mL) and water (3.6 mL) and the solution is stirred at RT. After 30 min, the reaction is concentrated under reduced pressure and the residue is purified by CombiFlash® Companion to give diol 2d (1.8 g, 84% yield).

Example 3

Synthesis of Alkyne 3a

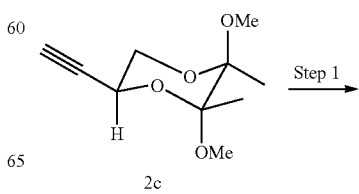

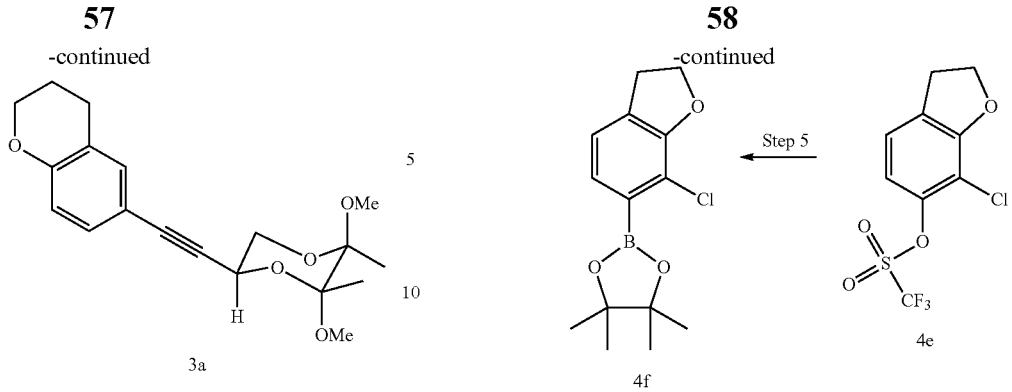

Step 1:

Solid Pd(PPh₃)₄ (444 mg, 0.385 mmol) and CuI (146 mg, 0.769 mmol) are successively added to a solution of 11c (10 g, 34 mmol) and alkyne 2c (11 g, 55 mmol) dissolved in DMF (23 mL) and diethylamine (115 mL). The reaction mixture is stirred overnight at RT and then concentrated, diluted with EtOAc (300 mL) and successively washed with brine, 1 N aqueous HCl and water (300 mL each). The organic layer is dried over Na₂SO₄ and the residue purified by CombiFlash® Companion to give alkyne 3a (10.8 g, 84% yield).

Example 4

Synthesis of Boronate Fragment 4f

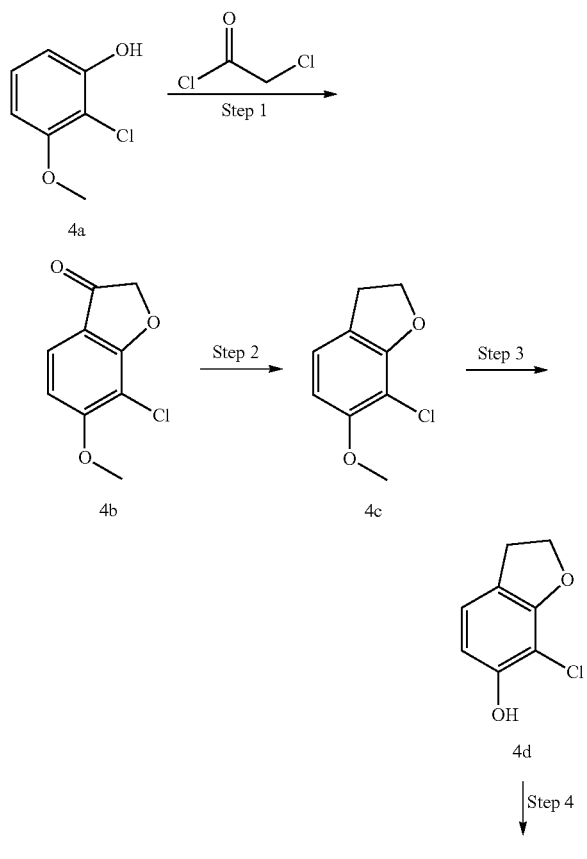

Step 1:

To a solution of 4a (6 g, 37 mmol) in nitrobenzene (12 mL), chloroacetyl chloride (4.6 mL, 57.5 mmol) is added, followed by the addition of AlCl₃ (20.4 g, 152 mmol). As the AlCl₃ is added, the mixture becomes viscous and gas evolution is observed. The resulting brown syrupy mixture is left to stir overnight at RT. (Reference: Y. Takeuchi et. al., *Chem. Pharm. Bull.* 1997, 45(12), 2011-2015.) The thick reaction mixture is cooled and ice water is added very carefully (Very exothermic) a few drops at a time. Once gas evolution and bubbling is subsided, cold water is further added followed by EtOAc. The mixture is stirred for 5 min and the product extracted with EtOAc (3×). The combined organic layers are washed with brine (1×), dried over Na₂SO₄, filtered and concentrated to afford the uncyclized chloroketone (24 g of crude; contaminated with some nitrobenzene) as a pale yellow solid. This intermediate is then taken up in EtOH (100 mL), NaOAc is added (20.4 g, 248 mmol) and the reaction is brought to reflux for 40 min. The EtOH is evaporated, the residue is taken up in EtOAc (300 mL) and washed with 5% K₂CO₃ (2×200 mL) and the aqueous layer then acidified with aqueous HCl (1 N; pH=~5). This acidic layer is extracted with EtOAc (2×250 mL), washed with brine (1×), dried over Na₂SO₄, filtered and concentrated to afford the crude product. This material is purified by CombiFlash® Companion (120 g) to afford intermediate 4b as a yellow solid (4.7 g).

Step 2:

The ketone 4b (127 mg, 0.64 mmol) is dissolved in EtOH (2 mL) and treated with hydrazine hydrate (500 μL, 16 mmol). The mixture is heated to reflux for 45 min before allowing it to cool to RT. The solvent is removed by evaporation and the residue is dissolved in diethylene glycol (1 mL) before being treated with KOH (108 mg, 1.92 mmol) and then heated to 110-120° C. for 2.5 h. The reaction mixture is diluted with EtOAc and the pH is adjusted with 1 N HCl to pH<4. The organic phase is separated, washed with saturated brine, dried over anhydrous MgSO₄, filtered and concentrated. The crude material is purified by CombiFlash® Companion (eluent: 0-50% EtOAc/hexanes) to give intermediate 4c as a yellow oil (62 mg).

Step 3:

A solution of 4c (61 mg, 0.33 mmol) is cooled to −78° C. in DCM (2 mL) and then treated with BBr₃ (1 M in DCM, 825 μL, 0.82 mmol). After ~15 min, the bath is removed and the reaction is allowed to reach RT. The reaction is then stirred for 1.5 h. The reaction is cooled to 0° C. before quenching by the careful dropwise addition of water. The mixture is treated with saturated NaHCO₃ (to about pH=8) and the phases separated. The organic phase is washed with saturated brine, dried over MgSO₄, filtered and concentrated to dryness. The product is purified by CombiFlash® Companion (0-50% EtOAc/ hexanes) to give intermediate 4d as colorless oil, which solidifies upon standing (40 mg, 71% yield).

Step 4:

The phenol 4d (40 mg, 0.23 mmol) is dissolved in DCM (2 mL), cooled to 0° C. and treated with pyridine (95 μL, 1.17 mmol), followed by Tf$_2$O (44 μL, 0.26 mmol). The reaction is allowed to stir at this temperature for 10 min before warming to RT over a period of 1 h. The reaction mixture is diluted with DCM and the organic phase washed with 10% citric acid and then brine. The organic phase is dried over anhydrous MgSO$_4$, filtered, concentrated and purified by CombiFlash® Companion (0-50% EtOAc/hexanes) to give 4e as a yellow oil (67 mg, 94% yield).

Step 5:

To a solution of the triflate 4e (66 mg, 0.22 mmol) in DMF (2 mL), bis-(pinacolato)diborane (72 mg, 0.28 mmol) and potassium acetate (64 mg, 0.65 mmol) are added. This solution is de-gassed (with bubbling Ar) for 10 min before adding PdCl$_2$(dppf)-CH$_2$Cl$_2$, (27 mg, 0.03 mmol, 0.15 eq). The mixture is de-gassed a further 5 min before being heated to 90° C. for 16 h. The mixture is cooled to RT and diluted with EtOAc/water. The organic phase is washed with saturated brine (3×), dried over anhydrous MgSO$_4$, filtered and concentrated. The crude material is purified by CombiFlash® Companion (0-70% EtOAc in hexanes) to afford the boronate 4f as a white solid (41 mg, 67% yield).

Example 5

Synthesis of Boronate Fragment 5f

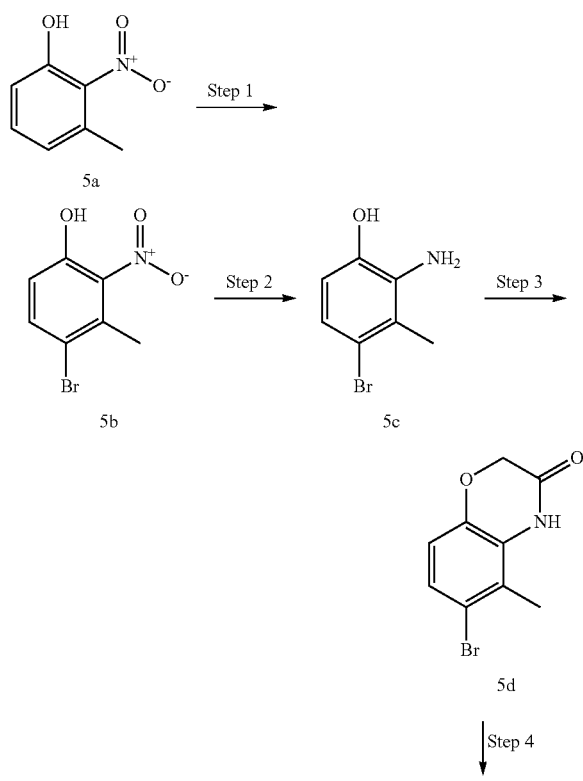

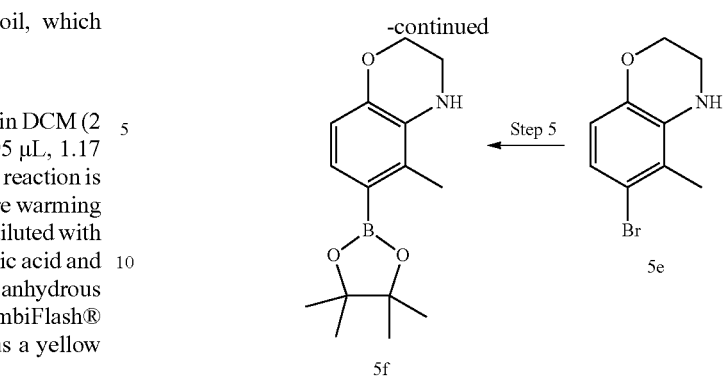

Step 1:

The nitrophenol 5a (5.23 g, 34.1 mmol) is dissolved in acetic acid (20 mL) and the solution is cooled in an ice bath. Bromine (1.75 mL, 34.15 mmol) dissolved in 5 mL acetic acid) is added dropwise with stirring. The mixture is stirred for 1 h at 0° C. before being poured into ice water (250 mL). The mixture is extracted with EtOAc (2×100 mL) and then washed with 5% NaHCO$_3$ (2×50 mL) before being dried over anhydrous MgSO$_4$, filtered and concentrated to give the desired crude product 5b as an orange solid (8.2 g, quantitative yield). This material is used in the next step without further purification.

Step 2:

To a well stirred ethanol solution (75 mL) of 5b (8.1 g, 34.9 mmol), SnCl$_2$ (20 g, 105 mmol) is added. The reaction mixture is stirred at reflux for 2.5 h. After that period, the transformation is incomplete, therefore, more SnCl$_2$ (2 g, 10 mmol) is added and the reaction mixture is heated at reflux for 1 h before being cooled to RT. The mixture is poured onto 250 g of ice and the pH adjusted to approximately 7.5 with aqueous 5% NaHCO$_3$. The product is extracted with EtOAc (3×100 mL) before being washed with saturated brine (2×100 mL). The organic phase is dried over anhydrous MgSO$_4$, filtered and concentrated to dryness to give the aniline intermediate 5c as a gray solid (8.25 g, ~100% yield; this material contained some tin residues, nonetheless, it is used as such for the following step).

Step 3:

To a stirring, ice cold, DMF (5 mL) suspension of potassium carbonate (2.05 g, 14.8 mmol) and aniline 5c (750 mg, 3.71 mmol) under nitrogen, chloroacetyl chloride (355 μL, 4.45 mmol) is added dropwise. The mixture is allowed to warm to RT over a period of 15 min and then heated to 60° C. for 1 h. The mixture is allowed to cool to RT, is poured into a mixture of ice/water (250 mL) and is stirred for approximately 15 min. The suspension is centrifuged, and the supernatant is discarded. The solid material is left drying under suction overnight to give intermediate 5d (280 mg, 31% yield).

Step 4:

To an ice cold THF (6 mL) solution of the cyclic amide 5d (280 mg, 1.16 mmol) under nitrogen, a borane-THF solution (1 M in THF, 1.74 mL, 1.74 mmol) is added slowly. The reaction mixture is slowly allowed to warm to RT, then is stirred at RT for 1.5 h and then gently heated to reflux for 1 h to complete the conversion. The mixture is cooled in an ice bath and is carefully quenched with aqueous 1 M NaOH (4 mL) over 10 min. The reaction mixture is partitioned between EtOAc (150 mL) and water (25 mL). The organic layer is washed with aqueous 1 N NaOH (20 mL), saturated aqueous NaCl, and finally dried over anhydrous MgSO$_4$, filtered and concentrated to give the crude 5e as an amber oil (212 mg, 81% yield). This product is used as such for next transformation.

Step 5:
A well stirred DMF (15 mL) solution of the arylbromide 5e (0.50 g, 2.19 mmol), potassium acetate (0.728 g, 7.67 mmol) and bis(pinacolato)diborane (0.83 g, 3.3 mmol) is degassed by bubbling Ar through the solution for 20 min. PdCl$_2$(dppf)-DCM (320 mg, 0.44 mmol) is added and degassing is continued for 15 min. The system is sealed (teflon screw cap vessel) under Ar and heated to 90° C. for 5 h. The reaction mixture is allowed to cool to RT, dilute with EtOAc (150 mL), washed with brine (3×100 mL) and water (2×100 mL), dried over anhydrous MgSO$_4$, filtered and concentrated to dryness. The residue is purified by CombiFlash® Companion (EtOAc/hexanes) to give the desired boronate 5f (389 mg, 65% yield) as a yellowish waxy solid.

Example 6

Synthesis of Boronate Fragment 6i

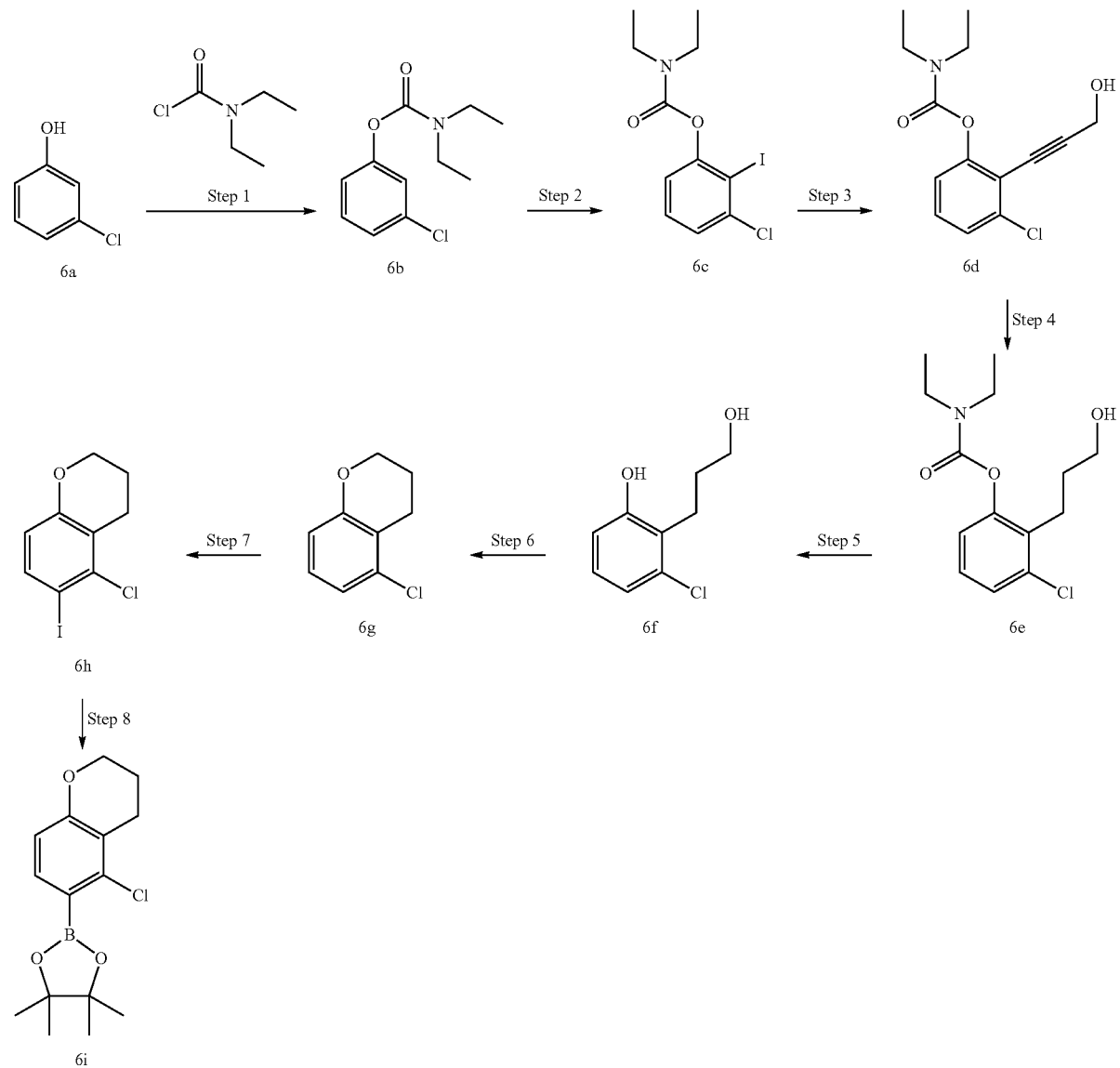

Step 1:
Sodium hydride (60%, 7.78 g, 194 mmol) is added to a well stirred suspension of 6a (12.5 g, 97.2 mmol) in THF (100 mL). After stirring the reaction mixture for 1 h, N,N-diethylcarbamoyl chloride (24.64 mL, 194 mmol) is added at RT. After stirring the reaction overnight, the reaction mixture is quenched with water (100 mL), extracted with EtOAc (3×50 mL), dried over anhydrous MgSO$_4$, filtered and evaporated under reduced pressure to obtain 6b (33 g, 75% yield) in high purity.

Step 2:

Diisopropylamine (21.0 mL, 121 mmol) in THF (330 mL) is treated with a solution of n-BuLi (2.5 M in hexanes, 48.2 mL, 121 mmol) at 0° C. After 30 min at this temperature, the solution is cooled to −78° C. and carbamate 6b (33.29 g, 109.7 mmol, 75% pure) is added. The reaction is stirred at this temperature for 30 min and then iodine (33.4 g, 132 mmol) is added. The solution is stirred for 30 min at 0° C. and is then warmed to RT. After 2 h, the reaction mixture is quenched with water (250 mL) and the volatile organic solvents are removed under reduced pressure. The aqueous phase is then extracted with EtOAc (3×100 mL), washed with 1 N HCl (1×200 mL), dry MgSO$_4$, filtered and evaporated under reduced pressure to obtain 6c (18.6 g, 39% yield).

Step 3:

The iodo 6c (10 g, 28 mmol), propargyl alcohol (3.3 mL, 56 mmol), Pd(PPh$_3$)$_4$ (3.27 g, 2.83 mmol) and copper iodide (1.08 g, 5.66 mmol) are combined in diisopropylamine (39 mL, 39 mmol) in a sealable tube under Ar and heated at 100° C. After 1 h, the reaction mixture is cooled to RT and poured into EtOAc (100 mL) and this mixture is extracted with 10% HCl (2×100 mL). The organic layer is dried over MgSO$_4$ and concentrated to dryness. The crude product is purified by CombiFlash® Companion to obtain 6d (3.65 g, 46% yield).

Step 4:

6d (3.63 g, 12.9 mmol) is dissolved in EtOAc (81 mL) and treated with Rh—Al$_2$O$_3$ (5% w/w, 3.45 g, 1.68 mmol). The flask is evacuated and charged with 1 atmosphere of H$_2$ (balloon) and the reaction is stirred overnight at RT. The reaction mixture is filtered through Celite® (EtOAc wash) and the filtrate is concentrated under reduced pressure. The residue is then purified by CombiFlash® Companion to obtain 6e (3.7 g, 71% yield).

Step 5:

Solid NaOH (920 mg, 23 mmol) is added to a solution of 6e (2.63 g, 9.20 mmoL) in EtOH (93 mL) and the mixture is heated to reflux and is stirred overnight. The mixture is then cooled to RT and the organic solvent removed under reduced pressure. Water is added (100 mL) and the mixture extracted with Et$_2$O (3×100 mL), dried over MgSO$_4$, filtered and evaporated under reduced pressure to obtain phenol 6f (869 mg, 51% yield).

Step 6:

Diethyl azodicarboxylate (953 μL, 6.05 mmol) is added dropwise to a solution of phenol 6f (869 mg, 4.66 mmol) and PPh$_3$ (1.59 g, 6.05 mmol) in THF (65 mL) and the reaction is stirred at RT. After 4 h, the reaction mixture is evaporated under reduced pressure. The residue is then purified by CombiFlash® Companion to obtain the chroman intermediate 6g (387 mg, 49% yield).

Step 7:

Iodine (583 mg, 2.29 mmol) is added to a solution of chroman 6g (387 mg, 2.29 mmol) and AgNO$_3$ (429 mg, 2.52 mmol) in MeOH (23 mL). After 20 min, a 0.5 M solution of sodium thiosulfate (10 mL) is added and the aqueous phase extracted with EtOAc (3×25 mL). The combined organic phases are washed with brine, then dried (MgSO$_4$), filtered and evaporated to obtain aryl iodide 6h (647 mg, 96% yield).

Step 8:

A solution of iodo intermediate 6h (647 mg, 2.20 mmol), bis(pinocolato)diborane (0.725 g, 2.86 mmol) and potassium acetate (0.626 g, 6.59 mmol) in DMF (17 mL) is degassed with Ar for 10 min. PdCl$_2$(dppf)-DCM complex (179 mg, 0.22 mmol) is then added and the mixture is degassed with Ar for approximately another 5 min. The reaction is then heated to 95° C. in a sealable tube and is stirred overnight. The reaction is cooled to RT and EtOAc (100 mL) is added. The solution is washed with brine (3×150 mL), water (1×150 mL), dried over MgSO$_4$, filtered and solvent removed under reduced pressure. The residue is purified by CombiFlash® Companion to afford boronate ester 6i (260 mg, 40% yield).

Example 7

Synthesis of Boronate Fragment 7d

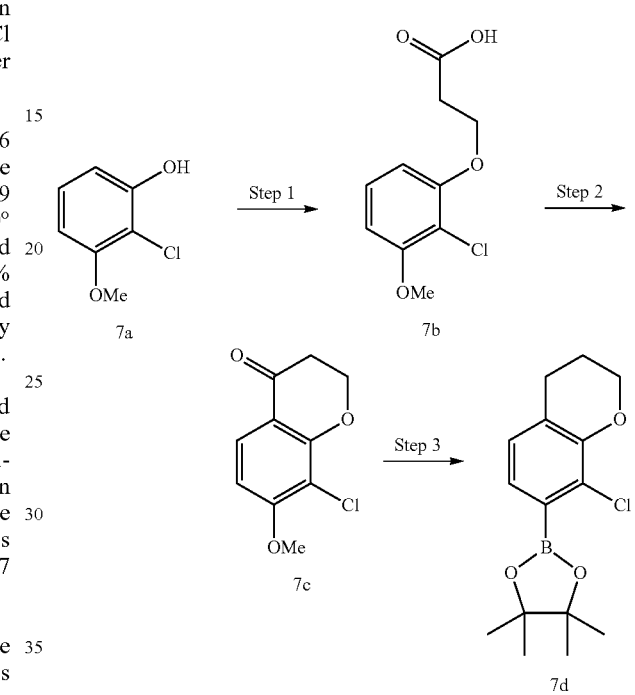

Step 1:

A solution of phenol 7a (0.91 g, 5.74 mmol) in dry DMF (1 mL) is added dropwise to a slurry of NaH (60% in oil, 0.60 g, 15 mmol) in dry DMF (1 mL) cooled to 10-15° C. (cold water bath) and the mixture is stirred for 20 min. This results in a thick, frothy white mixture. A solution of 3-bromopropionic acid (1.1 g, 6.9 mmol) in dry DMF (0.5 mL) is then added dropwise and the reaction stirred at RT overnight. After 16 h, methanol (1.2 mL) is added to help break up the thick, pasty reaction mixture which is then added to diluted HCl (12 mL, 1 N HCl in 100 mL water) and extracted with EtOAc (80 mL; the pH of the aqueous phase is adjusted to pH<3). The organic layer is dried over anhydrous Na$_2$SO$_4$ and evaporated to give 7b as a white solid material, contaminated with some unreacted SM (1.29 g of crude material). This material is used in the next step without purification.

Step 2:

The crude compound 7b (1.53 g, 6.63 mmol) is combined with polyphosphoric acid (approximately 7 g) and heated to 75° C. to give a cherry red colored solution. During the reaction time, the reaction mixture becomes viscous and stirring becomes difficult. After 4 h, the reaction is cooled; ice and water are slowly added with rapid stirring to give a thick suspension. This mixture is transferred to a separatory funnel where the product is extracted with EtOAc (100 mL) and washed with water (100 mL), saturated NaHCO$_3$ (2×100 mL) and brine (75 mL). The organic phase is dried over anhydrous MgSO$_4$ and evaporated to give a sticky violet solid 7c which is used as such (1.29 g crude).

Step 3:

Intermediate 7c is analogous to intermediate 4b in Example 4; those skilled in the art would recognize that the same synthetic methodologies used to convert 4b to the boronate 4f can be applied for the conversion of 7c to the corresponding boronate 7d.

Example 8

Synthesis of Boronate Fragment 8h

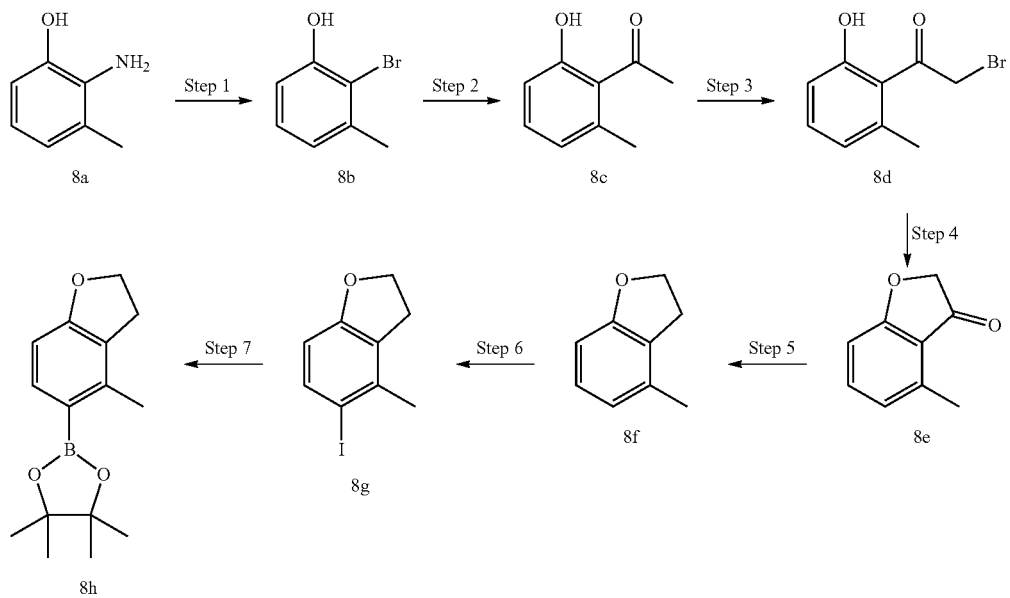

Step 1

2-Amino-m-cresol 8a (5.7 g, 46.3 mmol) is dissolved in H$_2$O (30 mL) and 1,4-dioxan (15 mL). The mixture is heated to reflux and then HBr (48%, 17 mL, 0.31 mol) is added dropwise over a period of 20 min. The reflux is maintained for an additional 15 min after the addition is complete. The reaction is cooled to 0° C., and NaNO$_2$ in H$_2$O (20 mL) is added over a period of 30 min. The stirring is continued for 15 min at 0° C., the mixture is then transferred in one shot to a stirring mixture of Cu(I)Br (7.64 g, 53.2 mmol) in H$_2$O (20 mL) and HBr (48%, 17 mL, 0.31 mol) at 0° C. (protected from light). The reaction is stirred for 15 min at 0° C., warmed to 60° C., stirred for an additional 15 min, cooled to RT and then stirred overnight. The reaction mixture is then transferred to a separatory funnel and extracted with EtOAc (3×). The organic layers are combined, washed with brine, dried over anhydrous MgSO$_4$, filtered and concentrated over silica to afford a mixture that is purified using the CombiFlash® Companion (20% EtOAc/hexanes) to afford the desired bromide 8b (1.46 g, 17% yield) as a red-brown oil.

Step 2:

To a solution of the bromide 8b (1.36 g, 7.27 mmol) and (PPh$_3$)$_2$PdCl$_2$ (766 mg, 1.09 mmol) in DMF (12 mL), 1-ethoxyvinyl-tri-n-butyltin (2.7 mL, 8.0 mmol) is added. The mixture is capped and heated in a microwave at 160° C. for 15 min. HPLC and LC-MS analysis indicate approximately 70% conversion. More 1-ethoxyvinyl-tri-n-butyltin (2.7 mL; 8.0 mmol) and catalyst (PPh$_3$)$_2$PdCl$_2$ (380 mg) are added and the solution is again subjected to the same microwave conditions. The reaction is quenched with 6N HCl (1.5 mL) and stirred at RT for 1 h to effect hydrolysis of the intermediate. The mixture is poured into EtOAc (150 mL), washed with brine (3×), dried over MgSO$_4$, filtered and concentrated over silica to afford the mixture that is purified using the CombiFlash® Companion (20% EtOAc/hexanes) to afford the desired ketone 8c (947 mg, 87% yield) as an orange oil.

Step 3:

The methyl ketone 8c (1.02 g, 6.8 mmol) is dissolved in EtOAc (15 mL) and CHCl$_3$ (15 mL) before being treated with Cu(II)Br$_2$ (3.03 g, 13.6 mmol). The mixture is heated to reflux for 16 h. The mixture is cooled to RT, the product filtered and washed with EtOAc (1×). The solution is concentrated over silica to afford the mixture that is purified using the CombiFlash® Companion (10% EtOAc/hexanes) to afford the α-bromoketone 8d (710 mg, 46% yield) as an orange oil. This material is used as is in the next step without purification.

Step 4:

To a solution of the bromoketone 8d (710 mg, 3.1 mmol) in anhydrous DMF (12 mL), KF (400 mg, 6.95 mmol) is added. The reaction is stirred at RT for 16 h. The mixture is taken up in EtOAc (150 mL), washed with brine (3×), dried over anhydrous MgSO$_4$, filtered and concentrated over silica to afford the mixture that is purified using the CombiFlash® Companion (20% EtOAc/hexanes) to afford the cyclic ketone 8e (280 mg, 61% yield) as a pale orange solid.

Step 5:

Zn dust pre-activation procedure: Zinc dust (20 g, 350 mesh) is placed in a round bottom flask and 1 N HCl (50 mL) is added. This suspension is sonicated for 1 min before decanting off the liquid. This procedure is repeated for a second time after which the solid is washed with EtOH (2×), Et$_2$O (2×) and dried under high vacuum. To a solution of the ketone 8e (280 mg, 1.89 mmol) in AcOH (10 mL) pre-activated Zn dust (1.24 g, 18.9 mmol) is added. The reaction mixture is then heated to 75° C. for 2 h. The reaction mixture is filtered (with EtOAc washing of the solids). The solvent is evaporated over silica and the mixture is directly purified using the CombiFlash® Companion (10% EtOAc/hexanes) to afford the desired dihyrobenzofuran 8f (174 mg, 69% yield) as a colorless oil.

Step 6:

To a solution of the dihydrobenzofuran 8f (240 mg, 1.8 mmol) in MeOH (5 mL), AgNO$_3$ (304 mg, 1.79 mmol) is added followed by iodine (453 mg, 1.79 mmol). The yellow mixture is stirred at RT for 1 h. To the reaction mixture is added a solution of 10% Na$_2$S$_2$O$_3$ and the mixture is stirred for 15 min at RT. The mixture is diluted with EtOAc (100 mL), and the organic layer is washed with brine (3×) and 10% Na$_2$S$_2$O$_3$ (2×). The organic phase is dried over anhydrous MgSO$_4$, filtered and concentrated over silica to give a mixture. This mixture is purified using the CombiFlash® Companion (10% EtOAc/hexanes) to afford the iodo derivative 8g (400 mg, 86% yield) as a white amorphous solid.

Step 7:

A mixture of the iodo derivative 8g (400 mg, 1.54 mmol), bis(pinocolato)diborane (585 mg, 2.31 mmol), potassium acetate (511 mg, 5.4 mmol) in DMF (20 mL) is degassed (Ar balloon and sonication for 5 min); then the catalyst (PdCl$_2$dppf, 188 mg, 0.23 mmol) is added with additional degassing (Ar balloon and sonication for 2 min). The mixture is then heated to approximately 95° C. for 4 h. The mixture is cooled, EtOAc (200 mL) is added, washed with brine (3×), water (2×), dried over anhydrous MgSO$_4$, filtered and solvent evaporation over silica affords the mixture that is purified using the CombiFlash® Companion (10% EtOAc/hexanes) to afford the desired boronate 8h (315 mg, 79% yield) as a yellow oil.

Example 9

Synthesis of Boronate Fragment 9b

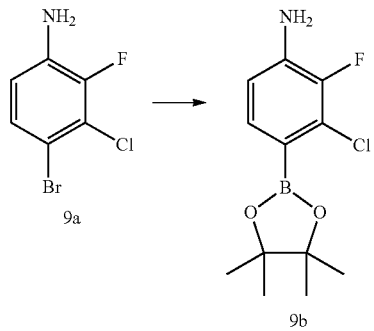 [SMILES: Nc1ccc(Br)c(Cl)c1F ; CC1(C)OB(c2ccc(N)c(F)c2Cl)OC1(C)C]

Anhydrous DMF (60 mL) is added to a flask charged with bromide 9a (5.00 g, 22.2 mmol), bis-(pinacolato)diborane (8.48 g, 33.4 mmol) and potassium acetate (6.35 g, 66.8 mmol) and the resulting suspension is deoxygenated by bubbling a stream of N$_2$ gas through the mixture for 45 min. 1,1'-bis(diphenylphosphino)ferrocene (2.73 g, 3.34 mmol) is then added and the mixture is deoxygenated for approximately a further 5 min and is then heated to 95° C. After 16 h, the dark reaction mixture is cooled, extracted with EtOAc (500 mL and 300 mL) and washed with 1:1 water/brine (600 mL) and brine (600 mL). The combined extracts are dried over anhydrous MgSO$_4$, filtered and evaporated to a black syrup which is purified by flash column chromatography (EtOAc/hexane) to afford the boronate 9b as white solid contaminated with <25% of the diboron reagent (4.24 g, 62% yield).

Example 10

Synthesis of Boronate Fragment 10g

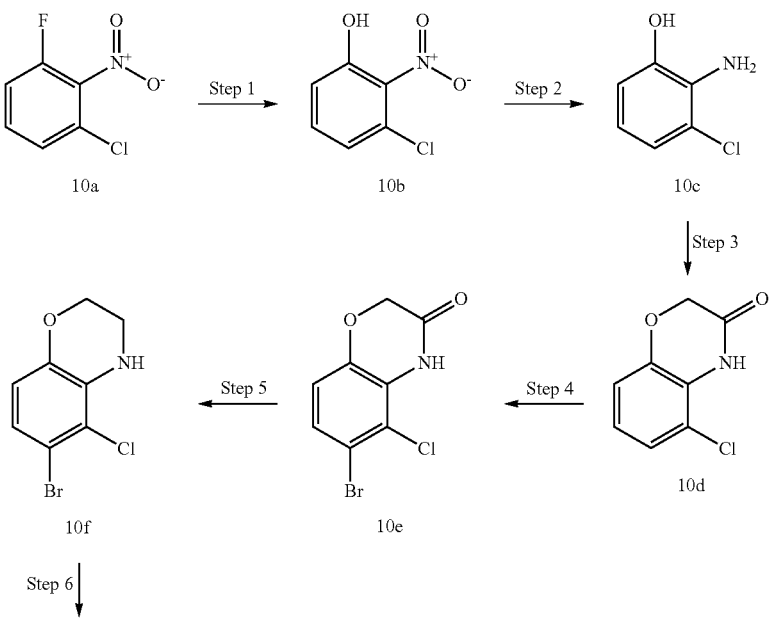

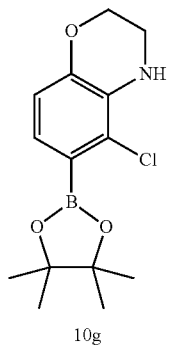

10g

Step 1:

2-Chloro-6-fluoronitrobenzene 10a (6.62 g, 37.7 mmol) and LiOH monohydrate (6.33 g, 151 mmol) are dissolved in THF (45 mL) and water (65 mL) and an aqueous solution of $H_2O_2$ (30%, 8.60 mL, 80.0 mmol) added. The resulting turbid solution is sealed and is heated to 60° C. with rapid stirring. After 3 days, the dark orange mixture is cooled and is added to half-saturated aqueous sodium thiosulfate (200 mL) and shaken vigorously in a separatory funnel. The mixture is then acidified to pH<3 with 1 N HCl, extracted with EtOAc (500 mL) and washed with brine (400 mL). The combined extracts are dried over magnesium sulfate, filtered and evaporated to a deep yellow oil (aminophenol 10b) containing some solid particles (residual starting material) which is used as such (6.37 g, 97% yield).

Step 2:

The crude aminophenol 10b (6.37 g, 36.7 mmol) is dissolved in THF (100 mL) and tin powder (17.4 g, 147 mmol) is added followed by 1 N HCl (220 mL, 220 mmol). The resulting mixture is stirred vigorously at RT. After 16 h, the reaction is cooled to 0° C., the acid neutralized with 10 N NaOH (22 mL) and the resulting milky suspension stirred vigorously for 15 min. The mixture is then filtered through a pad of Celite® and the solids washed thoroughly with EtOAc (4×200 mL). The filtrate is transferred to a separatory funnel and the aqueous phase acidified with 1 N HCl (4 mL), diluted with brine (400 mL) and the organic phase washed with brine (400 mL). The extract is then dried over sodium sulfate, filtered and evaporated to afford aminophenol 10c as a waxy, pale brown solid (2.91 g, 55% yield).

Step 3:

Chloroacetyl chloride (1.94 mL, 24.3 mmol) is added to an ice-cold mixture of aminophenol 10c (2.91 g, 20.3 mmol) and potassium carbonate (8.40 g, 60.8 mmol) in anhydrous DMF (200 mL) under a $N_2$ atmosphere. After 5 min, the reaction is allowed to warm to RT and, after a further 45 min, is heated to 50° C. After 15 h, the reaction is cooled and extracted with EtOAc (600 mL) and washed with water/brine (1 L), half-saturated sodium bicarbonate (1 L) and brine (600 mL). The organic phase is then dried over $MgSO_4$, filtered and evaporated to afford lactam 10d as a fibrous, pale-olive solid (3.15 g, 85% yield).

Step 4:

Bromine (1.8 mL; 35 mmol) is slowly added dropwise to a stirred solution of lactam 10d (3.15 g; 17.1 mmol) in anhydrous DCM (40 mL) at RT. After 3 h, the resulting suspension is slowly added to saturated aqueous sodium thiosulfate (200 mL) and extracted with DCM (4×100 mL). The combined extracts are then washed with brine (200 mL), dried over magnesium sulfate, filtered and evaporated to afford the bromide 10e as a pale beige powder (4.00 g, 89% yield).

Step 5:

A solution of borane in THF (1.0 M, 18.5 mL, 18.5 mmol) is added dropwise to an ice-cold solution of lactam 10e (4.00 g, 15.2 mmol) in anhydrous THF (75 mL), and the reaction is allowed to warm to RT. After 30 min, the solution is heated to gentle reflux under a $N_2$ atmosphere. After 2 h, the reaction is cooled to 0° C. and carefully quenched with 1 N NaOH (19 mL) and stirred for 15 min. The mixture is then diluted with water (30 mL) and the THF is evaporated. The aqueous residue is then extracted with EtOAc (400 mL+50 mL) and washed with water/brine (200 mL), 0.5 N NaOH (200 mL) and brine (100 mL). The combined extracts are dried over magnesium sulfate, filtered and evaporated to afford the morpholine derivative 10f as a yellow syrup (3.90 g, quantitative yield).

Step 6:

Anhydrous DMF (30 mL) is added to a flask charged with aryl bromide 10f (1.84 g, 7.42 mmol), bis(pinacolato)diborane (2.83 g, 11.1 mmol) and potassium acetate (2.47 g, 26.0 mmol) and the resulting suspension is then deoxygenated by bubbling a stream of $N_2$ gas through the mixture for 15 min. 1,1'-bis(diphenylphosphino)ferrocene (909 mg, 1.11 mmol) is then added and the mixture is deoxygenated for a further 5 min and then heated to 95° C. After 16 h, the dark reaction mixture is cooled, diluted with EtOAc (300 mL) and washed with 1:1 water/brine (500 mL) and brine (200 mL). The extract is then dried over $MgSO_4$, filtered and evaporated to a brown syrup which is chromatographed over silica gel (EtOAc/hexanes) to afford the boronate 10g as a white solid contaminated with 0.8 eq of the diboron reagent (1.52 g, 69% yield).

Example 11

Synthesis of Boronate Fragment 11d

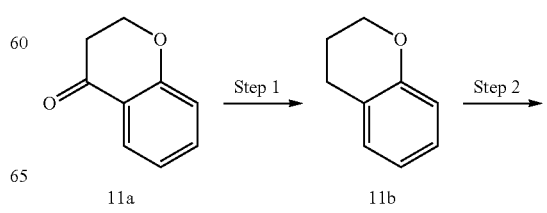

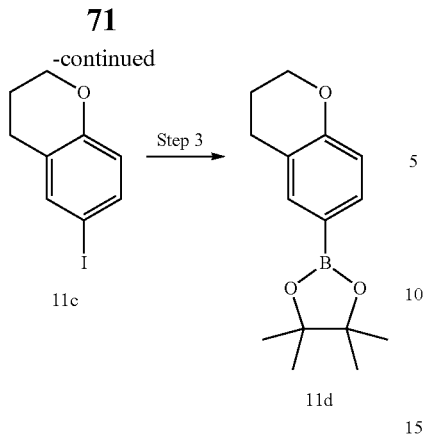

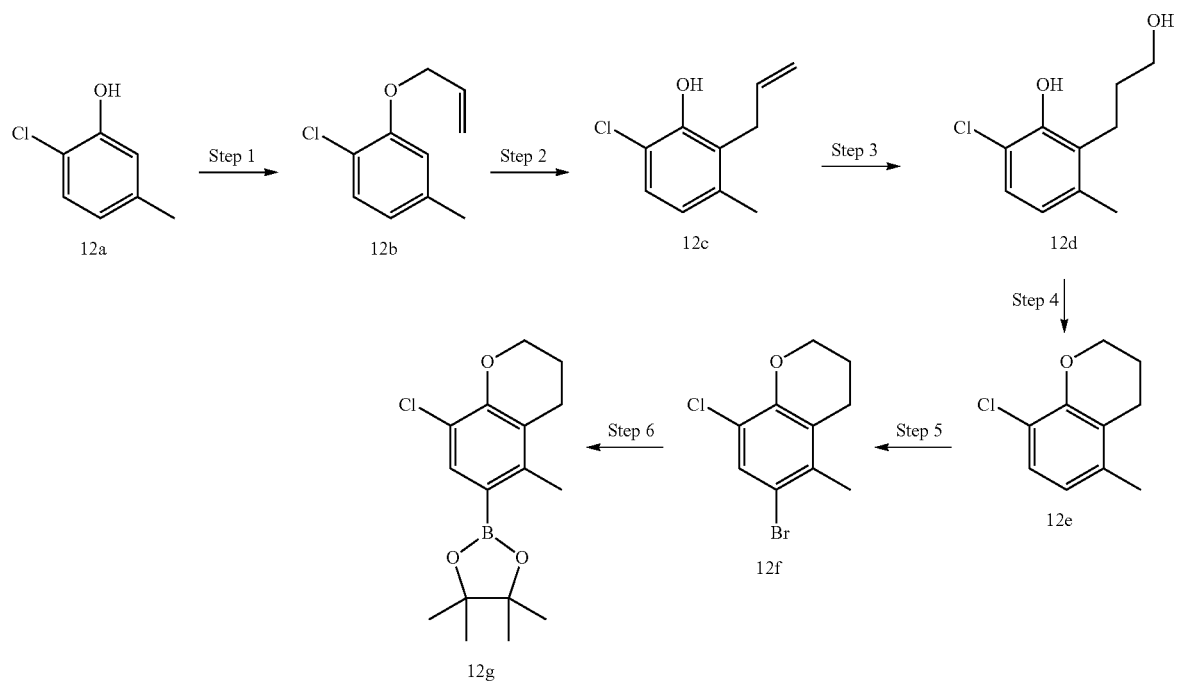

Example 12

Synthesis of Boronate Fragment 12g acetate (1.10 g, 11.5 mmol) in DMF (36 mL) is degassed with Ar for 5 min followed by the addition of the PdCl₂dppf-DCM complex (314 mg, 0.38 mmol). The reaction mixture is then degassed for an additional 5 min before being heated to 95° C. for 5 h. The reaction is then cooled to RT. The crude reaction mixture is diluted with water and the product is extracted with EtOAc (3×100 mL). The combined organics are washed with water (100 mL) and brine (100 mL). The organic phase is then dried over MgSO₄ and filtered and concentrated. The crude mixture is further purified by CombiFlash® Companion using a gradient of EtOAc/hexanes to afford the borane fragment 11d (840 mg, 84% yield).

Step 1:
Commercially available chromanone 11a (9.78 g, 66.0 mmol) dissolved in AcOH (20 mL) is added to a suspension of zinc dust (108 g, 1.65 mol) in AcOH (150 mL). The mixture is heated to 100° C. and is stirred mechanically overnight. The mixture is then filtered through Celite® (washed with EtOAc, 100 mL), diluted with PhMe (300 mL) and the solution is evaporated to give chroman intermediate 11b (8.45 g, 95% yield).

Step 2:
AgNO₃ (12.0 g, 70.6 mmol) and I₂ (15.8 g, 62.3 mmol) are added sequentially to a solution of 11b (8.45 g, 63.0 mmol) dissolved in MeOH (225 mL). The reaction is allowed to stir for 1 h, filtered on Celite® and the filtrate concentrated under reduced pressure. The crude mixture is diluted with EtOAc (250 mL) and washed with saturated sodium thiosulfate (250 mL). The organic layer is washed with water (200 mL) and then dried over Na₂SO₄, filtered and concentrated. The crude mixture is further purified by CombiFlash® Companion to give 6-iodochroman 11c (12.1 g, 74% yield).

Step 3:
A solution of the 6-iodochroman 11c (1.0 g, 3.85 mmol), bis[pinocolato]diborane (1.22 g, 4.81 mmol) and potassium Step 1:
The phenol 12a (6.75 g, 47.3 mmol) is dissolved in DMF (270 mL) and is treated with allyl bromide (6.55 mL, 75.7 mmol). To this solution, NaH (60%, 4 g, 99.4 mmol) is added portionwise and stirring is continued overnight. The reaction mixture is diluted with EtOAc (500 mL) and washed with H₂O (3×500 mL). The organic layer is dried over MgSO₄, filtered and concentrated to dryness to obtain the desired product 12b, which is used as such in the next step.

Step 2:
The ether 12b (9.67 g) is placed in a microwave vial neat with a stir bar and is heated to 240° C. for 20 min at which point the Claisen rearrangement reaction is complete. The crude product 12c (9.3 g) is used in the following step without further purification.

Step 3:
To a solution of the allyl intermediate 12c (9.3 g, 45.8 mmol) in anhydrous THF (300 mL) at 0° C., borane (1 M in THF, 96 mL, 96 mmol, 2.1 eq) is added. The solution is allowed to warm to RT and then is stirred for 2.5 h. The solution is then cooled to 0° C. and treated with 10 N NaOH dropwise, followed by slow addition of 30% $H_2O_2$ (104 ml, 916 mmol). The resulting mixture is allowed to warm to RT and then is stirred at RT for 1 h. The reaction mixture is diluted with HCl (10%, 100 mL) and extracted with EtOAc (3×200 mL). The combined organic phases are dried over $MgSO_4$ and concentrated. The crude product is purified by CombiFlash® Companion to give 12d (7.1 g, 77% yield).

Step 4:

To a solution of the diol 12d (7.1 g, 35.3 mmol) in THF (500 mL), $PPh_3$ (12 g, 45.9 mmol), followed by DEAD (7.2 mL, 45.9 mmol) are added. The solution is stirred at RT for 4 h. The reaction mixture is evaporated under reduced pressure and purified by CombiFlash® Companion to obtain the desired product 12e (5.26 g, 82% yield).

Step 5:

The chroman derivative 12e (5.26 g, 28.8 mmol) is dissolved in AcOH (70 mL) and is then treated with $Br_2$ in AcOH (40 mL). The reaction is stirred at RT for 15 min, then diluted with toluene and concentrated to dryness. The residue is taken up in EtOAc (25 mL) and washed with saturated $Na_2S_2O_3$ (25 mL) and saturated $NaHCO_3$ (25 mL). The organic layer is dried over $MgSO_4$, concentrated and purified by CombiFlash® Companion to obtain the desired product 12f (2.7 g, 36% yield).

Step 6:

The bromide 12f (2.71 g, 10.4 mmol) is dissolved in DMF (120 mL) and treated with bispinocolatoborane (4 g, 15.5 mmol) and potassium acetate (3.45 g, 36.3 mmol). The mixture is degassed (using an Ar balloon) before the introduction of the catalyst ($PdCl_2dppf$, 845 mg, 1.04 mmol). The mixture is then degassed again (using an Ar balloon) and heated to 95° C. for 16 h. The mixture is cooled to RT, diluted with $H_2O$ (300 mL) and extracted with EtOAc (2×300 mL). The combined organic layers are washed with water (3×300 mL) dried over $MgSO_4$, filtered and concentrated. The product is then purified by CombiFlash® Companion. The semi-purified product is then triturated with hexanes (3×50 mL) in order to remove the excess disborane and obtain clean compound 12g (1.74 g, 54% yield).

Example 13

Synthesis of Boronate Fragment 13a

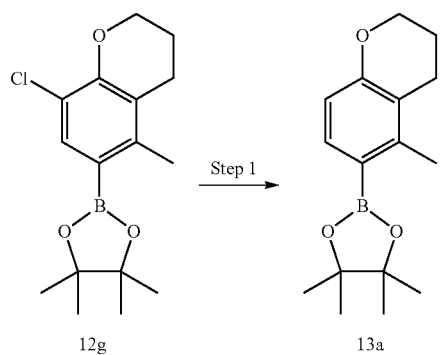

Step 1:

Palladium on activated charcoal (10% Pd by weight, 0.63 mg, 0.59 mmol) is added to a solution of aryl chloride 12g (0.91 g, 2.95 mmol) and ammonium formate (1.92 g, 30.4 mmol) dissolved in MeOH and the mixture is heated to reflux. After 15 min, the reaction is cooled to RT and filtered through Celite® (MeOH rinse). The filtrate is evaporated to dryness and the residue partitioned between water and EtOAc (10 mL each). The organic layer is dried over anhydrous $MgSO_4$ and concentrated to obtain boronic ester 13a (0.78 g, 97% yield).

Example 14

Synthesis of Boronate Fragment 14g

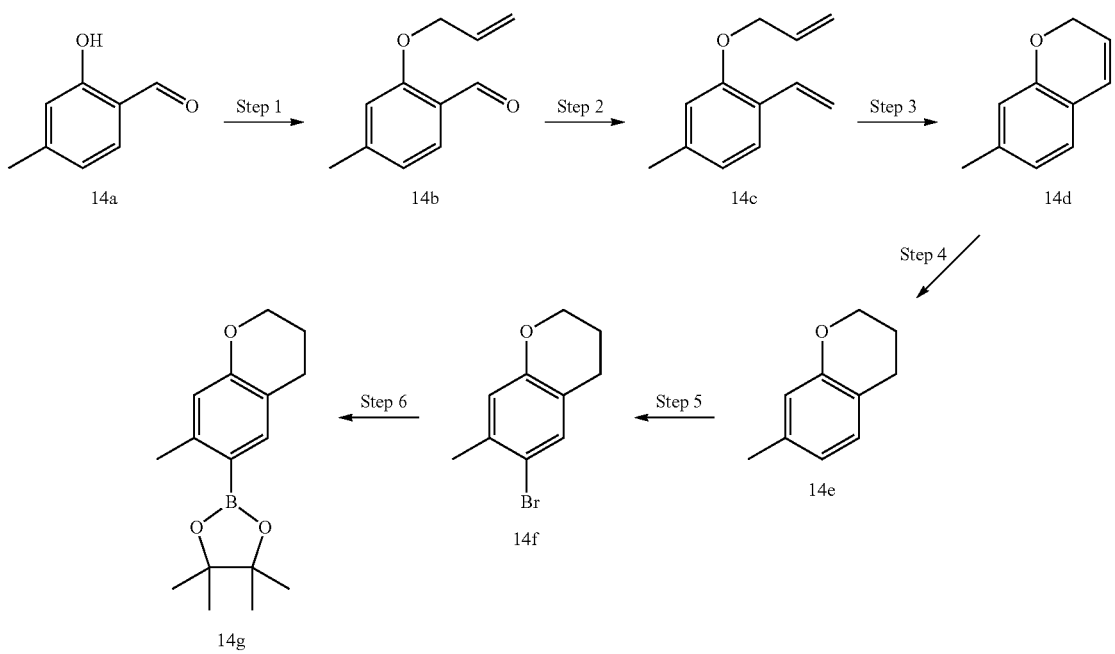

Step 1:

Allyl bromide (9.3 mL, 110 mmol) followed by potassium carbonate (20 g, 150 mmol) are added to a solution of 14a (10 g, 73 mmol) dissolved in DMF (110 mL). The reaction is allowed to stir under Ar at RT overnight. The reaction is diluted with water (400 mL) and extracted with EtOAc (400 mL). The organic layer is washed with water (2×400 mL), dried over $Na_2SO_4$ and concentrated. The product is then purified by CombiFlash® Companion in two batches to provide allyl ether 14b (12 g, 92% yield).

Step 2:

A solution of n-BuLi in hexanes (2.5 M, 6.4 mL, 16 mmol) is added dropwise to a precooled (−78° C.) suspension of methyltriphenylphosphonium bromide (6.6 g, 19 mmol) in THF (90 mL). The resulting bright yellow mixture is stirred for 5 min at −78° C., warmed to RT over approximately 5 min and then recooled to −78° C. Aldehyde 14b (2.4 g, 14 mmol) dissolved in THF (10 mL) is added dropwise and the reaction is allowed to proceed for 10 min at −78° C. before being allowed to warm to RT and stir overnight. The reaction is quenched with brine (100 mL), diluted with water (100 mL) and extracted with EtOAc (100 mL). The organic layer is then washed with water (2×100 mL), dried over $Na_2SO_4$ and concentrated. The crude yellow liquid is then taken up in EtOAc (1 mL) and diluted with hexanes (20 mL), after which $Ph_3PO$ precipitates as a white solid. The solid is removed by filtration, washed with 1:9 EtOAc:hexanes (50 mL) and the filtrates are evaporated to dryness. The product is purified by CombiFlash® Companion to give diene 14c (1.3 g, 54% yield).

Step 3:

Grubb's second generation catalyst (50 mg, 0.075 mmol) is added to a degassed solution of diene 14c (1.3 g, 7.5 mmol). After stirring under Ar for 2.5 h, the reaction is concentrated onto $SiO_2$ (about 2 g) and the product purified by CombiFlash® Companion to give benzopyran 14d (940 mg, 86% yield) as a clear oil.

Step 4:

Solid Pd—C (10% w/w, 680 mg, 0.64 mmol) is added to a solution of benzopyran 14d (940 mg, 6.4 mmol) in EtOH (8.5 mL) and the flask is evacuated and backfilled with $H_2$ gas (balloon). After stirring the reaction at RT for 2.5 h, the mixture is filtered through Celite® (EtOAc washing) and then the filtrate is concentrated to dryness. The product is purified by CombiFlash® Companion to provide chroman 14e (800 mg, 84% yield).

Step 5:

Neat $Br_2$ (275 µL, 5.4 mmol) is added dropwise to a solution of chroman 14e (800 mg, 5.4 mmol) dissolved in AcOH (25 mL). The reaction is then diluted with water (50 mL) and EtOAc (50 mL). The organic layer is washed with water (2×50 mL) and saturated $NaHCO_3$ (2×50 mL). The organic layer is dried over $Na_2SO_4$ and concentrated to dryness. The product is purified by CombiFlash® Companion to give bromide 14f as a mixture with the dibromide (1.3 g, 68% by mass 14f, 51% yield).

Step 6:

A solution of the bromide 14f (950 mg, 2.8 mmol), bis[pinocolato]diborane (840 mg, 3.3 mmol) and potassium acetate (920 g, 9.6 mmol) in DMF (30 mL) is degassed with Ar for 5 min followed by the addition of the $PdCl_2$dppf-DCM complex (290 mg, 0.36 mmol). The reaction mixture is then degassed for an additional 5 min before being heated to 95° C. for 3 h. The reaction is then cooled to RT. The crude reaction mixture is diluted with water and the product is extracted 3 times with EtOAc (3×20 mL). The combined organics are washed with water (2×20 mL). The organic phase is then dried over $Na_2SO_4$, filtered and concentrated. The crude mixture is further purified by CombiFlash® Companion to afford boronic ester 14g (403 mg, 53% yield) as a pale yellow solid.

Example 15

Synthesis of Boronate Fragment 15l

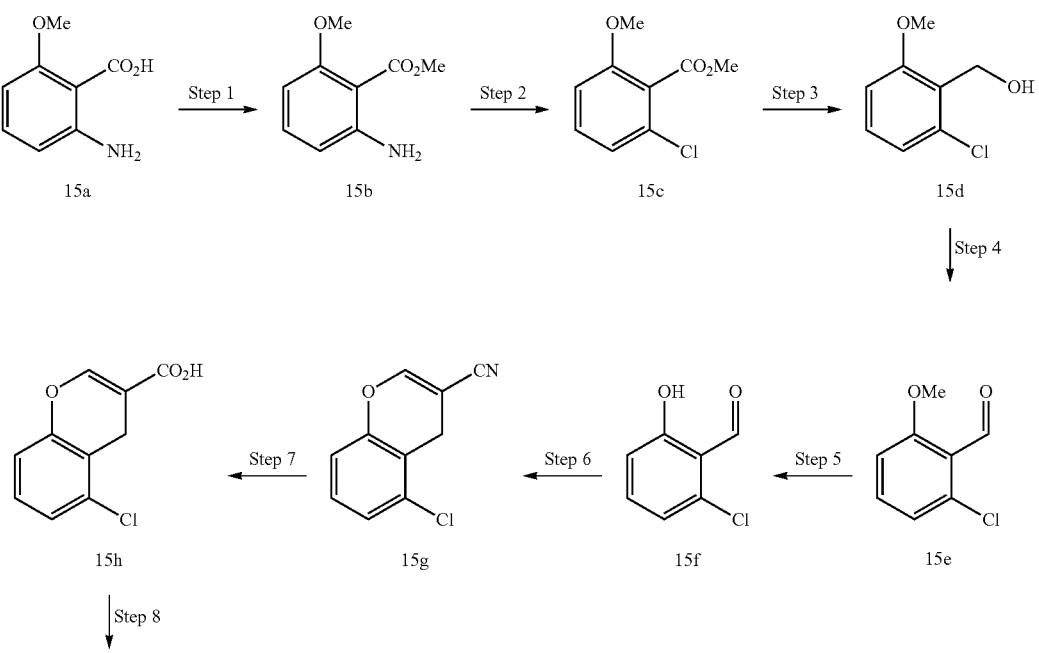

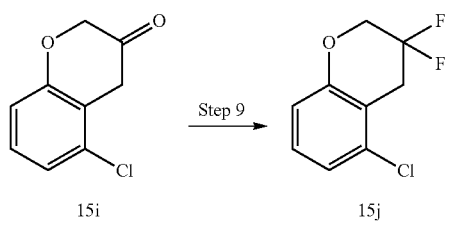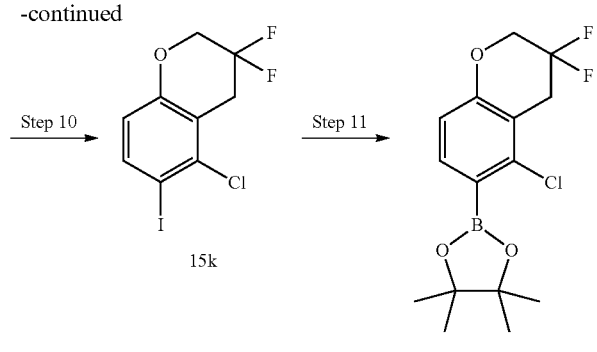

Step 1:
An ethereal solution of diazomethane (0.7 M, 100 mL) is added to a solution of 15a (5.0 g, 30 mmol) in ether (20 mL). After consumption of the SM (TLC monitoring), the reaction is concentrated onto $SiO_2$ (about 10 g) and the product purified by CombiFlash® Companion to yield ester 15b (5.2 g, 95% yield).

Step 2:
A solution of $NaNO_2$ (2.1 g, 30 mmol) in water (10 mL) is slowly added to a solution of aniline 15b (5.0 g, 28 mmol) dissolved in AcOH (50 mL) and 2 M HCl (75 mL) at 0° C. The resulting mixture is stirred at this temperature for 1 h. Solid CuCl (8.4 g, 85 mmol) is added portionwise (over 2 min). The reaction is allowed to come to RT, is stirred for 30 min and then is warmed to 60° C. for 40 min. The mixture is poured into water (200 mL) and extracted with EtOAc (2×200 mL). The organic layer is dried with $MgSO_4$, filtered and evaporated to dryness. The product is purified by CombiFlash® Companion to afford aryl chloride 15c (3.8 g, 68% yield).

Step 3:
A solution of DIBAL in DCM (1 M, 42 mL, 42 mmol) is added dropwise over a period of 25 min to a precooled (−78° C.) solution of ester 15c (3.8 g, 19 mmol) in dry $CH_2Cl_2$ (100 mL). The reaction is allowed to stir for 2 h at −78° C. The reaction is quenched at −78° C. by the dropwise addition of 1 N HCl (8 mL). The reaction is allowed to warm to RT and the organic phase washed with a 5% solution of Rochelle's salt (100 mL), dried over $MgSO_4$, filtered and concentrated under reduced pressure to give crude benzyl alcohol 15d (3.2 g, 99% yield), which is used in the next step without any further purification.

Step 4:
Solid Dess Martin reagent (8.7 g, 20 mmol) is added to a precooled (0° C.) solution of alcohol 15d in dry $CH_2Cl_2$ (100 mL). The reaction is allowed to stir for 2 h while slowly warming to RT. At this time, another 0.5 g of Dess Martin Periodinane is added and the reaction continues for another 1 h. A 1:1 mixture of saturated $NaHCO_3$ and 0.5 M $Na_2S_2O_3$ (100 mL) is added and this mixture is stirred vigorously until the phases become clear (approximately 30 min). The organic phase is separated and the aqueous phase is extracted with DCM (100 mL) and washed with saturated $NaHCO_3$ (100 mL). The combined organic phases are then dried over $MgSO_4$ and evaporated. The product is purified by CombiFlash® Companion to give aldehyde 15e (2.9 g, 90% yield).

Step 5:
A solution of methyl ether 15e (720 mg, 4.2 mmol) in anhydrous $CH_2Cl_2$ (20 mL) is added slowly to a precooled (−30° C.) solution of $BBr_3$ (1 M, 8.4 mL, 8.4 mmol). The solution is warmed to 0° C. and is stirred for 3 h. The reaction is quenched carefully with methanol (1 mL) and washed with saturated $NaHCO_3$ and then brine (25 mL each). The organic layer is dried over $MgSO_4$, filtered and concentrated and the product is purified by CombiFlash® Companion to give phenol 15f (530 mg, 80% yield).

Step 6:
A mixture of the aldehyde 15f (1.1 g, 7.2 mmol), acrylonitrile (2.4 mL, 36 mmol) and DABCO (190 mg, 1.7 mmol) are refluxed for 5 h. The reaction mixture is cooled to RT, diluted with EtOAc (50 mL) and washed with 1 N NaOH (20 mL) and then with 1 N HCl (20 mL). The organic phase is dried over $MgSO_4$ and concentrated to dryness. The product is purified by CombiFlash® Companion to afford the nitrile 15g (650 mg, 47% yield).

Step 7:
A mixture of nitrile 15g (650 mg, 3.4 mmol), 10% NaOH (10 mL, 25 mmol) and EtOH (95%, 0.5 mL) is heated to reflux for 5 days. The reaction is then cooled to RT and 1 N HCl is then added until pH 4. The precipitate is then collected by filtration, washed with water and dried in vacuo to give acid 15h (740 mg, >99% yield).

Step 8:
Triethylamine (0.56 mL, 4.0 mmol) and diphenylphosphoryl azide (0.75 mL, 3.5 mmol) are added successively to a solution of acid 15h (714 mg, 3.4 mmol) in dry toluene (40 mL). This mixture is heated to 85° C. for 2 h and then cooled to RT and treated with 6 N HCl (6 mL). The mixture is brought to reflux and is stirred at this temperature for 2 h. The reaction is then cooled to RT, diluted with EtOAc (100 mL) and washed with saturated $NaHCO_3$ (2×100 mL), water (2×100 mL) and brine (100 mL). The organic layer is dried over $MgSO_4$, filtered and evaporated to dryness. The product is then purified by CombiFlash® Companion to give ketone 15i (269 mg, 44% yield).

Step 9:
Deoxofluor® (0.54 mL, 2.9 mmol) is added to a solution of ketone 15i (270 mg, 1.5 mmol) in $CH_2Cl_2$ (0.6 mL) and EtOH (17 μL) in a sealed tube. The sealed tube is heated to 40° C. for 24 h. The tube is then unsealed, cooled to 0° C. and the reaction quenched by the slow (Exothermic) addition of saturated $NaHCO_3$ (1 mL). The crude reaction mixture is diluted with water (20 mL) and extracted with DCM (3×20 mL). The combined organics are washed with water (20 mL) and the organic phase is dried over $MgSO_4$, filtered and concentrated. The product is purified by CombiFlash® Companion to provide difluorochroman 15j (225 mg, 71% yield).

Step 10:
Solid silver nitrate (187 mg, 1.1 mmol) and iodine (279 mg, 1.1 mmol) are added successively to a solution of difluorochroman 15j (225 mg, 1.1 mmol) dissolved in MeOH (7.8 mL). The reaction is stirred at RT for 90 min and then filtered through a pad of Celite®. The filtrate is treated with a drop of 0.5 N Na₂S₂O₃ (orange color dissipated) then concentrated under reduced pressure. The residue is partitioned between H₂O, 0.5N Na₂S₂O₃ and EtOAc (20 mL each). The water layer is extracted with EtOAc (3×20 mL) and the combined organics are washed with brine (20 mL), dried over MgSO₄, filtered and concentrated. The product is purified by Combi-Flash® Companion to give aryl iodide 15k (158 mg, 44% yield).

Step 11:

A solution of the aryl iodide 15k (150 mg, 0.45 mmol), bis[pinocolato]diborane (150 mg, 0.59 mmol) and potassium acetate (130 mg, 1.4 mmol) in DMF (5 mL) is degassed with Ar for 5 min followed by the addition of the PdCl₂dppf-DCM complex (44 mg, 0.054 mmol). The reaction mixture is then degassed for an additional 5 min before being heated to 85° C. for 9 h. The reaction is then cooled to RT. The crude reaction mixture is diluted with water and the product is extracted with EtOAc (3×10 mL). The combined organics are washed with water (10 mL) and brine (10 mL). The organic phase is then dried over MgSO₄ and filtered and concentrated. The crude mixture is further purified by CombiFlash® Companion to afford boronic ester 15l (123 mg, 70% pure by NMR, 57% yield).

Example 16

Synthesis of Boronate Fragment 16c

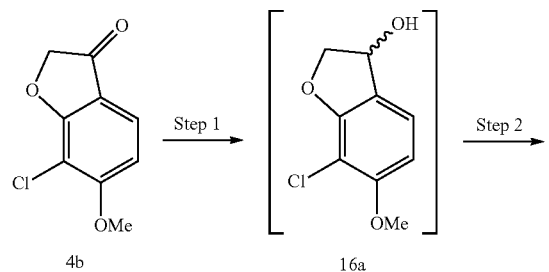

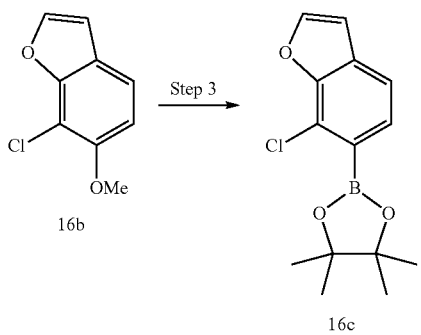

Step 1:

Solid NaBH₄ (342 mg, 9.0 mmol) is added to a solution of ketone 4b (1.5 g, 7.5 mmol) dissolved in MeOH (10 mL) and THF (25 mL) at 0° C. is then added. The reaction is warmed to RT and is allowed to stir for 1 h. The reaction is quenched with aqueous HCl (1 N, 5 mL), the MeOH is removed by concentration and the product extracted with EtOAc (2×50 mL). The organic layer is washed with brine (50 mL), dried over Na₂SO₄, filtered and concentrated to afford alcohol 16a (1.52 g>99% yield). This material is used as is in the next step.

Step 2:

TFA (2.9 mL) is added dropwise to a solution of crude alcohol 16a (1.5 g; 7.47 mmol) in DCM (28 mL) at 0° C. The solution is stirred for 30 min, then concentrated to dryness. The residue is taken up in EtOAc, washed with NaHCO₃ (saturated), brine, dried over Na₂SO₄, filtered and concentrated to a pale yellow gum. The product is purified by CombiFlash® Companion to afford benzofuran 16b (0.30 g, 22% yield) as a white solid.

Step 3:

Compound 16c is prepared from 16b following a synthetic sequence identical to steps 3 to 5 of Example 4.

Example 17

Synthesis of Boronate Fragment 17g

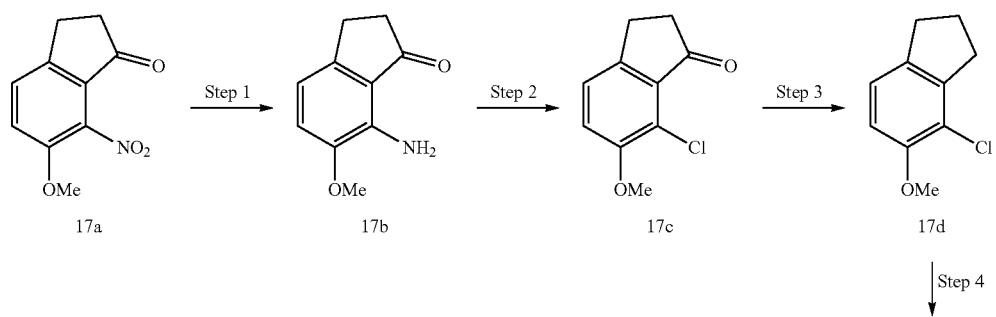

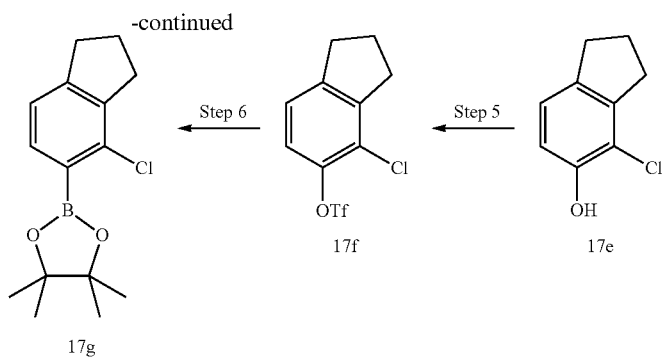

Step 1:
Zn dust (7.89 g, 121 mmol) is added to a solution of 17a (5.0 g, 24 mmol) in AcOH (100 mL). The reaction mixture is then heated to 100° C. and is stirred overnight. The reaction is cooled to RT and the mixture is filtered (EtOAc washing), the solvent is evaporated and the residue purified by Combi-Flash® Companion (30% EtOAc/hexanes) to afford aniline 17b (3.06 g, 72% yield) as a yellow solid.

Step 2:
A solution of NaNO$_2$ (640 mg, 9.3 mmol) in water (3 mL) is slowly added to a solution of aniline 17b (1.5 g, 8.5 mmol) dissolved in AcOH (12 mL) and 2 M HCl (25 mL) at 0° C. The resulting mixture is stirred at this temperature for 1 h. Solid CuCl (2.6 g, 26 mmol) is added portionwise (over 2 min) and the reaction is allowed to come to RT, is then stirred for 30 min and then is warmed to 60° C. for 40 min. The mixture is poured into water (100 mL) and extracted with EtOAc (2×100 mL). The organic layer is dried with MgSO$_4$, filtered and evaporated to dryness. The product is purified by Combi-Flash® Companion (40% EtOAc/hexanes) to afford aryl chloride 17c (1.11 g, 99% yield) as a pale yellow solid.

Step 3:
Solid pre-activated Zn dust is added to a solution of ketone 17c in AcOH. The reaction mixture is then heated to 100° C. and stirred at that temperature for 4 h. The reaction mixture is filtered (EtOAc washing), the filtrate is evaporated to dryness and the product purified by CombiFlash® Companion (10% EtOAc/hexanes) to afford indane 17d (902 mg, 88% yield) as a white crystalline solid.

Step 4:
A solution of BBr$_3$ in DCM (1 M, 9.9 mL, 9.9 mmol) is added dropwise to a precooled (−78° C.) solution of methyl ether 17d (902 mg, 4.9 mmol) dissolved in DCM (20 mL). The reaction solution is stirred at this temperature for 10 min and allowed to warm to RT. After stirring for 1.5 h, water (50 mL) is added (Exothermic) and the mixture is extracted with DCM (3×50 mL). The combined organic layers are dried over MgSO$_4$, filtered and evaporated to dryness. The product is purified by CombiFlash® Companion to afford phenol 17e (700 mg, 84% yield) as an off-white solid.

Step 5:
Tf$_2$O (1.05 mL, 12 mmol) is added to a precooled (0° C.) solution of phenol 17e (700 mg, 4.1 mmol) and Et$_3$N (1.7 mL, 12 mmol) in DCM (20 mL). The resulting dark solution is allowed to warm to RT. After 25 min, the reaction is quenched with saturated NaHCO$_3$ (10 mL), diluted with DCM, and the organic layer washed with water, brine, dried over MgSO$_4$ and evaporated to dryness. The product is purified by CombiFlash® Companion (10% EtOAc/hexanes) to afford triflate 17f (1.21 g, 97% yield) as a yellow oil.

Step 6:
A solution of triflate 17f (1.2 g, 4.0 mmol), bis[pinocolato]diborane (1.5 g, 6.0 mmol) and potassium acetate (1.3 g, 14 mmol) in DMF (20 mL) is degassed with Ar for 5 min followed by the addition of the PdCl$_2$dppf-DCM complex (490 mg, 0.60 mmol). The reaction mixture is then degassed for an additional 5 min before being heated to 95° C. for 5 h. The reaction is then cooled to RT. The crude reaction mixture is diluted with water and the product is extracted with EtOAc (3×100 mL). The combined organics are washed with water (100 mL) and brine (100 mL). The organic phase is then dried over MgSO$_4$ and filtered and concentrated. The crude mixture is further purified by CombiFlash® Companion (10% EtOAc/hexanes) to afford boronic ester 17g (593 mg, 53% yield) as a pale yellow solid.

Example 18

Synthesis of Boronate Fragment 18d

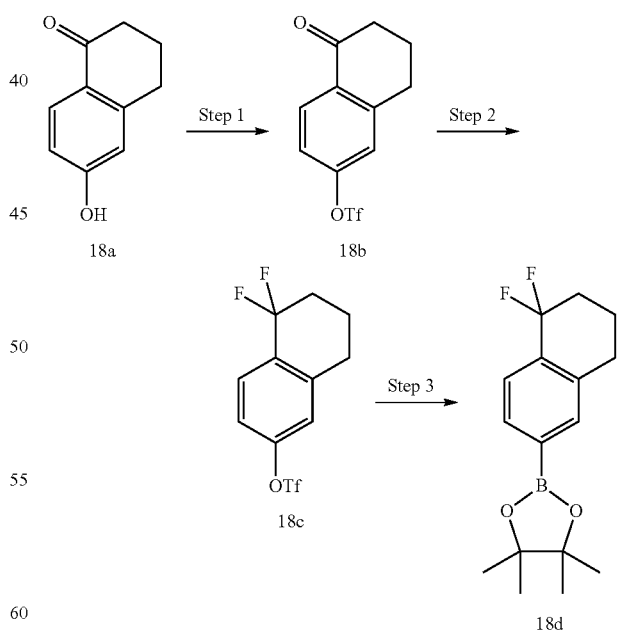

Step 1:
Neat Tf$_2$O (0.83 mL, 4.9 mmol) is added dropwise to a cooled (0° C.) solution of phenol 18a (0.50 g, 3.1 mmol) and pyridine (1.3 mL, 17 mmol) in DCM (15 mL). The reaction is allowed to warm to RT and stir overnight. The reaction is quenched by the addition of a 10% citric acid solution (50 mL) and the mixture is extracted with DCM (3×50 mL). The combined organics are washed with water (50 mL), dried over MgSO$_4$, filtered and concentrated. The product is purified by CombiFlash® Companion to give triflate 18b (500 mg, 94% yield).

Step 2:

Deoxyfluor® (0.83 mL, 4.2 mmol) followed by EtOH (10 uL, 0.2 mmol) are added to neat triflate 18b (500 mg, 1.7 mmol) in a sealable tube. The tube is sealed and the reaction is heated in an oil bath at 85° C. and is stirred overnight. The reaction is then cooled to 0° C. and quenched by the slow addition of NaHCO$_3$ (100 μL, Exothermic). The mixture is diluted with water (50 mL) and extracted with DCM (3×50 mL). The combined organic layers are washed with water (50 mL) and brine (50 mL). The organic phase is then dried over MgSO$_4$, filtered and concentrated. The crude product is purified by CombiFlash® Companion to provide the difluorotetrahydronaphtyl triflate 18c (175 mg, 33% yield).

Step 3:

Step three is performed exactly as in step 6 of Example 17 to provide boronic ester 18d.

Example 19

Synthesis of Boronate Fragment 19d

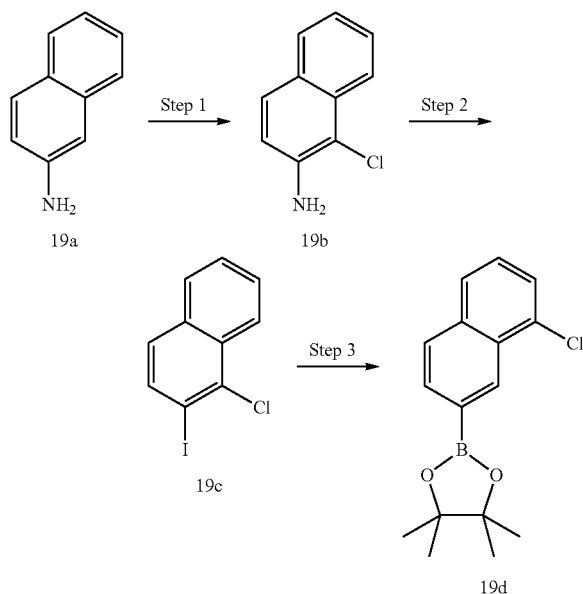

Step 1;

Solid N-chlorosuccinimide (2.2 g, 16 mmol) is added in portions over 5 min to a solution of naphthylamine 19a (2.3 g, 16 mmol) dissolved in CCl$_4$ (150 mL). The reaction is then heated to 50° C. and is stirred for 40 min. The reaction is then cooled to RT, solids are removed by filtration and the filtrate is washed with water (100 mL), dried over MgSO$_4$ and evaporated to dryness to provide chloroaniline 19b (2.8 g, 96% yield).

Step 2:

A solution of NaNO$_2$ (1.2 g, 17 mmol) in water (5 mL) is slowly added to a precooled (0° C.) suspension of aniline 19b (2.8 g, 15 mmol) in 12 N HCl (7 mL) and ice (9.7 g), so as to maintain the temperature below 5° C. The mixture is stirred for 15 min and then is transferred to a solution of KI (8.7 g, 52 mmol) in water (30 mL) and the resulting mixture is stirred for 2 h. The mixture is extracted with Et$_2$O (3×100 mL) and the combined organic layers washed successively with 3 N NaOH (2×50 mL), 5% NaHSO$_3$ (50 mL) and brine (100 mL). The organic phase is dried over MgSO$_4$, filtered and concentrated to dryness. The crude product is purified by flash chromatography (EtOAc/hexanes) to provide aryl iodide 19c (2.4 g, 54% yield).

Step 3:

Step three is carried out exactly as described in step 11 of Example 15 to provide boronic ester 19d.

Example 20

Synthesis of Boronate Fragment 20d

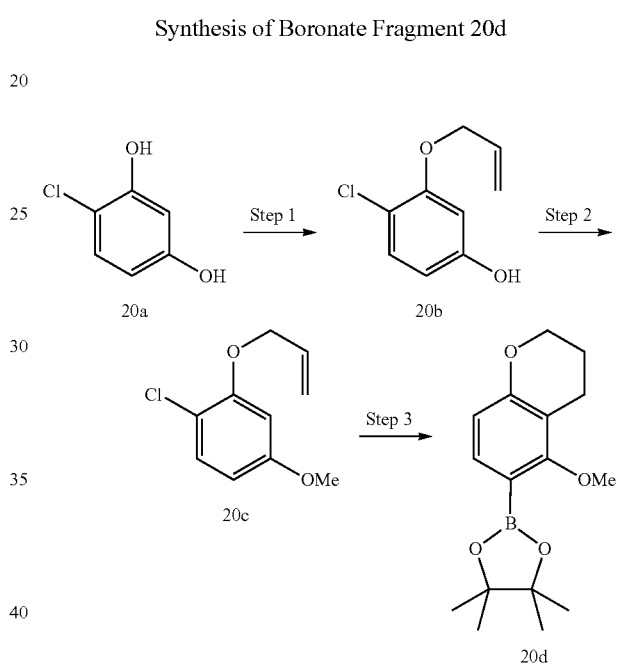

Step 1:

Allyl bromide (2.1 mL, 25 mmol) followed by potassium carbonate (7.2 g, 52 mmol) are added to a solution of 6-chlororesorcinol 20a (10 g, 69 mmol) dissolved in DMF (120 mL). The reaction is stirred overnight, diluted with EtOAc (500 mL) and washed with water (3×500 mL). The organic layer is dried over MgSO$_4$ and concentrated to dryness. The crude product is purified by CombiFlash® Companion to obtain allyl ether 20b (1.8 g, 40% yield).

Step 2:

Methyl iodide (1.2 mL, 20 mmol) followed by potassium carbonate (3.8 g, 27 mmol) are added to a solution of phenol 20b (1.8 g, 9.8 mmol) dissolved in DMF (12 mL). The reaction is stirred for 2 h, diluted with EtOAc (50 mL) and washed with water (3×50 mL). The organic layer is dried over MgSO$_4$ and concentrated to dryness. The crude product is purified by CombiFlash® Companion to obtain methyl ether 20c (1.8 g, 40% yield).

Step 3:

Step 3 is comprised of a sequence of steps identical to steps 2 through 6 of Example 12, followed by step 1 of Example 13 to provide boronic ester 20d.

Example 21

Synthesis of Boronate Fragment 21g

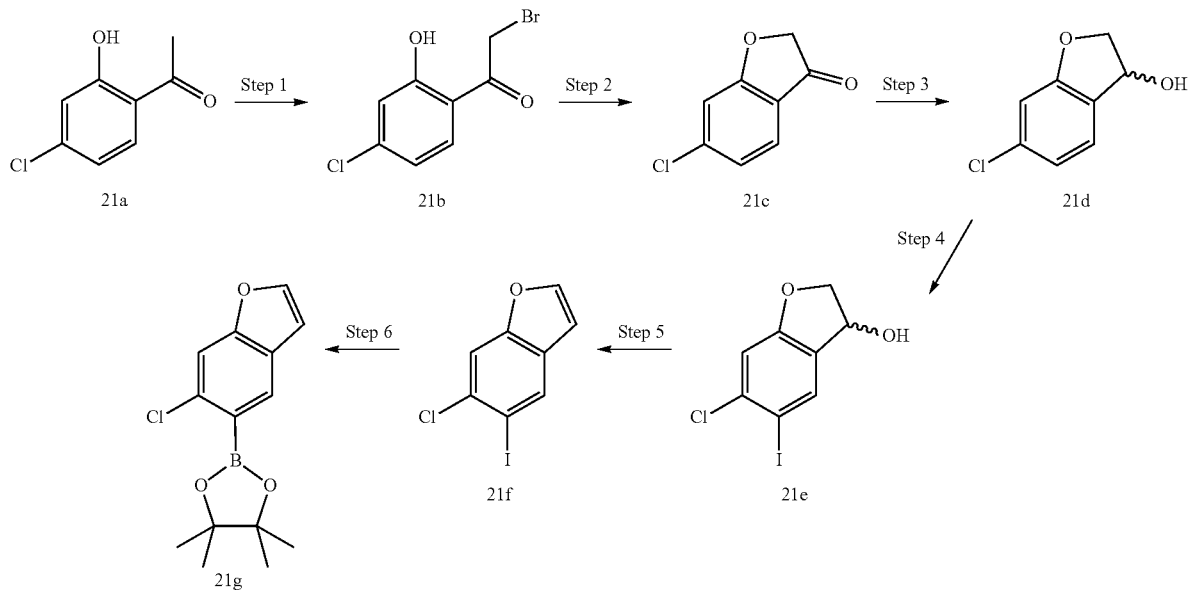

Step 1:
Solid CuBr$_2$ (7.9 g; 35 mmol) is added to a solution of 21a (4.0 g, 23 mmol) dissolved in EtOAc (32 mL) and CHCl$_3$ (32 mL). The mixture is heated to reflux and is stirred for 8 h. CuBr$_2$ (3.9 g) is then added and the mixture continues to stir at reflux for an additional 15 h. The mixture is cooled to RT, the solids removed by filtration (EtOAc washing). The filtrate is concentrated to afford the crude bromoketone 21b (6.3 g), which is used directly in the next step.

Step 2:
Solid KF (2.5 g, 43 mmol) is added to a solution of crude bromoketone 21b (6.3 g, 23 mmol) dissolved in DMF (21 mL). The reaction is stirred at RT for 3 h and then taken up in ether (300 mL), washed with brine (3×100 mL), dried over MgSO$_4$, filtered and concentrated to dryness. The crude product is purified by CombiFlash® Companion to afford ether 21c (2.1 g, 49% yield over two steps).

Step 3:
Solid NaBH$_4$ (270 mg, 7.1 mmol) is added to a precooled (0° C.) solution of ketone 21c (1.0 g, 5.9 mmol) dissolved in MeOH (20 mL). The reaction is allowed to stir for 1 h and then quenched with aqueous HCl (1 N, 1 mL). The volatiles are removed in vacuo and the product extracted with EtOAc (20 mL). The organic layer is washed with brine (20 mL), dried (Na$_2$SO$_4$), filtered and concentrated to afford the crude alcohol 21d (1.0 g), which is used directly in the next step.

Step 4:
Solid AgNO$_3$ (1.0 g, 6.1 mmol) followed by I$_2$ (1.6 g, 6.2 mmol) are added to a solution of alcohol 21d (1.0 g, 6.2 mmol) dissolved in MeOH (58 mL). The mixture is stirred at RT for 1 h and then a solution of Na$_2$S$_2$O$_4$ (0.5 M, 10 mL) is added and the mixture is stirred for 30 min. The MeOH is removed in vacuo and the residue taken up in EtOAc (50 mL), washed with water (1×50 mL), brine (1×50 mL), dried (Na$_2$SO$_4$), filtered and concentrated to afford aryl iodide 21e (1.6 g), which is used directly in the next step.

Step 5:
Crude alcohol 21e (1.6 g, 5 mmol) is dissolved in a mixture of DCM (20 mL) and TFA (2.2 mL). The reaction is stirred for 45 min and then concentrated to dryness. The residue is taken up in EtOAc (50 mL), washed with saturated NaHCO$_3$ (50 mL) and brine (50 mL). The organic layer is dried over Na$_2$SO$_4$, filtered and concentrated to dryness. The crude product is purified by CombiFlash® Companion to provide benzofuran 21f (978 mg, 65% yield over 3 steps).

Step 6:
Step 6 is carried out exactly as described for step 11 of Example 15 to provide boronic ester 21g.

Example 22

Synthesis of Boronate Fragment 22d

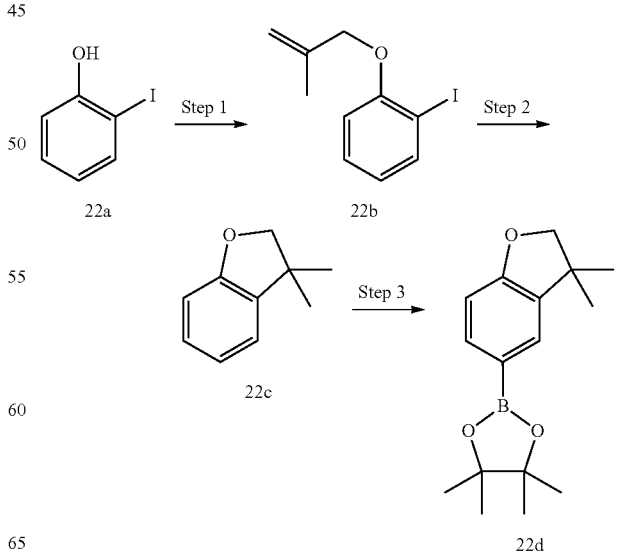

Step 1:

Neat 3-bromo-2-methylpropene (1.7 mL, 16 mmol) is added to a suspension of phenol 22a (3.0 g, 14 mmol) and potassium carbonate (5.6 g, 41 mmol) in DMF (35 mL). The reaction is stirred for 2 h and then quenched with water (100 mL) and extracted with hexanes (2×100 mL). The organic phase is washed with brine (2×100 mL) and concentrated to give ether 22b (3.3 g, 87% yield).

Step 2:

Neat tributyltin hydride (2.3 mL, 8.8 mmol) is added to a solution of aryliodide 22b (2.0 g, 7.3 mmol) and AIBN (120 mg, 0.73 mmol) in PhMe (40 mL) and the reaction is then stirred at reflux under $N_2$. After 1 h, the reaction is concentrated to dryness and the crude product purified by CombiFlash® Companion to provide dihydrobenzofuran 22c (785 mg, 73% yield).

Step 3:

Step 3 is comprised of a sequence of synthetic steps identical to steps 10 and 11 of Example 15 to provide boronic ester 22d.

Example 23

Synthesis of Boronate Fragment 23c

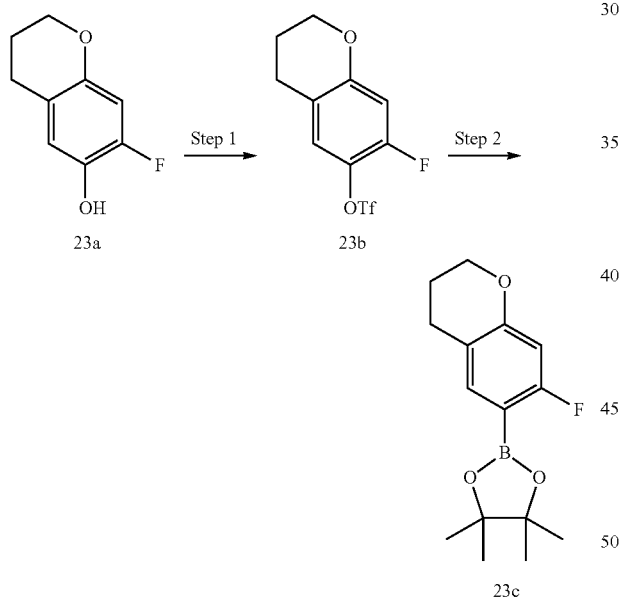

Step 1:

Neat $Tf_2O$ (0.56 mL, 3.3 mmol) is added dropwise to a cooled (0° C.) solution of phenol 23a (350 mg, 2.1 mmol; prepared according to Doi et al *Bull. Chem. Soc. Jpn.* 2004 77, 2257-2263) and pyridine (0.91 mL, 11 mmol) in DCM (10 mL) under an Ar atmosphere. The reaction is allowed to warm to RT and then is stirred for 2 h. The reaction is quenched by the addition of a 10% citric acid solution (20 mL) and extracted with DCM (3×20 mL). The combined organic layers are washed with water (20 mL), dried over $MgSO_4$, filtered and concentrated to dryness. The crude product is purified by CombiFlash® Companion to provide triflate 23b (512 mg, 82% yield).

Step 2:

A solution of the triflate 23b (510 mg, 1.7 mmol), bis[pinocolato]diborane (560 mg, 2.2 mmol) and potassium acetate (500 mg, 5.1 mmol) in DMF (18 mL) is degassed with Ar for 5 min followed by the addition of the $PdCl_2$dppf-DCM complex (140 mg, 0.17 mmol). The reaction mixture is then degassed for an additional 5 min before being heated to 100° C. by microwave irradiation for 10 min. The reaction is then cooled to RT. The crude reaction mixture is diluted with EtOAc (60 mL) and washed with brine (3×60 mL). The organic layer is dried over $MgSO_4$, filtered and concentrated. The crude mixture is further purified by CombiFlash® Companion to afford boronic ester 23c (200 mg, 42% yield).

Example 24

Synthesis of Boronate Fragment 24b

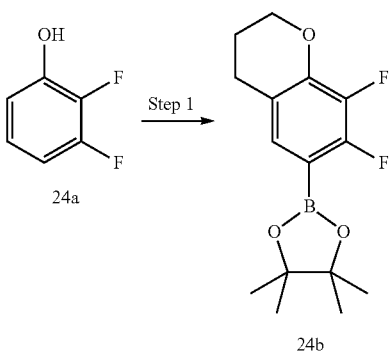 [SMILES: Oc1cccc(F)c1F ; CC1(C)OB(c2cc3c(c(F)c2F)OCCC3)OC1(C)C]

Step 1:

Compound 24b is prepared from 24a following a synthetic sequence identical to steps 1 to 6 of Example 12.

Example 25

Synthesis of Boronate Fragment 25b

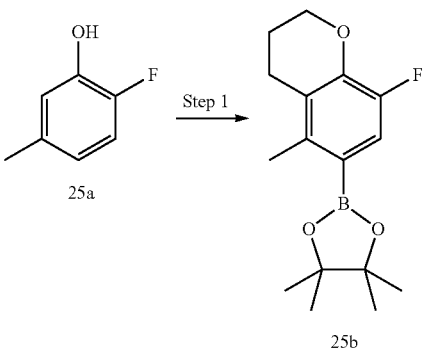

Step 1:
Compound 25b is prepared from 25a following a synthetic sequence identical to steps 1 to 6 of Example 12.

Example 26

Synthesis of Boronate Fragment 26b

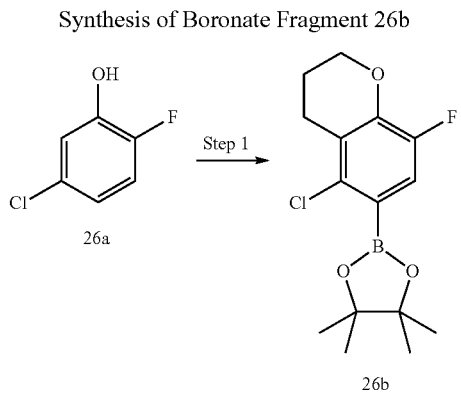

Step 1:
Compound 26b is prepared from 26a following a synthetic sequence identical to steps 1 to 6 of Example 12.

Example 27

Synthesis of Boronate Fragment 27b

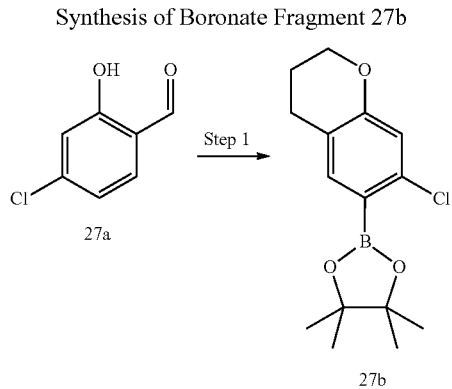

Step 1:
Compound 27b is prepared from 27a following a synthetic sequence identical to steps 1 to 6 of Example 14.

Example 28

Synthesis of Boronate Fragment 28b

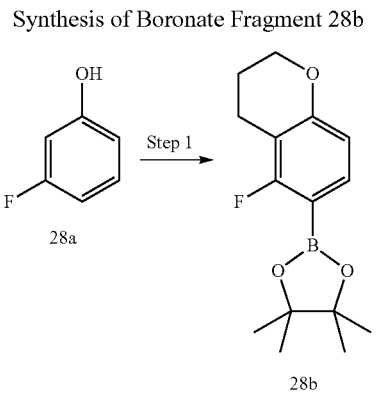

Step 1:
Compound 28b is prepared from 28a following a synthetic sequence identical to steps 1 to 8 of Example 6.

Example 29

Synthesis of Boronate Fragment 29b

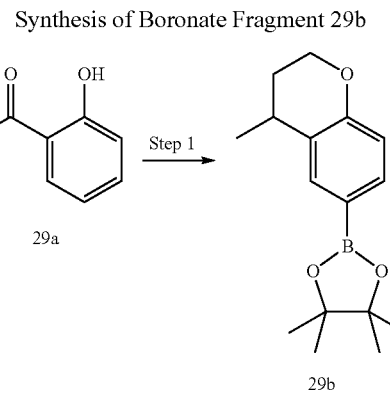

Step 1:
Compound 29b is prepared from 29a following a synthetic sequence identical to steps 1 to 6 of Example 14.

Example 30

Synthesis of Boronate Fragment 30b

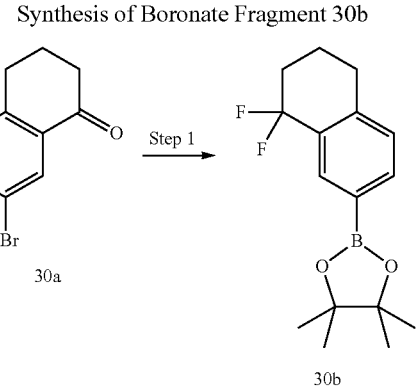

Step 1:
Compound 30b is prepared from 30a following a synthetic sequence identical to steps 2 and 3 of Example 18.

Example 31

Synthesis of Boronate Fragment 31b

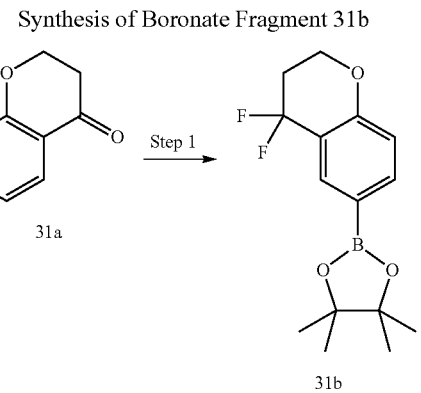

Step 1:
Compound 31b is prepared from 31a following a synthetic sequence identical to steps 9 to 11 of Example 15.

Example 32

Synthesis of Boronate Fragment 32b

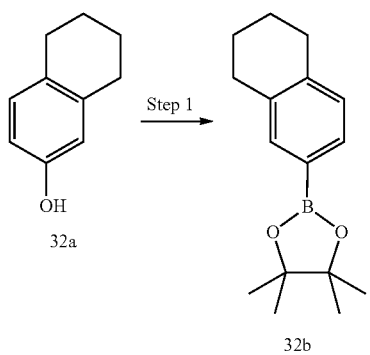 [SMILES: Oc1ccc2c(c1)CCCC2 ; CC1(C)OB(c2ccc3c(c2)CCCC3)OC1(C)C]

Step 1:
Compound 32b is prepared from 32a following a synthetic sequence identical to steps 5 to 6 of Example 17.

Example 33

Synthesis of Boronate Fragment 33b

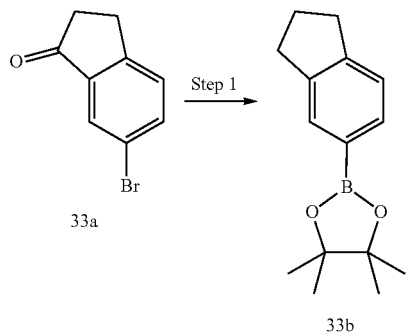 [SMILES: O=C1CCc2ccc(Br)cc21 ; CC1(C)OB(c2ccc3c(c2)CCC3)OC1(C)C]

Step 1:
Compound 33b is prepared from 33a following a synthetic sequence identical to steps 1 and 4 of Example 11.

Example 34

Synthesis of Boronate Fragment 34f

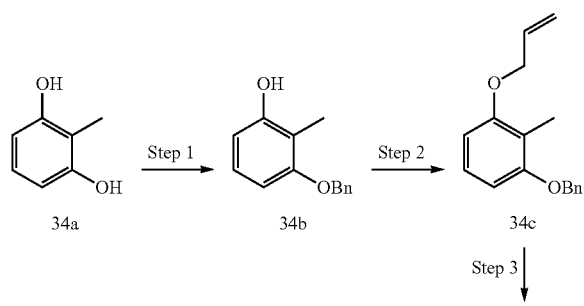

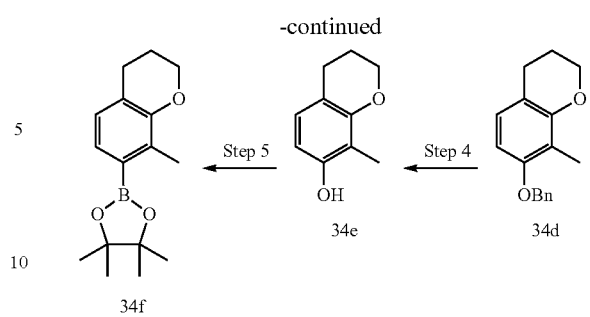

Step 1:
Benzyl bromide (25 mL, 210 mmol) followed by potassium carbonate (44 g, 320 mmol) are added to a solution of 2-methylresorcinol 34a (38 g, 310 mmol) dissolved in DMF (1 L). The reaction is stirred overnight, diluted with EtOAc (2 L) and washed with water (3×2 L). The organic layer is dried over $Na_2SO_4$ and concentrated to dryness. The crude product is purified by CombiFlash® Companion to obtain benzyl ether 34b (18.6 g, 39% yield).

Step 2:
Allyl bromide (3.0 mL, 35 mmol) followed by potassium carbonate (6.5 g, 47 mmol) are added to a solution of phenol 34b (5 g, 23 mmol) dissolved in DMF (100 mL). The reaction is stirred overnight, diluted with EtOAc (500 mL) and washed with water (3×500 mL). The organic layer is dried over $Na_2SO_4$ and concentrated to dryness. The crude product is purified by CombiFlash® Companion to obtain benzyl ether 34c (4.4 g, 75% yield).

Step 3:
Compound 34d is prepared from 34c following a synthetic sequence identical to steps 2 to 4 of Example 12.

Step 4:
Benzyl ether 34d and Pd—C (10% w/w, 100 mg, 0.094 mmol) are combined in EtOAc (5 mL) and the flask is evacuated and backfilled with a $H_2$ atmosphere (balloon). After stirring for 3 h, the reaction is filtered through Celite® (EtOAc washing) and the filtrated concentrated to give phenol 34e (145 mg, 95% yield).

Step 5:
Compound 34f is prepared from 34e following a synthetic sequence identical to steps 5 to 6 of Example 17.

Example 35

Synthesis of Boronate Fragment 35e

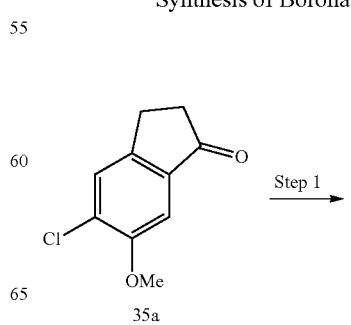

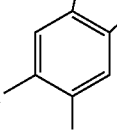

Steps 1 through 4 are done in analogy to steps 3 through 6 from Example 17.

Example 36

Synthesis of Boronate Fragment 36d

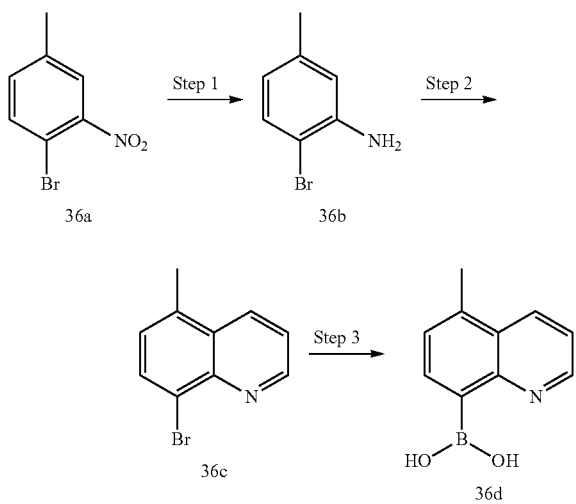

Step 1:

4-bromo-3-nitrotoluene 36a (5.0 g, 22.9 mmol) is dissolved in 50 mL ethyl acetate and solid tin(II) chloride dihydrate (20.0 g, 86.9 mmol) is added. The mixture is heated under nitrogen atmosphere at 70° C. for 2 h (note: temporary overheating to 100° C. is observed! Caution should be exercised!). The mixture is cooled down and is poured into 200 mL of ice-water. 5% aqueous $NaHCO_3$ (50 mL) solution is added (rapid foaming!), followed by 10 N aqueous NaOH to bring the pH ~7-8. Large volume of gelatinous yellowish precipitate is formed. This heterogeneous mixture is shaken with EtOAc (200 mL) and the mixture is centrifuged in 50 mL portions, resulting in good separation of a yellowish solid. The clear supernatant is decanted and is extracted with EtOAc. Combined organic phase is washed with brine, dried over sodium sulphate, filtered and concentrated under vacuum to give an orange oily residue. This residue is re-dissolved in 100 mL of ether and the solution is washed with 10% $Na_2CO_3$ (20 mL) followed by 2.5 M aqueous NaOH (20 mL). The dark brown organic solution is then stirred with $MgSO_4$ and active charcoal and filtered to give a light yellow solution, which darkened rapidly on standing in open flask. The solvent is removed under vacuum to give the desired compound 36b as a brown-red oil which is used in the next step without further purification (3.31 g, 78% yield).

Step 2:

A mixture of compound 36b (3.3 g, 17.7 mmol), glycerin (3.3 g, 35.5 mmol), nitrobenzene (2.2 g, 17.7 mmol) and 75% aqueous sulfuric acid (10 mL, 138 mmol) is stirred at 150° C. for 3 h (mixture turns black and viscous). The reaction mixture is cooled down, poured into ice-water (200 mL) and 10 N aqueous NaOH is added (30 mL, 300 mmol). The black mixture is then shaken with EtOAc (100 mL) and is centrifuged in 50 mL portions. The upper EtOAc layers are combined and the bottom aqueous layers containing the black tar are shaken with EtOAc and re-centrifuged. All EtOAc extracts are combined, washed with brine, dried over $Na_2SO_4$, filtered and concentrated under vacuum to give a brown-red oil. This material is chromatographed on 80 g silica gel column (CombiFlash® Companion apparatus, hexane-EtOAc gradient). The fractions containing the compound are concentrated under vacuum to afford compound 36c as a white solid (3.26 g, 83% yield).

Step 3:

To a cooled (−78° C.) solution of compound 36c (500 mg, 2.25 mmole) in anhydrous $Et_2O$ (20 mL), is added over 5 min under an Ar atmosphere a 1.6 M solution of n-BuLi in hexane (3.5 mL, 5.60 mmol). The mixture is stirred at −78° C. for 50 min, triisopropylborate (2.00 mL, 8.55 mmol) is then added dropwise and the mixture is stirred for 2 h at that temperature. The mixture is slowly allowed to reach RT over a 2 h period and it is poured into 1 M aqueous HCl (30 mL). The mixture is transferred into a separatory funnel, the organic layer is separated and the aqueous layer is washed with $Et_2O$. The aqueous layer is then transferred into a 500 mL Erlenmeyer flask and the pH of the solution is adjusted to 6.3 (measured with a pH meter) by slowly adding a saturated solution of $NaHCO_3$ in water (~25 mL, careful: foaming). The suspension is filtered off and the separated light-beige solid is washed with water and dried under high vacuum. This crude product (383 mg) is triturated with $Et_2O$/hexanes to give a first crop of the desired compound 36d as a free base (120 mg, 28% yield). The mother liquors are concentrated under vacuum and are purified by reversed-phase HPLC using a $CH_3CN/H_2O$ gradient containing 0.06% TFA (ODS-AQ, C-18 column, 75×30 mm, 5-µm particle size). After lyophilization, a second crop of compound 36d is obtained as a TFA salt (102 mg, 15% yield), (total yield: 43%).

Example 37

Synthesis of Boronate Fragment 37d

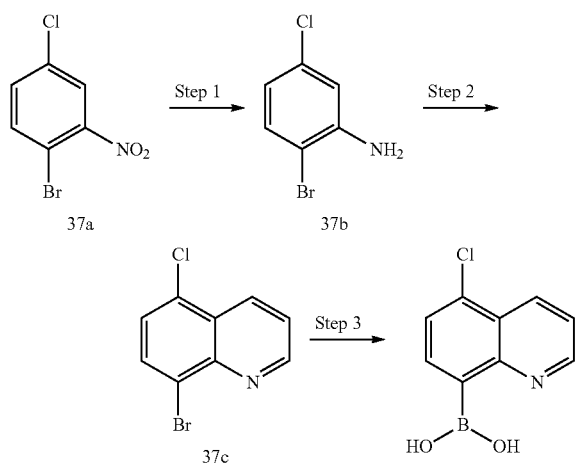

Step 1:

1-bromo-4-chloro-2-nitrobenzene 37a is transformed to compound 37b using the procedure of example 36b, except for the fact that $Et_2O$ is used for the extractions instead of EtOAc.

Step 2:

Compound 37b (4.2 g, 20.3 mmol) is melted at 50° C. in a 100 mL round-bottomed flask containing a stirring bar and immersed in an oil bath. A solution of zinc chloride (700 mg, 5.03 mmol) and ferric chloride (540 mg, 3.25 mmol) in water (3.3 mL) is added in one portion followed by absolute EtOH (20 mL). The flask is stoppered with a rubber septa and a needle is inserted to avoid any pressure build-up. The mixture is warmed to 80° C. and acrolein (1.68 mL, 24.4 mmol) is added via a syringe pump over a 2 h period. After the addition, the mixture is stirred at 80° C. for 1 h and an additional amount of solid ferric chloride is added (4.1 g, 25.3 mmol). The mixture is stirred at 80° C. for an extra 24 h and then concentrated under vacuum to give a semi-solid residue. Water (200 mL) is added followed by a 10 N aqueous solution of NaOH (20 mL) and DCM (200 mL). After shaking the mixture for a few min, the solid is filtered over a pad of Celite® and the filtrate is transferred into a separatory funnel. The organic layer is separated and the aqueous layer is extracted with DCM. The combined organic extracts are washed with brine, dried ($Na_2SO_4$), filtered and concentrated under vacuum to give a brown solid. This solid is triturated in hot $CH_3CN$ and filtered. The solid is discarded and the filtrate is concentrated under vacuum to give a brown semi-solid (2.3 g). This material is purified on a CombiFlash® Companion apparatus on 40 g silica gel column eluted with EtOAc/hexanes gradient. After evaporation of the solvent under vacuum, the desired compound 37c is isolated as a yellow solid (390 mg, 8% yield).

Step 3:

Compound 37c is transformed to compound 37d using the procedure of example 36d.

Example 38

Synthesis of Boronate Fragment 38c

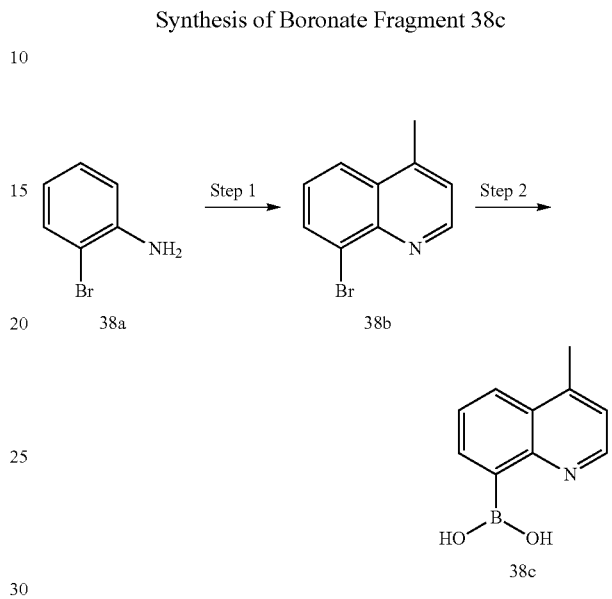

Step 1:

2-bromoaniline 38a is transformed to compound 39b using the procedure of example 37c except that methyl vinyl ketone is used instead of acrolein.

Step 2:

Compound 38b is transformed to compound 38c using the procedure of example 36d.

Example 39

Synthesis of Boronate Fragment 39k

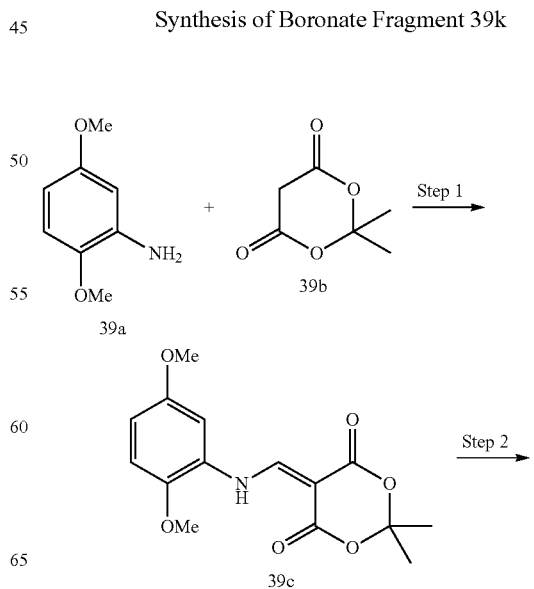

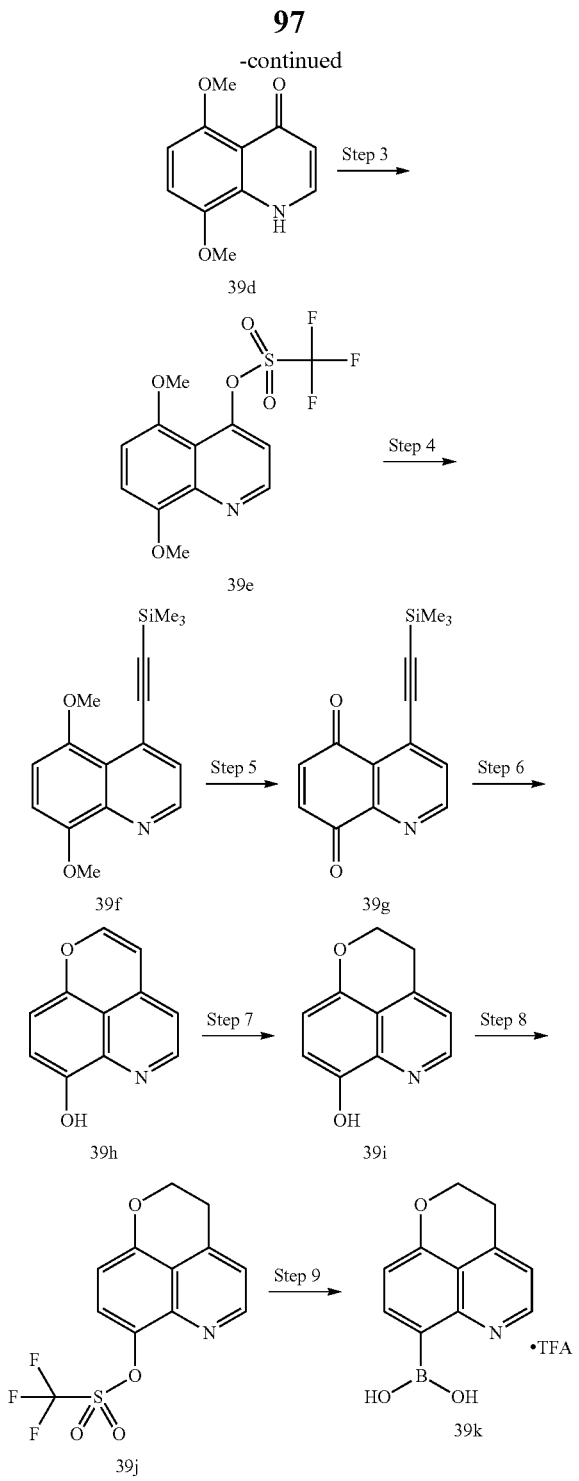

Step 2:
Compound 39c (62.00 g, 202 mmol) is dissolved in diphenyl ether (310 mL) and refluxed at 240° C. for 30 min. The mixture is then cooled down to RT and n-hexane is added, which causes a brown precipitate to form. This solid is separated by filtration and is washed with n-pentane and n-hexane to remove non-polar impurities and the remaining dark brown solid (compound 39d) is used as is in the next step (27 g, 65% yield).

Step 3:
A mixture of compound 39d (30.0 g, 146 mmol), DMAP (3.75 g, 30.7 mmol) and 2,6-lutidine (24.4 mL; 208 mmol) in DCM (1.4 L) is cooled to 0° C. and Tf$_2$O (29.6 mL, 175 mmol) is added slowly at 0° C. The resulting mixture is stirred at 0° C. for 2 h and at RT for 1 h. It is then diluted with DCM, washed with H$_2$O and brine and dried (Na$_2$SO$_4$). The solvent is removed under reduced pressure and the residue is purified by flash chromatography on silica gel (20% EtOAc/petroleum ether). The desired compound 39e is isolated as a yellow solid (35 g, 70% yield).

Step 4:
A mixture of diisopropylethyl amine (46.5 mL, 267 mmol) in dry DMF (250 mL) is degassed with argon for 30 min and is added to a mixture of compound 39e (30.0 g, 89.0 mmol), triphenylphosphine (7.70 g, 29.4 mmol), tris(dibenzylideneacetone)di-palladium(0)-chloroform adduct (9.21 g, 8.9 mmol). The resulting mixture is stirred for 5 min at 0° C. and TMS acetylene (13.4 g, 136 mmol) is added dropwise. The temperature is raised to RT and the mixture is stirred for 4 h. Diethyl ether and water is added, the aqueous layer is separated and washed with diethyl ether. The combined organic layers are washed with H$_2$O and brine. After drying on Na$_2$SO$_4$, the solvent is removed under reduced pressure and the residue is purified by flash chromatography on silica gel (30% EtOAc/petroleum ether). Compound 39f is isolated as a yellow solid (18 g, 70% yield).

Step 5:
A solution of ceric ammonium nitrate (42.3 g, 77.2 mmol) in H$_2$O (47 mL) is added under argon atmosphere to a solution of compound 39f (11.0 g, 38.3 mmol) in acetonitrile (366 mL). The reaction mixture is degassed with argon for 10 min and the mixture is stirred at RT for 20 min. Water is then added and the solution is extracted with DCM. The organic extracts are combined, washed with H$_2$O, brine and dried (Na$_2$SO$_4$). The solvent is removed under reduced pressure and the residue is purified by flash chromatography on silica gel (40% EtOAc/petroleum ether). The desired compound 39g is isolated as a yellow solid (5.0 g, 52% yield).

Step 6:
Compound 39g (1.80 g, 7.1 mmol) is taken in distilled acetic acid (72 mL) under argon atmosphere. Ammonium chloride (7.55 g, 141 mmol) is added and the reaction is refluxed for 45 min. The reaction mixture is cooled to RT, H$_2$O is added and the solution is washed with EtOAc. The aqueous layer is neutralized with a saturated aqueous solution of NaHCO$_3$ and is extracted with EtOAc. The combined organic extracts are washed with H$_2$O, brine and dried (Na$_2$SO$_4$). The solvent is removed under reduced pressure to afford compound 39h as a brown solid (250 mg, 20% yield).

Step 7:
Compound 39h (230 mg, 1.24 mmol) is dissolved in absolute EtOH (11 mL) and 10% palladium on carbon is added (46 mg) under nitrogen atmosphere. The mixture is stirred for 15 h under one atmosphere of hydrogen. The reaction is degassed with nitrogen, filtered through Celite®, and the Celite® bed is washed with an EtOH—CHCl$_3$ mixture. The solvent is removed under reduced pressure to give compound 39i as a brown sticky solid (200 mg, 86% yield).

Reference: Feliu, L.; Ajana, W.; Alvarez, M.; Joule, J. A. *Tetrahedron* 1997, 53, 4511.

Step 1:
Meldrum's acid 39b (47.04 g, 326 mmol) is dissolved in trimethyl orthoformate (360 mL) and refluxed for 2 h. Then 2,5-dimethoxy aniline 39a (50 g, 326 mmol) is added and the mixture is refluxed for an extra 5 h. The reaction mixture is cooled down to RT and the solid which formed upon cooling is collected by filtration. It is further crystallized from MeOH to afford compound 39c as a yellow solid (63 g, 63% yield).

Step 8:

Compound 39i (600 mg, 3.21 mmol) is taken in dry DCM (30 mL) under nitrogen atmosphere. The solution is cooled to 0° C. and triethylamine (0.89 mL, 6.42 mmol) is added dropwise followed by Tf$_2$O (0.65 mL, 3.87 mmol). The temperature is raised to RT and the reaction mixture is stirred for 2 h. The mixture is diluted with DCM and is washed with H$_2$O, brine and dried (Na$_2$SO$_4$). The solvent is removed under reduced pressure to afford a residue which is purified by flash chromatography (10% EtOAc/hexane). Compound 39j is isolated as a brown solid (630 mg, 61% yield).

Step 9:

In a dry (oven-dried for 30 min.) 5-mL glass microwave vessel containing a magnetic stirring bar, are added compounds 39j (250 mg, 0.078 mmol), bis(pinacolato)diborane (250 mg, 0.098 mmol), anhydrous potassium acetate (150 mg, 1.51 mmol), Pd(PCy$_3$)$_2$ (62.0 mg, 0.091 mmol) and anhydrous, deoxygenated (argon bubbling for 30 min) 1,4-dioxane (4 mL). The vial is capped tightly with a septum-cap and the vessel is flushed with argon. The mixture is stirred at 95° C. (oil bath temperature) under an atmosphere of argon for 16 h. The reaction mixture is then concentrated under vacuum, the brown oily residue is dissolved in glacial AcOH (7 mL) and is filtered via 45 μm membrane filter. The dark brown solution is divided into 5×1.5 mL portions and is injected on an automatic preparative reversed-phase HPLC-MS apparatus (CH$_3$CN/H$_2$O gradient containing 0.06% TFA, ODS-AQ, C-18 column, 50×19 mm, 5-μm particle size). The collected fractions are lyophylized to give the desired compound 39k as a yellow amorphous solid (115 mg, 45% yield for the TFA salt).

Example 40

Synthesis of Compound 1035

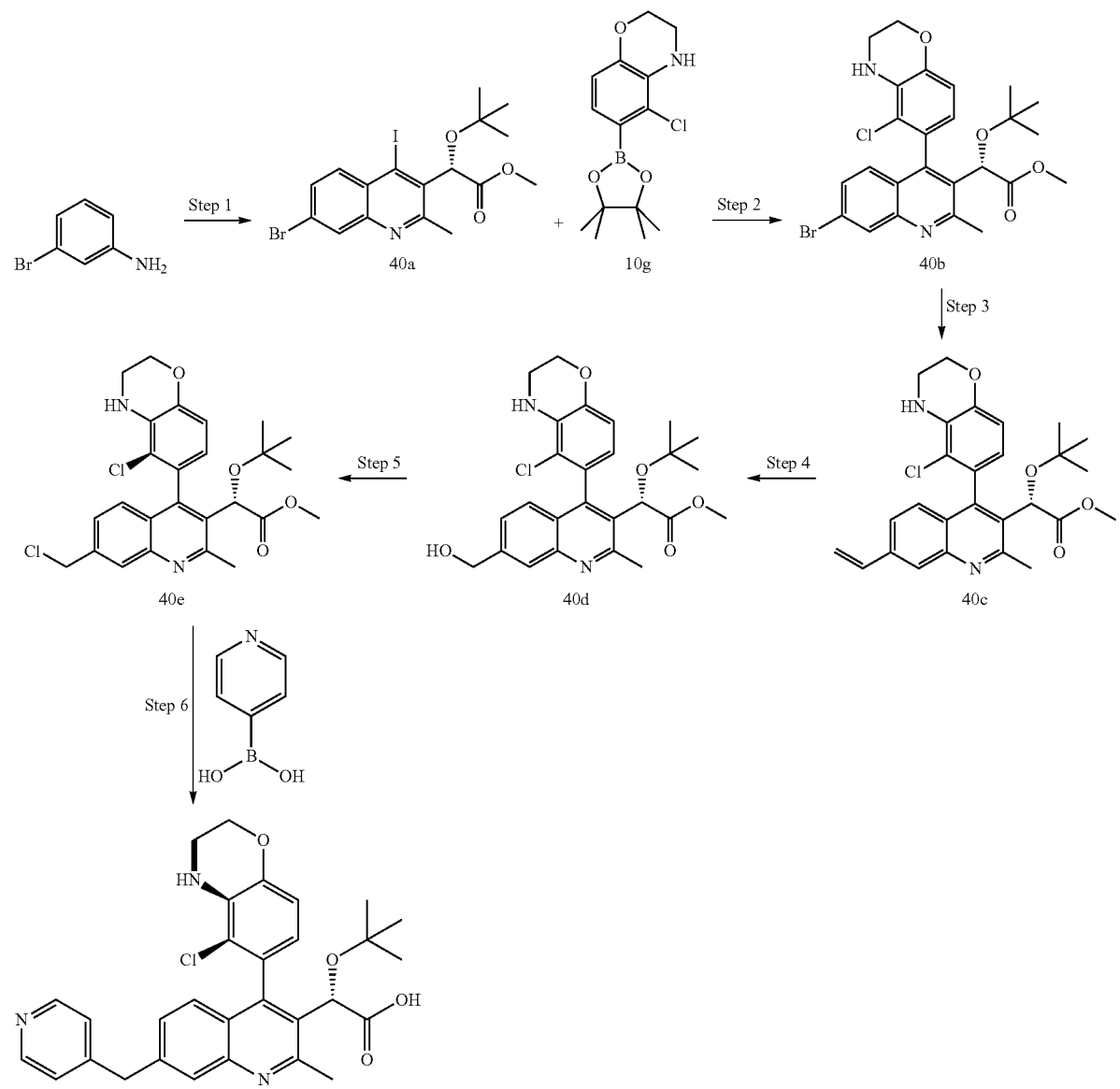

Step 1:
The 7-bromo-4-iodoquinoline 40a is synthesized from 3-bromoaniline using the same protocols as those described for the preparation of iodoquinoline fragment 1i in Example 1.

Step 2:
The 7-bromo-4-iodoquinoline 40a (2.9 g, 5.9 mmol) is combined with boronate 10g (2 g, 6.8 mmol), potassium carbonate (2.4 g, 17.6 mmol), and Pd[PPh$_3$]$_4$ (680 mg, 0.59 mmol) in DMF (24 mL). The solution is degassed (Ar) and then heated at 105° C. for 5 h. The cooled solution is diluted with EtOAc (200 mL) and washed with brine (3×). The organic phase is dried (MgSO$_4$), filtered and concentrated to dryness. The residue is purified by CombiFlash® Companion to afford compound 40b as a mixture of atropisomers (670 mg, 21% yield).

Step 3:
To a solution of bromide 40b (670 mg, 1.26 mmol) in THF (30 mL) is added vinyltributyltin (0.42 mL, 1.38 mmol). Following degassing by bubbling Ar for 10 min under sonication, PdCl$_2$-[PPh$_3$]$_2$ (0) (88 mg, 0.125 mmol) is added followed by degassing for another 5 min. The reaction mixture is stirred at 75° C. for 20 h before being concentrated to dryness. The residue is purified by CombiFlash® Companion to afford compound 40c (400 mg, 66% yield) which is used as in the following step.

Step 4:
To a solution of compound 40c (339 mg, 0.7 mmol) in THF (8 mL) and water (4 mL) at RT is added OsO$_4$ (177 µL, 2.5% soln in t-butanol, 0.014 mmol) followed by NMO (93 mg, 0.8 mmol). The reaction is stirred for 16 h but is not complete. The same quantities of OsO$_4$ and NMO are again added and stirring continues for an additional 1 h. Sodium periodate (196 mg, 0.92 mmol) is added to generate the intermediate aldehyde. The reaction mixture is poured into a saturated solution of aqueous Na$_2$S$_2$O$_3$ and water (50 mL) is added before it is extracted with DCM (3×). The solvent is filtered using a phase separator filter and concentrated. The residue is dissolved in MeOH (10 mL) and treated with NaBH$_4$ (80 mg, 2.1 mmol) at RT for 1 h to give the crude alcohol. A saturated solution of NH$_4$Cl is added, followed by water (50 mL) and the mixture then is extracted with DCM (3×). The phases are separated using a phase separator filter and the organic phase is concentrated. The residue is purified using the CombiFlash® Companion to afford the alcohol 40d (171 mg, 50% yield).

Step 5:
To a solution of alcohol 40d (171 mg, 0.35 mmol) in anhydrous DCM (5 mL) at RT is added anhydrous DMF (1 drop) followed by thionyl chloride (51.5 µL, 0.7 mmol). The resulting solution is stirred for 1 h before being diluted with DCM (5 mL) and then washed with a saturated solution of NaHCO$_3$ (5 mL). After being stirred for 1 min, the mixture is passed through a phase separator filter and concentrated to afford chloride 40e (160 mg, 90% yield) as a pale yellow solid, which is used as is in the following step.

Step 6:
In a vial suitable for microwave, the following are dissolved in anhydrous DMF (2 mL); benzyl chloride 40e (40 mg, 0.08 mmol), 4-pyridylboronic acid (24 mg, 0.2 mmol), K$_3$PO$_4$ (51 mg, 0.24 mmol), Pd(OAc)$_2$ (4 mg, 0.018 mmol), and triphenylphosphine (8.5 mg, 0.032 mmol). The vial is capped and is degassed by bubbling Ar under sonication for 5 min before being heated at 120° C. for 20 min in a microwave. The crude mixture is diluted with EtOAc (200 mL) and washed with brine (3×). The phases are filtered through a phase separator filter and concentrated to dryness. The residue is purified by CombiFlash® Companion to afford the mixture of atropisomeric methyl esters (33 mg, 76% yield) as a pale yellow oil. A solution of this mixture (33 mg) in THF (2 mL) and MeOH (1 mL) and 5N NaOH (72 µL, 0.36 mmol) is stirred at 45° C. for 3 h. Acetic acid is added until the solution is acidic and the resulting mixture is then concentrated. Final purification to separate the atropisomers (diastereomers) is performed by preparative HPLC to afford after lyophilization compound 1035 (1.25 mg, 4% yield) as an amorphous solid.

It would be obvious to those skilled in the art that intermediates 40a, 40b and 40e can be used to make a variety of other compounds. Intermediate 40a can be coupled to any of the boronate fragments described herein in Examples 4-39 via Suzuki coupling reaction to give intermediates analogous to 40b having different R$^4$ substituents. Intermediates 40b and 40e can then be further modified in a variety of ways that would be evident to those skilled in the art, including directly attached amines and benzylic-type amines derivatives via Buchwald-type coupling or direct alkylation, respectively, with the corresponding amine; the details of the synthesis of two compounds, 1074 (Example 41) and 1071 (Example 42) are described below.

Example 41

Synthesis of Compound 1074

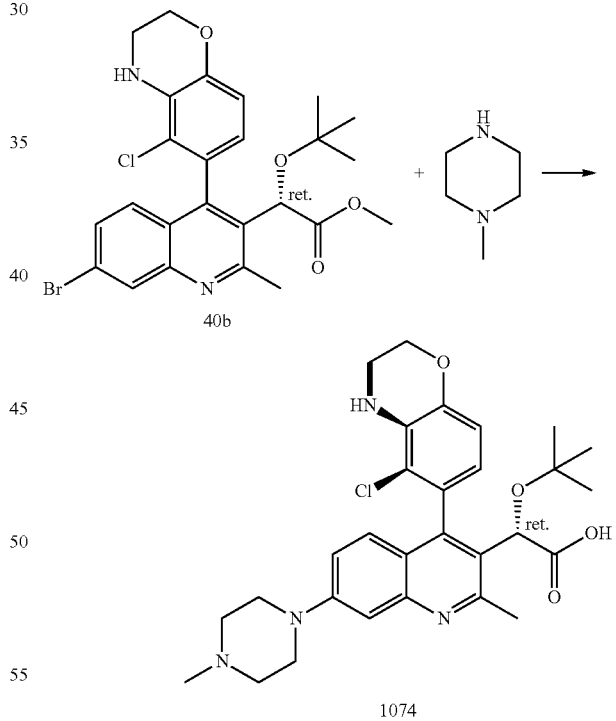

In a vial suitable for microwave reactions is added bromide 40b (15 mg, 0.028 mmol), acetyltrimethylammonium bromide (2.1 mg, 0.006 mmol), Pd[(tBu)$_3$P]$_2$ (2.6 mg, 0.003 mmol), 1-methylpiperazine (4 µL, 0.037 mmol), and a solution of 2 M sodium carbonate (21 µL, 0.042 mmol). The reagents are dissolved in toluene (1.0 mL) before being capped and then submitted directly to the following microwave conditions: 20 min at 145° C. The mixture is concentrated to dryness and purified by CombiFlash® Companion to afford the methyl esters of the atropisomeric mixture (8 mg, 52% yield) as a pale yellow oil. This mixture is dissolved in THF (3 mL) and MeOH (1.5 mL) before being treated with 5N NaOH (17 µL, 0.09 mmol). The solution is heated to 55° C. for 16 h before being acidified with AcOH and concentrated to dryness. The mixture is purified by preparative HPLC to separate the atropisomers (diastereomers) and afford after lyophilization, compound 1074 as a yellow amorphous solid (1 mg, 12% yield).

Example 42

Synthesis of Compound 1071

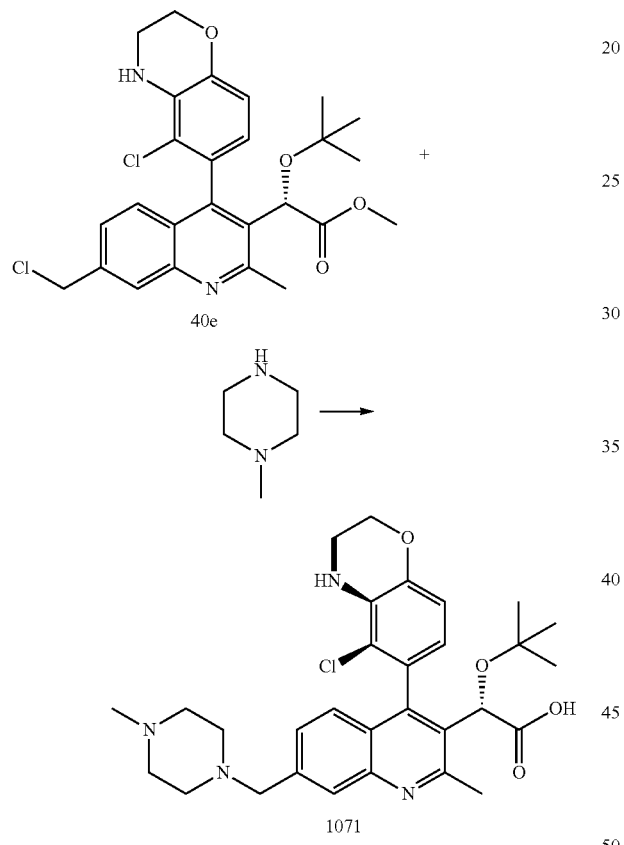

To a solution of chloride 40e (25 mg, 0.05 mmol) in DMF (3 mL) is added KI (2.5 mg, 0.015 mmol), 1-methylpiperazine (8.8 µL, 0.08 mmol), and triethylamine (17 µL, 0.12 mmol). The reaction mixture is stirred at RT for 24 h. The reaction mixture is diluted with EtOAc (40 mL) and washed with brine (3×). The mixture is filtered through a phase separator filter and concentrated to dryness to afford the atropisomeric mixture of esters (28 mg, 100% yield) as a pale yellow oil. The mixture of esters is dissolved in THF (3 mL) and MeOH (1.5 mL) and 5N NaOH (59 µL, 0.3 mmol) is added. The solution is heated to 55° C. for 16 h before being acidified with AcOH and concentrated. The atropisomers (diastereomers) are separated by preparative HPLC to afford (after lyophilization) compound 1071 as orange solid (8.5 mg, 30% yield).

Example 43

Synthesis of Compound 1057

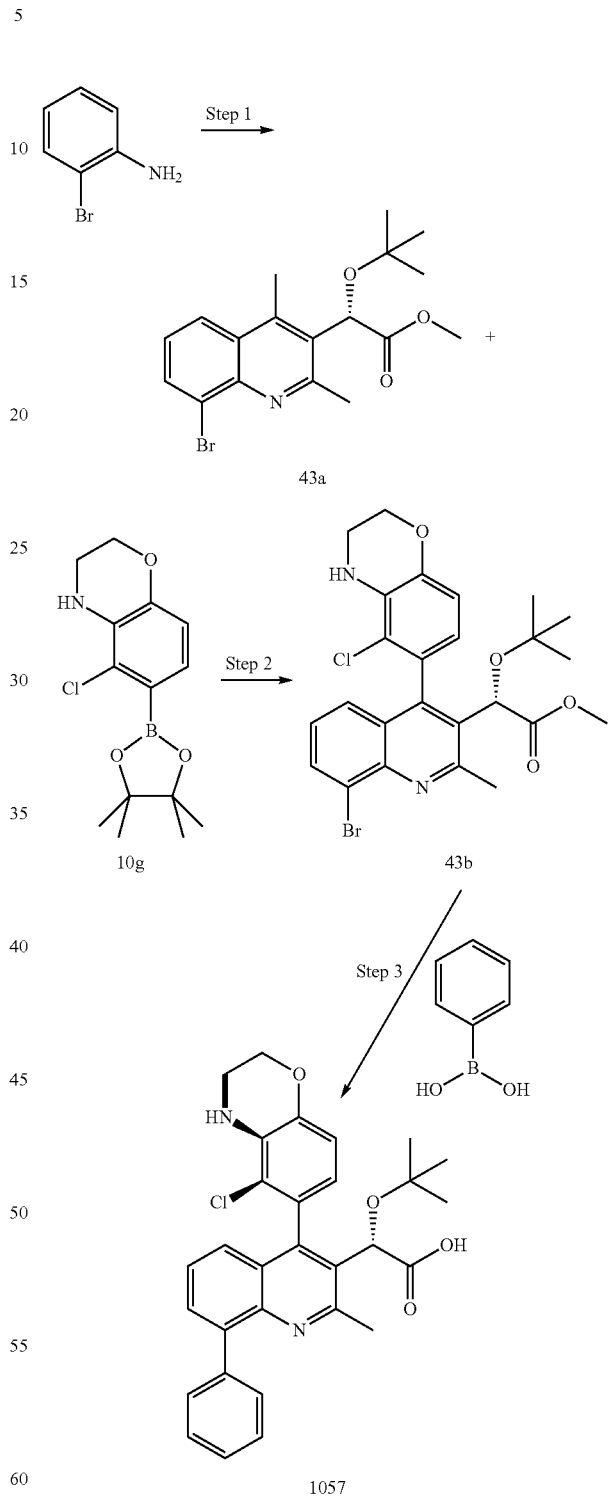

Step 1:

8-bromo-4-iodoquinoline 43a is synthesized from 2-bromoaniline using the same protocols as those described for the preparation of iodoquinoline fragment 1i in Example 1.

Step 2:

In a suitable microwave vessel, quinoline 43a (740 mg, 1.5 mmol) is added to boronic ester 10g (511 mg, 1.73 mmol), Pd[PPh$_3$]$_4$ (347 mg, 0.3 mmol) and K$_2$CO$_3$ (623 mg, 4.5 mmol) in DMF (8 mL). The vessel is sealed and heated for 25 min at 135° C. The cooled reaction mixture is filtered through Celite® and the filtrate is diluted with EtOAc. The organic phase is washed with water, brine, dried (MgSO$_4$), filtered and concentrated under vacuum. The crude product is purified by CombiFlash® Companion to afford a mixture of esters 43b (426 mg, 53% yield, mixture of two atropisomers).

Step 3:

A mixture of bromide 43b (60 mg, 0.011 mmol), phenylboronic acid (19.2 mg, 0.016), Pd[PPh$_3$]$_4$ (26 mg, 0.02 mmol) and K$_2$CO$_3$ (47 mg, 0.034 mmol) in DMF (1.5 mL) and water (0.2 mL) is heated to 125° C. for 13 min in a microwave. The cooled reaction mixture is filtered through Celite® and the filtrate is diluted with EtOAc. The organic phase is washed with water, brine, dried (MgSO$_4$), filtered and concentrated under vacuum. The crude product is purified by CombiFlash® Companion to give a crude product mixture (32.8 mg, 55% yield). This mixture is dissolved in THF/MeOH (3 mL/1.5 mL) and treated with 1.0 N NaOH (1 mL, 1.0 mmol). The reaction mixture is stirred at 60° C. for 4 h before being acidified to pH 4 with 1.0 N HCl. The mixture is then extracted with DCM, dried (MgSO$_4$), filtered and concentrated under vacuum. The residue is purified by preparative HPLC to afford after lyophilization compound 1057 as an orange solid (9.9 mg, 31% yield).

Example 44

Synthesis of C-2 Substituted Analogs

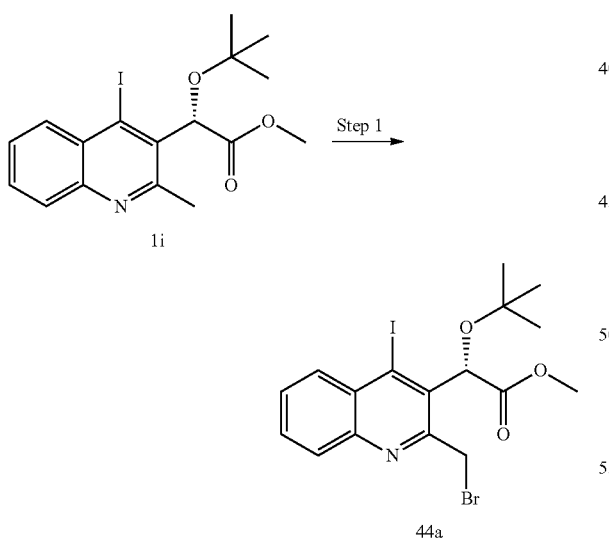

Step 1:

The 4-iodoquinoline 1i (3 g, 7.2 mmol) is dissolved in CCl$_4$ (30 mL) which is subsequently treated with recrystallized NBS (1.4 g, 7.9 mmol) followed by benzoyl peroxide (72 mg, 0.3 mmol). The solution is heated to 75° C. for 24 h. The solvent is removed and the crude product taken up in EtOAc (250 mL), washed with brine, before being dried (Na$_2$SO$_4$), filtered and concentrated to afford the crude product as an amber gum. This material is purified by CombiFlash® Companion to afford bromide 44a (2.5 g, 70% yield).

It is clear for a person skilled in the art that various analogs can be prepared from compound 44a using a variety of appropriate metal alkoxides (in the case of alcohols) or appropriate anions for nitrogen based nucleophiles; as an example, the synthesis of compound 2005 is shown below

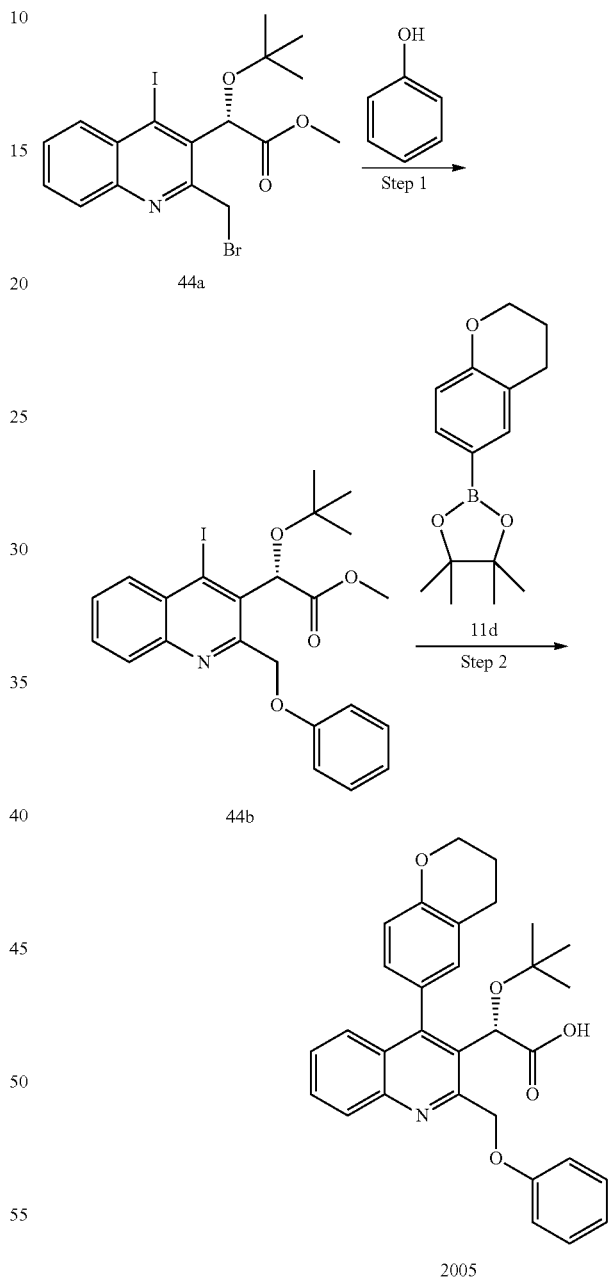

Step 1:

Phenol (19 mg, 0.20 mmol) is dissolved in DMF (1.0 mL) before being treated with K$_2$CO$_3$ (15 mg, 0.10 mmol). The potassium salt is allowed to pre-form over a period of 1 h before a solution of bromide 44a is added (50 mg, 0.10 mmol). The aryl ether is allowed to form overnight at RT. The mixture is taken up in EtOAc (15 mL) and washed with brine before being dried (Na$_2$SO$_4$), filtered and concentrated. The crude product is purified by CombiFlash® Companion to give the aryl ether 44b as a colorless gum (36 mg, 70% yield).

Step 2:

In a microwave vessel is added ether 44b (36 mg, 0.07 mmol), the boronic ester 11d (24 mg, 0.09 mmol), K$_2$CO$_3$ (29 mg, 0.21 mmol) and the catalyst Pd(PPh$_3$)$_4$ (8.3 mg, 0.01 mmol) all dissolved in DMF/H$_2$O (1 mL/0.1 mL). The vessel is capped and submitted to microwave conditions at 110° C. for 15 min. The reaction mixture is diluted with EtOAc and subsequently washed with water. The organic phase is further washed with brine, dried (MgSO$_4$), filtered and concentrated. The material is purified by CombiFlash® Companion to afford the methyl ester of the desired product (23 mg, 63% yield) as a white solid. This material is dissolved in THF (1 mL) and MeOH (0.6 mL) and NaOH (1 N, 0.33 mL, 0.33 mmol) is added. The mixture is stirred at 50° C. for 16 h. The mixture is concentrated in vacuo before being purified by reversed phase preparative HPLC to afford after lyophilization compound 2005 as a yellow amorphous solid (13.5 mg, 60% yield).

It would be obvious to those skilled in the art that intermediate 44a can be used with other nucleophiles to displace the primary bromide (as in the preparation of 44b from 44a), followed by Suzuki coupling with any boronate fragment described in this application to produce a variety of other compounds (for example, the production of compound 2005 from 44b).

Example 45

Synthesis of Compound 1046

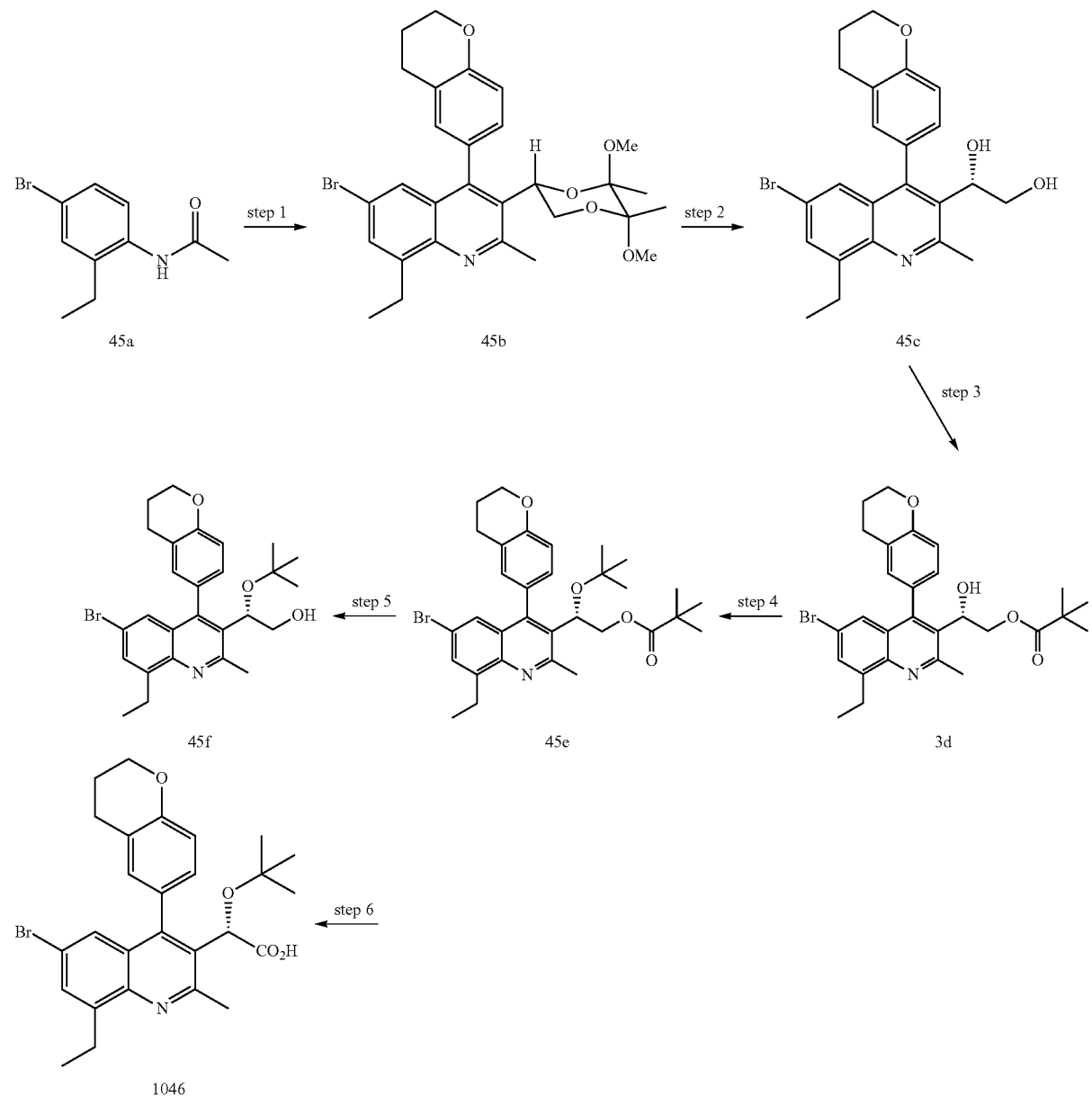

Step 1:

Triflic anhydride (190 μL, 1.13 mmol) is added via syringe over 1 min to a stirred mixture of amide 45a (250 mg, 1.0 mmol) and 2-chloropyridine (130 μL, 1.4 mmol) in DCM (2 mL) at −78° C. After 5 min, the reaction flask is placed in an ice-water bath and warmed to 0° C. Alkyne 2c (232 mg, 0.70 mmol) in DCM (1 mL) is added via syringe. The resulting solution is allowed to warm to RT. After stirring for 30 min, $Et_3N$ (1 mL) is added and the mixture partitioned between DCM (50 mL) and brine (50 mL). The organic layer is washed with brine (50 mL), dried over $Na_2SO_4$ and concentrated. The residue is then purified by CombiFlash® Companion giving quinoline 45b (380 mg, 97% yield).

Step 2:

Quinoline 45b (380 mg, 0.68 mmol) is dissolved in TFA/water (10:1, 10.5 mL) and the reaction is stirred at RT. After 30 min, the reaction mixture is concentrated under reduced pressure, diluted with saturated $NaHCO_3$ (5 mL) and extracted with DCM (3×10 mL). The combined organic layers are dried over $Na_2SO_4$ and concentrated to give diol 45c (299 mg, >99% yield).

Step 3:

Trimethylacetyl chloride (100 μL, 0.81 mmol) is added to a 0° C. solution of diol 45c (299 mg, 0.68 mmol) and $Et_3N$ (280 μL, 2.0 mmol) in DCM (3.8 mL). The reaction is allowed to come to RT and stir overnight. The reaction is quenched with water (10 mL) and washed with EtOAc (10 mL). The organic layer is dried over $Na_2SO_4$ and concentrated. The mixture is purified by CombiFlash® Companion to give ester 45d (85 mg, 24% yield).

Step 4:

One drop of 70% perchloric acid is added to a stirred solution of alcohol 45d (85 mg, 0.161 mmol) dissolved in tert-butyl acetate (1.8 mL) at RT and the mixture stirred overnight. The reaction is quenched by addition of saturated $NaHCO_3$ (5 mL) and the mixture extracted with EtOAc (5 mL). The organic layer is dried over $Na_2SO_4$, filtered and the solvent evaporated. The residue is purified by CombiFlash® Companion to give tent-butyl ether 45e (40 mg, 43% yield).

Step 5:

$LiBH_4$ in THF (2 M, 69 μL, 0.14 mmol) is added to a solution of ester 45e (40 mg, 0.069 mmol) dissolved in THF (1 mL) and the reaction mixture is stirred overnight at RT. Excess reagent is quenched with HCl (three drops, lots of effervescence) and the mixture neutralized with $NaHCO_3$ (10 mL) and extracted with EtOAc (3×10 mL). The combined organic layers are dried over $Na_2SO_4$ and concentrated to give crude alcohol 45f (27 mg, 79% yield), which was used directly in the next step.

Step 6:

Dess-Martin periodinane (30 mg, 0.07 mmol) is added to a solution of alcohol 45f (27 mg, 0.54 mmol) dissolved in DCM (0.4 mL). After 2 h, the reaction mixture is then applied to a plug of $SiO_2$ (1.5×1 cm) and the product eluted with 1:1 hexanes/EtOAc (20 mL). The filtrate is evaporated to give the crude aldehyde which is then dissolved in 1:1 THF/tBuOH (2 mL) and 2,3-dimethyl-2-butene (1M in THF, 0.5 mL, 0.5 mmol) is added. A separate solution of $NaClO_2$ (39 mg, 0.44 mmol) and $NaH_2PO_4$ (32 mg, 0.27 mmol) in water (1 mL) is added to the first solution and the reaction stirred at RT. After 20 min, the reaction is diluted with water (5 mL) and extracted with EtOAc (3×10 mL). The organic layer is dried over $Na_2SO_4$ and concentrated. The residue is purified by preparative HPLC to give carboxylic acid 1046 (6 mg, 20% yield).

Example 46

Alternative Synthesis of Boronate Fragment 39K

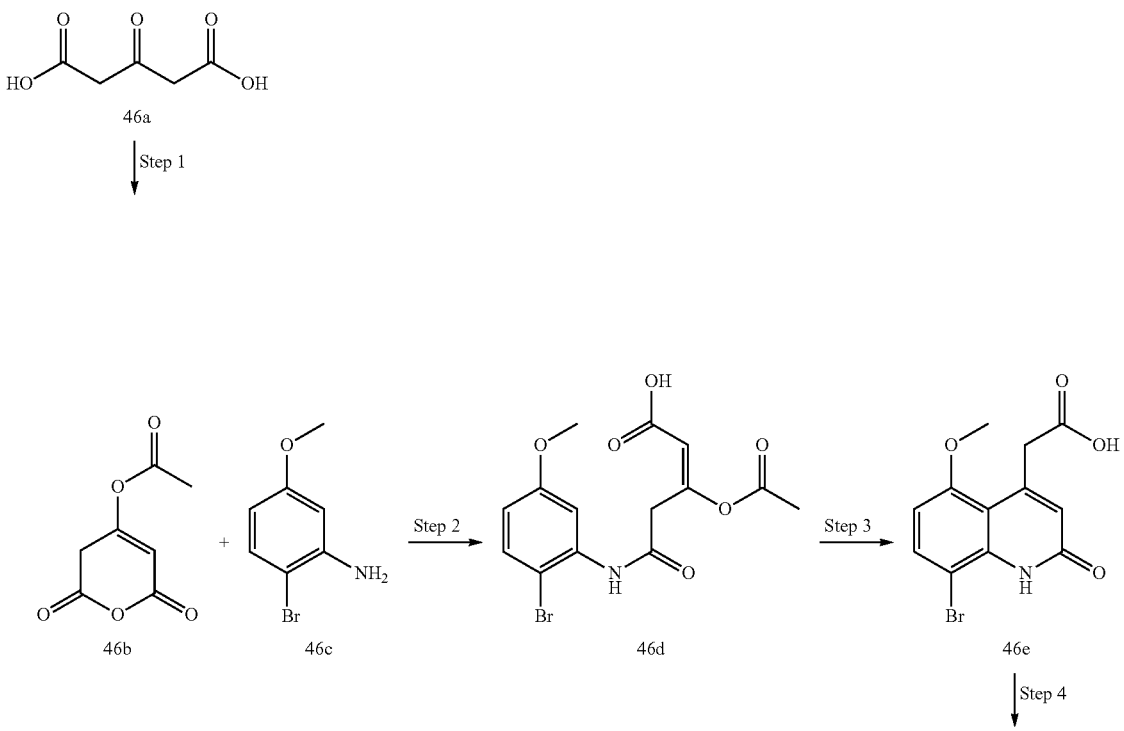

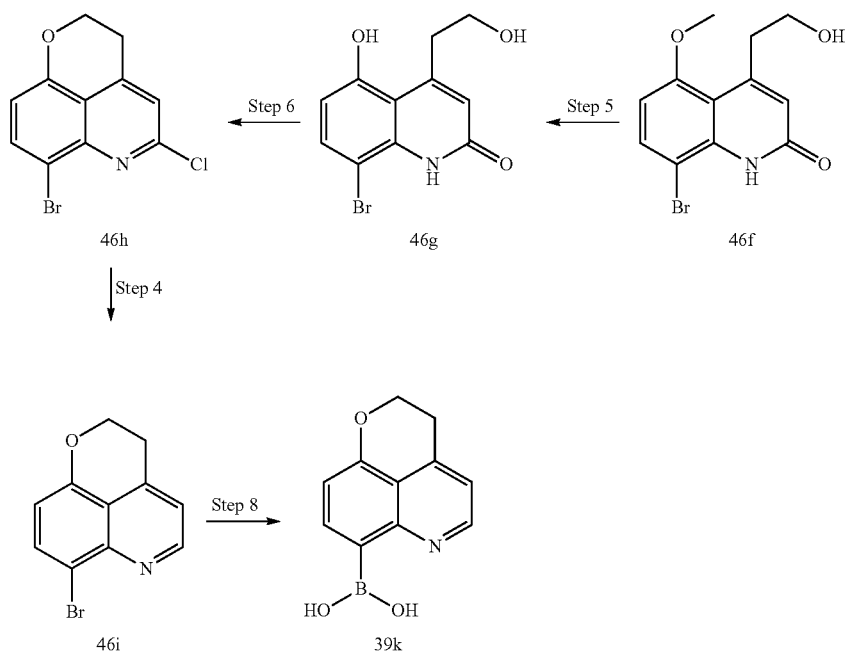

Step 1:

1,3-acetonedicarboxylic acid 46a (30 g, 205.3 mmol) is added in portions to acetic anhydride (55 g, 587.7 mmol) and the mixture is stirred at 35° C. for 23 h. The mixture is filtered and the filtrate is diluted with benzene (200 mL) and the solution stored at 5° C. for 3 h. The suspension formed is filtered and the solid is dried under vacuum to give compound 46b as a pale yellow solid (26.9 g, 70% yield).

Step 2:

To a stirred solution of aniline 46c (7.5 g, 44 mmol) in AcOH (50 mL) is added 46b (8.0 g, 40 mmol) portionwise. Following addition, the reaction mixture is warmed to 35° C. After 2 h, the reaction mixture is cooled to RT and poured in ice/water (600 mL). The resulting precipitate is isolated by filtration, rinsed with water (100 mL) and dried under vacuum to give 46d (9.1 g, 61% yield).

Step 3:

Compound 46d (5.7 g, 15.4 mmol) is added portionwise to concentrated sulfuric acid (20 mL) at RT, temperature of the reaction mixture is kept below 30° C. during addition. The mixture is stirred at RT for 30 min and then poured in ice/water (400 mL). The resulting precipitate is isolated by filtration, rinsed with water and dried under vacuum to give 46e (3.5 g, 72% yield) as a white solid.

Step 4:

The borane solution (1.0 M in THF, 10.5 ml, 10.5 mmol) is added dropwise to an ice cold solution of quinolone 46e (1.5 g, 4.8 mmol) in dry THF (40 mL) under a $N_2$ atmosphere. After the addition, the reaction is allowed to warm to RT and stirred for 22 h (reaction not completed by HPLC, 15% starting material). An extra equivalent of $BH_3$ is added at 0° C. and the reaction mixture is heated to 45° C. for 2 h. The reaction mixture is carefully quenched with 1.0 N NaOH (10 mL) and THF is removed under vacuum. The mixture is poured in EtOAc (100 mL) and the desired compound crashed out of the solution under these conditions. The solid recovered by filtration is dried under vacuum to give compound 46f as a grey solid (1.1 g, 79% yield).

Step 5:

To a solution of 46f (1.1 g, 3.8 mmol) in DCM (60 mL) at −78° C. is added dropwise a 1.0 M $BBr_3$ solution (23 mL, 23 mmol). The cooling bath is removed after 1 h and the mixture is stirred at RT for 16 h (by HPLC, ~30% cyclized product 46h is formed). The mixture is poured in ice/water (100 mL) and the white precipitate that formed is filtered and dried under vacuum to give 46g (773 mg, 71% yield).

Step 6:

To a solution of compound 46g (773 mg, 2.27 mmol) in THF (30 mL) is added $PPh_3$ (928 mg, 3.5 mmol) followed by DIAD (0.69 ml, 3.5 mmol) (dropwise) and the solution is stirred at RT for 2 h. The reaction mixture is concentrated under vacuum and the crude product is directly added portionwise to $POCl_3$ (2 mL) at RT. The reaction mixture is stirred at 100° C. for 45 min and then cooled to room temperature. The mixture is concentrated under vacuum (to remove $POCl_3$) and the crude product is diluted with DCM. The organic phase is washed with 1.0 N NaOH, water, and brine, dried ($MgSO_4$), filtered and concentrated under vacuum. The crude product is purified by CombiFlash® Companion (Hexanes/EtOAc 9/1 to 1/1) to give 46h as a pale yellow solid (445 mg, 91% yield).

Step 7:

To a solution of chloroquinoline 46h (30 mg, 0.1 mmol) in TFA (1 mL) is added zinc (34 mg; 0.5 mmol). The reaction mixture is stirred at RT for 16 h. The mixture is filtered, concentrated under vacuum, then diluted with 1.0 N NaOH (5 mL) and extracted with DCM (3×). The combined organic extracts are washed with water and brine, dried ($MgSO_4$), filtered and concentrated under vacuum. The crude product was purified by combi flash (Hexanes/EtOAc 6/4 to 4/6) to give 46i as a pale yellow solid (26 mg, quantitative yield).

Step 8:

The reaction is done following a similar procedure as described in step 9 of example 39 except starting with 46i and using Pd(Ph₃)₄ as catalyst to give 39k as a white solid.

Example 47

Synthesis of Compound 1093

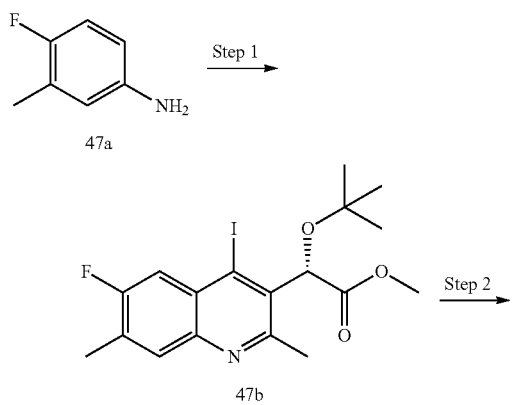

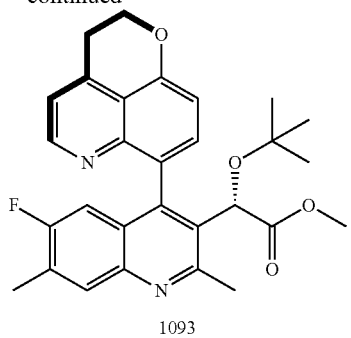

Step 1:
Iodoquinoline 47a is synthesized from aniline 46a using the same protocols as those described for the preparation of iodoquinoline fragment 1i in Example 1.

Step 2:
Reaction is carried out exactly as described in step 2 of example 43 using iodo 47b and boronic acid 39k to give compound 1093.

Example 48

Synthesis of Compound 1015 and 1016

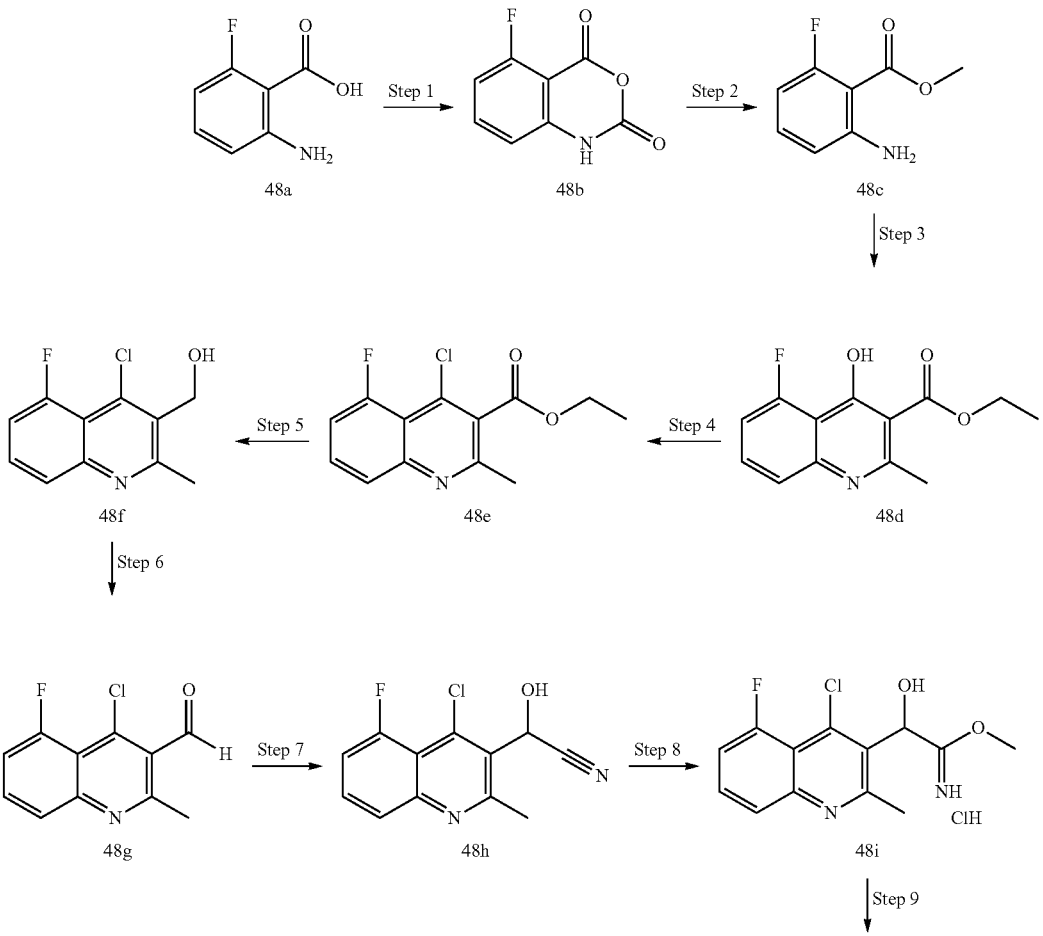

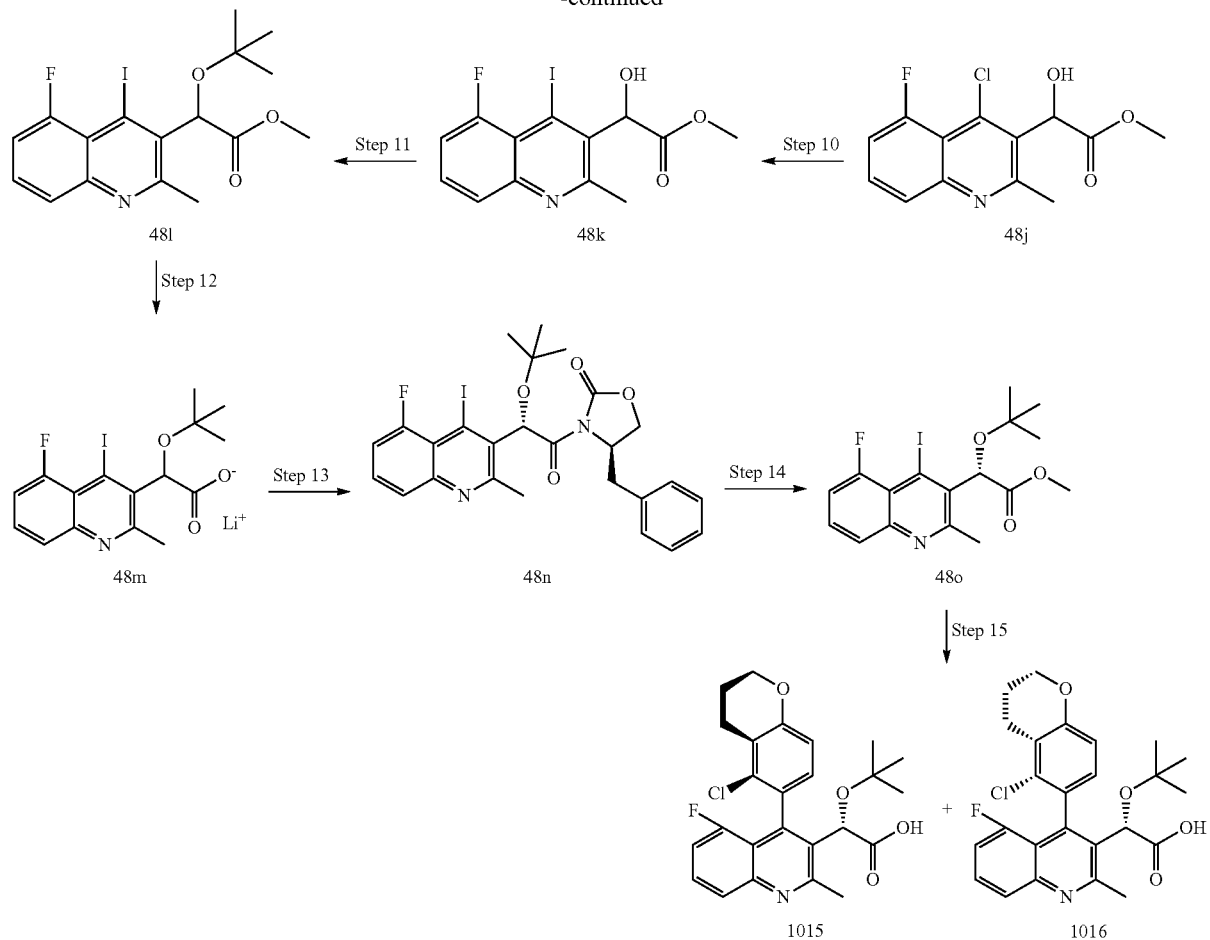

Step 1:

A 1.93 M phosgene solution in toluene (106.9 mL, 206.3 mmol) is added to a vigorously stirred suspension of anthranilate 48a (25.6 g, 165 mmol) in toluene (150 mL) in a pressure bottle. The reaction vessel is sealed and heated to 100° C. behind safety shield overnight. An additional amount of phosgene solution (42.7 mL; 82.5 mmol) is added to the cooled mixture and the reaction mixture is heated to 100° C. for an additional 4 h then is allowed to cool slowly to 0° C. The resulting suspension is filtered, the solid is washed with cold toluene and air dried overnight to give 48b (28.1 g, 94% yield) as a white solid.

Step 2:

A solution of 48b (28.1 g, 155 mmol) and DMAP (1.89 g, 15.5 mmol) in MeOH (500 mL) is heated at reflux for 24 h. The cooled reaction mixture is concentrated under reduced pressure and diluted with EtOAc (200 mL). The resulting solution is washed twice with phosphate buffer pH 6.0, dried (MgSO$_4$), filtered and concentrated under reduced pressure to give compound 48c (26.1 g, 99% yield).

Step 3:

A solution of 48c (26.0 g, 154 mmol), ethyl 3-ethoxybut-2-enoate (25.5 g, 161 mmol) and p-TsOH monohydrate (75.3 mg, 0.40 mmol) in o-xylene (500 mL) is heated (bath temp: 158° C.) for 15 h using a Dean-Stark trap to remove the produced EtOH. The mixture is cooled to RT and added slowly (25 min) to an ice-cold solution of 21% (w/w) NaOEt (60.26 mL, 161.5 mmol) in EtOH. The resulting brownish solution is heated to 80° C. for 4 h. The resulting suspension is allowed to cool to RT and is concentrated under reduced pressure. Water (400 mL) is added to the residual solid and the mixture is washed with Et$_2$O (2×400 mL). The aqueous phase is cooled to 0° C. and slowly acidified to pH 4 using 1 N HCl. The resulting suspension is filtered and the recovered solid is washed with dilute HCl (pH 4, 25 mL), dried under reduced pressure to give compound 48d (24.1 g, 63% yield) as a pale yellowish solid.

Step 4:

A mixture of 48d (24.1 g, 96.7 mmol) and POCl$_3$ (250 mL) is heated at reflux for 1 h. The cooled reaction mixture is concentrated under reduced pressure. The residue is poured into ice-water (500 mL) and stirred vigorously. The pH is adjusted to 6.5 using aqueous 5 N NaOH. The mixture is extracted with EtOAc and the combined organic layers are washed with brine, dried (MgSO$_4$), filtered and concentrated under reduced pressure to give compound 48e (25.2 g, 97% yield) as a black tar. The crude product is used as in next step.

Step 5:

A solution of 1 M DIBAL-H in toluene (200 mL, 200 mmol) is added (45 min) to a cold (−78° C.) solution of 48e (25.2 g, 94.1 mmol) in DCM (300 mL). The reaction mixture is stirred at RT for 30 min then re-cooled to −78° C. An aqueous 20% Rochelle salt solution (200 mL) is added and the mixture is allowed to warm to RT. The resulting suspension is diluted with DCM (300 mL) and the layers are separated. The aqueous layer is extracted twice with DCM. The combined organic layers are dried (MgSO$_4$), filtered and concentrated under reduced pressure. The resulting solid is dried at 50° C. under reduced pressure to give alcohol 48f (15.18 g, 71% yield) as a brown solid.
Step 6:
Et$_3$N (18.5 mL, 133 mmol) is added to a cool solution of 48f (10.0 g, 44.3 mmol) in DMSO (50 mL). Pyridine SO$_3$ complex (17.6 g, 111 mmol) is next added to the mixture in small portions over 5 min. The reaction mixture is stirred for 1 h then is poured in ice cold water (400 mL) and the resulting suspension is filtered. The solid is dissolved in DCM (200 ml) and the solution is dried (MgSO$_4$), filtered and concentrated under reduced pressure to give aldehyde 48g (9.01 g, 91% yield) as a brown solid.
Step 7:
ZnI$_2$ (6.42 g, 20.1 mmol) and TMSCN (10.7 mL, 80.5 mmol) are successively added to an ice-cold solution of aldehyde 48g (9.00 g, 40.2 mmol) in DCM (300 mL). The mixture is stirred at 0° C. for 1 h and at RT for 4 h. The reaction mixture is washed with water, dried (MgSO$_4$), filtered and concentrated under reduced pressure to give cyanohydrin 48h (12.0 g, 93% yield) as a tan crystalline solid.
Step 8:
A saturated solution of hydrogen chloride in MeOH (80 mL) is added to a suspension of 48h (12.2 g, 37.8 mmol) in MeOH (20 mL). The reaction mixture is stirred at RT for 2 h. N$_2$ is bubbled in the mixture for 30 min to remove excess HCl. The mixture is concentrated under reduced pressure to give compound 48i (11.1 g, 92% yield) as a tan crystalline solid.
Step 9:
A solution of 48i (11.05 g, 34.6 mmol) in aqueous 1 N HCl (150 mL) is stirred for 1 h at RT. The reaction mixture is diluted with water (100 mL) and filtered over Celite®. The pH of the aqueous filtrate is adjusted to 7.5 using aqueous 5 N NaOH. The solution is extracted twice with EtOAc. The combined organic layers are washed with brine, dried (MgSO$_4$), filtered and concentrated under reduced pressure to give methyl ester 48j (10.2 g, 104% yield) as a tan solid.
Step 10:
Chloroquinoline 48j (10.2 g, 36.0 mmol) is dissolved in a solution of 4 N HCl in 1,4-dioxan (100 mL). The solution was concentrated under reduced pressure. A mixture of the resulting HCl salt and NaI (27.0 g, 180 mmol) in MeCN (250 mL) is heated at reflux for 1 h. The cooled reaction mixture is diluted with EtOAc (300 mL) and the mixture is washed with aqueous 5% NaHCO$_3$ solution and aqueous 10% Na$_2$S$_2$O$_4$ solution. The organic layer is dried (MgSO$_4$), filtered and concentrated under reduced pressure to give iodoquinoline 48k (11.3 g, 84% yield) as a tan solid.
Step 11:
HClO$_4$ (1.17 mL, 13.6 mmol) is added to a suspension of 48k (3.40 g, 9.06 mmol) in t-butyl acetate (100 mL) and DCM (150 mL). The reaction mixture is stirred at RT overnight then is diluted with EtOAc (150 mL). The solution is washed twice with aqueous 5% NaHCO$_3$ solution, dried (MgSO$_4$), filtered and concentrated under reduced pressure. The residue is purified by flash chromatography (Combi-Flash; EtOAc/hexane) to give t-butylether 48l (2.76 g, 71% yield) as a white solid.
Step 12:
A mixture of ester 48l (5.01 g, 11.6 mmol) and LiOH hydrate (487 mg, 11.6 mmol) in THF (30 mL), MeOH (15 mL) and water (15 mL) is heated at reflux for 11 h. The reaction mixture is concentrated under reduced pressure. The residue is successively taken in EtOH (2×150 mL) and toluene (100 mL) and concentrated under reduced pressure to remove traces of water. The solid is dried under reduced pressure to give lithium salt 48m (5.10 g, 104% yield) as a pale yellow solid.
Step 13:
Pivaloyl chloride (1.43 mL, 11.6 mmol) is added to an ice-cold solution of 48m (5.08 g, 11.6 mmol) in THF (100 mL). The mixture is stirred at 0° C. for 30 min then cooled to −78° C. (mixed anhydride solution). A solution of 2.5 M n-BuLi in hexane (4.87 mL, 12.2 mmol) is added dropwise (until an orange color persisted) to a cold solution (−40° C.) of (R)-(+)-4-benzyl-2-oxazolidinone (2.16 g, 12.2 mmol) and triphenylmethane (10 mg) in THF (30 mL). The resulting mixture is cooled to −78° C. and rapidly cannulated into the mixed anhydride solution prepared previously. The reaction mixture is stirred at −78° C. for 30 min then is allowed to warm to RT and stirred at this temperature for 30 min. Aqueous 5% KHCO$_3$ solution (4 mL) is added and the mixture is concentrated under reduced pressure. The residue is diluted with EtOAc (250 mL) and the solution is successively washed with aqueous 5% KHCO$_3$ solution and brine, dried (MgSO$_4$), filtered and concentrated under reduced pressure. The residue is purified by flash chromatography (Combi-Flash; EtOAc/hexanes) to give the desired diasteroisomer 48n (1.34 g, 20% yield; higher retention time on reverse phase HPLC).
Step 14:
DBU (416 µL, 2.78 mmol) and NaI (1.74 g, 11.6 mmol) are successively added to a cold (−5° C.) solution of oxazolidinone 48n (1.34 g, 2.32 mmol) in THF (6 mL) and MeOH (12 mL). After 1 h the reaction mixture is concentrated under reduced pressure and EtOAc (100 mL) is added. The solution is washed with aqueous phosphate buffer pH 6.0 and brine, dried (MgSO$_4$), filtered and concentrated under reduced pressure. The residue is purified by flash chromatography (Combi-Flash; EtOAc/hexanes) to give methyl ester 48o (718 mg, 72% yield) as a yellowish crystalline solid.
Step 15:
Reaction is carried out exactly as described in step 2 of example 43 using iodo 48o and boronic acid 6i to give compound 1015 and 1016.

Example 49

C8166 HIV-1 Luciferase Assay (EC$_{50}$)

C8166 cells are derived from a human T-lymphotrophic virus type 1 immortalized but nonexpressing line of cord blood lymphocytes (obtained from J. Sullivan) and are highly permissive to HIV-1 infection. The pGL3 Basic LTR/TAR plasmid is made by introducing the HIV-1 HxB2 LTR sequence from nucleotide −138 to +80 (Sca1-HindIII) upstream of the luciferase gene in the pGL3 Basic Vector (a promoterless luciferase expression vector from Promega catalogue #E1751) with the gene for blasticidine resistance cloned in. The reporter cells are made by electroporating C8166 cells with pGL3 Basic LTR/TAR and selecting positive clones with blasticidine. Clone C8166-LTRIuc #A8-F5-G7 was selected by 3 consecutive rounds of limiting dilution under blasticidine selection. Cultures are maintained in complete media (consisting of: Roswell Park Memorial Institute medium (RPMI) 1640+10% FBS+10$^{-5}$ M β-mercaptoethanol+10 µg/mL gentamycin) with 5 µg/mL blasticidine, however, blasticidine selection is removed from the cells before performing the viral replication assay.
Luciferase Assay Protocol
Preparation of Compounds
Serial dilutions of HIV-1 inhibitor compounds are prepared in complete media from 10 mM DMSO stock solutions.

Eleven serial dilutions of 2.5× are made at 8× desired final concentration in a 1 mL deep well titer plate (96 wells). The 12$^{th}$ well contains complete media with no inhibitor and serves as the positive control. All samples contain the same concentration of DMSO 0.1% DMSO). A 25 µL aliquot of inhibitor is added, to triplicate wells, of a 96 well tissue culture treated clear view black microtiter plate (Corning Costar catalogue #3904). The total volume per well is 200 µL of media containing cells and inhibitor. The last row is reserved for uninfected C8166 LTRIuc cells to serve as the background blank control and the first row is media alone.

Infection of Cells

C8166 LTRIuc cells are counted and placed in a minimal volume of complete RPMI 1640 in a tissue culture flask (ex. 30×10$^6$ cells in 10 mL media/25 cm$^2$ flask). Cells are infected with HIV-1 or virus with variant integrase generated as described below at a molecules of infection (moi) of 0.005. Cells are incubated for 1.5 h at 37° C. on a rotating rack in a 5% CO$_2$ incubator and re-suspended in complete RPMI to give a final concentration of 25,000-cells/175 µL. 175 µL of cell mix is added to wells of a 96 well microtiter plate containing 25 µL 8× inhibitors. 25,000 uninfected C8166-LTRIuc cells/well in 200 µL complete RPMI are added to the last row for background control. Cells are incubated at 37° C. in 5% CO$_2$ incubator for 3 days.

Luciferase Assay

50 µL Steady Glo (luciferase substrate T$_{1/2}$=5 hours Promega catalogue #E2520) is added to each well of the 96 well plate. The relative light units (RLU) of luciferase is determined using the LUMIstar Galaxy luminometer (BMG LabTechnologies). Plates are read from the bottom for 2 seconds per well with a gain of 240.

The level of inhibition (% inhibition) of each well containing inhibitor is calculated as follows:

$$\% \cdot \text{inhibition} = \left(1 - \left[\frac{RLU \cdot \text{well} - RLU \cdot \text{blank}}{RLU \cdot \text{control} - RLU \cdot \text{blank}}\right]\right) * 100$$

The calculated % inhibition values are used to determine EC$_{50}$, slope factor (n) and maximum inhibition (I$_{max}$) by the non-linear regression routine NLIN procedure of SAS using the following equation:

$$\% \cdot \text{inhibition} = \frac{I_{max} \times [\text{inhibitor}]^n}{[\text{inhibitor}]^n + IC_{50}^n}$$

TABLES OF COMPOUNDS

Compounds of the invention shown in Tables 1 to 4 are integrase inhibitors. Representative compounds selected from Tables 1 to 3 below have EC$_{50}$ values of no more than 20 µM when tested in the HIV-1 luciferase assay of Example 46.

Retention times (t$_R$) for each compound are measured using the standard analytical HPLC conditions described in the Examples. As is well known to one skilled in the art, retention time values are sensitive to the specific measurement conditions. Therefore, even if identical conditions of solvent, flow rate, linear gradient, and the like are used, the retention time values may vary when measured, for example, on different HPLC instruments. Even when measured on the same instrument, the values may vary when measured, for example, using different individual HPLC columns, or, when measured on the same instrument and the same individual column, the values may vary, for example, between individual measurements taken on different occasions.

TABLE 1

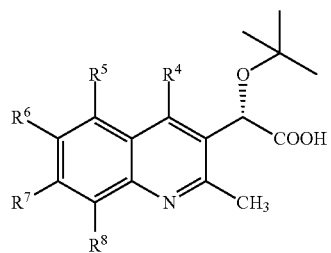

| Cpd | R$^4$ | R$^5$ | R$^6$ | R$^7$ | R$^8$ | t$_R$ (min) | MS (M + H)$^+$ |
|---|---|---|---|---|---|---|---|
| 1001 | 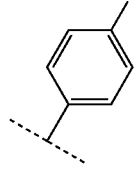 | F | H | H | H | 4.7 | 402.1/ 404.1 |
| 1002 | 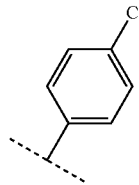 | H | —OCH$_3$ | H | H | 4.6 | 414.1/ 416.1 |

TABLE 1-continued
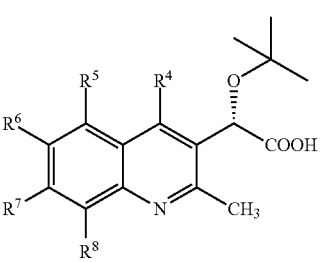
| Cpd | R⁴ | R⁵ | R⁶ | R⁷ | R⁸ | $t_R$ (min) | MS (M + H)⁺ |
|---|---|---|---|---|---|---|---|
| 1003 | 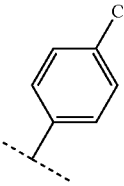 | H | H | —OCH₃ | H | 4.7 | 414.2/ 416.1 |
| 1004 | 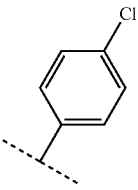 | H | H | H | F | 5.1 | 402.1/ 404.1 |
| 1005 | 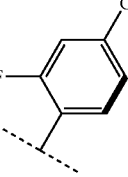 | F | H | H | H | 5.7 | 420.1/ 422.1 |
| 1006 | 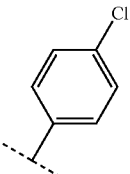 | H | —CH=CH₂ | H | H | 5.4 | 410.1/ 412.1 |
| 1007 | 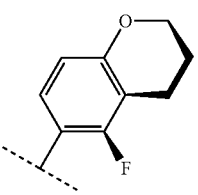 | F | H | H | H | 4.9 | 442.2 |
| 1008 | 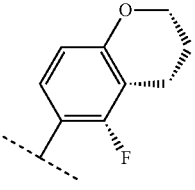 | F | H | H | H | 5.1 | 442.1 |

TABLE 1-continued
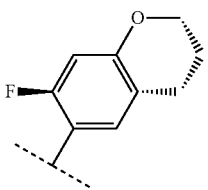
| Cpd | R⁴ | R⁵ | R⁶ | R⁷ | R⁸ | $t_R$ (min) | MS $(M+H)^+$ |
|---|---|---|---|---|---|---|---|
| 1009 | 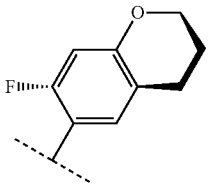 | F | H | H | H | 4.9 | 442.1 |
| 1010 | 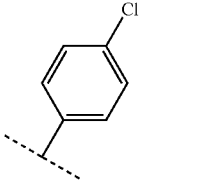 | F | H | H | H | 5.2 | 442.1 |
| 1011 | 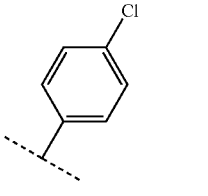 | H | —CN | H | H | 5.4 | 409.2/ 411.2 |
| 1012 | 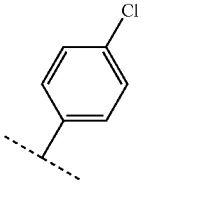 | H | —C(=O)H | H | H | 4.9 | 412.2/ 414.2 |
| 1013 | 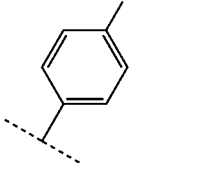 | H | —CH₂OH | H | H | 4.2 | 414.2/ 416.2 |
| 1014 |  | H | —C≡CH | H | H | 5.2 | 408.2/ 410.2 |

TABLE 1-continued

| Cpd | R⁴ | R⁵ | R⁶ | R⁷ | R⁸ | t_R (min) | MS (M + H)⁺ |
|---|---|---|---|---|---|---|---|
| 1015 | (6-Cl-chroman-8-yl) | F | H | H | H | 5.0 | 458.1/460.1 |
| 1016 | (8-Cl-chroman-7-yl) | F | H | H | H | 5.2 | 458.1/460.1 |
| 1017 | (8-Me-chroman-7-yl) | F | H | H | H | 4.9 | 438.2 |
| 1018 | (4-chlorophenyl) | H | H | H | Br | 8.8 | 462.1/464.1/466.1 |
| 1019 | (3-Cl-3,4-dihydro-2H-benzo[b][1,4]oxazin-6-yl) | F | H | H | H | 3.9 | 459.2/461.2 |
| 1020 | (5-Cl-3,4-dihydro-2H-benzo[b][1,4]oxazin-6-yl) | F | H | H | H | 4.2 | 459.2/461.2 |

TABLE 1-continued
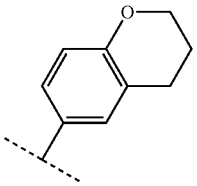
| Cpd | R⁴ | R⁵ | R⁶ | R⁷ | R⁸ | t_R (min) | MS (M + H)⁺ |
|---|---|---|---|---|---|---|---|
| 1021 | 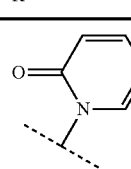 | H | H | 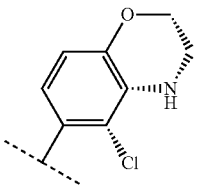 | H | 4.5 | 499.3 |
| 1022 | 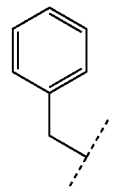 | H | H | 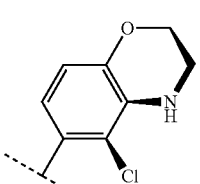 | H | 5.4 | 531.2/ 533.2 |
| 1023 | 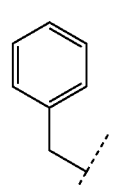 | H | H | 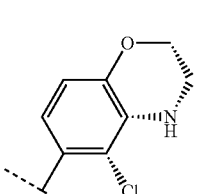 | H | 5.4 | 531.2/ 533.2 |
| 1024 | 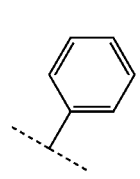 | H | H | 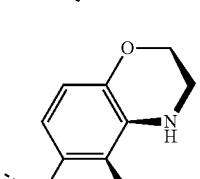 | H | 5.4 | 517.3/ 519.3 |
| 1025 | 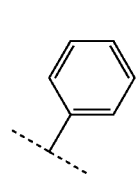 | H | H | 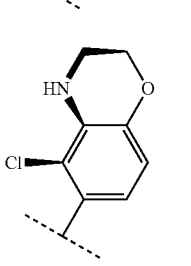 | H | 5.6 | 517.3/ 519.3 |
| 1026 | 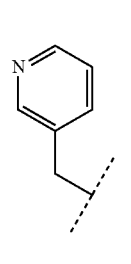 | H | H | (see structure) | H | 3.7 | 532.3/ 534.2 |

TABLE 1-continued
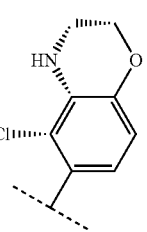
| Cpd | R⁴ | R⁵ | R⁶ | R⁷ | R⁸ | $t_R$ (min) | MS (M + H)⁺ |
|---|---|---|---|---|---|---|---|
| 1027 | 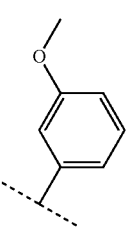 | H | H | 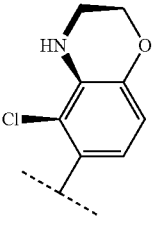 | H | 5.5 | 547.3/ 549.3 |
| 1028 | 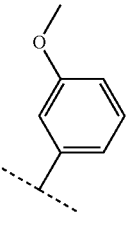 | H | H | 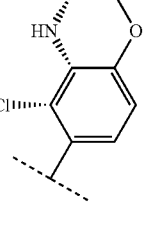 | H | 5.7 | 547.3/ 549.3 |
| 1029 | 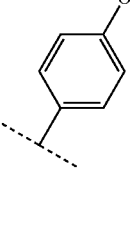 | H | H | 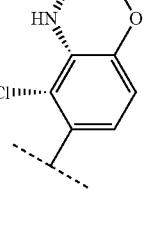 | H | 5.4 | 547.3/ 549.3 |
| 1030 | 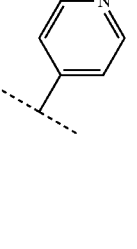 | H | H | 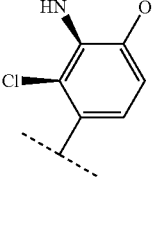 | H | 3.7 | 518.3/ 520.3 |
| 1031 |  | H | H |  | H | 3.8 | 518.3/ 520.3 |

TABLE 1-continued

| Cpd | R⁴ | R⁵ | R⁶ | R⁷ | R⁸ | t_R (min) | MS (M + H)⁺ |
|---|---|---|---|---|---|---|---|
| 1032 | chloro-dihydrobenzoxazine | H | H | pyridin-3-yl | H | 3.7 | 518.3/ 520.3 |
| 1033 | chloro-dihydrobenzoxazine | H | H | pyridin-3-yl | H | 3.8 | 518.3/ 520.3 |
| 1034 | chloro-dihydrobenzoxazine | H | H | pyridin-4-ylmethyl | H | 3.4 | 532.3/ 534.3 |
| 1035 | chloro-dihydrobenzoxazine | H | H | pyridin-4-ylmethyl | H | 3.6 | 532.3/ 534.3 |
| 1036 | chroman-6-yl | H | Br | H | —CH₃ | 5.4 | 498.2/ 500.2 |

TABLE 1-continued

| Cpd | R⁴ | R⁵ | R⁶ | R⁷ | R⁸ | t_R (min) | MS (M + H)⁺ |
|---|---|---|---|---|---|---|---|
| 1037 | (chloro-dihydro-benzoxazine) | H | | phenyl | H | 5.3 | 517.2/ 519.2 |
| 1038 | (chloro-dihydro-benzoxazine) | H | | phenyl | H | 5.5 | 517.2/ 519.2 |
| 1039 | (methyl-chromanyl) | H | H | 3-pyridyl | H | 4.2 | 497.3 |
| 1040 | (chromanyl) | H | t-Bu-NHC(O)CH₂ | H | H | 4.5 | 519.3 |
| 1041 | (chloro-chromanyl) | H | H | 3-pyridyl | H | 4.1 | 517.2/ 519.2 |

TABLE 1-continued
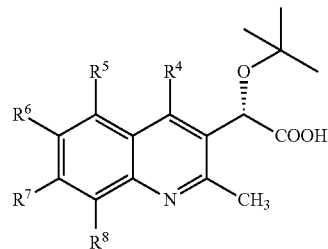
| Cpd | R⁴ | R⁵ | R⁶ | R⁷ | R⁸ | t_R (min) | MS (M + H)⁺ |
|---|---|---|---|---|---|---|---|
| 1042 | 8-Cl-chroman-6-yl (one stereo) | H | H | pyridin-3-yl | H | 4.2 | 517.2/ 519.2 |
| 1043 | 8-Cl-chroman-6-yl | H | H | pyridin-4-yl | H | 4.1 | 517.2/ 519.2 |
| 1044 | 8-Cl-chroman-6-yl (other stereo) | H | H | pyridin-4-yl | H | 4.2 | 517.2/ 519.2 |
| 1045 | chroman-6-yl | H | H | H | —CH₂CH₃ | 5.4 | 434.3 |
| 1046 | chroman-6-yl | H | Br | H | —CH₂CH₃ | 7.1 | 512.2/ 514.2 |

TABLE 1-continued

| Cpd | R⁴ | R⁵ | R⁶ | R⁷ | R⁸ | t_R (min) | MS (M + H)⁺ |
|---|---|---|---|---|---|---|---|
| 1047 | 8-Cl-chroman-7-yl | H | H | pyrimidin-5-yl | H | 4.8 | 518.2/520.2 |
| 1048 | 8-Cl-chroman-7-yl (epimer) | H | H | pyrimidin-5-yl | H | 4.8 | 518.2/520.2 |
| 1049 | 8-Cl-chroman-7-yl | H | H | phenyl | H | 5.9 | 516.2/518.2 |
| 1050 | 8-Cl-chroman-7-yl (epimer) | H | H | phenyl | H | 6.0 | 516.2/518.2 |
| 1051 | chroman-6-yl | H | Br | H | —OCF₃ | 8.2 | 568.1/570.1 |

TABLE 1-continued

| Cpd | R⁴ | R⁵ | R⁶ | R⁷ | R⁸ | t_R (min) | MS (M + H)⁺ |
|---|---|---|---|---|---|---|---|
| 1052 | 6-chromanyl | H | H | H | —CH₃ | 5.0 | 420.3 |
| 1053 | (8-Cl)-chroman-6-yl | H | H | thiazol-2-yl | H | 5.5 | 523.2/ 525.2 |
| 1054 | (8-Cl)-chroman-6-yl | H | H | thiazol-5-yl | H | 5.0 | 523.2/ 525.2 |
| 1055 | (8-Cl)-chroman-6-yl | H | H | 1-methylpyrrol-2-yl | H | 5.5 | 519.2/ 521.2 |
| 1056 | (3-Cl, 4-NH)-chroman-6-yl | H | H | H | phenyl | 5.3 | 517.2/ 519.2 |

TABLE 1-continued

| Cpd | R⁴ | R⁵ | R⁶ | R⁷ | R⁸ | t_R (min) | MS (M + H)⁺ |
|---|---|---|---|---|---|---|---|
| 1057 | 5-Cl-3,4-dihydro-2H-benzo[1,4]oxazin-8-yl | H | H | H | phenyl | 5.5 | 517.2/ 519.2 |
| 1058 | (3S,4R)-5-Cl-3,4-dihydro-2H-benzo[1,4]oxazin-8-yl | H | H | H | 3-methoxyphenyl | 5.3 | 547.2/ 549.2 |
| 1059 | 5-Cl-3,4-dihydro-2H-benzo[1,4]oxazin-8-yl | H | H | H | 3-methoxyphenyl | 5.6 | 547.2/ 549.2 |
| 1060 | (3S,4R)-5-Cl-3,4-dihydro-2H-benzo[1,4]oxazin-8-yl | H | H | H | 4-methoxyphenyl | 5.3 | 547.2/ 549.2 |
| 1061 | 5-Cl-3,4-dihydro-2H-benzo[1,4]oxazin-8-yl | H | H | H | 4-methoxyphenyl | 5.5 | 547.2/ 549.2 |

TABLE 1-continued

| Cpd | R⁴ | R⁵ | R⁶ | R⁷ | R⁸ | t_R (min) | MS (M + H)⁺ |
|---|---|---|---|---|---|---|---|
| 1062 | (chloro-chromane-NH, Cl trans) | H | H | H | 3-pyridyl-CH₂ | 4.3 | 518.2/ 520.2 |
| 1063 | (chloro-chromane-NH, Cl cis) | H | H | H | 3-pyridyl-CH₂ | 4.6 | 518.2/ 520.2 |
| 1064 | (chloro-chromane-NH, Cl trans) | H | H | H | benzyl-CH | 5.9 | 531.2/ 533.2 |
| 1065 | (chloro-chromane-NH, Cl cis) | H | H | H | benzyl-CH | 6.1 | 531.2/ 533.2 |
| 1066 | (chloro-chromane-NH, Cl trans) | H | H | H | 4-pyridyl-CH₂ | 4.3 | 518.2/ 520.2 |

TABLE 1-continued
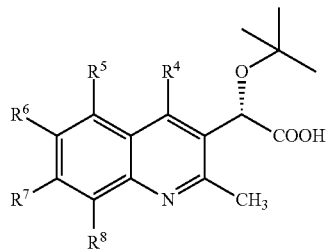
| Cpd | R⁴ | R⁵ | R⁶ | R⁷ | R⁸ | $t_R$ (min) | MS $(M+H)^+$ |
|---|---|---|---|---|---|---|---|
| 1067 | 5-Cl-3,4-dihydro-2H-benzo[b][1,4]oxazin-8-yl | H | H | H | pyridin-4-yl | 4.5 | 518.2/ 520.2 |
| 1068 | 8-Cl-chroman-6-yl | H | H | thiazol-2-yl | H | 5.4 | 523.2/ 525.2 |
| 1069 | 8-Cl-chroman-6-yl | H | H | thiazol-5-yl | H | 5.1 | 523.2/ 525.2 |
| 1070 | 8-Cl-chroman-6-yl | H | H | 1-methyl-1H-pyrrol-2-yl | H | 5.7 | 519.3/ 521.2 |
| 1071 | 5-Cl-3,4-dihydro-2H-benzo[b][1,4]oxazin-8-yl | H | H | 2-(4-methylpiperazin-1-yl)ethyl | H | 3.5 | 553.3/ 555.3 |

TABLE 1-continued

| Cpd | R⁴ | R⁵ | R⁶ | R⁷ | R⁸ | t_R (min) | MS (M + H)⁺ |
|---|---|---|---|---|---|---|---|
| 1072 | 4-Cl, 3-HN, 2-O benzoxazine (stereo) | H | H | H | Br | 5.6 | 519.1/521.1 |
| 1073 | 4-Cl, 3-HN, 2-O benzoxazine (stereo) | H | H | H | Br | 6.0 | 519.1/521.1 |
| 1074 | 4-Cl, 3-HN, 2-O benzoxazine (stereo) | H | H | 4-methylpiperazin-1-yl | H | 3.5 | 539.3/541.3 |
| 1075 | 4-Cl, 3-HN, 2-O benzoxazine (stereo) | H | H | H | 3-(methanesulfonamido)phenyl | 4.8 | 610.1/612.1 |
| 1076 | 4-Cl, 3-HN, 2-O benzoxazine (stereo) | H | H | H | 3-(methanesulfonamido)phenyl | 5.1 | 610.1/612.1 |

TABLE 1-continued

| Cpd | R⁴ | R⁵ | R⁶ | R⁷ | R⁸ | t_R (min) | MS (M + H)⁺ |
|---|---|---|---|---|---|---|---|
| 1077 | (3-chloro-3,4-dihydro-2H-benzo[b][1,4]oxazin-6-yl, trans) | H | H | H | 3-carbamoylphenyl | 4.5 | 560.2/ 562.2 |
| 1078 | (3-chloro-3,4-dihydro-2H-benzo[b][1,4]oxazin-6-yl, cis) | H | H | H | 3-carbamoylphenyl | 4.7 | 560.2/ 562.2 |
| 1079 | (3-chloro-3,4-dihydro-2H-benzo[b][1,4]oxazin-6-yl, trans) | H | H | H | 3-(N,N-dimethylcarbamoyl)phenyl | 4.8 | 588.2/ 590.2 |
| 1080 | (3-chloro-3,4-dihydro-2H-benzo[b][1,4]oxazin-6-yl, cis) | H | H | H | 3-(N,N-dimethylcarbamoyl)phenyl | 5.1 | 588.2/ 590.2 |
| 1081 | (3-chloro-3,4-dihydro-2H-benzo[b][1,4]oxazin-6-yl, trans) | H | H | H | 4-(morpholine-4-carbonyl)phenyl | 4.8 | 630.2/ 632.2 |

TABLE 1-continued

| Cpd | R⁴ | R⁵ | R⁶ | R⁷ | R⁸ | $t_R$ (min) | MS (M + H)⁺ |
|---|---|---|---|---|---|---|---|
| 1082 | 5-Cl-3,4-dihydro-2H-benzo[b][1,4]oxazin-6-yl | H | H | H | 4-(morpholine-4-carbonyl)phenyl | 5.0 | 630.2/ 632.2 |
| 1083 | (trans)-5-Cl-3,4-dihydro-2H-benzo[b][1,4]oxazin-6-yl | H | H | H | 5-Cl-3,4-dihydro-2H-benzo[b][1,4]oxazin-6-yl | 5.3 | 608.2/ 610.2/ 612.2 |
| 1084 | 5-Cl-3,4-dihydro-2H-benzo[b][1,4]oxazin-6-yl | H | H | H | 5-Cl-3,4-dihydro-2H-benzo[b][1,4]oxazin-6-yl | 5.5 | 608.2/ 610.2/ 612.2 |
| 1085 | chroman-6-yl | H | H | H | OCF₃ | 6.3 | 490.2 |
| 1086 | chroman-6-yl | H | H | | cyclohexa-2,4-dien-1-yl | 6.0 | 456.2 |

TABLE 1-continued
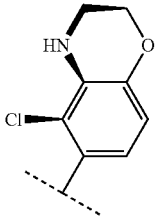
| Cpd | R⁴ | R⁵ | R⁶ | R⁷ | R⁸ | t_R (min) | MS (M + H)⁺ |
|---|---|---|---|---|---|---|---|
| 1087 |  | H | H | H | 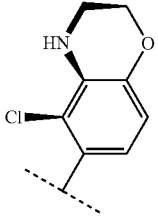 | 5.0 | 467.2/ 469.2 |
| 1088 |  | H | H | H | 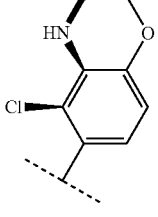 | 4.8 | 469.2/ 471.2 |
| 1089 | 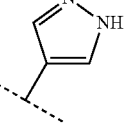 | H | H | H | 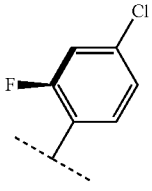 | 4.6 | 507.2/ 509.1 |
| 1090 | 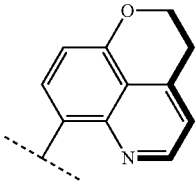 | F | H | H | H | 5.7 | 420.1/ 422.1 |
| 1091 | 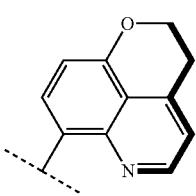 | F | H | H | H | 3.8 | 461.2 |
| 1092 | 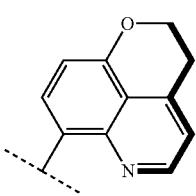 | H | H | Me | Cl | 5.0 | 491.2/ 493.2 |

TABLE 1-continued

| Cpd | R⁴ | R⁵ | R⁶ | R⁷ | R⁸ | t_R (min) | MS (M + H)⁺ |
|---|---|---|---|---|---|---|---|
| 1093 | (chromeno-pyridinyl) | H | F | Me | H | 2.9 | 475.1 |
| 1094 | (chromeno-pyridinyl) | H | H | CN | H | 4.3 | 468.0 |
| 1095 | (chromanyl) | H | H | CN | H | 5.5 | 431.1 |
| 1096 | (chromeno-pyridinyl) | H | H | —C(=O)—NH—t-Bu | H | 4.3 | 542.1 |

TABLE 2
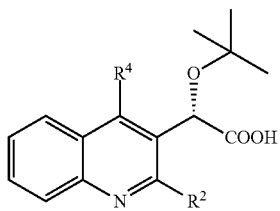
| Cpd | R² | R⁴ | t_R (min) | MS (M + H)⁺ |
|---|---|---|---|---|
| 2001 | morpholinylmethyl | 4-chlorophenyl | 5.1 | 469.3/ 471.3 |
| 2002 | morpholinylmethyl | chroman-6-yl | 5.0 | 491.4 |
| 2003 | imidazol-1-ylmethyl | chroman-6-yl | 5.0 | 472.4 |
| 2004 | 2-carboxybenzamidoethyl | chroman-6-yl | 5.2 | 569.3 |
| 2005 | phenoxyethyl | chroman-6-yl | 6.6 | 498.3 |
| 2006 | phenoxyethyl | dimethylchroman-6-yl | 6.8 | 512.3 |

TABLE 2-continued

| Cpd | R² | R⁴ | t_R (min) | MS (M + H)⁺ |
|---|---|---|---|---|
| 2007 | | | 6.8 | 512.3 |
| 2008 | | | 6.5 | 533.2/ 535.2 |
| 2009 | | | 6.7 | 533.2/ 535.2 |
| 2010 | | | 5.0 | 499.4 |
| 2011 | | | 6.0 | 500.3 |

TABLE 2-continued
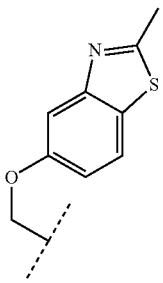
| Cpd | R² | R⁴ | $t_R$ (min) | MS (M + H)⁺ |
|---|---|---|---|---|
| 2012 | 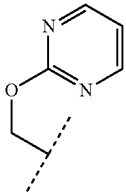 | 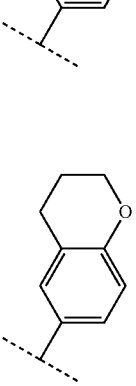 | 6.7 | 569.3 |
| 2013 | 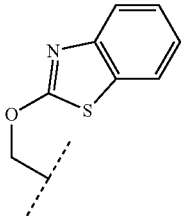 |  | 5.5 | 500.3 |
| 2014 |  | 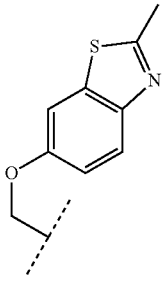 | 8.3 | 555.2 |
| 2015 | —CH₂OCH₃ | 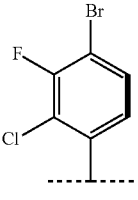 | 4.8 | 436.2 |
| 2016 |  |  | 8.2 | 643.0/ 645.0/ 647.0 |

TABLE 2-continued

[Structure: quinoline with R⁴ at 4-position, O-tBu and COOH substituents at 3-position, R² at 2-position]

| Cpd | R² | R⁴ | t_R (min) | MS (M + H)⁺ |
|---|---|---|---|---|
| 2017 | [2-methylbenzothiazol-6-yloxy-ethyl] | [4-bromo-3-fluoro-2-chlorophenyl] | 8.1 | 643.0/ 645.0/ 647.0 |

TABLE 3

[Structure: quinoline with R⁵, R⁶, R⁷, R⁸ on benzo ring, R⁴ at 4-position, O-tBu and COOH at 3-position, CH₃ at 2-position]

| Cpd | R⁴ | R⁵ | R⁶ | R⁷ | R⁸ | t_R (min) | MS (M + H)⁺ |
|---|---|---|---|---|---|---|---|
| 3001 | [4-chlorophenyl] | F | H | H | H | 4.7 | 402.0 |
| 3002 | [4-chlorophenyl] | H | H | H | F | 5.2 | 402.1 |
| 3003 | [4-chlorophenyl] | —OCH₃ | H | H | H | 4.5 | 414.2/ 416.2 |

TABLE 3-continued
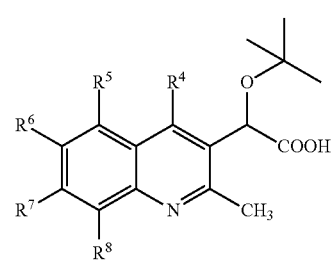
| Cpd | R⁴ | R⁵ | R⁶ | R⁷ | R⁸ | t_R (min) | MS (M + H)⁺ |
|---|---|---|---|---|---|---|---|
| 3004 | 4-Cl-C₆H₄- | H | —OCH₃ | H | H | 4.6 | 414.1/ 416.1 |
| 3005 | 4-Cl-C₆H₄- | H | H | —OCH₃ | H | 4.6 | 414.1/ 416.1 |
| 3006 | 4-Cl-C₆H₄- | H | H | H | —OCH₃ | 4.5 | 414.1/ 416.1 |
| 3007 | 4-Cl-C₆H₄- | H | H | H | —CH₃ | 4.7 | 398.1/ 400.1 |
| 3008 | 4-Cl-C₆H₄- | H | H | —CH=CH₂ | H | 4.9 | 410.2/ 412.2 |
| 3009 | 4-Cl-C₆H₄- | H | H | cyclopropyl | H | 5.2 | 424.2/ 426.2 |

TABLE 3-continued

| Cpd | R⁴ | R⁵ | R⁶ | R⁷ | R⁸ | t_R (min) | MS (M + H)⁺ |
|---|---|---|---|---|---|---|---|
| 3010 | 6-chromanyl | F | H | H | H | 5.0 | 424.2 |
| 3011 | 4-chlorophenyl | H | H | —NO₂ | H | 7.5 | 429.1/ 431.1 |
| 3012 | 4-chlorophenyl | H | H | —NH₂ | H | 5.2 | 399.1/ 401.1 |
| 3013 | 4-chlorophenyl | H | H | —CH₂OH | H | 4.9 | 414.1/ 416.1 |
| 3014 | 4-chlorophenyl | H | H | —C(=O)NH₂ | H | 4.7 | 427.1/ 429.1 |
| 3015 | 4-chlorophenyl | H | H | —CN | H | 6.5 | 409.1/ 411.1 |

TABLE 3-continued
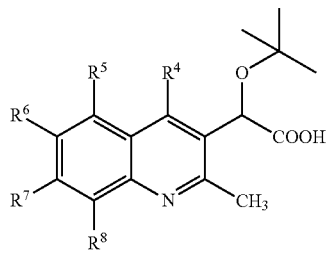
| Cpd | R⁴ | R⁵ | R⁶ | R⁷ | R⁸ | t_R (min) | MS (M + H)⁺ |
|---|---|---|---|---|---|---|---|
| 3016 | 4-chlorophenyl | H | H | —NHC(=O)CH₃ | H | 5.0 | 441.1/ 443.1 |
| 3017 | 4-chlorophenyl | —CH₃ | H | H | H | 4.0 | 398.3 |
| 3018 | chroman-6-yl | —CH₃ | H | H | H | 4.0 | 420.4 |
| 3019 | 4-chlorophenyl | H | H | H | 2-oxopyridin-1-yl 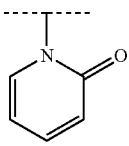 | 5.3 | 477.2/ 479.2 |

TABLE 4

| Cpd | R⁴ | R⁵ | R⁶ | R⁷ | R⁸ | R² |
|---|---|---|---|---|---|---|
| 4001 | (8-chloro-chroman-6-yl, Cl trans) | H | H | H | 1H-pyrazol-4-yl | CH₃ |
| 4002 | (8-chloro-chroman-6-yl, Cl trans) | H | H | 1H-pyrazol-4-yl | H | CH₃ |
| 4003 | (8-chloro-chroman-6-yl, Cl trans) | H | H | H | H | -CH₂CH₂OCH₃ |
| 4004 | (5-methyl-chroman-6-yl) | H | H | H | 1H-pyrazol-4-yl | CH₃ |
| 4005 | (5-methyl-chroman-6-yl) | H | H | 1H-pyrazol-4-yl | H | CH₃ |
| 4006 | (4-bromo-3-fluoro-2-chlorophenyl) | H | H | H | 1H-pyrazol-4-yl | CH₃ |

TABLE 4-continued

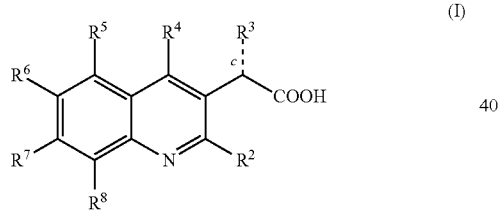

| Cpd | $R^4$ | $R^5$ | $R^6$ | $R^7$ | $R^8$ | $R^2$ |
|---|---|---|---|---|---|---|
| 4007 | (chroman-CH₃ substituted) | H | H | H | H | (methoxypropyl group) |

All of the documents cited herein are incorporated in to the invention as a reference, as if each of them is individually incorporated. Further, it would be appreciated that, in the above teaching of invention, the skilled in the art could make certain changes or modifications to the invention, and these equivalents would still be within the scope of the invention defined by the appended claims of the application.

The invention claimed is:
1. A compound of the formula (I)

(I)

wherein
$R^2$ is selected from:
  a) $(C_{2-6})$alkenyl, $(C_{2-6})$alkynyl, $(C_{1-6})$haloalkyl, $(C_{3-7})$cycloalkyl, aryl, Het, halo, nitro or cyano;
  b) —C(=O)—$R^{11}$, —C(=O)—O—$R^{11}$, —S—$R^{11}$, —SO—$R^{11}$, —SO₂—$R^{11}$, —$(C_{1-6})$alkylene-$R^{11}$, —$(C_{1-6})$alkylene-C(=O)—$R^{11}$, —$(C_{1-6})$alkylene-C(=O)—O—$R^{11}$, —$(C_{1-6})$alkylene-O—$R^{11}$, —$(C_{1-6})$alkylene-S—$R^{11}$, —$(C_{1-6})$alkylene-SO—$R^{11}$ or —$(C_{1-6})$alkylene-SO₂—$R^{11}$;
    wherein $R^{11}$ is in each instance independently selected from H, $(C_{1-6})$alkyl, $(C_{2-6})$alkenyl, $(C_{2-6})$alkynyl, $(C_{1-6})$haloalkyl, $(C_{3-7})$cycloalkyl, aryl and Het; and
    wherein each of the aryl and Het is optionally substituted with 1 to 3 substituents each independently selected from:
      i) halo, oxo, thioxo, $(C_{2-6})$alkenyl, $(C_{1-6})$haloalkyl, $(C_{3-7})$cycloalkyl, $(C_{3-7})$cycloalkyl-$(C_{1-6})$alkyl-, —OH, —O$(C_{1-6})$alkyl, —O$(C_{1-6})$haloalkyl, —SH, —S$(C_{1-6})$alkyl, —SO$(C_{1-6})$alkyl, —SO₂$(C_{1-6})$alkyl, —C(=O)—NH₂, —C(=O)—NH$(C_{1-4})$alkyl, —C(=O)—N$((C_{1-4})$alkyl$)_2$, —C(=O)-aryl, —C(=O)—Het, NH₂, —NH$(C_{1-6})$alkyl and —N$((C_{1-6})$alkyl$)_2$;
      ii) $(C_{1-6})$alkyl optionally substituted with —OH, —O—$(C_{1-6})$haloalkyl, or —O—$(C_{1-6})$alkyl; and
      iii) aryl or Het, wherein each of the aryl and Het is optionally substituted with halo, $(C_{1-6})$alkyl or COOH; and
  c) —O—$R^{8a}$
    wherein $R^{8a}$ is selected from H, $(C_{2-6})$alkenyl, $(C_{2-6})$alkynyl, $(C_{1-6})$haloalkyl, $(C_{3-7})$cycloalkyl, aryl and Het;
  d) —N$(R^9)R^{10}$, —C(=O)—N$(R^9)R^{10}$, —O—C(=O)—N$(R^9)R^{10}$, —SO₂—N$(R^9)R^{10}$, —$(C_{1-6})$alkylene-N$(R^9)R^{10}$, —$(C_{1-6})$alkylene-C(=O)—N$(R^9)R^{10}$, —$(C_{1-6})$alkylene-O—C(=O)—N$(R^9)R^{10}$, or —$(C_{1-6})$alkylene-SO₂—N$(R^9)R^{10}$ wherein
    $R^9$ is in each instance independently selected from H, $(C_{1-6})$alkyl and $(C_{3-7})$cycloalkyl; and
    $R^{10}$ is in each instance independently selected from $R^{11}$, —$(C_{1-6})$alkylene-$R^{11}$, —SO₂—$R^{11}$, —C(=O)—$R^{11}$, —C(=O)O$R^{11}$ and —C(=O)N$(R^9)R^{11}$; wherein $R^{11}$ and $R^9$ are as defined above; or $R^2$ may also be H, $(C_{1-6})$alkyl or —O—$(C_{1-6})$alkyl when one of $R^5$ or $R^8$ is other than H or when one of $R^6$ or $R^7$ is other than H, halo, $(C_{1-6})$alkyl or $(C_{1-6})$haloalkyl, $R^5$ and $R^8$ are each independently selected from:
  a) halo, nitro or cyano;
  b) $R^{11}$, —C(=O)—$R^{11}$, —C(=O)—O—$R^{11}$, —O—$R^{11}$, —S—$R^{11}$, —SO—$R^{11}$, —SO₂—$R^{11}$, —$(C_{1-6})$alkylene-$R^{11}$, —$(C_{1-6})$alkylene-C(=O)—$R^{11}$, —$(C_{1-6})$alkylene-C(=O)—O—$R^{11}$, —$(C_{1-6})$alkylene-O—$R^{11}$, —$(C_{1-6})$alkylene-S—$R^{11}$, —$(C_{1-6})$alkylene-SO—$R^{11}$ or —$(C_{1-6})$alkylene-SO₂—$R^{11}$;
    wherein $R^{11}$ is in each instance independently selected from H, $(C_{1-6})$alkyl, $(C_{2-6})$alkenyl, $(C_{2-6})$alkynyl, $(C_{1-6})$haloalkyl, $(C_{3-7})$cycloalkyl, aryl and Het; and
    wherein each of the aryl and Het is optionally substituted with 1 to 3 substituents each independently selected from:

i) halo, oxo, thioxo, $(C_{2-6})$alkenyl, $(C_{1-6})$haloalkyl, $(C_{3-7})$cycloalkyl, $(C_{3-7})$cycloalkyl-$(C_{1-6})$alkyl-, —OH, —O$(C_{1-6})$alkyl, —O$(C_{1-6})$haloalkyl, —SH, —S$(C_{1-6})$alkyl, —SO$(C_{1-6})$alkyl, —SO$_2$$(C_{1-6})$alkyl, —NH$_2$, —C(=O)—NH$(C_{1-4})$alkyl, —C(=O)—N(($C_{1-4}$)alkyl)$_2$, —C(=O)-aryl, —C(=O)—Het, NH$_2$, —NH$(C_{1-6})$alkyl and —N(($C_{1-6}$)alkyl)$_2$;

ii) $(C_{1-6})$alkyl optionally substituted with —OH, —O—$(C_{1-6})$haloalkyl, or —O—$(C_{1-6})$alkyl; and iii) aryl or Het, wherein each of the aryl and Het is optionally substituted with halo, $(C_{1-6})$alkyl or COOH; and c) —N(R$^9$)R$^{10}$, —C(=O)—N(R$^9$)R$^{10}$, —O—C(=O)—N(R$^9$)R$^{10}$, —SO$_2$—N(R$^9$)R$^{10}$, —$(C_{1-6})$alkylene-N(R$^9$)R$^{10}$, —$(C_{1-6})$alkylene-C(=O)—N(R$^9$)R$^{10}$, —$(C_{1-6})$alkylene-O—C(=O)—N(R$^9$)R$^{10}$, or —$(C_{1-6})$alkylene-SO$_2$—N(R$^9$)R$^{10}$ wherein R$^9$ is in each instance independently selected from H, $(C_{1-6})$alkyl and $(C_{3-7})$cycloalkyl; and R$^{10}$ is in each instance independently selected from R$^{11}$, —$(C_{1-6})$alkylene-R$^{11}$, —SO$_2$—R$^{11}$, —C(=O)—R$^{11}$, —C(=O)OR$^{11}$ and —C(=O)N(R$^9$)R$^{11}$; wherein R$^{11}$ and R$^9$ are as defined above;

R$^6$ is selected from:

a) $(C_{2-6})$alkenyl, $(C_{2-6})$alkynyl, $(C_{3-7})$cycloalkyl, nitro, cyano, aryl and Het;

b) —C(=O)—R$^{11}$, —C(=O)—O—R$^{11}$, —O—R$^{11}$, —S—R$^{11}$, —SO—R$^{11}$, —SO$_2$—R$^{11}$, —$(C_{1-6})$alkylene-R$^{11}$, —$(C_{1-6})$alkylene-C(=O)—R$^{11}$, —$(C_{1-6})$alkylene-C(=O)—O—R$^{11}$, —$(C_{1-6})$alkylene-O—R$^{11}$, —$(C_{1-6})$alkylene-S—R$^{11}$, —$(C_{1-6})$alkylene-SO—R$^{11}$ or —$(C_{1-6})$alkylene-SO$_2$—R$^{11}$;

wherein R$^{11}$ is in each instance independently selected from H, $(C_{1-6})$alkyl, $(C_{2-6})$alkenyl, $(C_{2-6})$alkynyl, $(C_{1-6})$haloalkyl, $(C_{3-7})$cycloalkyl, aryl and Het; and c) —N(R$^9$)R$^{10}$, —C(=O)—N(R$^9$)R$^{10}$, —O—C(=O)—N(R$^9$)R$^{10}$, —SO$_2$—N(R$^9$)R$^{10}$, —$(C_{1-6})$alkylene-N(R$^9$)R$^{10}$, —$(C_{1-6})$alkylene-C(=O)—N(R$^9$)R$^{10}$, —$(C_{1-6})$alkylene-O—C(=O)—N(R$^9$)R$^{10}$, or —$(C_{1-6})$alkylene-SO$_2$—N(R$^9$)R$^{10}$ wherein R$^9$ is in each instance independently selected from H, $(C_{1-6})$alkyl and $(C_{3-7})$cycloalkyl; and R$^{10}$ is in each instance independently selected from R$^{11}$, —$(C_{1-6})$alkylene-R$^{11}$, —SO$_2$—R$^{11}$, —C(=O)—R$^{11}$, —C(=O)OR$^{11}$ and —C(=O)N(R$^9$)R$^{11}$; wherein R$^{11}$ and R$^9$ are as defined above;

wherein each of the aryl and Het is optionally substituted with 1 to 3 substituents each independently selected from:

i) halo, oxo, thioxo, $(C_{2-6})$alkenyl, $(C_{1-6})$haloalkyl, $(C_{3-7})$cycloalkyl, $(C_{3-7})$cycloalkyl-$(C_{1-6})$alkyl-, —OH, —O$(C_{1-6})$alkyl, —O$(C_{1-6})$haloalkyl, —SH, —S$(C_{1-6})$alkyl, —SO$(C_{1-6})$alkyl, —SO$_2$$(C_{1-6})$alkyl, —NH$_2$, —NH$(C_{1-6})$alkyl and —N(($C_{1-6}$)alkyl)$_2$;

ii) $(C_{1-6})$alkyl optionally substituted with —OH, —O—$(C_{1-6})$haloalkyl, or —O—$(C_{1-6})$alkyl; and iii) aryl or Het, wherein each of the aryl and Het is optionally substituted with halo, $(C_{1-6})$alkyl or COOH; and R$^6$ may also be H, halo, $(C_{1-6})$alkyl, or $(C_{1-6})$haloalkyl when at least one of R$^5$ or R$^8$ is other than H or when R$^7$ is other than H, halo, $(C_{1-6})$alkyl, or $(C_{1-6})$haloalkyl or when R$^2$ is other than H, $(C_{1-6})$alkyl, or —O—$(C_{1-6})$alkyl;

R$^7$ may also be H, halo, $(C_{1-6})$alkyl, or $(C_{1-6})$haloalkyl when at least one of R$^5$ or R$^8$ is other than H or when R$^6$ is other than H, halo, $(C_{1-6})$alkyl, or $(C_{1-6})$haloalkyl or when R$^2$ is other than H, $(C_{1-6})$alkyl, or —O—$(C_{1-6})$alkyl;

or R$^5$ and R$^6$, together with the C to which they are attached, R$^6$ and R$^7$, together with the C to which they are attached, or R$^7$ and R$^8$, together with the C to which they are attached; may be linked to form a 5- or 6-membered carbocycle or a 4- to 7-membered heterocycle optionally further containing 1 to 3 heteroatoms each independently selected from N, O and S, wherein each S heteroatom may, independently and where possible, exist in an oxidized state such that it is further bonded to one or two oxygen atoms to form the groups SO or SO$_2$;

wherein the carbocycle or heterocycle is optionally substituted with 1 to 3 substituents each independently selected from halo, $(C_{1-6})$alkyl, $(C_{2-6})$alkenyl, $(C_{1-6})$haloalkyl, $(C_{3-7})$cycloalkyl, —OH, —O$(C_{1-6})$alkyl, —SH, —S$(C_{1-6})$alkyl, —NH$_2$, —NH$(C_{1-6})$alkyl and —N(($C_{1-6}$)alkyl)$_2$;

R$^3$ is $(C_{1-6})$alkyl, $(C_{1-6})$haloalkyl, $(C_{2-6})$alkenyl, $(C_{2-6})$alkynyl, $(C_{3-7})$cycloalkyl-$(C_{1-6})$alkyl-, aryl-$(C_{1-6})$alkyl-, Het-$(C_{1-6})$alkyl- or —Y—R$^{31}$, and bond c is a single bond; or R$^3$ is $(C_{1-6})$alkylidene and bond c is a double bond;

wherein Y is O or S and R$^{31}$ is $(C_{1-6})$alkyl, $(C_{1-6})$haloalkyl, $(C_{2-6})$alkenyl, $(C_{2-6})$alkynyl, $(C_{3-7})$cycloalkyl, aryl, $(C_{3-7})$cycloalkyl-$(C_{1-6})$alkyl-, aryl-$(C_{1-6})$alkyl- or Het-$(C_{1-6})$alkyl-;
wherein each of the $(C_{1-6})$alkylidene, $(C_{1-6})$alkyl, $(C_{1-6})$haloalkyl, $(C_{2-6})$alkenyl, $(C_{2-6})$alkynyl, $(C_{3-7})$cycloalkyl-$(C_{1-6})$alkyl-, aryl-$(C_{1-6})$alkyl-, Het-$(C_{1-6})$alkyl- and —Y—$R^{31}$ is optionally substituted with 1 to 3 substituents each independently selected from $(C_{1-6})$ alkyl, halo, cyano, oxo and —O$(C_{1-6})$alkyl;

$R^4$ is aryl or Het, wherein each of the aryl and Het is optionally substituted with 1 to 5 substituents each independently selected from halo, $(C_{1-6})$alkyl, $(C_{2-6})$alkenyl, $(C_{1-6})$haloalkyl, $(C_{3-7})$cycloalkyl, —OH, —O$(C_{1-6})$alkyl, —SH, —S$(C_{1-6})$alkyl, —NH$_2$, —NH$(C_{1-6})$ alkyl and —N$((C_{1-6})$alkyl$)_2$; wherein the $(C_{1-6})$alkyl is optionally substituted with hydroxy, —O$(C_{1-6})$alkyl, cyano or oxo;

wherein Het is a 4- to 7-membered saturated, unsaturated or aromatic heterocycle having 1 to 4 heteroatoms each independently selected from O, N and S, or a 7- to 14-membered saturated, unsaturated or aromatic heteropolycycle having wherever possible 1 to 5 heteroatoms, each independently selected from O, N and S; wherein each N heteroatom may, independently and where possible, exist in an oxidized state such that it is further bonded to an oxygen atom to form an N-oxide group and wherein each S heteroatom may, independently and where possible, exist in an oxidized state such that it is further bonded to one or two oxygen atoms to form the groups SO or SO$_2$;

or a pharmaceutically acceptable salt thereof.

2. A compound according to claim 1 of the formula (Ib),

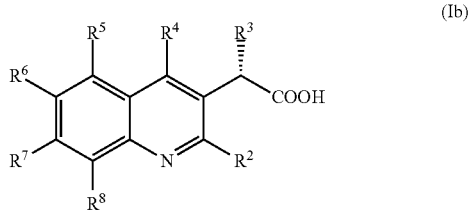

(Ib)

wherein $R^2$, $R^3$, $R^4$, $R^5$, $R^6$, $R^7$ and $R^8$ are as defined in claim 1, or a pharmaceutically acceptable salt thereof.

3. A compound according to claim 2, or a pharmaceutically acceptable salt thereof, wherein $R^2$ is selected from H, $(C_{1-6})$alkyl or —O—$(C_{1-6})$alkyl when one of $R^5$ or $R^8$ is other than H or when one of $R^6$ or $R^7$ is other than H, halo, $(C_{1-6})$alkyl or $(C_{1-6})$haloalkyl.

4. A compound according to claim 2, or a pharmaceutically acceptable salt thereof, wherein $R^3$ is selected from —O$(C_{1-6})$alkyl, —O—$(C_{1-6})$haloalkyl, —O$(C_{2-6})$alkenyl, —O$(C_{2-6})$alkynyl or —O—$(C_{3-7})$cycloalkyl;
wherein each of the —O$(C_{1-6})$alkyl and —O—$(C_{3-7})$cycloalkyl is optionally substituted with 1 to 3 substituents each independently selected from $(C_{1-3})$alkyl, cyano, oxo and —O$(C_{1-6})$ alkyl; and bond c is a single bond.

5. A compound according to claim 2, or a pharmaceutically acceptable salt thereof, wherein $R^4$ is selected from phenyl optionally substituted with 1 to 3 substituents each independently selected from halo, $(C_{1-4})$alkyl and $(C_{1-4})$haloalkyl.

6. A compound according to claim 2, or a pharmaceutically acceptable salt thereof, wherein $R^4$ is Het optionally substituted with 1 to 3 substituents each independently selected from halo and $(C_{1-6})$alkyl;
wherein the Het is a 5- or 6-membered heterocycle having 1 to 3 heteroatoms each independently selected from N, O and S; or the Het is a 9- or 10-membered heteropolycycle having 1 to 3 heteroatoms each independently selected from N, O and S.

7. A compound according to claim 2, or a pharmaceutically acceptable salt thereof, wherein $R^5$ is H, halo, $(C_{1-6})$alkyl, $(C_{1-6})$haloalkyl or —O$(C_{1-6})$ alkyl.

8. A compound according to any claim 2, or a pharmaceutically acceptable salt thereof, wherein $R^6$ is H when at least one of $R^5$ or $R^8$ is other than H or when $R^7$ is other than H, halo, $(C_{1-6})$alkyl, or $(C_{1-6})$haloalkyl or when $R^2$ is other than H, $(C_{1-6})$alkyl, or —O—$(C_{1-6})$alkyl.

9. A compound according to claim 2, or a pharmaceutically acceptable salt thereof, wherein $R^7$ is selected from:
a) $(C_{2-6})$alkenyl, $(C_{3-7})$cycloalkyl, nitro, cyano, aryl and Het;
b) —$(C_{1-6})$alkylene-$R^{11}$,
wherein $R^{11}$ is in each instance independently selected from H, $(C_{1-6})$alkyl, $(C_{2-6})$alkenyl, $(C_{2-6})$alkynyl, $(C_{1-6})$haloalkyl, $(C_{3-7})$cycloalkyl, aryl and Het; and
c) —N$(R^9)R^{10}$, —C(=O)—N$(R^9)R^{10}$, wherein
$R^9$ is in each instance independently selected from H, $(C_{1-6})$alkyl and $(C_{3-7})$cycloalkyl; and
$R^{10}$ is in each instance independently selected from $R^{11}$, —$(C_{1-6})$alkylene-$R^{11}$, —SO$_2$—$R^{11}$, —C(=O)—$R^{11}$, —C(=O)O$R^{11}$ and —C(=O)N$(R^9)R^{11}$;
wherein $R^{11}$ and $R^9$ are as defined above;
wherein each of the aryl and Het is optionally substituted with 1 to 3 substituents each independently selected from:
i) halo, oxo, thioxo, $(C_{2-6})$alkenyl, $(C_{1-6})$haloalkyl, $(C_{3-7})$cycloalkyl, $(C_{3-7})$cycloalkyl-$(C_{1-6})$alkyl-, —OH, —O$(C_{1-6})$alkyl, —O$(C_{1-6})$haloalkyl, —SH, —S$(C_{1-6})$alkyl, —SO$(C_{1-6})$alkyl, —SO$_2(C_{1-6})$alkyl, —NH$_2$, —NH$(C_{1-6})$alkyl and —N$((C_{1-6})$alkyl$)_2$;
ii) $(C_{1-6})$alkyl optionally substituted with —OH, —O—$(C_{1-6})$haloalkyl, or —O—$(C_{1-6})$alkyl; and
iii) aryl or Het, wherein each of the aryl and Het is optionally substituted with halo, $(C_{1-6})$alkyl or COOH;

$R^7$ may also be H, halo, $(C_{1-6})$alkyl, or $(C_{1-6})$haloalkyl when at least one of $R^5$ or $R^8$ is other than H or when $R^6$ is other than H, halo, $(C_{1-6})$alkyl, or $(C_{1-6})$haloalkyl or when $R^2$ is other than H, $(C_{1-6})$alkyl, or —O—$(C_{1-6})$alkyl.

10. A compound according to claim 2, or a pharmaceutically acceptable salt thereof, wherein $R^7$ is H, when at least one of $R^5$ or $R^8$ is other than H or when $R^6$ is other than H, halo, $(C_{1-6})$alkyl, or $(C_{1-6})$haloalkyl or when $R^2$ is other than H, $(C_{1-6})$alkyl, or —O—$(C_{1-6})$alkyl.

11. A compound according to claim 2, or a pharmaceutically acceptable salt thereof, wherein $R^8$ is selected from:
a) F, Cl, Br; and
b) H, $(C_{1-3})$alkyl, —O—$(C_{1-3})$haloalkyl, phenyl and Het, —$(C_{1-3})$alkylene-phenyl, —$(C_{1-3})$alkylene-Het;
wherein each of the aryl and Het is optionally substituted with 1 to 2 substituents each independently selected from:
i) oxo, thioxo, —O$(C_{1-6})$alkyl, —C(=O)—NH$_2$, —C(=O)—NH$(C_{1-4})$alkyl, —C(=O)—N$((C_{1-4})$alkyl$)_2$, —C(=O)-aryl, —C(=O)-Het; and
ii) $(C_{1-6})$alkyl.

12. A pharmaceutical composition comprising a therapeutically a compound according to claim 2, or a pharmaceutically acceptable salt thereof, and a pharmaceutically acceptable carrier.

13. A method for treating HIV in a host infected by HIV which method comprises administering to such host a therapeutically effective amount of a compound according to claim 2, or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 8,377,960 B2 | Page 1 of 1 |
| APPLICATION NO. | : 12/743138 | |
| DATED | : February 19, 2013 | |
| INVENTOR(S) | : Tsantrizos et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 249 days.

Signed and Sealed this
Sixteenth Day of December, 2014

Michelle K. Lee
*Deputy Director of the United States Patent and Trademark Office*